United States Patent
Bander

(10) Patent No.: US 7,192,586 B2
(45) Date of Patent: Mar. 20, 2007

(54) METHODS AND COMPOSITIONS FOR TREATING OR PREVENTING SKIN DISORDERS USING BINDING AGENTS SPECIFIC FOR PROSTATE SPECIFIC MEMBRANE ANTIGEN

(75) Inventor: Neil Bander, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 533 days.

(21) Appl. No.: 10/160,506

(22) Filed: May 30, 2002

(65) Prior Publication Data

US 2003/0161832 A1 Aug. 28, 2003

Related U.S. Application Data

(60) Provisional application No. 60/362,612, filed on Mar. 8, 2002, provisional application No. 60/324,100, filed on Sep. 20, 2001.

(51) Int. Cl.
*A61K 39/395* (2006.01)

(52) U.S. Cl. ............................... 424/155.1; 424/130.1; 424/133.1; 424/138.1; 424/141.1; 424/156.1

(58) Field of Classification Search ............ 424/130.1, 424/133.1, 138.1, 141.1, 155.1, 156.1
See application file for complete search history.

(56) References Cited

U.S. PATENT DOCUMENTS

| | | | |
|---|---|---|---|
| 4,454,106 A | 6/1984 | Gansow et al. | |
| 4,472,509 A | 9/1984 | Gansow et al. | |
| 4,579,844 A * | 4/1986 | Rovee et al. ............... | 514/171 |
| 4,814,275 A | 3/1989 | Durda et al. | |
| 4,855,353 A | 8/1989 | Kurami et al. | |
| 4,863,851 A | 9/1989 | McEwan et al. | |
| 4,863,854 A | 9/1989 | Mattes et al. | |
| 4,885,363 A | 12/1989 | Tweedle et al. | |
| 5,013,645 A | 5/1991 | Kim | |
| 5,053,503 A | 10/1991 | Dean et al. | |
| 5,057,302 A | 10/1991 | Johnson et al. | |
| 5,118,611 A | 6/1992 | Smith et al. | |
| 5,130,118 A | 7/1992 | Johnson et al. | |
| 5,162,504 A | 11/1992 | Horoszewicz | |
| 5,198,208 A | 3/1993 | Berg et al. | |
| 5,208,324 A | 5/1993 | Klaveness et al. | |
| 5,217,704 A | 6/1993 | Johnson et al. | |
| 5,227,471 A | 7/1993 | Wright, Jr. | |
| 5,229,289 A | 7/1993 | Kjeldsen et al. | |
| 5,314,996 A | 5/1994 | Wright, Jr. | |
| 5,342,924 A | 8/1994 | Chang | |
| 5,416,064 A | 5/1995 | Chari et al. | |
| 5,419,893 A | 5/1995 | Berg et al. | |
| 5,474,756 A | 12/1995 | Tweedle et al. | |
| 5,489,525 A | 2/1996 | Pastan | |
| 5,531,978 A | 7/1996 | Berg et al. | |
| 5,538,866 A | 7/1996 | Israeli et al. | |
| 5,565,562 A | 10/1996 | Parker et al. | |
| 5,578,484 A | 11/1996 | Horoszewicz | |
| 5,599,677 A | 2/1997 | Dowell et al. | |
| 5,639,879 A | 6/1997 | Mease et al. | |
| 5,660,827 A | 8/1997 | Thorpe et al. | |
| 5,674,470 A | 10/1997 | Tweedle et al. | |
| 5,697,902 A | 12/1997 | Goldenberg | |
| 5,763,202 A | 6/1998 | Horoszewicz | |
| 5,776,427 A | 7/1998 | Thorpe et al. | |
| 5,804,602 A | 9/1998 | Slusher et al. | |
| 5,846,519 A | 12/1998 | Tweedle et al. | |
| 5,855,866 A | 1/1999 | Thorpe et al. | |
| 5,863,538 A | 1/1999 | Thorpe et al. | |
| 5,877,289 A | 3/1999 | Thorpe et al. | |
| 5,935,818 A | 8/1999 | Israeli et al. | |
| 5,958,474 A | 9/1999 | Lee et al. | |
| 5,965,132 A | 10/1999 | Thorpe et al. | |
| 6,004,554 A | 12/1999 | Thorpe et al. | |
| 6,004,555 A | 12/1999 | Thorpe et al. | |
| 6,022,524 A | 2/2000 | Maisano et al. | |
| 6,036,955 A | 3/2000 | Thorpe et al. | |
| 6,051,230 A | 4/2000 | Thorpe et al. | |
| 6,093,399 A | 7/2000 | Thorpe et al. | |
| 6,136,311 A * | 10/2000 | Bander ..................... | 424/155.1 |
| 6,143,274 A | 11/2000 | Tweedle et al. | |
| 6,150,508 A | 11/2000 | Murphy et al. | |
| 6,168,778 B1 | 1/2001 | Janjic et al. | |

(Continued)

FOREIGN PATENT DOCUMENTS

EP 0 208 531 B1 1/1987

(Continued)

OTHER PUBLICATIONS

Li et al (Bioconjugate Chemistry, 5(2):101-104, Mar./Apr. 1994).*
Koo (J. Dermatol. 1999; 26: 723-733).*
Chang et al. (1999 ASCO Annual Meeting; Abs. No. 2399).*
Auerbach et al. (Clinical Chemistry 2003, 49:1,32-40.*
Jain et al. (Nat. Med. 1997, 3, 1203-1208).*
Fundamental Immunology 242 (William E. Paul, M.D. ed., 3rd ed. 1993).*
International Search Report, Jun. 6, 2003.
Barren et al. (1997), "Monoclonal Antibody 7E11.C5 Staining of Viable LNCaP Cells", Prostate 30(1):65-8.

(Continued)

*Primary Examiner*—Jeffrey Siew
*Assistant Examiner*—Brandon Fetterolf
(74) *Attorney, Agent, or Firm*—Fish & Richardson P.C.

(57) ABSTRACT

Methods and compositions for treating, preventing, or diagnosing epidermal or dermal disorders, e.g., psoriasis, are disclosed. The methods and compositions of the invention use binding agents, e.g., antibodies, specific for the extracellular domain of human prostate specific membrane antigen (PSMA).

62 Claims, 33 Drawing Sheets

U.S. PATENT DOCUMENTS

| | | | |
|---|---|---|---|
| 6,200,765 B1 | 3/2001 | Murphy et al. | |
| 6,261,535 B1 | 7/2001 | Thorpe et al. | |
| 6,331,175 B1 | 12/2001 | Goldenberg | |
| 6,342,221 B1 | 1/2002 | Thorpe et al. | |
| 6,824,780 B1 * | 11/2004 | Devaux et al. | 424/156.1 |

FOREIGN PATENT DOCUMENTS

| | | |
|---|---|---|
| EP | 0 232 751 B1 | 8/1987 |
| EP | 0 233 619 B1 | 8/1987 |
| EP | 0 279 397 B1 | 8/1988 |
| EP | 0 292 689 B1 | 11/1988 |
| EP | 0 299 795 A1 | 1/1989 |
| EP | 0 315 188 B1 | 5/1989 |
| EP | 0 382 583 B1 | 8/1990 |
| EP | 0 392 423 A2 | 10/1990 |
| EP | 0 466 200 AW | 1/1992 |
| EP | 0 495 878 B1 | 7/1992 |
| EP | 0 594 739 B1 | 5/1994 |
| EP | 0 882 454 AZ | 12/1998 |
| WO | WO 86/06384 | 11/1986 |
| WO | WO 88/02635 | 4/1988 |
| WO | WO 89/00557 | 1/1989 |
| WO | WO 89/06979 | 8/1989 |
| WO | WO 91/15466 | 10/1991 |
| WO | WO 93/17715 | 9/1993 |
| WO | WO 93/19668 | 10/1993 |
| WO | WO 94/04702 | 3/1994 |
| WO | WO 94/09820 | 5/1994 |
| WO | WO 94/26297 | 11/1994 |
| WO | WO 95/26206 | 10/1995 |
| WO | WO 95/31444 | 11/1995 |
| WO | WO 96/26272 | 8/1996 |
| WO | WO 96/39185 | 12/1996 |
| WO | WO 96/40245 | 12/1996 |
| WO | WO 97/32862 | 9/1997 |
| WO | WO 97/35616 | 10/1997 |
| WO | WO98/03873 | 1/1998 |
| WO | WO 9803873 A1 * | 1/1998 |
| WO | WO 99/43710 | 9/1999 |
| WO | WO00/14257 | 3/2000 |
| WO | WO 00/50457 | 8/2000 |
| WO | WO 00/52473 | 9/2000 |
| WO | WO 00/74729 | 12/2000 |

OTHER PUBLICATIONS

Carter et al. (1996), "Prostate-specific Membrane Antigen is a Hydrolase with Substrate and Pharmacologic Characteristics of a Neuropeptidase", Proc. Natl. Acad. Sci. U.S.A. 93:749-751.

Chang et al. (1999), "Five Different Anti-Prostate-specific Membrane Antigen (PSMA) Antibodies Confirm PSMA Expression in Tumor-associated Neovasculature", Cancer Research, 59(13):3192-3198.

Diamond et al. (1997), "Monoclonal Antibody 225 Blockade of Prostate Specific Membrane Antigen (PSM) Expression: Potential Novel Therapy for Prostate Cancer", Journal of Urology 157(4 suppl):226 (Abstract 884).

Dillman et al. (1988), "Toxicities Associated with Monoclonal Antibody Infusions in Cancer Patients", Mol. Biother. 1(2):81-85.

Dillman et al. (1994), "Human Anti-Mouse Antibody Response in Cancer Patients Following Single Low-Dose Injections of Radiolabeled Murine Monoclonal Antibodies", Cancer Biotherapy 9(1):17-28.

Fair et al. (1997), "Prostate Specific Membrane Antigen", Prostate 32(2):140-8.

Goldsmith and Bander, "Monoclonal Antibody Therapy", Nuclear Oncology: Diagnosis and Therapy. Chapter 32: Prostate Carcinoma. pp. 433-439. Lippincott Williams and Wilkins, Philadelphia, 2001.

Hamilton et al. (1998), "A novel humanized antibody against Prostate Specific Membrane Antigen (PSMA) for in vivo targeting and therapy", Proc. Amer. Assoc. Cancer Res. 39:440, Abstract #2997.

Harlow and Lane (1988), "Antibodies: A laboratory manual", Cold Spring Harbor Laboratory, p. 139-243.

Heston (1997), "Characterization and Glutamyl Preferring Carboxypeptidase Function of Prostate Specific Membrane Antigen: A Novel Folate Hydrolase", Urology 49(3A):104-112.

Holmes (2001), "PSMA specific antibodies and their diagnostic and therapeutic use", Exp. Opin. Invest. Drugs 10(3):511-19.

Horoszewicz et al. (1987), "Monoclonal Antibodies to a New Antigenic Marker in Epithelial Prostatic Cells and Serum of Prostatic Cancer Patients", Anticancer Research 7(5B):927-936.

Israeli et al. (1993), "Molecular Cloning of a Complementary DNA Encoding a Prostate-Specific Membrane Antigen", Cancer Research 53(2):227-230.

Israeli et al. (1994), "Expression of the Prostate-Specific Membrane Antigen", Cancer Research 54(7):1807-1811.

Israeli et al. (1997), "Prostate Specific Membrane Antigen and Other Prostatic Tumor Markers on the Horizon", Urological Clinics of North America 24(2):439-50.

Jain, R.K. (1990), "Vacular and interstitial barriers to delivery of therapeutic agents in tumors", Cancer and Metastasis Reviews 9(3):253-266.

Leek et al. (1995), "Prostate-Specific Membrane Antigen: Evidence for the Existence of a Second Related Human Gene", British Journal of Cancer 72:583-588.

Leung et al. (1986), "Selection of a Monoclonal Antibody to a New Prostate Cancer Marker for In Vivo Clinical Trials", 6th International Congress of Immunology, p. 516 (Abstract 4.15.19).

Liu et al. (1997), "Monoclonal Antibodies to the Extracellular Domain of Prostate-specific Membrane Antigen also React with Tumor Vascular Endothelium", Cancer Research 57(18):3629-3634.

Liu, et al. (1998), "Constitutive and Antibody-Induced Internalization of Prostate-Specific Membrane Antigen", Cancer Research 58(18):4055-4060.

Murphy et al. (1995), "Comparison of Prostate Specific Antigen, Prostate Specific Membrane Antigen, and LNCaP-Based Enzyme-Linked Immunosorbent Assays in Prostatic Cancer Patients and Patients With Benign Prostatic Enlargement", The Prostate 26:164-168.

Murphy et al. (1995), "Comparison of Prostate Specific Membrane Antigen, and Prostate Specific Antigen Levels in Prostatic Cancer Patients", Anticancer Res. 15:1473-1480.

Murphy et al. (1996), "Measurement of Prostate-Specific Membrane Antigen in the Serum With a New Antibody", The Prostate 28(4):266-271.

Pinto et al. (1996), "Prostate-Specific Membrane Antigen: A Novel Folate Hydrolase in Human Prostatic Carcinoma Cells", Clincal Cancer Research 2(9):1445-51.

Rochon et al. (1994), "Western Blot Assay for Prostate-Specific Membrane Antigen in Serum of Prostate Cancer Patients", The Prostate 25(4):219-223.

Schlom (1991), "Monoclonal antibodies: They're more and less than you think", Molecular Foundations of Oncology, ed. Broder, Williams & Wilkins, p. 95-134.

Smith (2001), "Technology evaluation: C242-DM1, ImmunoGen Inc.", Current Opin. In Mol Therapeutics 3(2):198-203.

Su et al. (1995), "Alternatively Spliced Variants of Prostate-specific Membrane Antigen RNA: Ratio of Expression as a Potential Measurement of Progression", Cancer Research 55:1441-1443.

Troyer et al. (1994), "Subcellular Localization of the 7E11-C5 Prostate Specific Antigen", Proc. Am. Assoc. Cancer Research 35:283 (Abstract 1688).

Troyer et al. (1995), "Biochemical Characterization and Mapping of the 7E11-C5.3 Epitope of the Prostate-Specific Membrane Antigen", Urol Oncol 1:29-37.

Troyer et al. (1995), "Detection and Characterization of the Prostate-Specific Membrane Antigen (PSMA) in Tissue Extracts and Body Fluids", International Journal of Cancer 62(5):552-558.

Troyer et al. (1997), "Location of prostate-specific membrane antigen in the LNCaP prostate carcinoma cell line", Prostate 30(4):232-242.

Uria et al. (1997), "Prostate Specific Membrane Antigen in Breast Carcinoma", The Lancet 349(9065):1601.

Wang et al. (1988), "Monoclonal Antibody Assays for Prostatic Tumor", Immunol Ser 39:195-219.

Wright (1990), "Characterization of a New Prostate Carcinoma-Associated Marker: 7E11-C5", Antibody Immunoconjugates and RadioPharmaceuticals 3:Abstract 193.

Wright et al. (1995), "Expression of Prostate-Specific Membrane Antigen in Normal, Benign, and Malignant Prostate Tissues", Urol Oncol, 1:18-28.

Yang et al. (1998), "Alpha particle emitter therapy of micrometastases: $^{213}$Bi-J5 (anti-PSMA) treatment of LNCaP spheroids", Proceedings of the American Association for Cancer Research 39:440 (Abstract #2996).

Bander, Oral Presentation: "mAb anti-PSMAext Therapy of Prostate Cancer", Oct. 1999.

Bander, CaPCURE Board Presentation: "Antibody Treatment of Prostate Cancer", Nov. 1999.

Bander, CaPCURE Board Presentation: "Monolconal Antibody Therapy of Prostate Cancer", 2001.

Bander, AACR Meeting Presentation: "mAb Therapy of Prostate Cancer Targeting PSMAext", Apr. 9, 2002.

Bander, ASCO Meeting Presentation: "Phase I Radioimmunotherapy Trials of mAb J591 to the Extracellular Domain of Prostate Specific Membrane Antigen (PSMAext) Radiolabeled with 90Y or 177Lu in Advanced Prostate Cancer", May 18-21, 2002.

Liu et al. (1998), "mAbs to the Extracellular Domain of Prostate Specific Membrane Antigen (PSMA)", 11$^{th}$ International Conference on Monoclonal Antibodies for Cancer, Mar. 19-21, Abstract 2.

* cited by examiner

Expression of PSMA on dermal vascular endothelium within a human psoriatic biopsy Amino Acid Sequence of Murine J591 Heavy Chain (CDRs are marked, numbering as Kabat)

EVQLQQSGPELKKPGTSVRISCKTS|GYTFTEYTIH|WVKQSHGKS
1        10        20        30            40
                                        CDR1

LEWIG|NINPNNGGTTYNQKFED|KATLTVDKSSSTAYMELRSLTS
       50           60         70        80
          CDR2

EDSAVYYCAA|GWNFDY|WGQGTTLTVSS
        90      100         110
              CDR3

FIG. 2A

Amino Acid Sequence of Murine J591 Light Chain (CDRs are marked, numbering as Kabat)

DIVMTQSHKFMSTSVGDRVSIIC|KASQDVGTAVD|WYQQKPGQSP
1        10        20           30           40
                              CDR1

KLLIY|WASTRHT|GVPDRFTGSGSGTDFTLTITNVQSEDLADYFC
       50        60         70         80
         CDR2

|QQYNSYPLT|FGAGTMLDLK
  90            100
   CDR3

FIG. 2B

Amino Acid Sequence of DeImmunised J591 Heavy Chain (CDRs are marked, numbering as Kabat)

```
EVQLVQSGPEVKKPGATVKISCKTS|GYTFTEYTIH|WVKQAPGKG
1        10        20          30         40
                                CDR1

LEWIG|NINPNNGGTTYNQKFED|KATLTVDKSTDTAYMELSSLRS
     50          60         70         80
           CDR2

EDTAVYYCAA|GWNFDY|WGQGTLLTVSS
       90       100       110
             CDR3
```

FIG. 3A

Amino Acid Sequence of DeImmunised J591 Light Chain (CDRs are marked, numbering as Kabat)

```
DIQMTQSPSSLSTSVGDRVTLTC|KASQDVGTAVD|WYQQKPGPSP
1        10        20          30         40
                                CDR1

KLLIY|WASTRHT|GIPSRFSGSGSGTDFTLTISSLQPEDFADYYC
     50       60         70         80
       CDR2

|QQYNSYPLT|FGPGTKVDIK
   90          100
  CDR3
```

FIG. 3B

Location of T cell epitopes in J591 VH

```
          1               10              20
     1    E V Q L Q Q S G P E L V K P G T S V R I S C K T S    J591 MoVH
     1    E V Q L V Q S G P E V K K P G T S V R I S C K T S    J591 DIVH
                    30              40              50
    26    G Y T F T E Y T I H W V K Q S H G K S L E W I G      J591 MoVH
    26    G Y T F T E Y T I H W V K Q A P G K G L E W I G      J591 DIVH
                    60              70
    51    I N P N N G G T T Y N Q K F E D K A T L T V D K S    J591 MoVH
    51    I N P N N G G T T Y N Q K F E D K A T L T V D K S    J591 DIVH
                    80              90              100
    76    S S T A Y M E L R S L T S E D S A V Y Y C A A G W    J591 MoVH
    76    T D T A Y M E L S S L R S E D T A V Y Y C A A G W    J591 DIVH
                          110
   101    N F D Y W G Q G T T L T V S S                        J591 MoVH
   101    N F D Y W G Q G T L L T V S S                        J591 DIVH
```

FIG. 4A

Location of T cell epitopes in J591 VK

```
           1          10         20                      
    1   D I V M T Q S H K F M S T S V G D R V S I I C K A   J591 MoVK
    1   D I Q M T Q S P S S L S T S V G D R V T L T C K A   J591 DIVK
                        30         40         50
   26   S Q D V G T A V D W Y Q Q K P G Q S P K L L I Y W   J591 MoVK
   26   S Q D V G T A V D W Y Q Q K P G Q P P K L L I Y W   J591 DIVK
                        60         70
   51   A S T R H T G V P D R F T G S G S G T D F T L T I   J591 MoVK
   51   A S T R H T G I P S R F S G S G S G T D F T L T I   J591 DIVK
                        80         90        100
   76   T N V Q S E D L A D Y F C Q Q Y N S Y P L T F G A   J591 MoVK
   76   S S L Q P E D F A D Y Y C Q Q Y N S Y P L T F G P   J591 DIVK
  101   G T M L D L K                                        J591 MoVK
  101   G T K V D I K                                        J591 DIVK
```

HindIII
```
AAGCTTATGAATATGCAAATCCTCTGAATCTACATGGTAAATATAGGTTTGTCTATACCACAAACAGAAAAACATGAGATCACAGTTCTC
         +         +         +         +         +         +         +         +         +
TTCGAATACTTATAGCGTTTAGGAGACTTAGATGTACCATTTATATCCAAACAGATAGGTGTTGTCTTTTTGTACTCTAGTGTCAAGAG
                                                                                              90
```

NcoI
```
TCTACAGTTACTGAGGACACAGGACCTCACCATGGGATGGAGCTGTATCATCCTCTTCTTGGTAGCAACAGCTACAGGTAAGGGCTCAC
         +         +         +         +         +         +         +         +         +
AGATGTCAATGACTCCTGTGTCCTGGAGTGGTACCCTACCTCGACATAGTAGGAGAAGAACCATCGTTGTCGATGTCCATTCCCGAGTG
                                                                                             180
                                          M  G  W  S  C  I  I  L  F  L  V  A  T  A  T
                                          └─────────────── Signal ─────────────────────
```

```
AGTAGCAGGCTTGAGGTCTGGACATATATATGGGTGACAATGACATCCACTTGCCTTTCTCTCCACAGGTGTCCACTCCGACATCCAGA
         +         +         +         +         +         +         +         +         +
TCATCGTCCGAACTCCAGACCTGTATATATACCCACTGTTACTGTAGGTGAACGGAAAGAGAGGTGTCCACAGGTGAGGCTGTAGGTCT
                                                                                             270
────────────── Intron ──────────────────────────────────────────────────  G  V  H  S  D  I  Q
                                                                          └─Signal─┘└── VK ──
```

|     |   |   |   |   |   |   |   |   |   |   |   |   |   |   |   |   |   |   |   |   |   |   |   |   |   |   |   |          |
|-----|---|---|---|---|---|---|---|---|---|---|---|---|---|---|---|---|---|---|---|---|---|---|---|---|---|---|---|----------|
|     | N | I | V | M | T | Q | F | P | K | S | M | S | A | S | A | G | E | R | M | T | L | T | C | K | A | S | E | Majority |
| 1   | N | I | V | M | T | Q | F | P | K | S | M | S | I | S | V | G | E | R | V | T | L | T | C | K | A | S | E | J415VK   |
| 1   | N | I | V | M | T | Q | S | P | K | S | M | S | A | S | A | G | E | R | M | T | L | T | C | K | A | S | E | J415DIVK1 |
| 1   | N | I | V | M | T | Q | S | P | K | S | M | S | A | S | A | G | E | R | M | T | L | T | C | K | A | S | E | J415DIVK2 |
| 1   | N | I | V | M | T | Q | S | P | K | S | M | S | A | S | A | G | E | R | M | T | L | T | C | K | A | S | E | J415DIVK3 |
| 1   | N | I | V | M | T | Q | S | P | K | S | M | S | A | S | A | G | E | R | M | T | L | T | C | K | A | S | E | J415DIVK4 |
| 1   | N | I | V | M | T | Q | F | P | K | S | M | S | A | S | A | G | E | R | M | T | L | T | C | K | A | S | E | J415DIVK5 |
| 1   | N | I | V | M | T | Q | F | P | K | S | M | S | A | S | A | G | E | R | M | T | L | T | C | K | A | S | E | J415DIVK6 |
| 1   | N | I | V | M | T | Q | F | P | K | S | M | S | A | S | A | G | E | R | V | T | L | T | C | K | A | S | E | J415DIVK7 |
| 1   | N | I | V | M | T | Q | F | P | K | S | M | S | A | S | A | G | E | R | M | T | L | T | C | K | A | S | E | J415DIVK8 |

|     |   |   |   |   |   |   |   |   |   |   |   |   |   |   |   |   |   |   |   |   |   |   |   |   |          |
|-----|---|---|---|---|---|---|---|---|---|---|---|---|---|---|---|---|---|---|---|---|---|---|---|---|----------|
|     | N | V | G | T | Y | V | S | W | Y | Q | Q | K | P | T | Q | S | P | K | M | L | I | Y | G | A | S | N | R | Majority |
| 28  | N | V | G | T | Y | V | S | W | Y | Q | Q | K | P | E | Q | S | P | K | M | L | I | Y | G | A | S | N | R | J415VK |
| 28  | N | S | G | T | Y | V | S | W | Y | Q | Q | K | P | T | Q | S | P | K | M | L | I | Y | G | A | S | N | R | J415DIVK1 |
| 28  | N | V | G | T | Y | V | S | W | Y | Q | Q | K | P | T | Q | S | P | K | M | L | I | Y | G | A | S | N | R | J415DIVK2 |
| 28  | N | V | G | T | Y | V | S | W | Y | Q | Q | K | P | T | Q | S | P | K | M | L | I | Y | G | A | S | N | R | J415DIVK3 |
| 28  | N | V | G | T | Y | V | S | W | Y | Q | Q | K | P | T | Q | S | P | K | M | L | I | Y | G | A | S | N | R | J415DIVK4 |
| 28  | N | V | G | T | Y | V | S | W | Y | Q | Q | K | P | T | Q | S | P | K | M | L | I | Y | G | A | S | N | R | J415DIVK5 |
| 28  | N | V | G | T | Y | V | S | W | Y | Q | Q | K | P | E | Q | S | P | K | M | L | I | Y | G | A | S | N | R | J415DIVK6 |
| 28  | N | V | G | T | Y | V | S | W | Y | Q | Q | K | P | T | Q | S | P | K | M | L | I | Y | G | A | S | N | R | J415DIVK7 |
| 28  | N | S | G | T | Y | V | S | W | Y | Q | Q | K | P | E | Q | S | P | K | M | L | I | Y | G | A | S | N | R | J415DIVK8 |

|     |   |   |   |   |   |   |   |   |   |   |   |   |   |   |   |   |   |   |   |   |   |   |   |   |   |   |          |
|-----|---|---|---|---|---|---|---|---|---|---|---|---|---|---|---|---|---|---|---|---|---|---|---|---|---|---|----------|
|     | F | T | G | V | P | D | R | F | S | G | S | G | S | G | T | D | F | I | L | T | I | S | S | V | Q | A | E | Majority |
| 55  | F | T | G | V | P | D | R | F | T | G | S | G | S | A | T | D | F | I | L | T | I | S | S | V | Q | T | E | J415VK |
| 55  | F | T | G | V | P | D | R | F | S | G | S | G | S | G | T | D | F | I | L | T | A | S | S | V | Q | A | E | J415DIVK1 |
| 55  | F | T | G | V | P | D | R | F | S | G | S | G | S | G | T | D | F | I | L | T | A | S | S | V | Q | A | E | J415DIVK2 |
| 55  | F | T | G | V | P | D | R | F | S | G | S | G | S | G | T | D | F | I | L | T | A | S | S | V | Q | A | E | J415DIVK3 |
| 55  | F | T | G | V | P | D | R | F | S | G | S | G | S | G | T | D | F | I | L | T | I | S | S | V | Q | A | E | J415DIVK4 |
| 55  | F | T | G | V | P | D | R | F | S | G | S | G | S | G | T | D | F | I | L | T | I | S | S | V | Q | A | E | J415DIVK5 |
| 55  | F | T | G | V | P | D | R | F | S | G | S | G | S | G | T | D | F | I | L | T | I | S | S | V | Q | A | E | J415DIVK6 |
| 55  | F | T | G | V | P | D | R | F | S | G | S | G | S | G | T | D | F | I | L | T | I | S | S | V | Q | A | E | J415DIVK7 |
| 55  | F | T | G | V | P | D | R | F | S | G | S | G | S | G | T | D | F | I | L | T | I | S | S | V | Q | A | E | J415DIVK8 |

|     |   |   |   |   |   |   |   |   |   |   |   |   |   |   |   |   |   |   |   |   |   |   |   |          |
|-----|---|---|---|---|---|---|---|---|---|---|---|---|---|---|---|---|---|---|---|---|---|---|---|----------|
|     | D | L | V | D | Y | Y | C | G | Q | S | Y | T | F | P | Y | T | F | G | G | G | T | K | L | E | M | K | Majority |
| 82  | D | L | V | D | Y | Y | C | G | Q | S | Y | T | F | P | Y | T | F | G | G | G | T | K | L | E | M | K | J415VK |
| 82  | D | P | V | D | Y | Y | C | G | Q | S | Y | T | F | P | Y | T | F | G | G | G | T | K | L | E | M | K | J415DIVK1 |
| 82  | D | P | V | D | Y | Y | C | G | Q | S | Y | T | F | P | Y | T | F | G | G | G | T | K | L | E | M | K | J415DIVK2 |
| 82  | D | L | V | D | Y | Y | C | G | Q | S | Y | T | F | P | Y | T | F | G | G | G | T | K | L | E | M | K | J415DIVK3 |
| 82  | D | L | V | D | Y | Y | C | G | Q | S | Y | T | F | P | Y | T | F | G | G | G | T | K | L | E | M | K | J415DIVK4 |
| 82  | D | L | V | D | Y | Y | C | G | Q | S | Y | T | F | P | Y | T | F | G | G | G | T | K | L | E | M | K | J415DIVK5 |
| 82  | D | L | V | D | Y | Y | C | G | Q | S | Y | T | F | P | Y | T | F | G | G | G | T | K | L | E | M | K | J415DIVK6 |
| 82  | D | L | V | D | Y | Y | C | G | Q | S | Y | T | F | P | Y | T | F | G | G | G | T | K | L | E | M | K | J415DIVK7 |
| 82  | D | L | V | D | Y | Y | C | G | Q | S | Y | T | F | P | Y | T | F | G | G | G | T | K | L | E | M | K | J415DIVK8 |

```
                  HindIII                                          BamHI
                     |                                               |
     GAAGTGAAGCTTGAGGAGTCTGGAGGAGGCTTGGTGCAACCTGGAGGATCCATGAAACTC
     ++++++++++++++++++++++++++++++++++++++++++++++++++++++++++++  60
     CTTCACTTCGAACTCCTCAGACCTCCTCCGAACCACGTTGGACCTCCTAGGTACTTTGAG E  V  K  L  E  E  S  G  G  G  L  V  Q  P  G  G  S  M  K  L
     ++++++++++++++++++++++++++++++++++++++++++++++++++++++++++++
     TCCTGTGTTGCCTCTGGATTCACTTTCAGTAATTACTGGATGAACTGGGTCCGCCAGTCT  120
     ++++++++++++++++++++++++++++++++++++++++++++++++++++++++++++
     AGGACACAACGGAGACCTAAGTGAAAGTCATTAATGACCTACTTGACCCAGGCGGTCAGA ┌──────CDR 1──────▷
       S  C  V  A  S  G  F  T  F  S  N  Y  W  M  N  W  V  R  Q  S
     ++++++++++++++++++++++++++++++++++++++++++++++++++++++++++++
     CCAGAGAAGGGGCTTGAGTGGGTTGCTGAAATTAGATCGCAATCTAATAATTTTGCAACA  180
     ++++++++++++++++++++++++++++++++++++++++++++++++++++++++++++
     GGTCTCTTCCCCGAACTCACCCAACGACTTTAATCTAGCGTTAGATTATTAAAACGTTGT ┌─────────CDR 2─────────
       P  E  K  G  L  E  W  V  A  E  I  R  S  Q  S  N  N  F  A  T
     ++++++++++++++++++++++++++++++++++++++++++++++++++++++++++++
     CATTATGCGGAGTCTGTGAAAGGGAGGGTCATCATCTCAAGAGATGATTCCAAGAGTAGT  240
     ++++++++++++++++++++++++++++++++++++++++++++++++++++++++++++
     GTAATACGCCTCAGACACTTTCCCTCCCAGTAGTAGAGTTCTCTACTAAGGTTCTCATCA ─────────CDR 2─────────▷
       H  Y  A  E  S  V  K  G  R  V  I  I  S  R  D  D  S  K  S  S
     ++++++++++++++++++++++++++++++++++++++++++++++++++++++++++++
     GTCTACCTGCAAATGAACAACTTGAGAGCTGAAGACACTGGCATTTATTACTGTACCAGG  300
     ++++++++++++++++++++++++++++++++++++++++++++++++++++++++++++
     CAGATGGACGTTTACTTGTTGAACTCTCGACTTCTGTGACCGTAAATAATGACATGGTCC V  Y  L  Q  M  N  N  L  R  A  E  D  T  G  I  Y  Y  C  T  R
     ++++++++++++++++++++++++++++++++++++++++++++++++++++++++++++
     CGATGGAATAATTTCTGGGGCCAAGGCACCACTCTCACAGTCTCCTCA
     ++++++++++++++++++++++++++++++++++++++++++++++++  348
     GCTACCTTATTAAAGACCCCGGTTCCGTGGTGAGAGTGTCAGAGGAGT ┌─────CDR 3─────▷                                  FIG. 8B
       R  W  N  N  F  W  G  Q  G  T  T  L  T  V  S  S
     ++++++++++++++++++++++++++++++++++++++++++++++++
```

```
        E V K L E E S G G G L V Q P G G S M K L S C V A S G F T F S    Majority
                      10                  20                  30

1      E V K L E E S G G G L V Q P G G S M K L S C V A S G F T F S    J415vh
 1      E V K L E E S G G G L V Q P G G S M K L S C V A S G F T F S    MUVHIIIO

N Y W M N W V R Q S P E K G L E W V A E I R L Q S D N F A T    Majority
                      40                  50                  60

31      N Y W M N W V R Q S P E K G L E W V A E I R S Q S N N F A T    J415vh
31      N Y W M N W V R Q S P E K G L E W V A E I R L K S D N Y A T    MUVHIIIO

H Y A E S V K G R V I I S R D D S K S S V Y L Q M N N L R A    Majority
                      70                  80                  90

61      H Y A E S V K G R V I I S R D D S K S S V Y L Q M N N L R A    J415vh
61      H Y A E S V K G R F T I S R D D S K S S V Y L Q M N N L R A    MUVHIIIO

E D T G I Y Y C T T G G Y G G R R S W N A F W G Q G T L V T    Majority
                     100                 110                 120

91      E D T G I Y Y C T - - - - - - - R R W N N F W G Q G T T L T    J415vh
91      E D T G I Y Y C T T G G Y G G R R S W F A Y W G Q G T L V T    MUVHIIIO

V S S                                                          Majority

114     V S S                                                          J415vh
121     V S S                                                          MUVHIIIO
```

```
                                                                BstEII
                                                                |
AACATTGTAATGACCCAATTTCCCAAATCCATGTCCATTTCAGTAGGAGAGAGGGTCACC
                                                                     60
TTGTAACATTACTGGGTTAAAGGGTTTAGGTACAGGTAAAGTCATCCTCTCTCCCAGTGG

N   I   V   M   T   Q   F   P   K   S   M   S   I   S   V   G   E   R   V   T

TTGACCTGCAAGGCCAGTGAGAATGTGGGTACTTATGTGTCCTGGTATCAACAGAAACCA
                                                                     120
AACTGGACGTTCCGGTCACTCTTACACCCATGAATACACAGGACCATAGTTGTCTTTGGT

┌──────── CDR 1 ────────►
    L   T   C   K   A   S   E   N   V   G   T   Y   V   S   W   Y   Q   Q   K   P
```

```
                                                                PvuI
                                                                |
GAACAGTCTCCTAAGATGTTGATATACGGGGCATCCAACCGGTTCACTGGGGTCCCCGAT
                                                                     180
CTTGTCAGAGGATTCTACAACTATATGCCCCGTAGGTTGGCCAAGTGACCCCAGGGGCTA

┌──────── CDR 2 ────────►
    E   Q   S   P   K   M   L   I   Y   G   A   S   N   R   F   T   G   V   P   D

CGCTTCACAGGCAGTGGATCTGCAACAGATTTCATTCTGACCATCAGCAGTGTGCAGACT
                                                                     240
GCGAAGTGTCCGTCACCTAGACGTTGTCTAAAGTAAGACTGGTAGTCGTCACACGTCTGA

R   F   T   G   S   G   S   A   T   D   F   I   L   T   I   S   S   V   Q   T

GAAGACCTTGTAGATTATTACTGTGGACAGAGTTACACCTTTCCGTACACGTTCGGAGGG
                                                                     300
CTTCTGGAACATCTAATAATGACACCTGTCTCAATGTGGAAAGGCATGTGCAAGCCTCCC

┌──────── CDR 3 ────────►
    E   D   L   V   D   Y   Y   C   G   Q   S   Y   T   F   P   Y   T   F   G   G
```

```
GGGACCAAGCTGGAAATGAAG
                      321
CCCTGGTTCGACCTTTACTTC

```
       D I V M T Q S P S S L A V S A G E K V T L S C K A S E S L L     Majori
                         |                                     |
                        10                                    30
       N I V M T Q F P K S M S I S V G E R V T L T C K A S E - - -     J415vk
       D I V M T Q S P S S L A V S A G E K V T M S C K S S Q S L L     Muvk1
                         |                                     |
 1                      20                                    30
 1

N V G N Q K T Y V A W Y Q Q K P G Q S P K L L I Y G A S T R     Majori
                         |                                     |
                        40                                    60
       - T Y V S W Y Q Q K P E Q S P K M L I Y G A S N R                J415vk
       N S G N Q K N Y L A W Y Q Q K P G Q S P K L L I Y W A S T R     Muvk1
                         |                                     |
28                      40                                    60
31

E S G V P D R F T G S G S G T D F I L T I S S V Q A E D L A     Majori
                         |                                     |
                        70                                    90
       F T G V P D R F T G S G S A T D F I L T I S S V Q T E D L V     J415vk
       E S G V P D R F T G S G S G T D F T L T I S S V Q A E D L A     Muvk1
                         |                                     |
55                      70                                    90
61

V Y Y C G N S Y S F P L T F G G G T K L E L K                    Majori
                         |
                       100                   110

D Y Y C G Q S Y T F P Y T F G G G T K L E M K                    J415vk
       V Y Y C Q N D Y S Y P L T F G A G T K L E L K                    Muvk1
                         |                     |
85                     100                   110
91
```

FIG. 9C

```
                    PvuII PstI
                      |    |
       GAGGTCCAGCTGCAGCAGTCTGGACCTGAGCTGGTTAAGCCTGGGGCTTCAGTGAAGATG
                                                                         60
       CTCCAGGTCGACGTCGTCAGACCTGGACTCGACCAATTCGGACCCCGAAGTCACTTCTAC

E  V  Q  L  Q  Q  S  G  P  E  L  V  K  P  G  A  S  V  K  M

TCCTGCAAGGCTTCTGGATACACATTCACTGGCTATGTTATGCACTGGGTGAAGCAGAAG
                                                                        120
       AGGACGTTCCGAAGACCTATGTGTAAGTGACCGATACAATACGTGACCCACTTCGTCTTC

┌─────CDR 1─────▶
         S  C  K  A  S  G  Y  T  F  T  G  Y  V  M  H  W  V  K  Q  K

CCTGGACAGGTCCTTGAGTGGATTGGATATATTAATCCTTACAATGATGTTACTAGGTAT
                                                                        180
       GGACCTGTCCAGGAACTCACCTAACCTATATAATTAGGAATGTTACTACAATGATCCATA

┌─────────CDR 2
         P  G  Q  V  L  E  W  I  G  Y  I  N  P  Y  N  D  V  T  R  Y

AATGGGAAGTTCAAAGGCAAGGCCACACTGACCTCAGACAAATATTCCAGCACAGCCTAC
                                                                        240
       TTACCCTTCAAGTTTCCGTTCCGGTGTGACTGGAGTCTGTTTATAAGGTCGTGTCGGATG

──────CDR 2─────▶
         N  G  K  F  K  G  K  A  T  L  T  S  D  K  Y  S  S  T  A  Y

SacI
                    |
       ATGGAGCTCAGCGGCCTGACCTCTGAGGACTCTGCGGTCTATTACTGTGCAAGAGGGGAG
                                                                        300
       TACCTCGAGTCGCCGGACTGGAGACTCCTGAGACGCCAGATAATGACACGTTCTCCCCTC

┌──CDR
         M  E  L  S  G  L  T  S  E  D  S  A  V  Y  Y  C  A  R  G  E

AACTGGTACTACTTTGACTCCTGGGGCCGAGGCGCCACTCTCACAGTCTCCTCA
                                                                        354
       TTGACCATGATGAAACTGAGGACCCCGGCTCCGCGGTGAGAGTGTCAGAGGAGT

┌──────CDR 3─────▶
         N  W  Y  Y  F  D  S  W  G  R  G  A  T  L  T  V  S  S         FIG. 10A
```

```
    E V Q L Q Q S G P E L V K P G A S V K I S C K A S G Y T F T        Majori
    |                   |                   |
                       10                  20                  30
  1 E V Q L Q Q S G P E L V K P G A S V K M S C K A S G Y T F T        j533vh
  1 E V Q L Q Q S G P E L V K P G A S V K[I]S C K A S G Y T F T        Muvhii G Y V M N W V K Q S P G Q V L E W I G D I N P G N G G T S          Majori
    |                   |                   |
                       40                  50                  60
 31 G Y V V M H[-]W V K Q K P G Q V L E W I G Y I N P Y N D V T R      j533vh
 31[D][Y][M N]N W V K Q[S]P G[K S]L E W I G[D]I N P G[N G G T][S]      Muvhii Y N G K F K G K A T L T V D K S S S T A Y M E L S G L T S E        Majori
    |                   |                   |
                       70                  80                  90
 60 Y N G K F K G K A T L T S D K Y S S T A Y M E L S G L T S E        j533vh
 61 Y N[Q]K F K G K A T L T[V]D K[S]S S T A Y M[Q]L S[S]L T S E        Muvhii D S A V Y Y C A R G E N S S S Y M A Y Y A F D S W G Q G A T        Majori
    |                   |                   |
                      100                 110                 120
 90 D S A V Y Y C A R G E N[- - -]W Y Y F D S W G R G A T              j533vh
 91 D S A V Y Y C A R G[Y]S S S Y M A Y Y[A]F D[Y]W G[Q]G[T T]         Muvhii V T V S S                                                          Majori
114 L T V S S                                                          j533vh
121[V]T V S S                                                          Muvhii
```

FIG. 10B

```
CAGGTGCAGCTAAAGGAGTCAGGACCTGGCCTGGTGGCGTCCTCACAGAGCCTGTCCATC
                                                              60
GTCCACGTCGATTTCCTCAGTCCTGGACCGGACCACCGCAGGAGTGTCTCGGACAGGTAG

Q  V  Q  L  K  E  S  G  P  G  L  V  A  S  S  Q  S  L  S  I

ACATGCACCGTCTCAGGATTCTCATTAACCGCCTATGGTATTAACTGGGTTCGCCAGCCT
                                                              120
TGTACGTGGCAGAGTCCTAAGAGTAATTGGCGGATACCATAATTGACCCAAGCGGTCGGA
```

CDR 1

T  C  T  V  S  G  F  S  L  T  A  Y  G  I  N  W  V  R  Q  P

```
CCAGGAAAGGGTCTGGAGTGGCTGGGAGTGATATGGCCTGATGGAAACACAGACTATAAT
                                                              180
GGTCCTTTCCCAGACCTCACCGACCCTCACTATACCGGACTACCTTTGTGTCTGATATTA
```

CDR 2

P  G  K  G  L  E  W  L  G  V  I  W  P  D  G  N  T  D  Y  N

```
TCAACTCTCAAATCCAGACTGAACATCTTCAAGGACAACTCCAAGAACCAAGTTTTCTTA
                                                              240
AGTTGAGAGTTTAGGTCTGACTTGTAGAAGTTCCTGTTGAGGTTCTTGGTTCAAAAGAAT
```

CDR 2

S  T  L  K  S  R  L  N  I  F  K  D  N  S  K  N  Q  V  F  L

```
AAAATGAGCAGTTTCCAAACTGATGACACAGCCAGATACTTCTGTGCCAGAGATTCGTAT
                                                              300
TTTTACTCGTCAAAGGTTTGACTACTGTGTCGGTCTATGAAGACACGGTCTCTAAGCATA
```

CDR 3

K  M  S  S  F  Q  T  D  D  T  A  R  Y  F  C  A  R  D  S  Y

```
GGTAACTTCAAGAGGGGTTGGTTTGACTTCTGGGGCCAGGGCACCACTCTCACAGTCTCC
                                                              360
CCATTGAAGTTCTCCCCAACCAAACTGAAGACCCCGGTCCCGTGGTGAGAGTGTCAGAGG
```

CDR 3

G  N  F  K  R  G  W  F  D  F  W  G  Q  G  T  T  L  T  V  S

```
TCA
    363
AGT
```

```
     1                    10                  20                  30
Majori   Q V Q L K E S G P G L V A S S Q S L S I T C T V S G F S L T
E99vh    Q V Q L K E S G P G L V A S S Q S L S I T C T V S G F S L T
Muvhib   Q V Q L K E S G P G L V A [P] S Q S L S I T C T V S G F S L T 31                   40                  50                  60
Majori   A Y G V N V S W V R Q P P G K G L E W L G V I W A G G S T D
E99vh  31 A Y G I N [-] [-] W V R Q P P G K G L E W L G V I W A G  S T D
Muvhib 31 [S] Y G [V] [H] [V] S W V R Q P P G K G L E W L G V I W A G [N] [S] [T] [N]

59/61                70                  80                  90
Majori   Y N S A L K S R L S I S K D N S K S Q V F L K M S S L Q T D
E99vh  59 Y N S T L K S R L N I F K D N S K N Q V F L K M S S F Q T D
Muvhib 61 Y N S A L [M] S R L [S] I [S] K D N S K [S] Q V F L K M [N] S [L] Q T D 89/91                100                 110                 120
Majori   D T A R Y F C A R D S G G N F K S G Y F A M D F W G Q G T S
E99vh    D T A R Y F C A R D S Y G N F K R G W F [-] [-] D F W G Q G T T
Muvhib 91 D T A M [Y] C A R D [R] G R Y Y Y S G [Y Y A] M D [Y] W G Q G T [S]

Majori   V T V S S
E99vh 117 L T V S S
Muvhib 121 [V] T V S S
```

```
                                                                              BstEII
                                                                              |
AACATTGTGATGACCCAGTCTCAAAAATTCATGTCCACATCACCAGGAGACAGGGTCAGG
                                                                                   60
TTGTAACACTACTGGGTCAGAGTTTTTAAGTACAGGTGTAGTGGTCCTCTGTCCCAGTCC

N  I  V  M  T  Q  S  Q  K  F  M  S  T  S  P  G  D  R  V  R

GTCACCTGCAAGGCCAGTCAGAATGTGGGTTCTGATGTAGCCTGGTATCAAGCGAAACCA
                                                                                  120
CAGTGGACGTTCCGGTCAGTCTTACACCCAAGACTACATCGGACCATAGTTCGCTTTGGT

[CDR 1 ———————————>]
   V  T  C  K  A  S  Q  N  V  G  S  D  V  A  W  Y  Q  A  K  P

GGACAATCTCCTAGAATACTGATTTACTCGACATCCTACCGTTACAGTGGGGTCCCTGAT
                                                                                  180
CCTGTTAGAGGATCTTATGACTAAATGAGCTGTAGGATGGCAATGTCACCCCAGGGACTA

[CDR 2 ————————>]
   G  Q  S  P  R  I  L  I  Y  S  T  S  Y  R  Y  S  G  V  P  D

CGCTTCACAGCCTATGGATCTGGGACAGATTTCACTCTCACCATTACCAATGTGCAGTCT
                                                                                  240
GCGAAGTGTCGGATACCTAGACCCTGTCTAAAGTGAGAGTGGTAATGGTTACACGTCAGA

R  F  T  A  Y  G  S  G  T  D  F  T  L  T  I  T  N  V  Q  S

GAAGACTTGACAGAGTATTTCTGTCAGCAATATAATAGCTATCCTCTCACGTTCGGTGCT
                                                                                  300
CTTCTGAACTGTCTCATAAAGACAGTCGTTATATTATCGATAGGAGAGTGCAAGCCACGA

[CDR 3 ——————————>]
   E  D  L  T  E  Y  F  C  Q  Q  Y  N  S  Y  P  L  T  F  G  A

GGGACCAAGCTGGAGCTGAAA
                     321
CCCTGGTTCGACCTCGACTTT                              FIG. 13A

G  T  K  L  E  L  K
```

```
         D I V M T Q S Q S S L A V S A G D K V T V S C K A S Q S L L    Majori
                   |         |         |
                   10        20        30
    1    N I V M T Q S Q K F M S T S P G D R V R V T C K A S Q - - -    e99VK
    1    D I V M T Q S P S S L A V S A G E K V T M S C K S S Q S L L    Muvkl N V G S D K N Y V A W Y Q A K P G Q S P K L L I Y S A S T R    Majori
                   |         |         |
                   40        50        60
   28    - V A W Y Q A K P G Q S P R I L I Y S T S Y R                  e99VK
   31    N S G N Q K N Y L A W Y Q Q K P G Q S P K L L I Y W A S T R    Muvkl E S G V P D R F T G S G S G T D F T L T I S S V Q A E D L A    Majori
                   |         |         |
                   70        80        90
   55    Y S G V P D R F T A Y G S G T D F T L T I T N V Q S E D L T    e99VK
   61    E S G V P D R F T G S G S G T D F T L T I S S V Q A E D L A    Muvkl V Y F C Q N D N S Y P L T F G A G T K L E L K R R A            Majori
                   |         |
                   100       110
   85    E Y F C Q Q Y N S Y P L T F G A G T K L E L K                  e99VK
   91    V Y C Q N D Y S Y P L T F G A G T K L E L K                    Muvkl

FIG. 13B
```

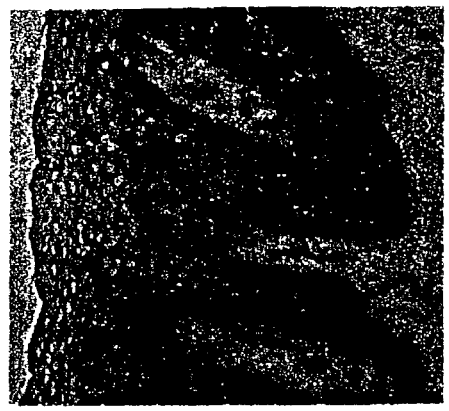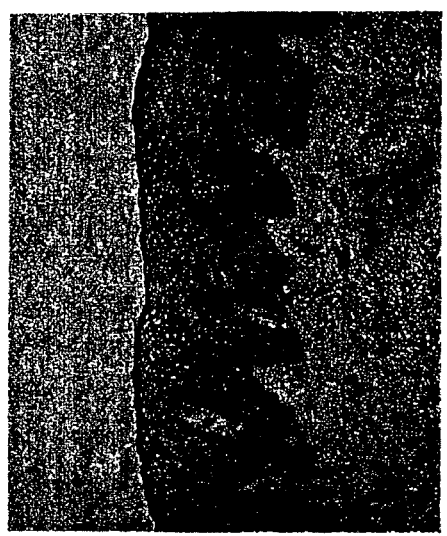
FIG. 15

METHODS AND COMPOSITIONS FOR TREATING OR PREVENTING SKIN DISORDERS USING BINDING AGENTS SPECIFIC FOR PROSTATE SPECIFIC MEMBRANE ANTIGEN

RELATED APPLICATIONS

This application claims priority to U.S. provisional application No. 60/324,100 filed on Sep. 20, 2001 and No. 60/362,612 filed on Mar. 8, 2002, the contents of which are incorporated herein by reference.

FIELD OF THE INVENTION

The invention relates to the use of a binding agent specific for prostate specific membrane antigen (PSMA) to treat or prevent a skin disorder, e.g., psoriasis.

BACKGROUND OF THE INVENTION

The skin is composed of the epidermis, an epithelial layer of ectodermal origin, and the dermis, a layer of connective tissue of mesodermal origin. See generally Fitzpatrick (1999) *Dermatology in General Medicine,* 5th ed., McGraw Hill. The junction of dermis and epidermis is mostly irregular, and projections of the dermis, known as papillae, interdigitate with evaginations of the epidermis known as epidermal ridges.

The epidermis consists mainly of a stratified keratinized epithelium populated primarily by keratinocytes, which are keratinizing epidermal cells. See id. The epidermis also harbors a number of other cell populations such as melanocytes, Langerhans cells, Merkel cells, and other cellular migrants. From the dermis outward, the epidermis consists of five layers of keratinocytes known as the stratum basale (stratum germinativum), stratum spinosum, stratum granulosum, stratum lucidum and stratum corneum.

The dermis is composed of the connective tissue that supports the epidermis and binds it to the subjacent layer, known as subcutaneous tissue or hypodermis. See id. The dermis has a rich network of blood and lymph vessels. The dermis contains vascular networks situated in parallel to the skin surface at various levels and connected by vertical communicating vessels. The dermis contains two layers with rather indistinct boundaries: the outermost papillary layer and the deeper reticular layer. The papillary layer is composed of a number of different cell types, including loose connective tissue cells, fibroblasts and other connective tissue cells, as well as mast cells and macrophages. Extravasated leukocytes are also detected in the papillary layer. The reticular layer is thicker than the papillary layer and is composed of irregular dense connective tissue (mainly type I collagen).

Many pathologic reactions of the skin involve a combination of epidermal and dermal components. See id. However, frequently one component is more predominantly involved in a given pathological reaction over the other, thus leading to certain clinical diagnoses. See id. For example, a hyperplastic epidermis is characteristic of psoriatic plaques. Examples of pathologic reactions involving superficial skin layers include vesicular dermitis (eczema), contact dermatitis, psoriasis, interface dermatitis, erythema multiforme, lupus erythematosus, lichen planus and dermatitis herpetiformis. Examples of pathologic reactions involving the dermis include acute febrile neutrophilic dermatosis (Sweet's Syndrome), erythema elevatum diutinum, cutaneous eosinophilic disease, granuloma, malignant atrophic papulosis, dermal neoplasm, dermal pseudoneoplasm, dermal hyperplasia, dermal vascular anomaly, Kaposi's sarcoma, anetoderma and atrophic disorder of the skin.

Skin disorders, such as psoriasis, eczema, and lichen planus, are known to affect one to two percent of the U.S. population, with as many as 150,000–260,000 new cases occurring annually ("Research Needs in 11 Major Areas in Dermatology" I. Psoriasis. *J. Invest. Dermatol.* 73:402–13, 1979). Presently known therapies for the above mentioned skin diseases are limited. Steroids or cyclosporin A are commonly used in the treatment of psoriasis, lichen planus, urticaria, atopic dermatitis, UV damage, pyoderma gangrenosum, vitiligo, ocular cicatricial pemphigoid, alopecia areata, allergic and irritant contact dermatitis and cutaneous T cell lymphoma. In addition, for some of these skin conditions, various therapies include retinoids, PUVA, nitrogen mustard, interferon, chemotherapy, methotrexate, light therapy (e.g., UV light and PUVA), antibiotics and antihistamines. See id. UV light therapies, both UVA and UVB therapy, expose the skin to UV radiation between 320–400 nm (UVA radiation) and 290–320 nm (UVB radiation). PUVA therapy is a form of photochemotherapy that involves repeated topical application of psoralen or a psoralen-based compound to an affected region of skin, followed by exposure of that region to UVA radiation. Another method used to treat proliferative skin diseases, particularly psoriasis and mycosis fungoides, is photodynamic therapy (PDT).

Side effects to these therapies are known. Most commonly encountered drawbacks for cyclosporin A include toxicity due to immunosuppression and renal and neural toxicity. Steroids have well known side effects including induction of Cushing Syndrome. Side effects of certain of the other aforementioned therapies include skin cancer, bone marrow and constitutional toxicities, ligament calcification, liver fibrosis and other disorders. With respect to light therapy, prolonged treatment of skin diseases using these types of therapies can result in significant acute and chronic adverse effects including erythema, pruritus, skin cancer, and chronic light-induced damage of the skin (Stern et al. (1979) *N.E. J. of Med.* 300:809–812).

Accordingly, there exists a need for improved therapeutic modalities for preventing and treating skin disorders.

SUMMARY OF THE INVENTION

The invention is based, in part, on the discovery that administration to a subject of an antibody to the extracellular domain of human prostate specific membrane antigen (PSMA) reduced the severity of psoriatic lesions. A reduction in the severity of the lesion was detected after administration of either anti-PSMA antibody alone or conjugated to a cytotoxic moiety. Enhanced expression of PSMA protein was detected in the basal and immediately suprabasal keratinocytes, as well as vascular cells, of psoriatic patients as compared to control patients. Accordingly, the invention provides methods and compositions for treating or preventing epidermal or dermal disorders using binding agents, e.g., antibodies or antigen binding fragments thereof, specific for PSMA, e.g., the extracellular region of PSMA.

The invention also features a method of treating, e.g., ablating or killing, a cell, e.g., a cell in the skin (e.g., an aberrant PSMA-expressing epidermal or a dermal cell), or a non-malignant, non-prostatic, hyperproliferative cell. Methods of the invention include contacting the cell, or a nearby cell, e.g., a vascular endothelial cell proximate to the cell, with a binding agent, e.g., an antibody or antigen-binding fragment thereof, that specifically binds PSMA in an amount sufficient to treat, e.g., ablate or kill, the cell. Methods of the invention can be used, for example, to treat or prevent a disorder, e.g., a skin disorder (e.g., psoriasis) or a non-malignant, non-prostatic hyperproliferative disorder, by administering to a subject a PSMA-binding agent, e.g., an anti-PSMA antibody or antigen-binding fragment thereof, in an amount effective to treat or prevent such disorder.

The subject method can be used on cells in culture, e.g. in vitro or ex vivo. For example, epidermal or dermal cells (e.g., dermal endothelial cells or keratinocytes, e.g., basal and immediately suprabasal keratinocytes) can be cultured in vitro in culture medium and the contacting step can be effected by adding the PSMA-binding agent, to the culture medium. The method can be performed on cells (e.g., dermal or epidermal cells) present in a subject, e.g., cells present in the epidermal layer (e.g., basal and immediately suprabasal layer) or dermal layer (e.g., the dermal vasculature) as part of an in vivo (e.g., therapeutic or prophylactic) protocol. For in vivo embodiments, the contacting step is effected in a subject and includes administering the binding agent to the subject under conditions effective to permit both binding of the binding agent to the cell, or the vascular endothelial cell proximate to the cell, and the treating, e.g., the killing or ablation, of the cell.

The method of the invention can be used to treat or prevent a skin disorder, e.g., a dermal, epidermal, hypodermal disorder or a disorder in the dermal-epidermal junction. The skin disorder can be one or more of: a hyperproliferative skin disorder (e.g., a malignant or benign hyperproliferative skin disorder), an allergic or hypersensitive inflammatory skin disorder, a chronic inflammatory disorder, an autoimmune disorder, e.g., a rheumatologic disorder, or a cutaneous disorder of altered reactivity.

Examples of skin disorders that can be treated or prevented using the methods of the invention include psoriasis, psoriatic arthritis, dermatitis (eczema), e.g., exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria and prokeratosis. Preferably, the disorder is dermatitis, e.g., atopic dermatitis or allergic dermatitis, or psoriasis. Most preferably, the disorder is psoriasis.

In other embodiments, the skin disorder is an inflammatory or a neoplastic disorder of the epidermis or dermis. For example, the skin disorder is an epidermal precancerous or cancerous lesion.

In other embodiments, the skin disorder is a cutaneous disorder of altered reactivity, or a skin manifestation of an autoimmune disorder, e.g., a rheumatologic disorder. In other embodiments, the skin disorder occurs in response to an irritant, e.g., a drug, an infectious agent, food, or environmental irritant. In one embodiment, the irritant is poison ivy. For example, the disorder can be allergic or irritant contact dermatitis.

In preferred embodiments, the binding agent used in the methods and compositions of the invention, interacts with, e.g., binds to, to PSMA, preferably human PSMA, with high affinity and specificity. For example, the binding agent binds to human PSMA with an affinity constant of at least $10^7$ $M^{-1}$, preferably, between $10^8$ $M^{-1}$ and $10^{10}$ $M^{-1}$, or about $10^9$ $M^{-1}$. Preferably, the binding agent binds to the extracellular domain of PSMA, and most preferably, the extracellular domain of human PSMA (e.g., amino acids 44–750 of human PSMA).

The binding agent can be an antibody (e.g., a monospecific, or a recombinant or modified antibody) or an antigen-binding fragment thereof, a small molecule, or a PSMA ligand. Preferably, the modified antibodies are those having one or more complementarity determining regions (CDRs) from a J591, J415, J533 or E99 antibody.

In a preferred embodiment, the binding agent is an anti-PSMA monospecific antibody (e.g., a monoclonal antibody) or an antigen-binding fragment thereof. The anti-PSMA antibodies (e.g., recombinant or modified antibodies) can be full-length (e.g., an IgG (e.g., an IgG1, IgG2, IgG3, IgG4), IgM, IgA (e.g., IgA1, IgA2), IgD, and IgE, but preferably an IgG) or can include only an antigen-binding fragment (e.g., a Fab, F(ab')$_2$ or scFv fragment, or one or more CDRs). An antibody, or antigen-binding fragment thereof, can include two heavy chain immunoglobulins and two light chain immunoglobulins, or can be a single chain antibody. The antibodies can, optionally, include a constant region chosen from a kappa, lambda, alpha, gamma, delta, epsilon or a mu constant region gene. A preferred anti-PSMA antibody includes a heavy and light chain constant region substantially from a human antibody, e.g., a human IgG1 constant region or a portion thereof. In some embodiments, the anti-PSMA antibodies are human antibodies.

The antibody (or fragment thereof) can be a murine or a human antibody. Examples of preferred murine monoclonal antibodies that can be used include a E99, J415, J533 and J591 antibody, which are produced by hybridoma cell lines having an ATCC Accession Number HB-12101, HB-12109, HB-12127, and HB-12126, respectively. Also within the scope of the invention are methods and composition using antibodies, or antigen-binding fragments thereof, which bind overlapping epitopes of, or competitively inhibit, the binding of the anti-PSMA antibodies disclosed herein to PSMA, e.g., antibodies which bind overlapping epitopes of, or competitively inhibit, the binding of monoclonal antibodies E99, J415, J533 or J591 to PSMA. Any combination of anti-PSMA antibodies can be used, e.g., two or more antibodies that bind to different regions of PSMA, e.g., antibodies that bind to two different epitopes on the extracellular domain of PSMA.

In some embodiments, the binding agent is an anti-PSMA antibody that binds to all or part of the epitope of an antibody described herein, e.g., a J591, E99, J415, and J533 antibody. The anti-PSMA antibody can inhibit, e.g., competitively inhibit, the binding of an antibody described herein, e.g., a J591, E99, J415, and J533 antibody, to human PSMA. An anti-PSMA antibody may bind to an epitope, e.g., a conformational or a linear epitope, which epitope when bound prevents binding of an antibody described herein, a J591, E99, J415, and J533 antibody. The epitope can be in close proximity spatially or functionally associated, e.g., an overlapping or adjacent epitope in linear sequence or conformationally to the one recognized by the J591, E99, J415, or J533 antibody.

In one embodiment, the anti-PSMA antibody binds to an epitope located wholly or partially within the region of about amino acids 120 to 500, preferably 130 to 450, more preferably, 134 to 437, or 153 to 347, of human PSMA. Preferably, the epitope includes at least one glycosylation site, e.g., at least one N-linked glycosylation site (e.g., the N-linked glycosylation site located at about amino acids 190–200, preferably at about amino acid 195, of human PSMA).

In other embodiments, the antibodies (or fragments thereof) are a recombinant or modified anti-PSMA antibody chosen from, e.g., a chimeric, a humanized, a deimmunized, or an in vitro generated antibody. As discussed herein, the modified antibodies can be CDR-grafted, humanized, deimmunized, or more generally, antibodies having CDRs from a non-human antibody, e.g., murine J591, J415, J533 or E99 antibody and a framework that is selected as less immunogenetic in humans, e.g., less antigenic than the murine framework in which a murine CDR naturally occurs. In one embodiment, a modified antibody is a deimmunized anti-PSMA antibody, e.g., a deimmunized form of E99, J415, J533 or J591 (e.g., a deimmunized form of an antibody produced by a hybridoma cell line having an ATCC Accession Number HB-12101, HB-12109, HB-12127 and HB-12126, respectively). Preferably, the antibody is a deimmunized form of J591 or J415 (referred to herein as "deJ591" or "deJ415" respectively). Most preferably, the antibody is a deimmunized form of J591.

The binding agent, e.g., the anti-PSMA antibody, or antigen-binding fragment thereof, described herein can be used alone, e.g., can be administered to a subject, or used in vitro, in non-derivatized or unconjugated forms. For example, the unconjugated form of an anti-PSMA antibody can ablate or kill the PSMA-expressing cell by antibody dependent-cell killing mechanisms such as complement mediated cell lysis and/or effector cell-mediated cell killing. Preferably, the anti-PSMA antibody binds to the cell surface of the cell that expresses PSMA (e.g., a dermal or epidermal cell), and, in particular, to the cell surface of living cells.

In some embodiments, the binding agent, e.g., an anti-PSMA antibody or fragment thereof, is also internalized with PSMA which permits intercellular delivery of a molecular entity conjugated to the antibody. The binding agent, e.g., an anti-PSMA antibody, or antigen-binding fragment thereof, can be derivatized or linked to another molecular entity, typically a label or a therapeutic (e.g., a cytotoxic or cytostatic) agent. The molecular entity can be, e.g., another peptide, protein, a non-peptide chemical compound, isotope, etc. The anti-PSMA antibody, or antigen-binding fragment thereof, can be functionally linked, e.g., by chemical coupling, genetic fusion, non-covalent association or otherwise, to one or more other molecular entities. For example, the anti-PSMA antibody, or antigen-binding fragment thereof, can be coupled to a label, such as a fluorescent label, a biologically active enzyme label, a radioisotope (e.g., a radioactive ion), a nuclear magnetic resonance active label, a luminescent label, or a chromophore. In other embodiments, the anti-PSMA antibody, or antigen-binding fragment thereof, can be coupled to a therapeutic agent, e.g., a cytotoxic moiety, e.g., a therapeutic drug, a radioisotope, molecules of plant, fungal, or bacterial origin, or biological proteins (e.g., protein toxins), or mixtures thereof. The therapeutic agent can be an intracellularly drug or other agent, such as short-range radiation emitters, including, for example, short-range, high-energy α-emitters, as described herein. In some preferred embodiments, the anti-PSMA antibody, or antigen binding fragment thereof, can be coupled to a molecule of bacterial origin, e.g., a maytansinoid (e.g., maytansinol or the DM1 maytansinoid, see FIG. 15). A radioisotope can be an α-, β-, or γ-emitter, or an β- and γ-emitter. Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99m}$Tc), phosphorus ($^{32}$P), carbon ($^{14}$C), and tritium ($^{3}$H), or one of the therapeutic isotopes listed above. The anti-PSMA antibody, or antigen-binding fragment thereof can also be linked to another antibody to form, e.g., a bispecific or a multispecific antibody.

The subject can be mammal, e.g., a primate, preferably a higher primate, e.g., a human (e.g., a patient having, or at risk of, a disorder described herein, e.g., a skin disorder). In one embodiment, the subject is a patient having an epidermal or a dermal condition (e.g., a patient suffering from a mild, moderate or severe form of psoriasis).

The PSMA binding agent, e.g., a PSMA binding agent as described herein, can be administered to the subject systemically (e.g., intravenously, intramuscularly, by infusion, e.g., using an infusion device, subcutaneously, transdermally, or by inhalation). In those embodiments where the PSMA binding agent is a small molecule, it can be administered orally. In other embodiment, the PSMA binding agent is administered locally (e.g., topically) to an affected area, e.g., a psoriatic lesion.

The methods of the invention can further include the step of monitoring the subject, e.g., for a reduction in one or more of: a reduction in size, redness, inflammation, irritation, etc. of a psoriatic lesion; a reduction in the subject's symptoms, e.g., reduced itch; reduced number of proliferating cells, e.g., keratinocytes, or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the same PSMA binding agent or for additional treatment with additional agents. Generally, a decrease in one or more of the parameters described above is indicative of the improved condition of the subject.

The methods of the invention can further include the step of analyzing a nucleic acid or protein from the subject, e.g., analyzing the genotype of the subject. In one embodiment, a nucleic acid encoding human PSMA and/or an upstream or downstream component(s) of human PSMA signaling, e.g., an extracellular or intracellular activator or inhibitor of human PSMA, is analyzed. The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the PSMA binding agent to thereby determine appropriate dosage(s) and treatment regimen(s) of the PSMA binding agent (e.g., amount per treatment or frequency of treatments) for prophylactic or therapeutic treatment of the subject.

The methods and compositions of the invention can be used in combination with other therapeutic modalities. Accordingly, the methods of the invention include administering to the subject a PSMA binding agent, e.g., a PSMA binding agent as described herein, in combination with a cytotoxic agent, in an amount effective to treat or prevent said disorder. The binding agent and the cytotoxic agent can be administered simultaneously or sequentially.

Exemplary cytotoxic agents that can be administered in combination with the PSMA binding agents include antimetabolite, an alkylating agent, cyclophosphamide, busulfan, dibromomannitol, streptozotocin, mitomycin C, cis-dichlorodiamine platinum (II) (DDP) cisplatin), anthracyclines, and an anti-mitotic agent.

Other examples of cytotoxic agents that can be administered in combination with the PSMA binding agents include phototherapy therapy (PUVA or UV radiation, e.g., UVA or UVB radiation), methotrexate, retinoids, macrolides, cyclosporine, etretinate, nonsteroidal anti-inflammatory drugs (NSAIDs), gold salts, and sulfasalizine.

In yet other embodiments, the methods can be used in combination with immunomodulatory agents, e.g., interleukin-2 (IL-2) or interferon (IFN).

In one embodiment, the PSMA binding agent can be administered in combination with a topically applied agent selected from the group consisting of a steroid (e.g., a glucocorticoid or a retinoid), vitamin (e.g., vitamin D), tar, keratolytic agent and anthralin.

In other embodiments, the PSMA binding agent can be administered in combination with a systemic agent selected from the group consisting of systemic glucocorticoids, sulfones, aminoquinolines, cytotoxic agents, antimetabolic agents, retinoids, antihistamines, immunosuppressive drugs, immunomodulatory drugs, and thalidomide.

Any combination and sequence of topical and/or systemic agents can be used. The PSMA binding agent and the topical and/or systemic agents can be administered during periods of active disorder, or during a period of remission or less active disease. The PSMA binding agent and the topical and/or systemic agents can be administered before treatment, concurrently with treatment, posttreatment, or during remission of the disorder.

In another aspect, the invention features a composition for topical use for treating a disorder, e.g., a skin disorder. The composition includes a binding agent that binds specifically to PSMA, e.g., a binding agent as described herein, and an agent (or second agent), e.g., a carrier or an agent, which enhances the effectiveness of the binding agent. Preferably, the second agent increases the permeability of the binding agent into a subject's skin. In other embodiments, the second agent reduces, ameliorates, or prevents a disorder, e.g., a skin disorder. Examples of second agents include, but are not limited to, steroids, vitamins, tar, keratolytic agents and anthralins.

The invention also features a composition for systemic administration, which includes a binding agent which binds specifically to PSMA, e.g., a binding agent as described herein, and an agent (or second agent) that reduces, ameliorates, or prevents a skin disorder. Examples of second agents that can be used in the compositions of the invention include, but are not limited to anti-inflammatory, antihistamine, immunosuppressive, cytotoxic, antimetabolic or immunomodulatory agents. For example, the second agent can be a systemic glucocorticoid, sulfone, aminoquinoline, retinoid, and thalidomide.

The composition of the invention can further include a pharmaceutically acceptable carrier, excipient or stabilizer.

In another aspect, the invention features a kit, which includes a PSMA binding agent, e.g., a PSMA binding agent as described herein, for use alone or in combination with a topical and/or a systemic agent, e.g., a second agent as described herein, along with instructions on how to use the PSMA binding agent or the combination of such agents.

In another aspect, the invention features methods for detecting the presence of a PSMA nucleic acid, e.g., mRNA or cDNA, or PSMA protein, in a sample, in vitro (e.g., a biological sample, such as plasma, tissue biopsy, e.g., a psoriatic lesion). The subject method can be used to evaluate, e.g., diagnose or stage a disorder described herein, e.g., a skin disorder (e.g., psoriasis). The method includes: (i) contacting the sample (and optionally, a reference, e.g., a control sample) with an agent specific for a PSMA nucleic acid, e.g., a probe or a primer, or a PSMA binding agent, under conditions that allow interaction of the agent and the PSMA nucleic acid, e.g., mRNA or cDNA, or protein to occur; and (ii) detecting formation of a complex between the agent, and the sample (and optionally, a reference, e.g., a control sample). Formation of the complex is indicative of the presence of PSMA nucleic acid or protein, and can indicate the suitability or need for a treatment described herein. For example, a statistically significant change in the formation of the complex in the sample relative to the control sample is indicative of the presence of PSMA in the sample. In one embodiment, the PSMA-binding agent is an anti-PSMA antibody, or antigen-binding fragment thereof, e.g., an anti-PSMA antibody, or antigen-binding fragment thereof as described herein. In other embodiments, the agent is a nucleic acid that specifically hybridizes to the PSMA nucleic acid.

In yet another aspect, the invention provides a method for detecting the presence of PSMA, in vivo (e.g., in vivo imaging in a subject). The subject method can be used to evaluate, e.g., diagnose or stage a disorder described herein, e.g., a skin disorder in a subject, e.g., a mammal, e.g., a primate, e.g., a human. The method includes: (i) administering to a subject (and optionally, a reference, e.g., a control subject) a PSMA binding agent, under conditions that allow interaction of the binding agent and the PSMA protein to occur; and (ii) detecting formation of a complex between the PSMA binding agent and PSMA statistically significant change in the formation of the complex in the subject relative to the reference, e.g., the control subject or subject's baseline, is indicative of the presence of PSMA.

In other embodiments, a method of diagnosing or staging, a disorder described herein, e.g., a skin disorder (e.g., psoriasis), is provided. The method includes: (i) identifying a subject having, or at risk of having, a skin disorder; (ii) obtaining a sample of a tissue or cell affected with the disorder; (iii) contacting said sample or a control sample with a labeled agent specific for a PSMA nucleic acid, e.g., a probe or a primer, or a labeled PSMA binding agent, under conditions that allow interaction of the binding agent and the PSMA nucleic acid, e.g., cDNA, mRNA, or PSMA protein to occur, and (iv) detecting formation of a complex. A statistically significant increase in the formation of the complex between the labeled agent with respect to a control sample is indicative of the skin disorder or the stage of the disorder.

Preferably, the agent, e.g., the PSMA binding agent, e.g., the anti-PSMA antibody or fragment thereof, is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials. In some embodiments, the modified anti-PSMA antibody or fragment thereof is coupled to a radioactive ion, e.g., indium ($^{111}$In), iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), technetium ($^{99}$mTc), praseodymium, or phosphorous ($^{32}$P).

Other features and advantages of the instant invention will become more apparent from the following detailed description and claims.

BRIEF DESCRIPTION OF THE DRAWINGS

FIGS. 2A–2B depict the amino acid sequence of murine J591 heavy and light chain variable region, respectively. The location of the CDRs is indicated in the Figures; the amino acid numbering is according the Kabat numbering (see, Kabat, E. A., et al. (1991) *Sequences of Proteins of Immunological Interest, Fifth Edition*, U.S. Department of Health and Human Services, NIH Publication No. 91–3242). Note that the CDRs are considered to encompass the Chothia loops and the Kabat hypervariable regions together and the sequences have been annotated accordingly. Heavy Chain: CDR1 is depicted in SEQ ID NO:1; CDR2 is depicted in SEQ ID NO:2; CDR3 is depicted in SEQ ID NO:3; the framework excluding CDR regions is depicted in SEQ ID NO:7; and the framework including CDR regions is depicted in SEQ ID NO:19. Light Chain: CDR1 is depicted in SEQ ID NO:4; CDR2 is depicted in SEQ ID NO:5; CDR3 is depicted in SEQ ID NO:6; the framework excluding CDR regions is depicted in SEQ ID NO:8; and the framework including CDR regions is depicted in SEQ ID NO:20.

FIGS. 3A–3B depict the amino acid sequence of deimmunized J591 heavy and light chain variable region, respectively. The location of the CDRs is indicated in the Figures; the amino acid numbering is according the Kabat numbering (see, Kabat, E. A., et al. (1991) supra). Note that the CDRs are considered to encompass the Chothia loops and the Kabat hypervariable regions together and the sequences have been annotated accordingly. Heavy Chain: CDR1 is depicted in SEQ ID NO:1; CDR2 is depicted in SEQ ID NO:2; CDR3 is depicted in SEQ ID NO:3; framework 1 is depicted in SEQ ID NO:9; framework 2 is depicted in SEQ ID NO:10; framework 3 is depicted in SEQ ID NO:11; framework 4 is depicted in SEQ ID NO:12; the framework excluding CDR regions is depicted in SEQ ID NO:17; and the framework including CDR regions is depicted in SEQ ID NO:21. Light Chain: CDR1 is depicted in SEQ ID NO:4; CDR2 is depicted in SEQ ID NO:5; CDR3 is depicted in SEQ ID NO:6; framework 1 is depicted in SEQ ID NO:13; framework 2 is depicted in SEQ ID NO:14; framework 3 is depicted in SEQ ID NO:15; framework 4 is depicted in SEQ ID NO:16; the framework excluding CDR regions is depicted in SEQ ID NO:18; and the framework including CDR regions is depicted in SEQ ID NO:22.

FIGS. 4A–4B depict an alignment of the murine J591 and deimmunized heavy chain variable regions, respectively (4A; SEQ ID NO:19 and 21, respectively) and light chain variable regions (4B; SEQ ID NO:20 and 22, respectively). Potential T cell epitopes (identified using a peptide threading program) in murine J591 VH and VK are shown in FIGS. 4A–4B, respectively. The 13-mer peptides predicted to bind to MHC class II are marked by the underlining, the CDRs are located at residues 26 to 35, 50 to 66 and 99 to 104 of FIG. 4A, and residues 24 to 34, 50 to 56 and 89 to 97 of FIG. 4B, and residues altered in the deimmunized heavy and light chain variable regions are boxed. Where possible, amino acid substitutions are those commonly used in human germline VH regions. The amino acid numbering is linear, not according to Kabat.

FIG. 5A shows an alignment of the coding and noncoding nucleotide strands of deimmunized J591 heavy chain variable region (SEQ ID NOs:23 and 24, respectively) with the corresponding amino acid sequence (SEQ ID NO:27). FIG. 5B shows an alignment of the coding and noncoding nucleotide strands of deimmunized J591 light chain variable region (SEQ ID NOs:25 and 26, respectively) with the corresponding amino acid sequence (SEQ ID NO:28). The location of the signal peptide and CDRs 1–3 is indicated in each alignment.

FIG. 6 depicts an alignment of the amino acid sequences for the murine and several deimmunized heavy chain variable regions of the J415 antibody. The murine amino acid sequence is shown as J415VH (SEQ ID NO:47); the deimmunized sequences are depicted as J415DIVH1 (amino acid residues 18 to 133 of SEQ ID NO:54), J415DIVH2 (SEQ ID NO:59), J415DIVH3 (SEQ ID NO:60), and J415DIVH4 (SEQ ID NO:49). The preferred sequence is J415DIVH4 (SEQ ID NO:49). The amino acid replacements are indicated by the boxed residues. A consensus sequence is labeled "majority" (SEQ ID NO:61).

FIG. 7 depicts an alignment of the amino acid sequences for the murine and several deimmunized light chain variable regions of the J415 antibody. The murine amino acid sequence is shown as J415VK (SEQ ID NO:48); the deimmunized sequences are depicted as J415DIVK1 (amino acid residues 18 to 124 of SEQ ID NO:57), J415DIVK2 (SEQ ID NO:62), J415DIVK3 (SEQ ID NO:63), J415DIVK4 (SEQ ID NO:64), J415DIVK5 (SEQ ID NO:50), J415DIVK6 (SEQ ID NO:65), J415DIVK7 (SEQ ID NO:66), and J415DIVK8 (SEQ ID NO:67). The preferred sequence is J415DIVK5 (SEQ ID NO:50). The amino acid replacements are indicated by the boxed residues. A consensus sequence is labeled "majority" (SEQ ID NO:68).

FIG. 8B depicts the nucleic acid coding sequence, the amino acid sequence, and the nucleic acid reverse complement sequence of the murine J415 heavy chain variable region (SEQ ID NO:125, 47, and 126, respectively). The relative locations of the CDRs and some restriction sites are indicated.

FIG. 8C depicts an alignment of the amino acid sequence of the murine J415 heavy chain variable region (SEQ ID NO:47) and a consensus sequence for Kabat subgroup murine VHIIIC (MUVHIII, SEQ ID NO:69). A consensus majority sequence based on the alignment is also shown (SEQ ID NO:70).

FIG. 9B depicts the nucleic acid coding sequence, the amino acid sequence, and the nucleic acid reverse complement sequence of the murine J415 light chain variable region (SEQ ID NOs:127, 48, and 128, respectively). The relative locations of the CDRs and some restriction sites are also indicated.

FIG. 9C depicts an alignment of the amino acid sequence of the murine J415 light chain variable region (SEQ ID NO:48) and a consensus sequence for Kabat subgroup murine variable light chain (MuVKI, SEQ ID NO:71). A consensus majority sequence based on the alignment is also shown (SEQ ID NO:72).

FIG. 10A depicts the nucleic acid coding sequence, the amino acid sequence, and the nucleic acid reverse complement sequence of the murine J533 heavy chain variable region (SEQ ID NO:73–75, respectively). The relative locations of the CDRs and restriction sites are indicated.

FIG. 10B depicts an alignment of the amino acid sequence of the murine J533 heavy chain variable region (SEQ ID NO:74) and a consensus sequence for Kabat subgroup murine variable heavy chain (MuVHIIA, SEQ ID NO:79). A consensus majority sequence based upon the alignment is also shown (SEQ ID NO:80).

FIG. 12A depicts the nucleic acid coding sequence, the amino acid sequence, and the nucleic acid reverse complement sequence of the murine E99 heavy chain variable region (SEQ ID NO:83–85, respectively). The relative locations of the CDRs and some restriction sites are indicated.

FIG. 12B depicts an alignment of the amino acid sequence of the murine E99 heavy chain variable region (SEQ ID NO:84) and a consensus sequence for Kabat subgroup murine variable heavy chain (MuVHIB, SEQ ID NO:89). A consensus majority sequence based upon the alignment is also shown (SEQ ID NO:90).

FIG. 13A depicts the nucleic acid coding sequence, the amino acid sequence, and the nucleic acid reverse complement sequence of the murine E99 light chain variable region (SEQ ID NO:86–88, respectively). The relative locations of the CDRs and some restriction sites are indicated.

FIG. 13B depicts an alignment of the amino acid sequence of the murine E99 light chain variable region (SEQ ID NO:87) and a consensus sequence for Kabat subgroup murine variable light chain (MuVKI, SEQ ID NO:91). A consensus majority sequence based upon the alignment is also shown (SEQ ID NO:92).

FIG. 15 is a panel of immunohistochemical stains from two psoriatic patients. Increased anti-PSMA staining was detected in psoriatic lesions, more specifically in basal and immediately suprabasal keratinocytes, dermal endothelial cells, as well as vascular cells (indicated by the arrow), compared to the weak staining detected in non-lesional control areas from the same patients.

DETAILED DESCRIPTION OF THE INVENTION

Figure 14A:
FIGS. 14A–14B are photographs depicting the psoriatic area involving the left middle finger of a patient before and after, respectively, two treatments with isotope-conjugated deimmunized J591 antibody. After treatment, the patient's psoriatic affected lesions in the inguinal areas also substantially improved.
Figure 14B:
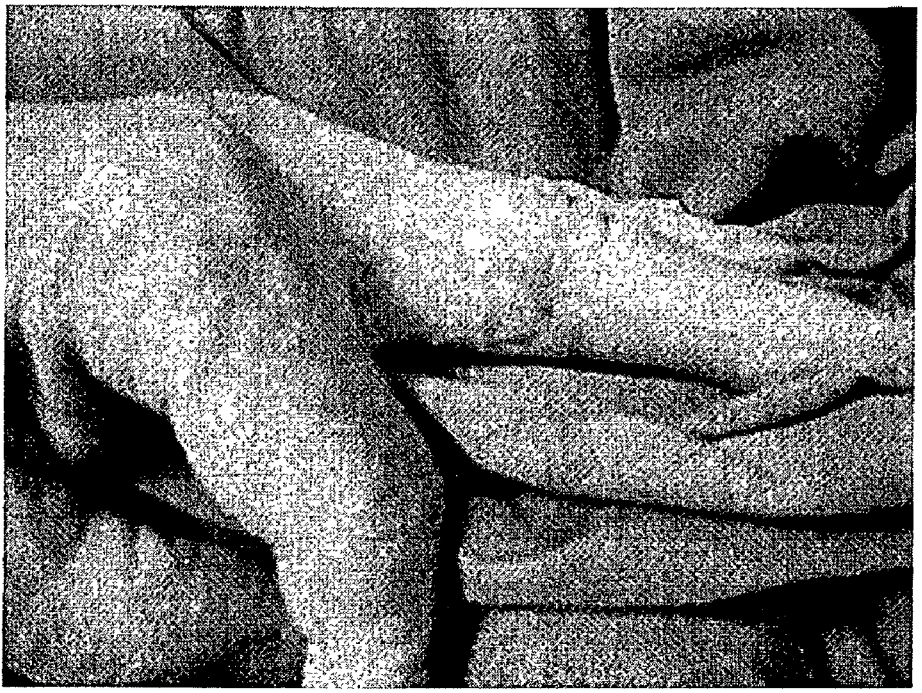
Figure 16:
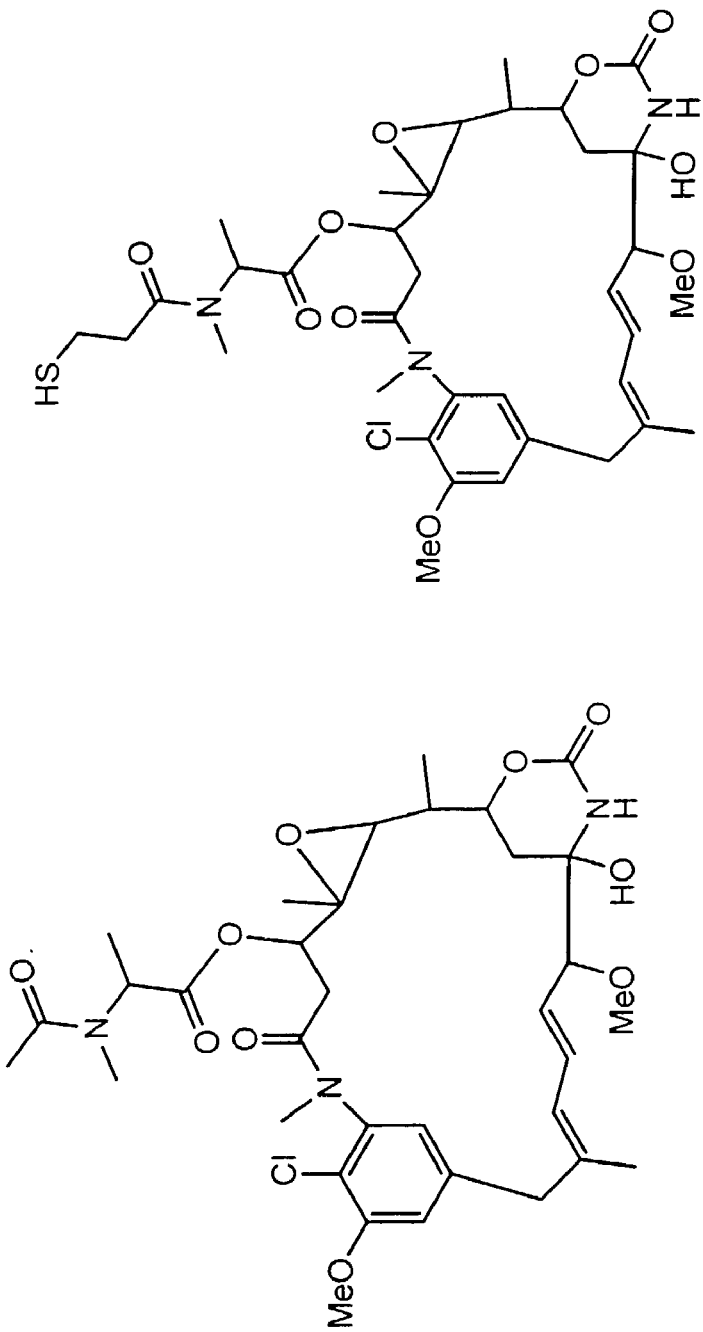
FIG. 16 depicts the chemical structures of DM1 and maytansine, a related molecule that lacks the thiol reactive group of DM1 used to conjugate DM1 to antibodies.

The invention is based, in part, on the discovery that administration to a subject of an antibody to the extracellular domain of prostate specific membrane antigen (PSMA), alone or conjugated to a cytotoxic moiety, reduced the severity of psoriatic lesions (Examples 1–2, and FIGS. 14A–14B). Expression of PSMA protein on hyperproliferative basal and immediately suprabasal keratinocytes, dermal endothelial cells, as well as vascular cells, was detected on the epidermis of a psoriatic lesion from a human subject (Example 3, and FIGS. 1 and 15). The intensity of the staining appears to localize more to less differentiated cells as compared to more differentiated cells. Methods of using the PSMA binding agents to treat, e.g., ablate or kill, PSMA-expressing cells in vitro or in vivo, are encompassed by the invention. Accordingly, in one aspect, the invention provides methods and compositions for treating or preventing skin disorders, e.g., epidermal or dermal disorders, using binding agents, e.g., antibodies or antigen-binding fragments thereof, specific for PSMA.

In order that the present invention may be more readily understood, certain terms are first defined. Additional definitions are set forth throughout the detailed description.

As used herein, "PSMA" or "prostate-specific membrane antigen" protein refers to mammalian PSMA, preferably human PSMA protein. Human PSMA includes the two protein products, PSMA and PSM', encoded by the two alternatively spliced mRNA variants (containing about 2,653 and 2,387 nucleotides, respectively) of the PSMA cDNA disclosed in Israeli et al. (1993) *Cancer Res.* 53:227–230; Su et al. (1995) *Cancer Res.* 55:1441–1443; U.S. Pat. Nos. 5,538,866, U.S. Pat. No. 5,935,818, and WO 97/35616, the contents of which are hereby incorporated by reference. The long transcript of PSMA encodes a protein product of about 100–120 kDa molecular weight characterized as a type II transmembrane receptor having sequence identity with the transferrin receptor and having NAALA-Dase activity (Carter et al. (1996) *Proc. Natl. Acad. Sci. USA* 93:749–753). Accordingly, the term "human PSMA" refers to at least two protein products, human PSMA and PSM', which have or are homologous to (e.g., at least about 85%, 90%, 95% identical to) an amino acid sequence as shown in Israeli et al. (1993) *Cancer Res.* 53:227–230; Su et al. (1995) *Cancer Res.* 55:1441–1443; U.S. Pat. No. 5,538,866, U.S. Pat. No. 5,935,818, and WO 97/35616; or which is encoded by (a) a naturally occurring human PSMA nucleic acid sequence (e.g., Israeli et al. (1993) *Cancer Res.* 53:227–230 or U.S. Pat. No. 5,538,866); (b) a nucleic acid sequence degenerate to a naturally occurring human PSMA sequence; (c) a nucleic acid sequence homologous to (e.g., at least about 85%, 90%, 95% identical to) the naturally occurring human PSMA nucleic acid sequence; or (d) a nucleic acid sequence that hybridizes to one of the foregoing nucleic acid sequences under stringent conditions, e.g., highly stringent conditions.

A "PSMA binding agent" is an agent which interacts with (e.g., binds to) PSMA, preferably human PSMA. Preferably, the PSMA binding agent interact with, e.g., binds to, the extracellular domain of PSMA, e.g., the extracellular domain of human PSMA located at about amino acids 44–750 of human PSMA (amino acid residues correspond to the human PSMA sequence disclosed in U.S. Pat. No. 5,538,866). Preferably, the interaction, e.g., binding, occurs with high affinity, e.g., affinity constant of at least $10^7$ M$^{-1}$, preferably, between $10^8$ M$^{-1}$ and $10^{10}$ M$^{-1}$, or about $10^9$ M$^{-1}$, and specificity. Preferably, the PSMA binding agent treats, e.g., ablates or kills, a cell, e.g., a PSMA-expressing cell (e.g., a skin cell, e.g., a dermal or epidermal). The mechanism by which the PSMA binding agent treats, e.g., ablates or kills, the cell is not critical to the practice of the invention. In one embodiment, the PSMA binding agent may bind to and be internalized with the PSMA expressed in the cells and/or vascular endothelial cells proximate to the cells. In those embodiments, the binding agent can be used to target a second moiety, e.g., a cytotoxic agent, to the cell. In other embodiments, the PSMA binding agent may mediate host mediated-killing, e.g., complement- or ADCC-mediated killing, of the cell and/or the vascular cell proximate thereto, upon binding to the extracellular domain of PSMA. The cell can be killed directly by the PSMA binding agent by binding directly to the cell (e.g., dermal or epidermal cell) or the vascular endothelial cells proximate thereto. Alternatively, the PSMA binding agent can treat, e.g., kill or ablate, or otherwise change the properties of the vascular endothelial cells to which it binds so that blood flow to the cells proximate thereto is reduced, thereby causing the cells to be killed or ablated. Examples of PSMA binding agents include anti-PSMA antibodies (e.g., monospecific, monoclonal (e.g., human or rodent), recombinant or modified, e.g., chimeric, CDR-grafted, humanized, deimmunized, in vitro generated antibodies; small molecules or peptidomimetics.

An "anti-PSMA antibody" is an antibody that interacts with (e.g., binds to) PSMA, preferably human PSMA protein. Preferably, the anti-PSMA antibody interacts with, e.g., binds to, the extracellular domain of PSMA, e.g., the extracellular domain of human PSMA located at about amino acids 44–750 of human PSMA (amino acid residues correspond to the human PSMA sequence disclosed in U.S. Pat. No. 5,538,866). In one embodiment, the anti-PSMA antibody binds all or part of the epitope of an antibody described herein, e.g., J591, E99, J415, and J533. The anti-PSMA antibody can inhibit, e.g., competitively inhibit, the binding of an antibody described herein, e.g., J591, E99, J415, and J533, to human PSMA. An anti-PSMA antibody may bind to an epitope, e.g., a conformational or a linear epitope, which epitope when bound prevents binding of an antibody described herein, J591, E99, J415, and J533. The epitope can be in close proximity spatially or functionally-associated, e.g., an overlapping or adjacent epitope in linear sequence or conformationally to the one recognized by the J591, E99, J415, or J533 antibody. In one embodiment, the anti-PSMA antibody binds to an epitope located wholly or partially within the region of about amino acids 120 to 500, preferably 130 to 450, more preferably, 134 to 437, or 153 to 347, of human PSMA (amino acid residues correspond to the human PSMA sequence disclosed in U.S. Pat. No. 5,538,866). Preferably, the epitope includes at least one glycosylation site, e.g., at least one N-linked glycosylation site (e.g., the N-linked glycosylation site located at about amino acids 190–200, preferably at about amino acid 195, of human PSMA) (amino acid residues correspond to the human PSMA sequence disclosed in U.S. Pat. No. 5,538,866).

In a preferred embodiment, the interaction, e.g., binding, between an anti-PSMA antibody and PSMA occurs with high affinity (e.g., affinity constant of at least $10^7$ M$^{-1}$, preferably, between $10^8$ M$^{-1}$ and $10^{10}$, or about $10^9$ M$^{-1}$) and specificity. Preferably, the anti-PSMA antibody treats, e.g., ablates or kills, a cell, e.g., a PSMA-expressing cell (e.g., a skin cell, e.g., a dermal or epidermal cell). The mechanism by which the anti-PSMA antibody treats, e.g., ablates or kills, the cell is not critical to the practice of the invention. In one embodiment, the anti-PSMA antibody may bind to and be internalized with the PSMA expressed in the cells and/or vascular endothelial cells proximate to the cells. In those embodiments, the anti-PSMA antibody can be used to target a second moiety, e.g., a cytotoxic or labeling agent, to the cell. In other embodiments, the anti-PSMA antibody may mediate host-mediated-killing, e.g., complement- or ADCC-mediated killing, of the cell and/or the vascular cell proximate thereto, upon binding to the extracellular domain of PSMA. The cell can be killed directly by the anti-PSMA antibody by binding directly to the cell or the vascular endothelial cells proximate thereto. Alternatively, the anti-PSMA antibody can treat, e.g., kill or ablate, or otherwise change the properties of the vascular endothelial cells to which it binds so that blood flow to the cells proximate thereto is reduced, thereby causing the cells to be killed or ablated. Examples of anti-PSMA antibodies include, e.g., monospecific, monoclonal (e.g., human), recombinant or modified, e.g., chimeric, CDR-grafted, humanized, deimmunized, and in vitro generated anti-PSMA antibodies.

As used herein, the term "treat" or "treatment" is defined as the application or administration of a PSMA binding agent to a subject, e.g., a patient, or application or administration to an isolated tissue or cell from a subject, e.g., a patient, which is returned to the patient. The binding agent can be administered alone or in combination with, a second agent. The subject can be a patient having a disorder (e.g., a disorder as described herein), a symptom of a disorder or a predisposition toward a disorder. The treatment can be to cure, heal, alleviate, relieve, alter, remedy, ameliorate, improve or affect the disorder, the symptoms of the disorder or the predisposition toward the disorder. While not wishing to be bound by theory, treating is believed to cause the inhibition, ablation, or killing of a cell in vitro or in vivo, or otherwise reducing capacity of a cell, e.g., an aberrant cell, to mediate a disorder, e.g., a disorder as described herein (e.g., a skin disorder, e.g., psoriasis).

As used herein, an amount of a PSMA binding agent, e.g., an anti-PSMA antibody, effective to treat a disorder, or a "therapeutically effective amount" refers to an amount of the agent which is effective, upon single or multiple dose administration to a subject, in treating a cell, e.g., a skin cell (e.g., a PSMA-expressing skin cell, or a vascular cell proximate thereto), or in prolonging curing, alleviating, relieving or improving a subject with a disorder as described herein beyond that expected in the absence of such treatment. As used herein, "inhibiting the growth" of the lesion refers to slowing, interrupting, arresting or stopping its growth and does not necessarily indicate a total elimination of the growth or lesion.

As used herein, an amount of a PSMA binding agent, e.g., an anti-PSMA antibody, effective to prevent a disorder, or a "prophylactically effective amount" of the agent refers to an amount of a binding agent, e.g., an anti-PSMA antibody, e.g., an anti-PSMA antibody as described herein, which is effective, upon single- or multiple-dose administration to the subject, in preventing or delaying the occurrence of the onset or recurrence of a disorder, e.g., a skin disorder as described herein, or treating a symptom thereof.

The terms "induce", "inhibit", "potentiate", "elevate", "increase", "decrease" or the like, e.g., which denote quantitative differences between two states, refer to a difference, e.g., a statistically significant difference, between the two states. For example, "an amount effective to inhibit the proliferation of the PSMA-expressing hyperproliferative cells" means that the rate of growth of the cells will be different, e.g., statistically significantly different, from the untreated cells.

As used herein, "specific binding" refers to the property of the binding agent, preferably the antibody, to: (1) to bind to PSMA, e.g., human PSMA protein, with an affinity of at least $1\times10^7$ $M^{-1}$, and (2) preferentially bind to PSMA, e.g., human PSMA protein, with an affinity that is at least two-fold, 50-fold, 100-fold, 1000-fold, or more greater than its affinity for binding to a non-specific antigen (e.g., BSA, casein) other than PSMA.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901–917, which are incorporated herein by reference). Preferably, each VH and VL is composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH— terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having: CDRs from a non-human source, e.g., from a non-human antibody, e.g., from a mouse immunoglobulin or another non-human immunoglobulin, from a consensus sequence, or from a sequence generated by phage display, or any other method of generating diversity; and having a framework that is less antigenic in a human than a non-human framework, e.g., in the case of CDRs from a non-human immunoglobulin, less antigenic than the non-human framework from which the non-human CDRs were taken. The framework of the immunoglobulin can be human, humanized non-human, e.g., a mouse, framework modified to decrease antigenicity in humans, or a synthetic framework, e.g., a consensus sequence. These are sometimes referred to herein as modified immunoglobulins. A modified antibody, or antigen binding fragment thereof, includes at least one, two, three or four modified immunoglobulin chains, e.g., at least one or two modified immunoglobulin light and/or at least one or two modified heavy chains. In one embodiment, the modified antibody is a tetramer of two modified heavy immunoglobulin chains and two modified light immunoglobulin chains.

As used herein, "isotype" refers to the antibody class (e.g., IgM or IgG1) that is encoded by heavy chain constant region genes.

The term "antigen-binding fragment" of an antibody (or simply "antibody portion," or "fragment"), as used herein, refers to a portion of an antibody which specifically binds to PSMA (e.g., human PSMA), e.g., a molecule in which one or more immunoglobulin chains is not full length but which specifically binds to PSMA (e.g., human PSMA protein). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423–426; and Huston et al. (1988) Proc. Natl. Acad. Sci. USA 85:5879–5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

The term "recombinant" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, deimmunized, in vitro generated (e.g., by phage display) antibodies, and may optionally include constant regions derived from human germline immunoglobulin sequences.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), *J. Mol. Biol.* 48:444–453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation of the invention) are a Blossum 62 scoring matrix with a gap penalty of 12, a gap extend penalty of 4, and a frameshift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the binding agent polypeptides of the invention may have additional conservative or non-essential amino acid substitutions, which do not have a substantial effect on the polypeptide functions. Whether or not a particular substitution will be tolerated, i.e., will not adversely affect desired biological properties, such as binding activity can be determined as described in Bowie, J U et al. (1990) *Science* 247:1306–1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

Anti-PSMA Antibodies

Many types of anti-PSMA antibodies, or antigen-binding fragments thereof, are useful in the methods of this invention. The antibodies can be of the various isotypes, including: IgG (e.g., IgG1, IgG2, IgG3, IgG4), IgM, IgA1, IgA2, IgD, or IgE. Preferably, the antibody is an IgG isotype. The antibody molecules can be full-length (e.g., an IgG1 or IgG4 antibody) or can include only an antigen-binding fragment (e.g., a Fab, F(ab')$_2$, Fv or a single chain Fv fragment). These include monoclonal antibodies, recombinant antibodies, chimeric antibodies, humanized antibodies, deimmunized antibodies, as well as antigen-binding fragments of the foregoing.

As described in more detail below, antibodies (preferably, monoclonal antibodies from differing organisms, e.g., rodent, sheep, human) against a predetermined antigen can be produced using art-recognized methods. Once the antibodies are obtained, the variable regions can be sequenced. The location of the CDRs and framework residues can be determined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901–917, which are incorporated herein by reference). The light and heavy chain variable regions can, optionally, be ligated to corresponding constant regions. A light and the heavy immunoglobulin chains can be generated and co-expressed into the appropriate host cells.

Monoclonal anti-PSMA antibodies can be used in the methods of the invention. Preferably, the monoclonal antibodies bind to the extracellular domain of PSMA (i.e., an epitope of PSMA located outside of a cell). Examples of preferred murine monoclonal antibodies to human PSMA include, but are not limited to, E99, J415, J533 and J591, which are produced by hybridoma cell lines having an ATCC Accession Number HB-12101, HB-12109, HB-12127, and HB-12126, respectively, all of which are disclosed in U.S. Pat. Nos. 6,107,090 and US 6,136,311, the contents of which are expressly incorporated by reference. Most preferably, the murine monoclonal antibody is J591, produced by HB-12126.

Additional monoclonal antibodies to PSMA can be generated using techniques known in the art. Monoclonal antibodies can be produced by a variety of techniques, including conventional monoclonal antibody methodology e.g., the standard somatic cell hybridization technique of Kohler and Milstein, *Nature* 256: 495 (1975). See generally, Harlow, E. and Lane, D. (1988) *Antibodies: A Laboratory Manual*, Cold Spring Harbor Laboratory Press, Cold Spring Harbor, N.Y. Although somatic cell hybridization procedures are preferred, in principle, other techniques for producing monoclonal antibody can be employed e.g., viral or oncogenic transformation of B lymphocytes. The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Useful immunogens for the purpose of this invention include PSMA (e.g., human PSMA)-bearing cells (e.g., dermal or epidermal cells from a subject with psoriasis or prostate tumor cell lines, e.g., LNCap cells); isolated or purified PSMA, e.g., human PSMA, e.g., biochemically isolated PSMA, or a portion thereof, e.g., the extracellular domain of PSMA. Techniques for generating antibodies to PSMA are described in U.S. Pat. Nos. 6,107,090, US 6,136, 311, the contents of all of which are expressly incorporated by reference.

Human monoclonal antibodies (mAbs) directed against human proteins can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368: 856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Bruggeman et al. 1991 *Eur J Immunol* 21:1323–1326).

Anti-PSMA antibodies or fragments thereof useful in the present invention may also be recombinant antibodies produced by host cells transformed with DNA encoding immunoglobulin light and heavy chains of a desired antibody. Recombinant antibodies may be produced by known genetic engineering techniques. For example, recombinant antibodies may be produced by cloning a nucleotide sequence, e.g., a cDNA or genomic DNA sequence, encoding the immunoglobulin light and heavy chains of the desired antibody from a hybridoma cell that produces an antibody useful in this invention. The nucleotide sequence encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding may be renaturable according to well known methods (Kim and Baldwin, "Specific Intermediates in the Folding Reactions of Small Proteins and the Mechanism of Protein Folding", *Ann. Rev. Biochem.* 51, pp. 459–89 (1982)). It is possible that the host cells will produce portions of intact antibodies, such as light chain dimers or heavy chain dimers, which also are antibody homologs according to the present invention.

It will be understood that variations on the above procedure are useful in the present invention. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for PSMA binding, e.g., the constant region may be modified by, for example, deleting specific amino acids. The molecules expressed from such truncated DNA molecules are useful in the methods of this invention. In addition, bifunctional antibodies may be produced in which one heavy and one light chain are anti-PSMA antibody and the other heavy and light chain are specific for an antigen other than PSMA, or another epitope of PSMA.

Chimeric antibodies, including chimeric immunoglobulin chains, can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041–1043); Liu et al. (1987) *PNAS* 84:3439–3443; Liu et al., 1987, *J. Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J. Natl Cancer Inst.* 80:1553–1559).

An antibody or an immunoglobulin chain can be humanized by methods known in the art. Once the murine antibodies are obtained, the variable regions can be sequenced. The location of the CDRs and framework residues can be determined (see, Kabat, E. A., et al. (1991) *Sequences of Proteins of Immunological Interest, Fifth Edition*, U.S.

Department of Health and Human Services, NIH Publication No. 91–3242, and Chothia, C. et al. (1987) J. Mol. Biol. 196:901–917, which are incorporated herein by reference). The light and heavy chain variable regions can, optionally, be ligated to corresponding constant regions.

Murine anti-PSMA antibodies can be sequenced using art-recognized techniques. As an example, hybridomas expressing murine antibodies J533, J415 and E99 were propagated in culture in RPMI 1640 medium supplemented with 10% fetal calf serum. The isotype of the antibodies secreted was confirmed as IgG1κ, IgG1κ, and IgG3κ respectively. These monoclonal antibodies, like J591, bind to the external domain of prostate specific membrane antigen. J591, J533 and E99 recognize the same epitope, while J415 recognizes an independent epitope. Total RNA for each monoclonal was prepared from $10^7$ hybridoma cells. $V_H$ and $V_K$ cDNA was prepared using reverse transcriptase and mouse κ constant region and mouse IgG constant region primers. The first strand cDNAs were amplified by PCR using a variety of mouse signal sequence primers (6 for $V_H$ and 7 for $V_K$). The amplified DNAs were gel-purified and cloned into the vector pT7Blue. The $V_H$ and $V_K$ clones obtained were screened for correct inserts by PCR and the DNA sequence of selected clones determined by the dideoxy chain termination method (see Table 1).

The DNA and amino acid sequences for the heavy and light chain variable regions from J415 were obtained and are shown in FIGS. 8B ($V_H$) and 9B ($V_K$) (also, see Table 1). The location of the CDRs is shown. J415 $V_H$ can be assigned to Mouse Heavy Chains Subgroup IIIC (Kabat E A et al; ibid). The sequence of J415 $V_H$ compared to the consensus sequence for this subgroup is shown in FIG. 8C. J415 $V_K$ can be assigned to Mouse Kappa Chains Subgroup I (Kabat E A et al; ibid). The sequence of J415 $V_K$ compared to the consensus sequence for this subgroup is shown in FIG. 9C.

The DNA and amino acid sequences encoding the heavy and light chain variable regions of J533 were obtained and are shown in FIGS. 10A ($V_H$) and 11A ($V_K$) (see also Table 1). The location of the CDRs is shown in each figure. J533 $V_H$ can be assigned to Mouse Heavy Chains Subgroup IIA (Kabat E A et al; Sequences of proteins of Immunological Interest, US Department of Health and Human Services, 1991). The sequence of J533 $V_H$ compared to the consensus sequence for this subgroup is shown in FIG. 10B. J533 $V_K$ can be assigned to Mouse Kappa Chains Subgroup III (Kabat E A et al; ibid). The sequence of J533 $V_K$ compared to the consensus sequence for this subgroup is shown in FIG. 11B.

The DNA and amino acid sequences of the heavy and light chain variable regions of E99 were obtained and are shown in FIGS. 12A ($V_H$) and 13A ($V_K$) (see also Table 1). The location of the CDRs is shown. E99 $V_H$ can be assigned to Mouse Heavy Chains Subgroup IB (Kabat E A et al; ibid). The sequence of E99 $V_H$ compared to the consensus sequence for this subgroup is shown in FIG. 12B. E99 $V_K$ can be assigned Mouse Kappa Chains Subgroup I (Kabat E A et al; ibid). The sequence of E99 $V_K$ compared to the consensus sequence for this subgroup is shown in FIG. 13B.

The amino acid sequence and nucleotide sequences encoding the variable region of antibodies J415, deJ415, J591, deJ591, J533 and E99 are provided below in Table 1.

TABLE 1

Antibody variable chain sequences

| NAME | Organism | FIG. | SEQ ID NO: | SEQUENCE |
|---|---|---|---|---|
| $V_H$ J415 | Mus musculus | FIG. 8B | 125 | gaagtgaagcttgaggagtctggaggaggcttggtgcaacctgg aggatccatgaaactctcctgtgttgcctctggattcactttcagtaat tactggatgaactgggtccgccagtctccagagaagggcttgag tgggttgctgaaattagatcgcaatctaataattttgcaacacattatg cggagtctgtgaaagggagggtcatcatctcaagagatgattcca agagtagtgtctacctgcaaatgaacaacttgagagctgaagaca ctggcatttattactgtaccaggcgatggaataatttctggggccaa ggcaccactctcacagtctcctca |
| $V_H$ Variable Region J591 | Mus musculus | FIG. 2A | 19 | EVQLQQSGPELKKPGTSVRISCKTSGYTFT EYTIHWVKQSHGKSLEWIGNINPNNGGTT YNQKFEDKATLTVDKSSSTAYMELRSLTS EDSAVYYCAAGWNFDYWGQGTTLTVSS |
| $V_H$ J415 (complementary strand of SEQ ID NO: 125) | Mus musculus | FIG. 8B | 126 | Tgaggagactgtgagagtggtgccttggcccccagaaattattcca tcgcctggtacagtaataaatgccagtgtcttcagctctcaagttgtt catttgcaggtagacactactcttggaatcatctcttgagatgatgac cctcccttttcacagactccgcataatgtgttgcaaaattattagattg cgatctaatttcagcaacccactcaagccccttctctggagactgg cggacccagttcatccagtaattactgaaagtgaatccagaggca acacaggagagtttcatggatcctccaggttgcaccaagcctcctc cagactcctcaagcttcacttc |
| $V_L$ J415 | Mus musculus | FIG. 9B | 127 | aacattgtaatgacccaatttcccaaatccatgtccatttcagtagga gagagggtcaccttgacctgcaaggccagtgagaatgtgggtact tatgtgtcctggtatcaacagaaaccagaacagtctcctaagatgtt gatatacggggcatccaaccggttcactgggtcccgatcgctt cacaggcagtggatctgcaacagatttcattctgaccatcagcagt gtgcagactgaagacccttgtagattattactgtggacagagttacac ctttccgtacacgttcggaggggggaccaagctggaaatgaag |
| $V_L$ Variable Region J591 | Mus musculus | FIG. 2B | 20 | DIVMTQSHKFMSTSVGDRVSIICKASQDV GTAVDWYQQKPGQSPKLLIYWASTRHTG VPDRFTGSGSGTDFTLTITNVQSEDLADYF CQQYNSYPLTFGAGTMLDLK |

TABLE 1-continued

Antibody variable chain sequences

| NAME | Organism | FIG. | SEQ ID NO: SEQUENCE |
|---|---|---|---|
| V$_L$ J415 (complementary strand of SEQ ID NO: 127) | Mus musculus | FIG. 9B | 128 cttcatttccagcttggtcccccctccgaacgtgtacggaaaggtgt aactctgtccacagtaataatctacaaggtcttcagtctgcacactg ctgatggtcagaatgaaatctgttgcagatccactgcctgtgaagc gatcggggacccccagtgaaccggttggatgccccgtatatcaaca tcttaggagactgttctggtttctgttgataccaggacacataagtac ccacattctcactggccttgcaggtcaaggtgaccctctctcctact gaaatggacatgggatttgggaaattgggtcattacaatgtt |
| V$_H$ Variable Region (Deimm) J591 | Artificial - deimmunized heavy chain J591 | FIG. 3A | 21 EVQLVQSGPEVKKPGATVKISCKTSGYTFT EYTIHWVKQAPGKGLEWIGNINPNNGGTT YNQKFEDKATLTVDKSTDTAYMELSSLRS EDTAVYYCAAGWNFDYWGQGTLLTVSS |
| V$_L$ Variable Region (Deimm) J591 | Artificial - deimmunized light chain J591 | FIG. 3B | 22 DIQMTQSPSSLSTSVGDRVTLTCKASQDV GTAVDWYQQKPGPSPKLLIYWASTRHTGI PSRFSGSGSGTDFTLTISSLQPEDFADYYCQ QYNSYPLTFGPGTKVDIK |
| V$_H$ Deimmunized J591 CDS (122-166) & CDS (249-605) | Artificial - deimmunized heavy chain J591 | FIG. 5A | 23 Aagcttatgaatatgcaaatcctctgaatctacatggtaaatatagg tttgtctataccacaaacagaaaaacatgagatcacagttctctctac agttactgagcacacacaggacctcaccatgggatggagctgtatcat cctcttcttggtagcaacagctacaggtaaggggctcacagtagca ggcttgaggtctggacatatatatgggtgacaatgacatccactttg cctttctctccacaggtgtccactccgaggtccaactggtacagtct ggacctgaagtgaagaagcctggggctacagtgaagatatcctg caagcttctggatacacattcactgaatataccatacactgggtga agcaggcccctggaaagggccttgagtggattggaaacatcaatc ctaacaatggtggtaccacctacaatcagaagttcgaggacaagg ccacactaactgtagacaagtccaccgatacagcctacatggagc tcagcagcctaagatctgaggatactgcagtctattattgtgcagct ggttggaactttgactactggggccaagggaccctgctcaccgtct cctcaggtgagtccttacaacctctctcttctattcagcttaaatagat tttactgcatttgttggggggaaatgtgtgtatctgaatttcaggtca tgaaggactagggacaccttgggagtcagaaagggtcattggga gcccgggctgatgcagacagacatcctcagctcccagacttcatg gccagagatttataggatcc |
| V$_H$ Deimmunized (complementary strand of SEQ ID NO:23) J591 | Artificial - deimmunized heavy chain J591 | FIG. 5A | 24 ggatcctataaatctctggccatgaagtctgggagctgaggatgtc tgtctgcatcagcccgggctcccaatgacccttctgactcccaag gtgtccctagtccttcatgacctgaaattcagatacacacatttccc cccaacaaatgcagtaaaatctatttaagctgaatagaaagagag gttgtaaggactcacctgaggagacggtgagcagggtcccttggc cccagtagtcaaagttccaaccagctgcacaataatagactgcagt atcctcagatcttaggctgctgagctccatgtaggctgtatcggtgg acttgtctacagttagtgtggccttgtcctcgaacttctgattgtaggt ggtaccaccattgttaggattgatgtttccaatccactcaaggccctt tccaggggcctgcttcacccagtgtatggtatattcagtgaatgtgt atccagaagtcttgcaggatatcttcactgtagccccaggcttcttc acttcaggtccagactgtaccagttggacctcggagtggacacct gtggagaaaggcaaagtggatgtcattgtcacccatatatatgt ccagacctcaagcctgctactgtgagccccttacctgtagctgttgc taccaagaagaggatgatacagctccatccatggtgaggtcctgt gtgctcagtaactgtagagagaactgtgatctcatgttttctgtttgt ggtatagacaaacctatatttaccatgtagattcagaggatttgcata ttcataagctt |
| V$_L$ Deimmunized J591 CDS (122-166) & CDS (249-581) | Artificial - deimmunized light chain J591 | FIG. 5B | 25 aagcttatgaatatgcaaatcctctgaatctacatggtaaatatagg tttgtctataccacaaacagaaaaacatgagatcacagttctctctac agttactgagcacacaggacctcaccatgggatggagctgtatcat cctcttcttggtagcaacagctacaggtaaggggctcacagtagca ggcttgaggtctggacatatatatgggtgacaatgacatccactttg cctttctctccacaggtgtccactccgacatccagatgacccagtct ccctcatccctgtccacatcagtaggagacagggtcaccctcacct gtaaggccagtcaagatgtgggtactgctgtagactggtatcaaca gaaaccaggaccatctcctaaactactgatttattgggcatccactc ggcacactggaatccctagtcgcttctcaggcagtggatctggga cagacttcactctcaccatttctagtcttcagcctgaagactttgcag attattactgtcagcaatataacagctatcctctcacgttcggtcctg ggaccaaggtggacatcaaacgtgagtagaatttaaactttgcttc ctcagttggatcc |

TABLE 1-continued

Antibody variable chain sequences

Figures 2, 5A:
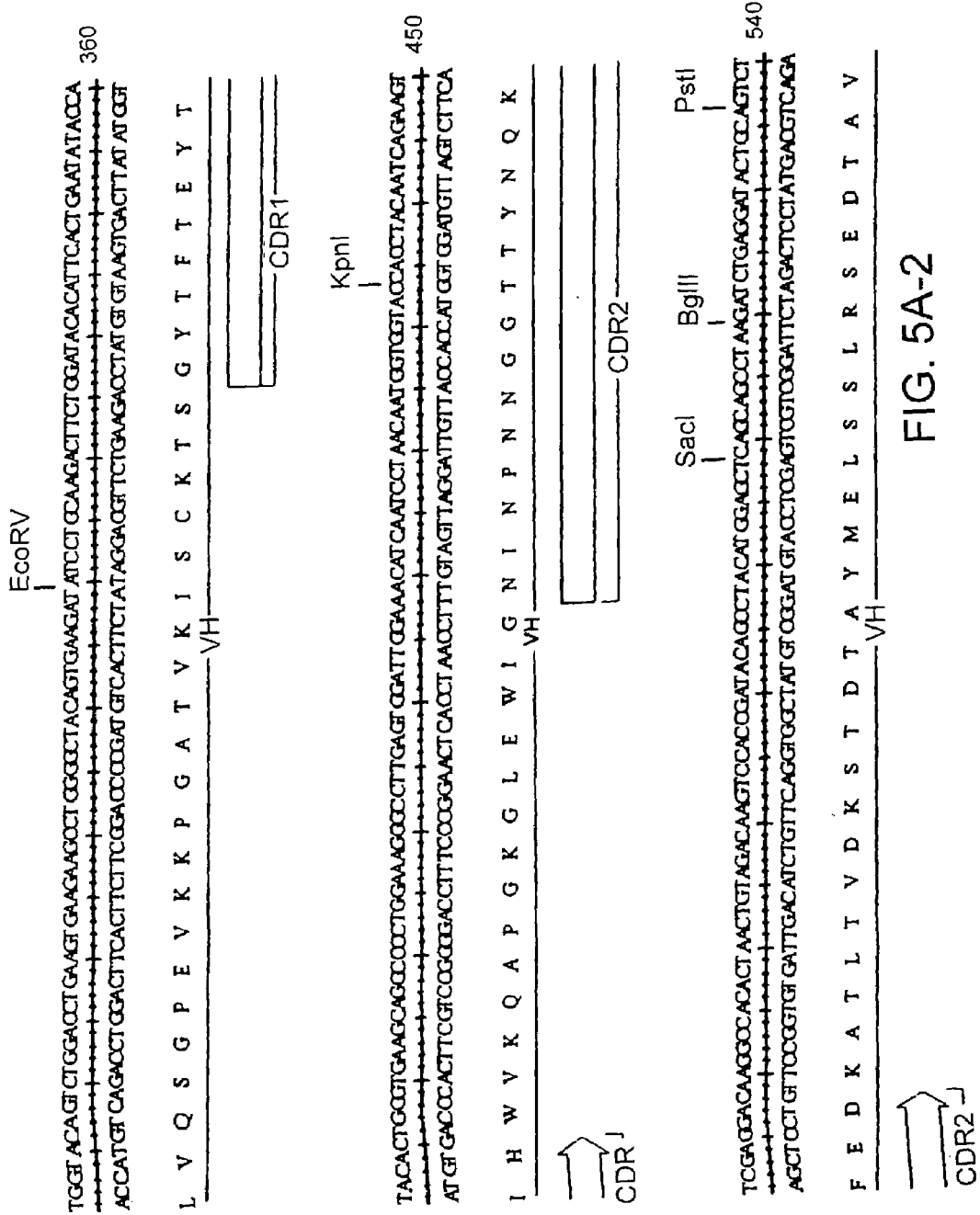
FIGS. 5A–5B depict the nucleotide sequences of the deimmunized J591 heavy and light chain variable region, respectively.
Figures 3, 5A:
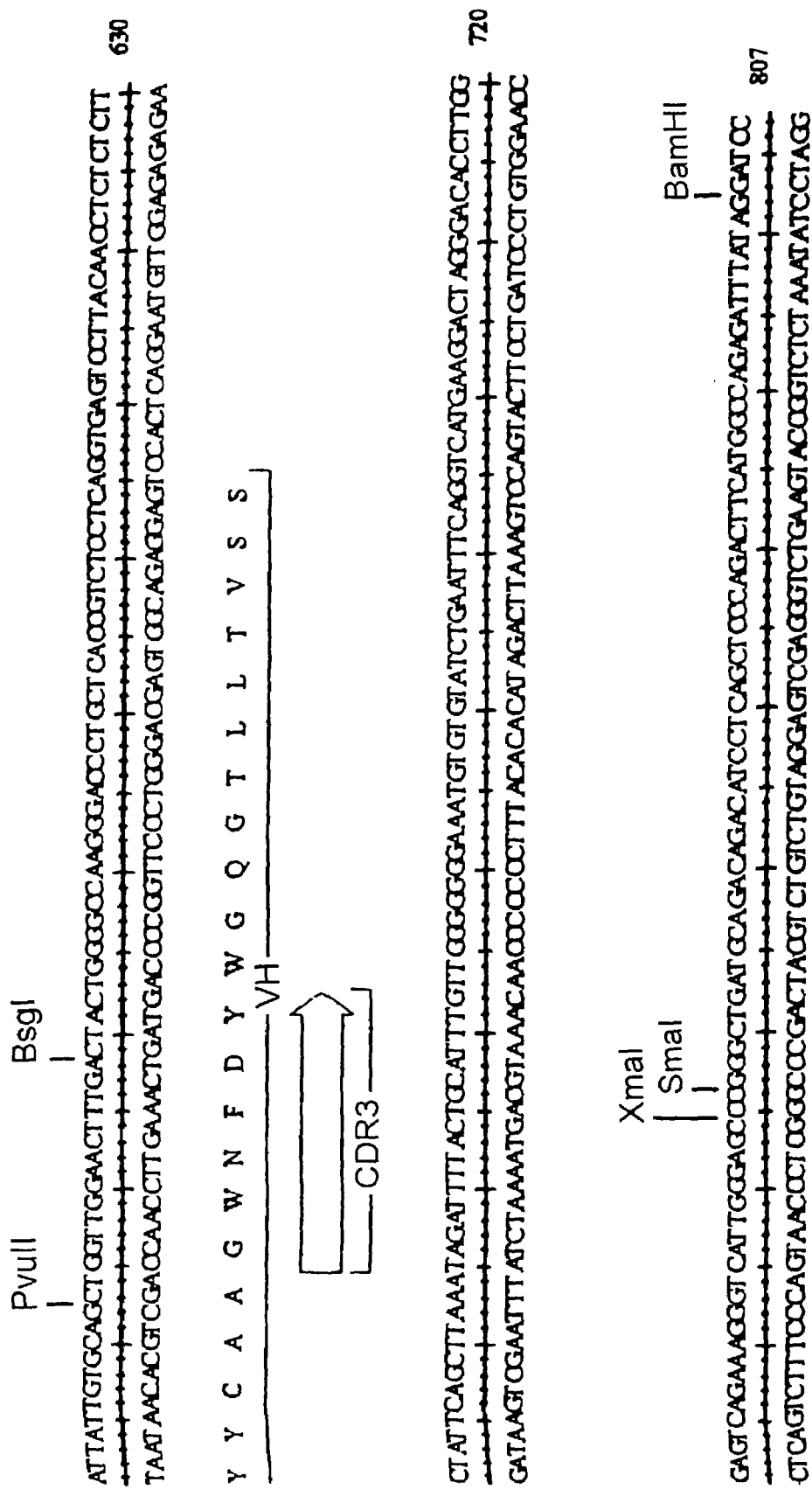
Figures 2, 5B:
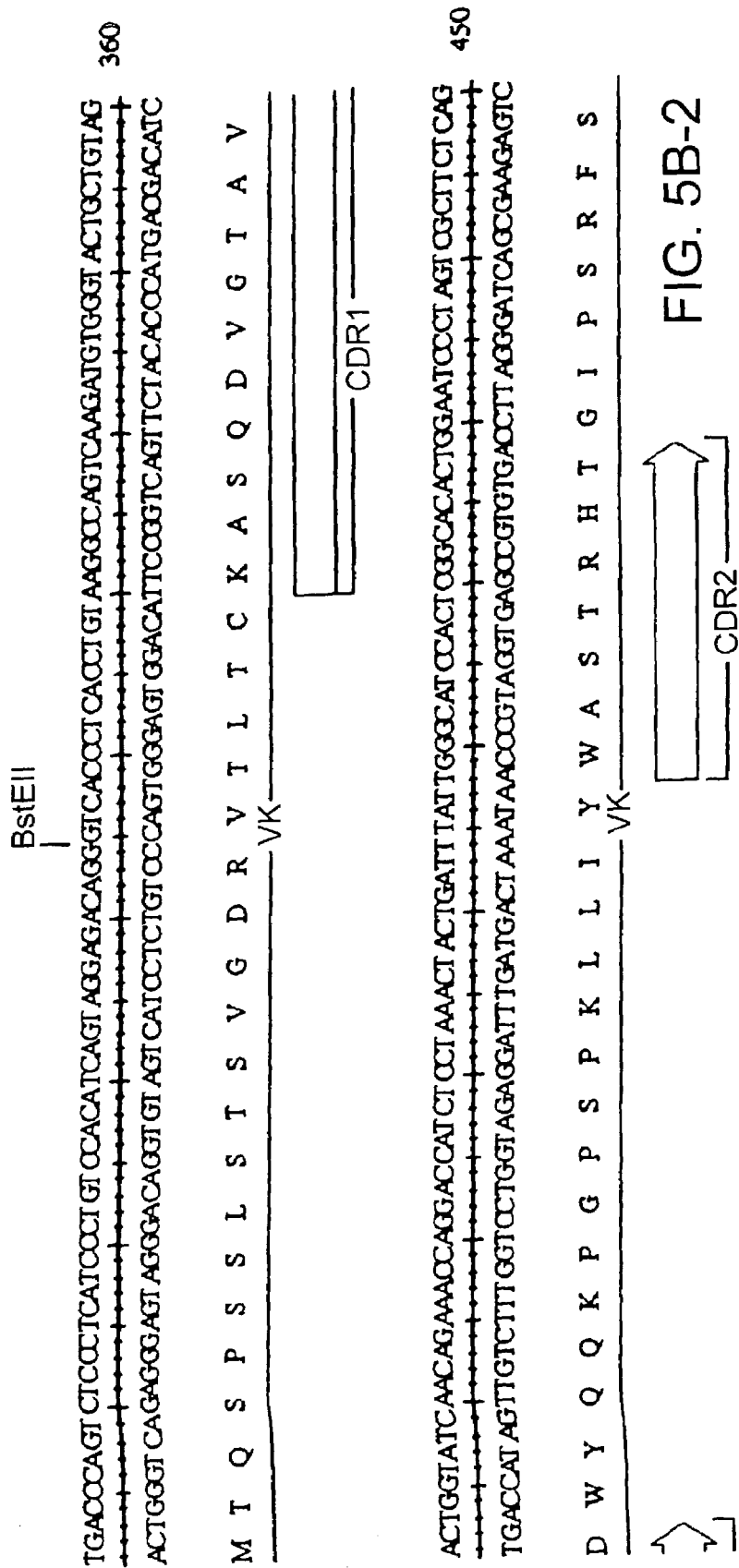
Figures 3, 5B:
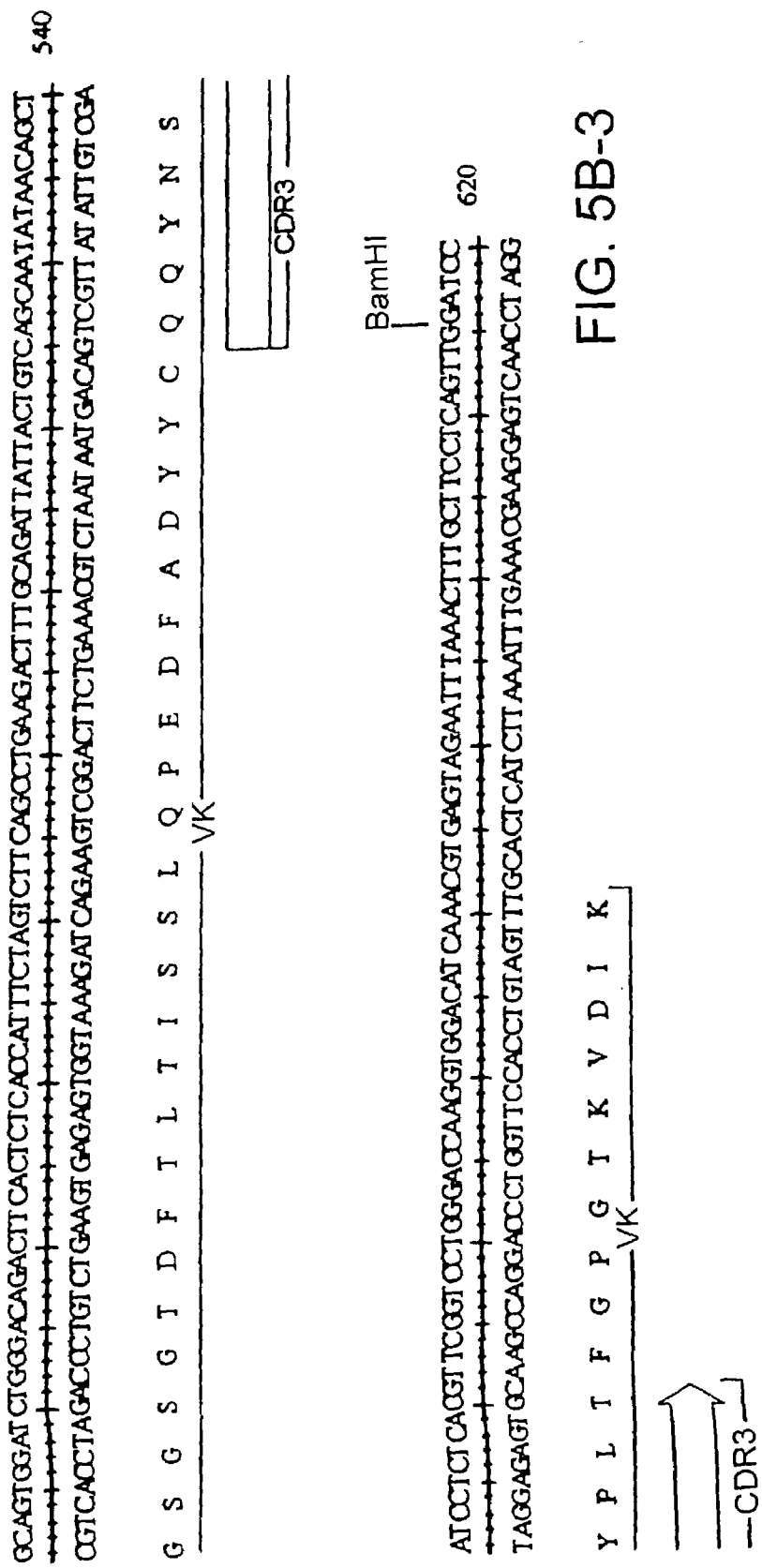
Figures 2, 8A:
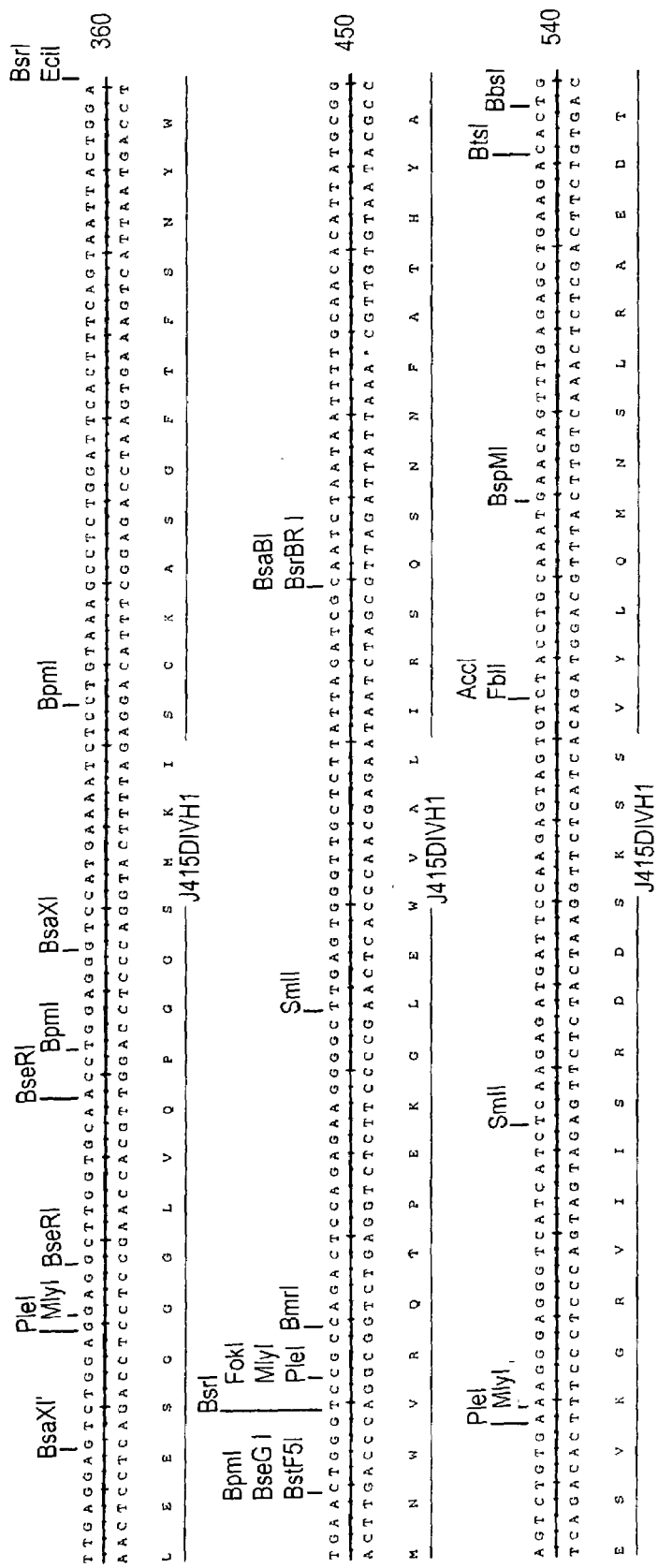
FIG. 8A depicts the nucleic acid coding sequence, the amino acid sequence, and the nucleic acid reverse complement sequence of the deimmunized J415 heavy chain variable region (J415DIVH1) (SEQ ID NO:53–55, respectively). The relative location of the signal sequence, intron and J415DIVH1 amino acid sequence is indicated, as well as some restriction sites.
Figures 3, 8A:
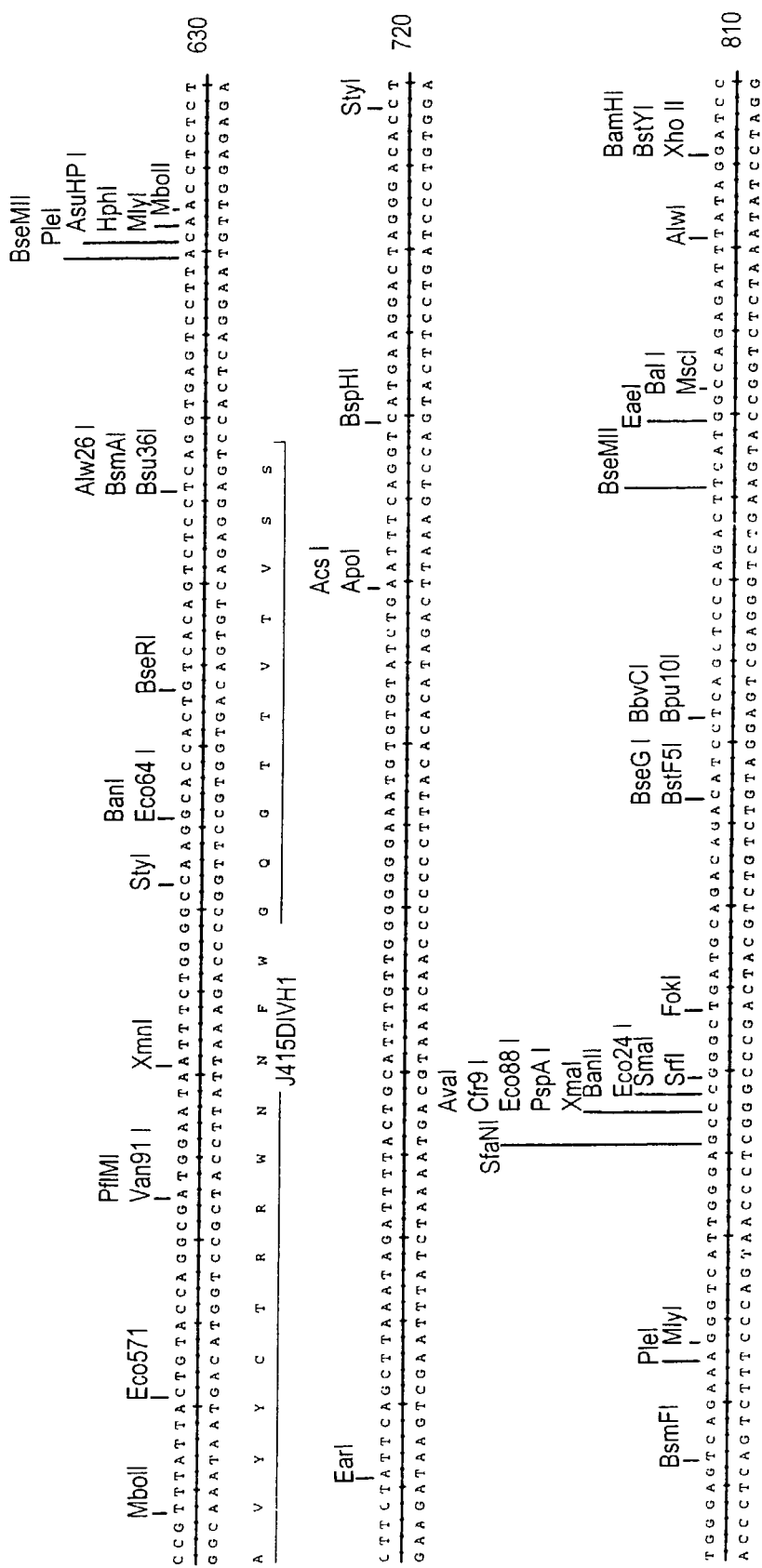

| NAME | Organism | FIG. | SEQ ID NO: | SEQUENCE |
|---|---|---|---|---|
| $V_L$ Deimmunized (complimentary strand of SEQ ID NO:25) J591 | Artificial - deimmunized light chain J591 | FIG. 5B | 26 | ggatccaactgaggaagcaaagtttaaattctactcacgtttgatgt ccaccttggtcccaggaccgaacgtgagaggatagctgttatattg ctgacagtaataatctgcaaagtcttcaggctgaagactagaaatg gtgagagtgaagtctgtcccagatccactgcctgagaagcgacta gggattccagtgtgccgagtggatgcccaataaatcagtagtttag gagatggtcctggtttctgttgataccagtctacagcagtacccaca tcttgactggccttacaggtgagggtgaccctgtctcctactgatgt ggacaggatgagggagactgggtcatctggatgtcggagtgga cacctgtggagagaaaggcaaagtggatgtcattgtcacccatata tatgtccagacctcaagcctgctactgtgagccccttacctgtagct gttgctaccaagaagaggatgatacagctccatcccatggtgagg tcctgtgtgctcagtaactgtagagagaactgtgatctcatgtttttct gtttgtggtatagacaaacctatatttaccatgtagattcagaggattt gcatattcataagctt |
| $V_H$ Deimmunized (predicted a.a. of SEQ ID NO:23) J591 | Artificial - deimmunized heavy chain J591 | FIG. 3A | 27 | MGWSCIILFLVATATGVHSEVQLVQSGPE VKKPGATVKISCKTSGYTFTEYTIHWVKQ APGKGLEWIGNINPNNGGTTYNQKFEDKA TLTVDKSTDTAYMELSSLRSEDTAVYYCA AGWNFDYWGQGTLLTVSS |
| $V_L$ Deimmunized (predicted a.a. of SEQ ID NO:25) J591 | Artificial - deimmunized light chain J591 | FIG. 3B | 28 | MGWSCIILFLVATATGVHSDIQMTQSPSSL STSVGDRVTLTCKASQDVGTAVDWYQQK PGPSPKLLIYCASTRHTGIPSRFSGSGSGTD FTLTISSLQPEDFADYYCQQYNSYPLTFGP GTKVDTK |
| $V_H$ Variable Region J415 | Mus musculus | FIG. 6 | 47 | EVKLEESGGGLVQPGGSMKLSCVASGFTF SNYWMNWVRQSPEKGLEWVAEIRSQSNN FATHYAESVKGRVIISRDDSKSSVYLQMN NLRAEDTGIYYCTRRWNNFWGQGTTLTV SS |
| $V_L$ Variable Region J415 | Mus musculus | FIG. 7 | 48 | NIVMTQFPKSMSISVGERVTLTCKASENVG TYVSWYQQKPEQSPKMLIYGASNRFTGVP DRFTGSGSATDFILTISSVQTEDLVDYYCG QSYTFPYTFGGGTKLEMK |
| $V_H$ Variable Region (Deimm) J415-4 | Artificial - deimmunized heavy chain J415-4 | FIG. 6 | 49 | EVKLEESGGGLVQPGGSMKISCVASGFTFS NYWMNWVRQSPEKGLEWVAEIRSQSNNF ATHYAESVKGRVIISRDDSKSSVYLQMNS LRAEDTAVYYCTRRWNNFWGQGTTVTVS S |
| $V_L$ Variable Region (Deimm) J415-5 | Artificial - deimmunized light chain J415-5 | FIG. 7 | 50 | NIVMTQFPKSMSASAGERMTLTCKASENV GTYVSWYQQKPTQSPKMLIYGASNRFTGV PDRFSGSGSGTDFILTISSVQAEDLVDYYC GQSYTFPYTFGGGTKLEMK |
| $V_H$ Deimmunized J415-4 | Artificial - deimmunized heavy chain J415-4 | | 51 | gaagtgaaacttgaggagtctgtgaggaggcttggtgcaacctgg agggtccatgaaaatctcctgtgttgcctctggattcactttcagtaa ttactggatgaactgggtccgccagtctccagagaaggggcttga gtgggttgctgaaattagatcgcaatctaataattttgcaacacattat gcggagtctgtgaaagggagggtcatcatctcaagagatgattcc aagagtagtgtctacctgcaaatgaacagtttgagagctgaagcactgccgttattactgtaccaggcgatggaataatttctggggccaa ggcaccactgtcacagtctcctca |
| $V_L$ Deimmunized J415-5 | Artificial - deimmunized light chain J415-5 | | 52 | aacattgtaatgacccaatttcccaaatccatgtccgcctcagcagg agagaggatgaccttgacctgcaaggccagtgagaatgtgggta cttatgtgtcctggtatcaacagaaaccaacacagtctcctaagatg ttgatatacggggcatccaaccggttcactggggtcccagatcgct tctccggcagtggatctggaacagatttcattctgaccatcagcagt gtgcaggcagaagaccttgtagattattactgtggacagagttaca cctttccgtacacgttcggaggggggaccaagctggaaatgaag |
| $V_H$ Deimmunized J415-1 CDS (122-160) & CDS (249-608) | Artificial - deimmunized heavy chain J415-1 | FIG. 8A | 53 | aagcttatgaatatgcaaatcctctgaatctacatgtaaatataggt ttgtctataccacaaacagaaaaacatgagatcacagttctctctac agttactgagcacacaggacctcaccatgggatggagctgtatca tcctcttcttggtagcaacagctacaggtaaggggctcacagtagc aggcttgaggtctggacatatatatgggtgacaatgaacatccacttt gccttttctctccacaggtgtccactccgaagtgaaacttgaggagt ctggaggaggcttggtgcaacctggagggtccatgaaaatctcct gtaaagcctctggattcactttcagtaattactggatgaactgggtcc gccagactccagagaagggcttgagtgggttgctcttattagatc gcaatctaataattttgcaacacattatgcggagtctgtgaaaggga |

TABLE 1-continued

Antibody variable chain sequences

Figures 2, 9A:
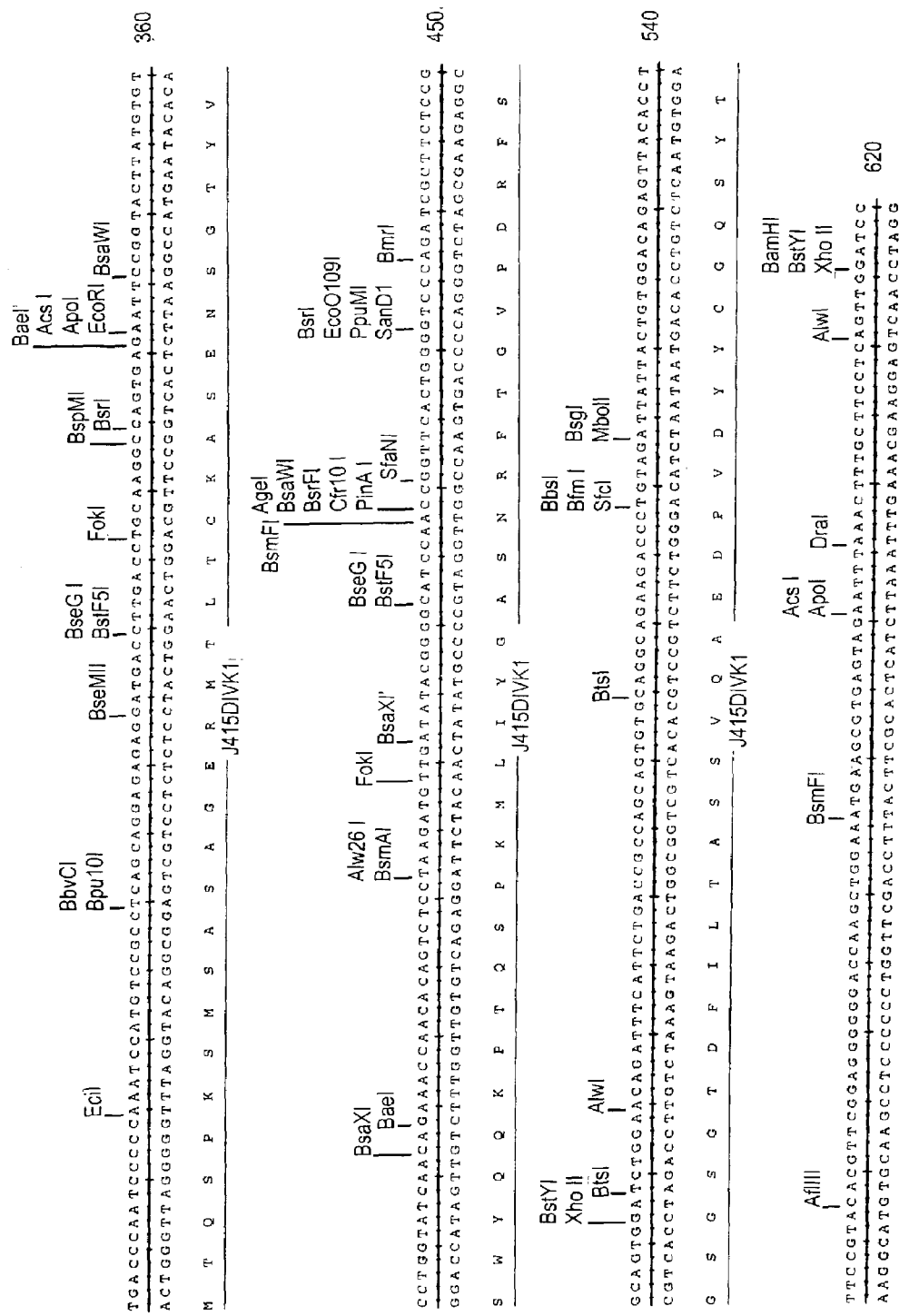
FIG. 9A depicts the nucleic acid coding sequence, the amino acid sequence, and the nucleic acid reverse complement sequence of the deimmunized J415 light chain variable region (J415DIVK1) (SEQ ID NO:56–58, respectively). The relative location of the signal sequence, intron and J415DIVK1 amino acid sequence is indicated, as well as some restriction sites.

| NAME | Organism | FIG. | SEQ ID NO: | SEQUENCE |
|---|---|---|---|---|
| Mature (18-133) | | | | gggtcatcatctcaagagatgattccaagagtagtgtctacctgca aatgaacagtttgagagctgaagacactgccgtttattactgtacca ggcgatggaataatttctggggccaaggcaccactgtcacagtct cctcaggtgagtccttacaacctctctcttctattcagcttaaatagat tttactgcatttgttgggggggaaatgtgtgtatctgaatttcaggtca tgaaggactagggacaccttgggagtcagaaagggtcattggga gcccgggctgatgcagacagacatcctcagctcccagacttcatg gccagagatttataggatcc |
| V<sub>H</sub> Deimmunized (predicted a.a. of SEQ ID NO:53) J415-1 | Artificial - deimmunized heavy chain J415-1 | FIG. 8A | 54 | MGWSCIILFLVATGVHSEVKLEESGGGLV QPGGSMKISCKASGFTFSNYWMNWVRQT PEKGLEWVALIRSQSNNFATHYAESVKGR VIISRDDSKSSVYLQMNSLRAEDTAVYYC TRRWNNFWGQGTTVTVSS |
| V<sub>H</sub> Deimmunized (complimentary strand of SEQ ID NO: 53) J415-1 | Artificial - deimmunized heavy chain J415-1 | FIG. 8A | 55 | ggatcctataaatctctggccatgaagtctgggagctgaggatgtc tgtctgcatcagcccgggctcccaatgacccttctgactcccaag gtgtccctagtccttcatgacctgaaattcagatacacacatttcccc ccaacaaatgcagtaaaatctatttaagctgaatagaagagagag gttgtaaggactcacctgaggagactgtgacagtggtgccttggc cccagaaattattccatcgcctggtacagtaataaacggcagtgtct tcagctctcaaactgttcatttgcaggtagacactactcttggaatca tctcttgagatgatgaccctcccctttcacagactccgcataatgtgtt gcaaaattattagattgcgatctaataagagcaacccactcaagcc ccttctctggagtctggcggacccagttcatccagtaattactgaaa gtgaatccagaggcctttacaggagattttcatggaccctccaggttg caccaagcctcctccagactcctcaagtttcacttcggagtggaca cctgtggagagaaaggcaaagtggatgtcattgtcacccatatata tgtccagacctcaagcctgctactgtgagccccttacctgtagctgt tgctaccaagaagaggatgatacagctccatcccatggtgaggtc ctgtgtgctcagtaactgtagagagaactgtgatctcatgttttctgt ttgtggtatagacaaacctatatttaccatgtagattcagaggatttg catattcataagctt |
| V<sub>L</sub> Deimmunized J415-1 CDS (122-160) & CDS (249-581) | Artificial - deimmunized light chain J415-1 | FIG. 9A | 56 | aagcttatgaatatgcaaatcctctgaatctacatggtaaatataggt ttgtctataccacaaacagaaaaacatgagatcacagttctctctac agttactgagcacacaggacctcaccatgggatggagctgtatca tcctcttcttggtagcaacagctacaggtaaggggctcacagtagc aggcttgaggtctggacatatatatgggtgacaatgaatcccactttt gccttttctctccacaggtgtccactccaacattgtaatgacccaatc ccccaaatccatgtccgcctcagcaggagagaggatgaccttgac ctgcaaggccagtgagaattccggtacttatgtgtcctggtatcaac agaaaccaacagtctcctaagatgttgatatacggggcatccaa ccggttcactggggtcccagatcgcttctccggcagtggatctgga acagatttcattctgaccgccagcagtgtgcaggcagaagaccct gtagattattactgtggacagagttacacctttccgtacacgttcgga gggggaccaagctggaaatgaagcgtgagtagaatttaaacttt gcttcctcagttggatcc |
| V<sub>L</sub> Deimmunized (predicted a.a. of SEQ ID NO :56) J415-1 | Artificial - deimmunized light chain J415-1 | FIG. 9A | 57 | MGWSCIILFLVATGVHSNIVMTQSPKSMS ASAGERMTLTCKASENSGTYVSWYQQKP TQSPKMLIYGASNRFTGVPDRFSGSGSTD FILTASSVQAEDPVDYYCGQSYTFPYTFGG GTKLEMK |
| V<sub>L</sub> Deimmunized (complimentary strand of SEQ ID NO:56) J415-1 | Artificial - deimmunized light chain J415-1 | FIG. 9A | 58 | ggatccaactgaggaagcaaagtttaaattctactcacgcttcatttc cagcttggtccccccctccgaacgtgtacggaaaggtgtaactctgt ccacagtaataatctacaggtcttctgcctgcacactgctggcgg tcagaatgaaatctgttccagatccactgccggagaagcgatctgg gacccagtgaaccggttggatgccccgtatatcaacatcttagga gactgtgttggtttctgttgatacccaggacacataagtaccggaatt ctcactggccttgcaggtcaaggtcatcctctctcctgctgaggcg gacatggatttggggattgggtcattacaatgttggagtggacac ctgtggagagaaaggcaaagtggatgtcattgtcacccatatatat gtccagacctcaagcctgctactgtgagccccttacctgtagctgtt gctaccaagaagaggatgatacagctccatcccatggtgaggtcc tgtgtgctcagtaactgtagagagaactgtgatctcatgttttctgttt gtggtatagacaaacctatatttaccatgtagattcagaggatttgca tattcataagctt |
| V<sub>H</sub> Deimmunized J415-2 | Artificial - deimmunized heavy chain J415-2 | FIG. 6 | 59 | EVKLEESGGGLVQPGGSMKISCVASGFTFS NYWMNWVRQTPEKGLEWVALIRSQSNNF ATHYAESVKGRVIISRDDSKSSVYLQMNS LRAEDTAVYYCTRRWNNFWGQGYTTVTVS S |

TABLE 1-continued

Antibody variable chain sequences

| NAME | Organism | FIG. | SEQ ID NO: SEQUENCE |
|---|---|---|---|
| V$_H$ Deimmunized J415-3 | Artificial - deimmunized heavy chain J415-3 | FIG. 6 | 60 EVKLEESGGGLVQPGGSMKISCVASGFTFS NYWMNWVRQTPEKGLEWVAEIRSQSNNF ATHYAESVKGRVIISRDDSKSSVYLQMNS LRAEDTAVYYCTRRWNNFWGQGTTVTVS S |
| J415 V$_H$ (DI) majority sequence | Artificial - majority sequence | FIG. 6 | 61 EVKLEESGGGLVQPGGSMKISCVASGFTFS NYWMNWVRQTPEKGLEWVAEIRSQSNNF ATHYAESVKGRVIISRDDSKSSVYLQMNS LRAEDTAVYYCTRRWNNFWGQGTTVTVS S |
| V$_L$ Deimmunized J415-2 | Artificial - deimmunized light chain J415-2 | FIG. 7 | 62 NIVMTQSPKSMSASAGERMTLTCKASENV GTYVSWYQQKPTQSPKMLIYGASNRFTGV PDRFSGSGSGTDFILTASSVQAEDPVDYYC GQSYTFPYTFGGGTKLEMK |
| V$_L$ Deimmunized J415-3 | Artificial - deimmunized light chain J415-3 | FIG. 7 | 63 NIVMTQSPKSMSASAGERMTLTCKASENV GTYVSWYQQKPTQSPKMLIYGASNRFTGV PDRFSGSGSGTDFILTASSVQAEDLVDYYC GQSYTFPYTFGGGTKLEMK |
| V$_L$ Deimmunized J415-4 | Artificial - deimmunized light chain J415-4 | FIG. 7 | 64 NIVMTQSPKSMSASAGERMTLTCKASENV GTYVSWYQQKPTQSPKMLIYGASNRFTGV PDRFSGSGSGTDFILTISSVQAEDLVDYYC GQSYTFPYTFGGGTKLEMK |
| V$_L$ Deimmunized J415-6 | Artificial - deimmunized light chain J415-6 | FIG. 7 | 65 NIVMTQFPKSMSASAGERMTLTCKASENV GTYVSWYQQKPEQSPKMLIYGASNRFTGV PDRFSGSGSGTDFILTISSVQAEDLVDYYC GQSYTFPYTFGGGTKLEMK |
| V$_L$ Deimmunized J415-7 | Artificial - deimmunized light chain J415-7 | FIG. 7 | 66 NIVMTQFPKSMSASAGERVTLTCKASENV GTYVSWYQQKPTQSPKMLIYGASNRFTGV PDRFSGSGSGTDFILTISSVQAEDLVDYYC GQSYTFPYTFGGGTKLEMK |
| V$_L$ Deimmunized J415-8 | Artificial - deimmunized light chain J415-8 | FIG. 7 | 67 NIVMTQFPKSMSASAGERMTLTCKASENS GTYVSWYQQKPEQSPKMLIYGASNRFTGV PDRFSGSGSGTDFILTISSVQAEDLVDYYC GQSYTFPYTFGGGTKLEMK |
| J415 V$_L$ (DI) majority sequence | Artificial - majority sequence | FIG. 7 | 68 NIVMTQFPKSMSASAGERMTLTCKASENV GTYVSWYQQKPTQSPKMLIYGASNRFTGV PDRFSGSGSGTDFILTISSVQAEDLVDYYC GQSYTFPYTFGGGTKLEMK |
| MuV$_H$IIIC | Mus musculus | FIG. 8C | 69 EVKLEESGGGLVQPGGSMKLSCVASGFTF SNYWMNWVRQSPEKGLEWVAEIRLKSDN YATHYAESVKGRFTISRDDSKSSVYLQMN NLRAEDTGIYYCTTGGYGGRRSWFAYWG QGTLVTVSS |
| J415V$_H$/MuV$_H$IIIC majority sequence | Artificial - majority sequence | FIG. 8C | 70 EVKLEESGGGLVQPGGSMKLSCVASGFTF SNYWMNWVRQSPEKGLEWVAEIRLQSDN FATHYAESVKGRVIISRDDSKSSVYLQMN NLRAEDTGIYYCTTGGYGGRRSWNAFWG QGTLVTVSS |
| MuV$_L$1 | Mus musculus | FIG. 9C | 71 DIVMTQSPSSLAVSAGEKVTMSCKSSQSLL NSGNQKNYLAWYQQKLPGQSPKLLIYWAS TRESGVPDRFTGSGSGTDFTLTISSVQAED LAVYYCQNDYSYPLTFGAGTKLELK |
| J415V$_L$/MuV$_L$1 majority sequence | Artificial - majority sequence | FIG. 9C | 72 DIVMTQSPSSLAVSAGEKVTLSCKASESLL NVGNQKTYVAWYQQKPGQSPKLLIYGAS TRESGVPDRFTGSGSGTDFILTISSVQAEDL AVYYCGNSYSFPLTFGGGTKLELK |
| J533 V$_H$ CDS (1-354) | Mus musculus | FIG. 10A | 73 gaggtccagctgcagcagtctggacctgagctggttaagcctggg gcttcagtgaagatgtcctgcaaggcttctggatacacattcactgg ctatgttatgcactgggtgaagcagaagcctggacaggtccttgag tggattggatatattaatccttacaatgatgttactaggtataatggga agttcaaaggcaaggccacactgacctcagacaaatattccagca cagcctacatggagctcagcggcctgacctctgaggactctgcg tctattactgtgcaagaggggagaactggtactactttgactcctgg ggccgaggcgccactctcacagtctcctca |
| J533 V$_H$ (predicted amino acid of SEQ ID NO: 73) | Mus musculus | FIG. 10A | 74 EVQLQQSGPELVKPGASVKMSCKASGYTF TGYVMHWVKQKPGQVLEWIGYINPYNDV TRYNGKFKGKATLTSDKYSSTAYMELSGL TSEDSAVYYCARGENWYYFDSWGRGATL TVSS |

TABLE 1-continued

Antibody variable chain sequences

| NAME | Organism | FIG. | SEQ ID NO: SEQUENCE |
|---|---|---|---|
| J533 V<sub>H</sub> (complementary strand of SEQ ID NO: 73) | Mus musculus | FIG. 10A | 75 tgaggagactgtgagagtggcgcctcggccccaggagtcaaagt agtaccagttctcccctcttgcacagtaatagaccgcagagtcctc agaggtcaggccgctgagctccatgtaggctgtgctggaatatttg tctgaggtcagtgtggccttgcctttgaacttcccattatacctagta acatcattgtaaggattaatatatccaatccactcaaggacctgtcc aggcttctgcttcacccagtgcataacatagccagtgaatgtgtatc cagaagccttgcaggacatcttcactgaagccccaggcttaacca gctcaggtccagactgctgcagctggacctc |
| J533 V<sub>L</sub> CDS (1–333) | Mus musculus | FIG. 11A | 76 gacattgtgctgacccaatctccagcttctttggctgtgtctctagga cagagggccaccatatcctgcagagccagtgaaagtattgatagtt atgacaatacttttatgcactggtaccagcagaaaccaggacagcc acccaacctcctcatctttcgtgcatccatcctagaatctgggatcc ctgccaggttcagtggcagtgggtctgggacagacttcaccctca ccatttatcctgtggaggctgatgatgttgcaacctattactgtcacc aaagtattgaggatccgtacacgttcggaggggggaccaagctg gaaataaaa |
| J533 V<sub>L</sub> (predicted amino acid of SEQ ID NO:76) | Mus musculus | FIG. 11A | 77 DIVLTQSPASLAVSLGQRATISCRASESIDS YDNTFMHWYQQKPGQPPNLLIFRASILES GIPARFSGSGSGTDFTLTIYPVEADDVATY YCHQSIEDPYTFGGGTKLEIK |
| J533 V<sub>L</sub> (complementary strand of SEQ ID NO:76) | Mus musculus | FIG. 11A | 78 ttttatttccagcttggtccccctccgaacgtgtacggatcctcaat actttggtgacagtaataggttgcaacatcatcagcctccacaggat aaatggtgagggtgaagtctgtcccagacccactgccactgaacc tggcagggatcccagattctaggatggatgcacgaaagatgagg aggttgggtggctgtcctggtttctgctggtaccagtgcataaaagt attgtcataactatcaatactttcactggctctgcaggatatggtggc cctctgtcctagagacacagccaaagaagctggagattgggtcag cacaatgtc |
| MuV<sub>H</sub>II | Mus musculus | FIG. 10B | 79 EVQLQQSGPELVKPGASVKISCKASGYTFT DYYMNNWVKQSPGKSLEWIGDINPGNGG TSYNQKFKGKATLTVDKSSSTAYMQLSSL TSEDSAVYYCARGYYSSSYMAYYAFDYW GQGTTVTVSS |
| J533V<sub>H</sub>/MuV<sub>H</sub>II majority sequence | Artificial - majority sequence | FIG. 10B | 80 EVQLQQSGPELVKPGASVKISCKASGYTFT GYVMNNWVKQSPGQVLEWIGDINPGNGG TSYNGKFKGKATLTVDKSSSTAYMELSGL TSEDSAVYYCARGENSSSYMAYYAFDSW GQGATVTVSS |
| MUV<sub>L</sub>-3 | Mus musculus | FIG. 11B | 81 DIVLTQSPASLAVSLGQRATISCRASESVDS YGNSFMHWYQQKPGQPPKLLIYAASNLES GVPARFSGSGSGTDFTLNIHPVEEDDAATY YCQQSNEDPPWTFGGGTKLEIK |
| J533V<sub>L</sub>/ MuV<sub>L</sub>-3 majority sequence | Artificial - majority sequence | FIG. 11B | 82 DIVLTQSPASLAVSLGQRATISCRASESVDS YGNSFMHWYQQKPGQPPNLLIFAASILES GVPARFSGSGSGTDFTLTIHPVEADDAATY YCQQSIEDPPYTFGGGTKLEIK |
| E99 V<sub>H</sub> CDS (1–363) | Mus musculus | FIG. 12A | 83 caggtgcagctaaaggagtcaggacctggcctggtggcgtcctc acagagcctgtccatcacatgcaccgtctcaggattctcattaacc gcctatggtattaactgggttcgccagcctccaggaaagggtctgg agtggctgggagtgatatggcctgatggaaacacagactataattc aactctcaaatccagactgaacatcttcaaggacaactccaagaac caagtttttcttaaaaatgagcagtttccaaactgatgacacagccag atacttctgtgccagagattcgtatggtaacttcaagagggggttggtt tgacttctggggccaggcaccactctcacagtctcctca |
| E99 V<sub>H</sub> (predicted amino acid of SEQ ID NO:83) | Mus musculus | FIG. 12A | 84 QVQLKESGPGLVASSQSLSITCTVSGFSLT AYGINWVRQPPGKGLEWLGVIWPDGNTD YNSTLKSRLNIFKDNSKNQVFLKMSSFQT DDTARYFCARDSYGNFKRGWFDFWGQGT TLTVSS |
| E99 V<sub>H</sub> (complementary strand of SEQ ID NO: 83) | Mus musculus | FIG. 12A | 85 tgaggagactgtgagagtggtgcctggccccagaagtcaaacc aaccctcttgaagttaccatacgaatctctggcacagaagtatctg gctgtgtcatcagtttggaaactgctcattttttaagaaaacttggttctt ggagttgtccttgaagatgttcagtctggatttgagagttgaattata gtctgtgtttccatcaggccatatcactcccagccactccagaccct ttcctggaggctggcgaacccagttaataccataggcggttaatga gaatcctgagacggtgcatgtgatggacaggctctgtgaggacgc caccaggccaggtcctgactcctttagctgcacctg |

TABLE 1-continued

Antibody variable chain sequences

| NAME | Organism | FIG. | SEQ ID NO: SEQUENCE |
|---|---|---|---|
| E99 V$_L$ CDS (1-321) | Mus musculus | FIG. 13A | 86 aacattgtgatgacccagtctcaaaaattcatgtccacatcaccagg agacagggtcagggtcacctgcaaggccagtcagaatgtgggtt ctgatgtagcctggtatcaagcgaaaccaggacaatctcctagaat actgatttactcgacatcctaccgttacagtggggtccctgatcgctt cacagcctatggatctgggacagatttcactctcaccattaccaatg tgcagtctgaagacttgacagagtatttctgtcagcaatataatagct atcctctcacgttcggtgctgggaccaagctggagctgaaa |
| E99 V$_L$ (predicted amino acid of SEQ ID NO:86) | Mus musculus | FIG. 13A | 87 NIVMTQSQKFMSTSPGDRVRVTCKASQNV GSDVAWYQAKPGQSPRILIYSTSYRYSGVP DRFTAYGSGTDFTLTITNVQSEDLTEYFCQ QYNSYPLTFGAGTKLELK |
| E99 V$_L$ (complementary strand of SEQ ID NO:86) | Mus musculus | FIG. 13A | 88 tttcagctccagcttggtcccagcaccgaacgtgagaggatagcta ttatattgctgacagaaatactctgtcaagtcttcagactgcacattg gtaatggtgagagtgaaatctgtcccagatccataggctgtgaagc gatcagggaccccactgtaacggtaggatgtcgagtaaatcagta ttctaggagattgtcctggtttcgcttgataccaggctacatcagaac ccacattctgactggccttgcaggtgaccctgaccctgtctcctggt gatgtggacatgaattttgagactgggtcatcacaatgtt |
| MuV$_H$IB | Mus musculus | FIG. 12B | 89 QVQLKESGPGLVASSQSLSITCTVSGFSLT AYGINWVRQPPGKGLEWLGVIWPDGNTD YNSTLKSRLIFKDNSKNQVFLKMSSFQT DDTARYFCARDSYGNFKRGWFDFWGQGT TLTVSS |
| E99V$_H$/MuV$_H$ IB majority sequence | Artificial - majority sequence | FIG. 12B | 90 QVQLKESGPGLVASSQSLSITCTVSGFSLT AYGINWVRQPPGKGLEWLGVIWPDGNTD YNSTLKSRLNIFKDNSKNQVFLKMSSFQT DDTARYFCARDSYGNFKRGWFDFWGQGT TLTVSS |
| MuV$_L$-1 | Mus musculus | FIG. 13B | 91 DIVMTQSPSSLAVSAGEKVTMSCKSSQSLL NSGNQKNYLAWYQQKPGQSPKLLIYWAS TRESGVPDRFTGSGSGTDFTLTISSVQAED LAVYYCQNDYSYPLTFGAGTKLELK |
| E99V$_L$/MuV$_L$ -1 majority sequence | Artificial - majority sequence | FIG. 13B | 92 DIVMTQSQSSLAVSAGDKVTVSCKASQSL LNVGSDKNYVAWYQAKPGQSPKLLIYSAS TRESGVPDRFTGSGSGTDFTLTISSVQAED LAVYFCQNDNSYPLTFGAGTKLELKRA |

Humanized or CDR-grafted antibody molecules or immunoglobulins can be produced by CDR-grafting or CDR substitution, wherein one, two, or all CDRs of an immunoglobulin chain can be replaced. See e.g., U.S. Pat. No. 5,225,539; Jones et al. 1986 Nature 321:552–525; Verhoeyan et al. 1988 Science 239:1534; Beidler et al. 1988 J. Immunol. 141:4053–4060; Winter U.S. Pat. No. 5,225,539, the contents of all of which are hereby expressly incorporated by reference.

Winter describes a CDR-grafting method that may be used to prepare the humanized antibodies of the present invention (UK Patent Application GB 2188638A, filed on Mar. 26, 1987; Winter U.S. Pat. No. 5,225,539), the contents of which are expressly incorporated by reference. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, Science 229:1202–1207, by Oi et al., 1986, BioTechniques 4:214, and by Queen et al. U.S. Pat. Nos. 5,585,089, US 5,693,761 and US 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

Also within the scope of the invention are humanized antibodies in which specific amino acids have been substituted, deleted or added. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the contents of which are hereby incorporated by reference. The acceptor framework can be a mature human antibody framework sequence or a consensus sequence. As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

Other techniques for humanizing immunoglobulin chains, including antibodies, are described in Padlan et al. EP 519596 A1, published on Dec. 23, 1992.

The anti-PSMA antibody, or antigen fragment thereof, may also be modified by specific deletion of human T cell epitopes or "deimmunization" by the methods disclosed in WO 98/52976 and WO 00/34317, the contents of which are specifically incorporated by reference herein. Briefly, the murine heavy and light chain variable regions of an anti-PSMA antibody can be analyzed for peptides which bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the murine $V_H$ and $V_L$ sequences, as described in WO 98/52976 and WO 00/34317. These motifs bind to any of the 18 major MHC class II DR allotypes, and thus, constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al. (1992) *J. Mol. Biol.* 227:776–798; Cook, G. P. et al. (1995) *Immunol. Today Vol.* 16 (5): 237–242; Chothia, D. et al. (1992) *J. Mol. Bio.* 227:799–817. The V BASE directory provides a comprehensive directory of human immunoglobulin variable region sequences (compiled by Tomlinson, I. A. et al. MRC Centre for Protein Engineering, Cambridge, UK). After the deimmunized $V_H$ and $V_L$ of an anti-PSMA antibody are constructed by mutagenesis of the murine $V_H$ and $V_L$ genes. The mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region.

The recombinant deimmunized antibody can be transfected into a suitable host cell for expression, for example, NSO or CHO cells, to produce complete recombinant antibodies.

In one embodiment, deimmunized $V_H$ and $V_L$ of murine J591 regions were constructed by mutagenesis of the murine $V_H$ and $V_L$ genes. The murine J591 variable region sequences are shown in FIGS. 2A–2B. Potential epitopes (identified using a peptide threading program) in murine J591 heavy chain and light chain variable regions are shown in FIGS. 3A and 3B, respectively. The 13-mer peptides predicted to bind to MHC class II are indicated by the underline, the CDRs are located at residues 26 to 35, 50 to 66, and 99 to 104 of FIG. 3A and residues 24 to 34, 50 to 56, and 89 to 97 of FIG. 3B, and residues altered in the deimmunized heavy and light chain variable regions are boxed. Where possible, amino acid substitutions are those commonly used in human germline heavy and light chain variable regions. In addition to the in silico analysis using the peptide threading software, a database of human MHC class II binding peptides was searched for motifs present in the murine J591 sequence.

The following 13-mers (labeled by first linear residue number of the 13-mer) of the murine J591 heavy chain variable region were predicted to bind to MHC Class II were 2, 10, 16, 30, 32, 35, 43, 46, 58, 62, 70, 81, 84, 91, and 100 (FIG. 3A). An explanation of the rationale behind changes made to the residues in the murine J591 heavy chain variable region is set forth below (note residues altered are identified under the Kabat numbering system):

5Q→V removes the potential epitope at residue 2;
11,12LV→VK remove the potential epitope at residue 10;
12V→K is also changed to remove a motif from the database of human MHC class II binding peptides;
16,17TS→AT, and 19R→K remove the potential epitope at residue 16;
the epitope at residue 30 spans CDR1 and is therefore unaltered;
40,41SH→AP removes potential epitopes at residues 32 and 35;
44S→G reduces binding score for epitope at 43, this 13 mer spans CDR2;
the epitopes at residues 46, 58 and 62 span CDR2, and are thus unaltered;
75,76SS→TD remove the potential epitope at residue 70;
82aR→S, 83T→R remove potential epitopes at residues 81 and 84;
87S→T this change made to remove a motif from the database of human MHC class II binding peptides;
the epitope at residue 91 spans CDR3 and is therefore unaltered; and
108T→L removes the potential epitope at residue 100.

The following 13-mers (labeled by first linear residue number of the 13-mer) of the murine J591 light chain variable region that were predicted to bind to MHC Class II molecules were 1, 8, 17, 27, 30, 31, 35, 45, 47, 56, 60, 71, 73, 81, 94 (FIG. 3B). An explanation of the rationale behind changes made to the residues in the murine J591 light chain variable region is set forth below (note residues altered are identified under the Kabat numbering system):
- 3V→Q removes potential epitope at residue 1;
- 8-11HKFM→PSSL removes potential epitope at residue 8(13);
- 20-22SII→TLT removes potential epitopes at residues 17 and 20;
- 21I→L is also changed to remove a motif from the database of human MHC class II binding peptides;
- the epitope at residue 27 spans CDR1 and is therefore unaltered;
- 42Q→P reduces the binding score for the epitope at residue 31;
- the epitopes at residues 44 and 47 span CDR2 and are thus unaltered;
- 58V→I is changed to remove a motif from the database of human MHC class II binding peptides;
- 60D→S, 62T→S removes the epitopes at residues 56 and 60;
- 76-78TNV→SSL, 80S→P, 83L→F removes the epitopes at residues 71, 73, 76, and 81;
- 87F→YI is changed to remove a motif from the database of human MHC class II binding peptides;
- 100 A→P and 103 M→K remove the epitope at residue 94; and
- 104 L→V and 106 L→I are changed to remove a motif from the database of human MHC class II binding peptides.

The amino acid and nucleotide sequences for the deimmunized J591 heavy and light chain variable regions are shown in FIGS. 3A–3B and 5A–5B, respectively (see also Table 1).

Human IgG1 or κ constant regions were added and the composite genes transfected into NSO cells to produce complete recombinant anti-PSMA antibodies. These antibodies bound to PSMA (on LNCap cells) as efficiently as the original murine antibody, and have reduced or no immunogenicity in man.

The design of deimmunized J415 was similar to the making of the deimmunized J591 antibody. The heavy and light chain sequences were cloned from the hybridoma designated HB-12109. These sequences were cloned, sequenced and expressed as a chimeric antibody for use as a control antibody. The murine V region sequences were subjected to peptide threading to identify potential T cell epitopes, through analysis of binding to 18 different human MHC class II allotypes. The results of the peptide threading analysis for the murine sequences are shown in Table 2.

TABLE 2

Potential T cell epitopes in murine J415 sequences

| Sequence | Number of potential T cell | Location of potential epitopes+ (no. of potential MHC binders from 18 groups tested) |
|---|---|---|
| Murine J415 $V_H$ | 12 | 10(17), 16(13), 21(9), 30(6), 35(16), 43(8), 46(6), 49(8), 64(6), 80(15), 86(15), 104(6) |
| Murine J415 $V_K$ | 13 | 5(5), 11(18), 13(11), 17(5), 27(8), 31(7), 56(15), 60(12), 70(5), 71(11), 73(17), 76(7), 81(17) |

+first amino acid of potential epitope, numbering E or N amino acid number1 to S or K amino acid number 107 and 116 for $V_H$ and $V_K$ respectively.

Primary deimmunized $V_H$ and $V_L$ sequences were defined (J415D1VH1, J415D1VK1). As generation of the primary deimmunized sequences requires a small number of amino acid substitutions that might affect the binding of the final deimmunized molecule, three other variant $V_H$S and seven other $V_L$S were designed (see FIGS. 6 and 7). The nucleotide sequences for the primary deimmunized $V_H$ and $V_L$ regions are shown in FIGS. 8A and 9A, respectively. Comparisons of the amino acid sequences of the murine and deimmunized V regions of J415 are shown in FIG. 6 for $V_H$ and FIG. 7 for $V_L$.

An explanation of the rational behind some of the changes made to the residues in the murine J415 heavy chain variable region is set forth below (note residues altered are identified according to the linear numbering shown in FIG. 6):
- 20L→I removes the potential epitope at residues 10 and 16;
- 87N→S removes the potential epitopes at residues 80 and 86;
- 94,95GI→AV remove the potential epitope at residue 86; and
- 112L→V removes the potential epitope at residue 104.

Changes to Residues of Murine J415

An explanation of the rational behind some of the changes made to the residues in the murine J415 light chain variable region is set forth below (note residues altered are identified according to the linear numbering shown in FIG. 7):
- 13I A removes the potential epitopes at residues 5, 11 and 13;
- 15V A removes the potential epitopes at residues 5, 11, and 13;
- 19V-M removes the potential epitopes at residues 11, 13, and 17;
- 41E-T removes the potential epitope at residue 31;
- 63T-S removes the potential epitopes at residues 56 and 60;
- 68A-G removes the potential epitopes at residues 56 and 60; and
- 80T-A removes the potential epitopes at residues 70, 71, 73, and 76;

The deimmunized variable regions for J415 were constructed by the method of overlapping PCR recombination. The cloned murine $V_H$ and $V_K$ genes were used as templates for mutagenesis of the framework regions to the required deimmunized sequences. Sets of mutagenic primer pairs were synthesized encompassing the regions to be altered. The vectors VH-PCR1 and VK-PCR1 (Riechmann et al. (1988) *Nature* 332:323–7) were used as templates to introduce 5' flanking sequence including the leader signal peptide, leader intron and the murine immunoglobulin promoter, and 3' flanking sequence including the splice site, and intron sequences. The deimmunized V regions produced were cloned into pUC19 and the entire DNA sequence was confirmed to be correct for each deimmunized $V_H$ and $V_L$.

The deimmunized heavy and light chain V-region genes were excised from pUC19 as HindIII to BamHI fragments, which include the murine heavy chain immunoglobulin promoter, the leader signal peptide, leader intron, the $V_H$ or $V_L$ sequence and the splice site. These were transferred to the expression vectors pSVgpt and pSVhyg, which include human IgG1 or κ constant regions respectively and markers for selection in mammalian cells. The DNA sequence was confirmed to be correct for the deimmunized $V_H$ and $V_L$ in the expression vectors.

For the transfection of expression vectors pSVgptJ415VHHuIgG1 and pSVhygJ415VKHuCK into NSO (a non-immunoglobulin producing mouse myeloma, obtained from the European Collection of Animal Cell Cultures, Porton UK (ECACC No. 85110505)) cells, 3 and 6 μg of plasmid DNA respectively was prepared and then linearized with PvuI to improve transfection efficiency. The ethanol precipitated DNA was then mixed with a semi-confluent flask of NSO cells that had been harvested by centrifugation and resuspended in 0.5 ml of non-selective Dulbecco's Modified Eagle's Medium (DMEM)(Life Technologies Inc.) in a 0.4 cm gene pulser cuvette. The cells and DNA were chilled on ice for 5 minutes before a pulse of 17OV, 960 μF was applied. The cuvette was returned to ice for a further 20 minutes before being transferred to a 75 cm² flask containing 20 mls non-selective DMEM to recover for 24 hours. The cells were then harvested and resuspended in selective DMEM and plated over 4×96 well plates, 200 μl/well.

To culture NSO cell lines, selection and expansion the cells are grown at 37° C., 5% $CO_2$ and 10% FBS. To prepare non-selective medium for routine culture of NSO cells, the culture medium is Dulbecco's Modification of Eagle's Medium (DMEM)(Life Technologies, Catalogue No: 31965–023) supplemented with 10% fetal bovine serum of USA origin (Life Technologies, Fetal Bovine Serum Cat No: 16000), Antibiotic/Antimycotic solution (Life Technologies, Cat No: 15240), Gentamycin (Life Technologies, catalogue No: 15710), Sodium pyruvate (Life Technologies, Catalogue No: 11360–039). When growing NSO cells up to saturation for antibody production do not add the xanthine and mycophenolic acid and the FBS is reduced to 5%.

To prepare selective medium for culture of NSO transfectomas, the culture medium is Dulbecco's Modification of Eagle's Medium (DMEM)(Life Technologies, Catalogue No: 31965–023) supplemented with 10% fetal bovine serum of USA origin (Life Technologies, Fetal Bovine Serum Cat No: 16000), Antibiotic/Antimycotic solution (Life Technologies, Cat No: 15240), Gentamycin (Life Technologies, catalogue No: 15710), Sodium pyruvate (Life Technologies, Catalogue No: 11360–039), 250 μg/ml xanthine (Sigma Catalogue No: X-3627, stock made up at 25 mg/ml in 0.5M NaOH), and 0.8 μg/ml mycophenolic acid (Sigma Catalogue No: M-3536, stock made up at 2.5 mg/ml in 100% ethanol).

After approximately 10 days the cell colonies expressing the gpt gene were visible to the naked eye. The plates were then screened for antibody production using the following protocol for human IgG1/κ Screening ELISA. 6 single colonies were picked from wells with high ODs greater than 0.7 into a 24 well cell culture plate. Within 5–6 days the cells were expanded into a 25 cm² flask. The antibody productivity of the selected clones was assayed using the following protocol for human IgG1/κ ELISA from saturated cultures in the 24 well and 25 cm² flasks.

The details of the protocol are as follows. ELISA plates (Dynatech Immulon 2) are coated with 100 μL per well with sheep α human κ antibody (The Binding Site Cat No: AU015) diluted 1:1000 in carbonate/bicarbonate coating buffer pH 9.6 (Sigma Cat: C-3041). The coated plate is incubated at 4° C. overnight or 1 hr at 37° C. The plate is then washed 3 times with PBST (PBS with 0.05% Tween 20). The samples are added, 100 μL per well from 24 well plates, 25 μL+75 μL PBST for 96 well plates. Blank wells are treated with PBST only. The reaction mixture is incubated at room temperature for 1 hr. Then, the plate is wash 3 times with PBST (PBS with 0.05%Tween 20). The secondary antibody, peroxidase conjugated sheep α human IgG γ chain specific is added (The Binding Site Cat No: APO04) at a ratio of 1:1000 in PBST, 100 μL per well. The mixture is incubated at room temperature for 1 hour. The mixture is then washed 3 times with PBST (PBS with 0.05% Tween 20).

To make up the substrate, one tablet (20 mg) of OPD (o-PHENYLENE DIAMINE) (Sigma Cat No: P-7288) is dissolved in 45 ml of $H_2O$ plus 5 ml 10×peroxidase buffer (make 10×peroxidase buffer with Sigma phosphate citrate buffer tablets pH 5.0, P-4809), add 10 μL 30%(w/w) hydrogen peroxide (Sigma Cat No: H 1109) just before use. The substrate is then added at 100 μL per well and incubate RT for 5 min or as required. When the color develops, the reaction can be stopped by adding 25 μL 12.5% $H_2SO_4$. The results are read at 492 nm.

Expression and expansion of J415 Deimmunized Antibodies

The clones with the highest productivity were expanded into a 75 cm² flask and then into 2×175 cm² flasks. The cells from one of the 175 Cm² flask was used to inoculate 4×triple layer flasks (500 cm², Nalge Nunc International) containing non selective DMEM containing 5% FBS, cells from the other were frozen as detailed in the protocol for freezing NSO cells detailed below.

To cryoprotect mammalian cells and resurrect cells from liquid nitrogen, the following materials are needed: Fetal Bovine serum (Life Technologies Cat No: 16000), DMSO (Sigma, Cat No: D4540), 2 ml cryotubes (Nunc or Greiner), and polystyrene box with walls 1–2 cm thick. Briefly, actively growing cells are harvested by centrifugation (1000 rpm, 5 min) and resuspended at about $10^7$ cells/ml in 10% DMSO/90% FBS. As a rough guide, cells grown to a semi-confluency should be resuspended in 1 ml for a 75 cm² flask or 2.5 ml for a 175 cm² flask. A required number of tubes are cooled and labeled in ice. 1 ml portions are aliquoted to labeled cryotubes. The cryotubes are placed in polystyrene box at −70° C. for at least 4 h, or overnight. The vials are transferred to canes and place in liquid nitrogen. A record of the storage should be made both in the canister index and the central cell line indexing system.

To thaw the cells from liquid nitrogen, the vial is removed from liquid nitrogen and contents are thawed quickly by incubation at 37° C., while swirling in a waterbath. The outside of the vial is cleaned with 70% methylated spirits. The suspension is transferred to a universal container. 10 ml of the medium to be used to propagate the cell line is added dropwise, swirling to mix. The cells are harvested by centrifugation (1000 rpm, 5 min). The supernatant is discarded. The cells are resuspended in 20 ml growth medium and transferred to a 75 cm² flask. If low viability is suspected, extra serum can be added to the growth medium to 20%, use only 5 ml, and transfer to a 25 cm² flask.

After 10–14 days the 500 ml to 1 liter static saturated cultures were harvested. Antibody was purified, by ProSepA (Millipore Ltd.) affinity chromatography using the following protocol for antibody purification. The purified antibody preparation was sterilized by filtration and stored at 4° C.

The antibody purification protocol is as follows: NSO transfectoma cell line producing antibody is grown in DMEM 5% FCS in Nunc Triple layer flasks, 250 ml per flask (total volume 1 L) for 10–14 days until nearing saturation. Conditioned medium collected and spun at 3000 rpm for 5 min in bench centrifuge 5 minutes to remove cells. $\frac{1}{10}^{th}$ volume 1M Tris-HCl pH 8 (Sigma Cat: T3038) is then added to cell supernatant to make this 0.1 M Tris-HCl pH 8. 0.5 to 1 ml Prosep A (Millipore Cat: 113 111824) is added and stirred overnight at room temperature. Prosep A collected by spinning at 3000 rpm for 5 minutes then packed into a Biorad Poly-Prep column (Cat: 73 1–1550). The column is washed with 10 ml PBS, then eluted in 1 ml fractions with 0.1M Glycine pH 3.0. Each fraction is collected into a tube containing 100 microL 1M Tris-HCl pH 8 (Sigma, as above). Absorbance of each fraction is measured at 280 nm. Fractions containing the antibody are pooled and dialyzed against PBS overnight at room temperature. The preparation is sterilized by filtration through a 0.2 micron syringe filter and the absorbance of each fraction is measured at 280 nm. The antibody concentration is determined by ELISA for human IgG.

The purified antibody can be quantified using the protocol for Human IgG1/κ ELISA described above.

Testing of J415 Deimmunized Antibodies

The J415 deimmunized antibodies were tested in an ELISA for binding to LNCap membrane preparation following the protocol as detailed above. ELISA plates were coated with LNCap membrane preparation and blocked with 5% BSA in phosphate buffered saline. Doubling dilutions of the J415 chimeric antibody (murine variable heavy and light chain regions fused to human constant heavy and light chain regions, respectivley) and the deimmunized antibodies were applied. Detection was with horseradish peroxidase conjugated goat anti-human IgG and donkey anti-mouse for chimeric and mouse antibodies respectively. Color was developed with o-phenylene diamine substrate.

The antibody composed of deimmunized J415 heavy chain version 4 (also referred to as "J415DIVH4") combined with deimmunized J415 light chain version 5 (also referred to as "J415DIVK5") shows equivalent binding to LNCap cells as compared to the chimeric antibody. Also, when DIVK5 is combined with heavy chain versions 1 and 2 (also referred to as "J415DIVH1" and "J415DIVH2", respectively), binding to LNCap cells is equivalent to that of the chimeric antibody when tissue culture supernatant is analyzed. These data can be confirmed with purified antibody. When light chains 1, 2, 3 were combined with any of the J415 heavy chain versions 1, 2, 3, and 4 no antibody was produced. Deimmunized J415 light chain versions 1, 2, and 3 ("J415DIVK1", "J415DIVK2", and "J415DIVK3", respectively) may be defective on structural grounds. The best chain combination for higher affinity and decreased immunogenicity is DIVH4/DIVK5.

The antibody composed of deimmunized heavy chain version 4 combined with deimmunized light chain version 5 showed equivalent binding to LNCap compared to the chimeric antibody. Also, when DIVK5 is combined with heavy chain versions 1 and 2, binding to LNCap cells is two-fold less than that of the chimeric when purified antibody is analyzed.

In some embodiments, the anti-PSMA antibody, e.g., the modified anti-PSMA antibody or antigen-binding fragment thereof, includes at least one light or heavy chain immunoglobulin (or preferably, at least one light chain immunoglobulin and at least one heavy chain immunoglobulin). Preferably, each immunoglobulin includes a light or a heavy chain variable region having at least one, two and, preferably, three CDRs substantially identical to a CDR from a non-human anti-PSMA light or heavy chain variable region, respectively. For example, the antibody or antigen-binding fragment thereof can have at least one, two and preferably three CDRs from: the heavy chain variable region of murine J591 (see SEQ ID NO:1, 2, and 3, depicted in FIG. 2A); the light chain variable region of murine J591 (see SEQ ID NO:4, 5, and 6, depicted in FIG. 2B); the heavy chain variable region of murine J415 (see SEQ ID NO:29, 30, and 31, depicted in FIG. 6); the light chain variable region of murine J415 (see SEQ ID NO:32, 33, and 34, depicted in FIG. 7); the heavy chain variable region of murine J533 (see SEQ ID NO:93, 94, and 95, depicted in FIG. 10A); the light chain variable region of murine J533 (see SEQ ID NO:96, 97, and 98, depicted in FIG. 11A); the heavy chain variable region of murine E99 (see SEQ ID NO:99, 100, and 101, depicted in FIG. 12A); or the light chain variable region of murine E99 (see SEQ ID NO:102, 103, and 104, depicted in FIG. 13A). In other embodiments, the modified antibody or antigen-binding fragment thereof can have at least one, two, and preferably three CDRs from the light or heavy chain variable region of the antibody produced by the cell line having ATCC Accession Number HB-12126 or the deimmunized J591 antibody produced by the cell line having ATCC Accession Number PTA-3709. In other embodiments, the modified antibody or antigen-binding fragment thereof can have at least one, two and preferably three CDRs from the light or heavy chain variable region of the antibody produced by the cell line having ATCC Accession Number HB-12109 or the deimmunized J415 antibody produced by a cell line having ATCC Accession Number PTA-4174. In still other embodiments, the modified antibody or antigen-binding fragment thereof can have at least one, two and preferably three CDRs from the light or heavy chain variable region of the antibody produced by the cell line having ATCC Accession Number HB-12127 or the antibody produced by a cell line having ATCC Accession Number HB-12101.

In one preferred embodiment, the modified antibody or antigen-binding fragment thereof includes all six CDRs from the same non-human anti-PSMA antibody, e.g., the murine J591, J415, J533 or E99 antibody. In some embodiments, the CDRs have the amino acid sequences of SEQ ID NO:1, 2, 3, 4, 5 and 6 (corresponding to murine J591 heavy and light chain CDRs), the amino acid sequences of the CDRs of the antibody produced by the cell line having ATCC Accession number HB-12126 or the deimmunized J591 antibody produced by the cell line having ATCC Accession Number PTA-3709, or sequences substantially identical thereto. In other embodiments, the CDRs have the amino acid sequences of SEQ ID NO:29, 30, 31, 32, 33, and 34 (corresponding to murine J415 heavy and light chain CDRs), the amino acid sequences of the CDRs of the antibody produced by the cell line having ATCC Accession Number HB-12109 or the deimmunized J415 antibody produced by the cell line having ATCC Accession Number PTA-4174, or sequences substantially identical thereto. In other embodiments, the CDRs have the amino acid sequences of SEQ ID NO:93, 94, 95, 96, 97, and 98 (corresponding to murine J533 heavy and light chain CDRs), the amino acid sequences of the CDRs of the antibody produced by the cell line having ATCC Accession Number HB-12127, or sequences substantially identical thereto. In still other embodiments, the CDRs have the amino acid sequences of SEQ ID NO:99, 100, 101, 102, 103, and 104 (corresponding to murine E99 heavy and light chain CDRs), the amino acid sequences of the CDRs of the antibody produced by the cell line having ATCC Accession Number HB-12101, or sequences substantially identical thereto.

The amino acid sequence of the CDRs for antibodies J591, J415, J533 and E99 are provided below in Table 3.

TABLE 3

CDR Sequences

Figure 11A:
FIG. 11A depicts the nucleic acid coding sequence, the amino acid sequence, and the nucleic acid reverse complement sequence of the murine J533 light chain variable region (SEQ ID NO:76–78, respectively). The relative locations of the CDRs and some restriction sites are indicated.
Figure 11B:
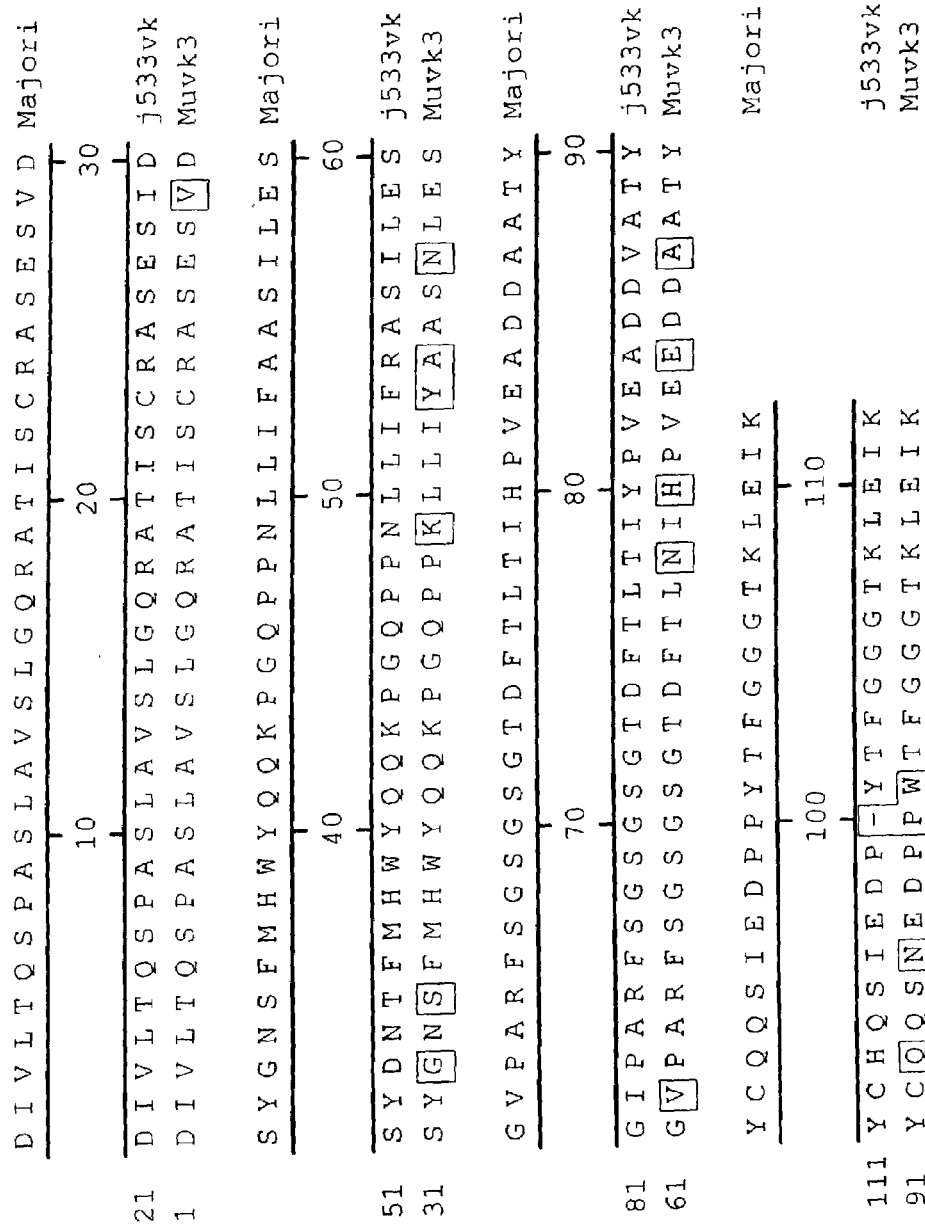
FIG. 11B depicts an alignment of the amino acid sequence of the murine J533 light chain variable region (SEQ ID NO:77) and a consensus sequence for Kabat subgroup murine MuVKIII, SEQ ID NO:81). A consensus majority sequence based upon the alignment is also shown (SEQ ID NO:82).

| NAME | Organism | FIG. | SEQ ID NO: | SEQUENCE |
|------|----------|------|------------|----------|
| V_H CDR1 J591 | Mus musculus | FIG. 2A | 1 | GYTFTEYTIH |
| V_H CDR2 J591 | Mus musculus | FIG. 2A | 2 | NINPNNGGTTYNQKFED |
| V_H CDR3 J591 | Mus musculus | FIG. 2A | 3 | GWNFDY |
| V_L CDR1 J591 | Mus musculus | FIG. 2B | 4 | KASQDVGTAVD |
| V_L CDR2 J591 | Mus musculus | FIG. 2B | 5 | WASTRHT |
| V_L CDR3 J591 | Mus musculus | FIG. 2B | 6 | QQYNSYPLT |
| V_H CDR1 J415 | Mus musculus | FIG. 6 | 29 | GFTFSNYWMN |
| V_H CDR2 J415 | Mus musculus | FIG. 6 | 30 | EIRSQSNNFATHYAESVKG |
| V_H CDR3 J415 | Mus musculus | FIG. 6 | 31 | RWNNF |
| V_L CDR1 J415 | Mus musculus | FIG. 7 | 32 | KASENVGTYVS |
| V_L CDR2 J415 | Mus musculus | FIG. 7 | 33 | GASNRFT |
| V_L CDR3 J415 | Mus musculus | FIG. 7 | 34 | GQSYTFPYT |
| V_H CDR1 J533 | Mus musculus | FIG. 10A | 93 | GYTFTGYVMH |
| V_H CDR2 J533 | Mus musculus | FIG. 10A | 94 | YINFPYNDVTRYNGKFKG |
| V_H CDR3 J533 | Mus musculus | FIG. 10A | 95 | GENWYYFDS |
| V_L CDR1 J533 | Mus musculus | FIG. 11A | 96 | RASESIDSYDNTFMH |
| V_L CDR2 J533 | Mus musculus | FIG. 11A | 97 | RASILES |
| V_L CDR3 J533 | Mus musculus | FIG. 11A | 98 | HQSIEDPYT |
| V_H CDR1 E99 | Mus musculus | FIG. 12A | 99 | GFSLTAYGIN |
| V_H CDR2 E99 | Mus musculus | FIG. 12A | 100 | VIWPDGNTDYNSTLKS |
| V_H CDR3 E99 | Mus musculus | FIG. 12A | 101 | DSYGNFKRGWFDF |
| V_L CDR1 E99 | Mus musculus | FIG. 13A | 102 | KASQNVGSDVA |
| V_L CDR2 E99 | Mus musculus | FIG. 13A | 103 | STSYRYS |
| V_L CDR3 E99 | Mus musculus | FIG. 13A | 104 | QQYNSYPLT |

The light or heavy chain immunoglobulin of the modified anti-PSMA antibody or antigen-binding fragment thereof can further include a light chain or a heavy chain variable framework sequence from a light chain or heavy chain variable framework present in a human or a non-human, e.g., rodent, antibody (e.g., the murine J591, J415, J533 or E99 antibody heavy chain or light chain variable framework). In some embodiments, the light chain or the heavy chain variable framework can be chosen from:

i a light or heavy chain variable framework including at least 5, 10, 20, 30, 40, 50, 60, 70, or 80 amino acid residues from a human light or heavy chain variable framework, e.g., a light or heavy chain variable framework residue from a mature human antibody, a human germline antibody sequence, or a human consensus antibody sequence;

ii a light or heavy chain variable framework including at least 5, but less than 30, amino acid residues from a human light chain or heavy chain variable framework, e.g., a light chain or heavy chain variable framework residue from a mature human antibody, a human germline antibody sequence, or a human consensus antibody sequence;

iii a light or heavy chain variable framework including at least 5, 10, 20, 30, 40, 50, 60, 75 or more amino acid residues from a light or heavy variable framework from a non-human antibody, e.g., a murine antibody (e.g., an anti-PSMA antibody having the framework amino acid sequence shown in SEQ ID NO:7 or 8 (from the heavy and light chain, respectively, of murine J591; see FIGS. 2A and 2B), SEQ ID NO:35 or 36 (from the heavy and light chain, respectively, of murine J415; see FIGS. 6 and 7), SEQ ID NO:109 or 114 (from the heavy and light chain, respectively, of murine J533; see FIGS. 10A and 11A), or SEQ ID NO:119 or 124 (from the heavy and light chain, respectively, of murine E99; see FIGS. 12A and 13A)), or the framework of a murine antibody described herein (e.g., a murine J591, J415, J533, or E99 antibody produced by a hybridoma cell line having an ATCC Accession Number HB-12126, HB-12109, HB-12127 or HB-12101);

iv a light or heavy chain variable framework, which has at least 60%, 65%, 70%, 72%, 75%, 80%, 85%, 90%, 95%, 96%, 97%, 98%, 99% or more identity with, or which has an amino acid sequence which differs by at least 1, 2, 5, or more residues, but less than 10, 20, 30 or 40 residues from, the sequence of the framework of a light or heavy chain variable region of a non-human antibody, e.g., a murine antibody (e.g., an anti-PSMA antibody having the framework amino acid sequence shown in SEQ ID NO:7 or 8 (from the heavy and light chain, respectively, of murine J591; see FIGS. 2A and 2B), SEQ ID NO:35 or 36 (from the heavy and light chain, respectively, of murine J415; see FIGS. 6 and 7), SEQ ID NO:109 or 114 (from the heavy and light chain, respectively, of murine J533; see FIGS. 10A and 11A), or SEQ ID NO:119 or 124 (from the heavy and light chain, respectively, of murine E99; see FIGS. 12A and 13A)), or the framework of a murine antibody described herein (e.g., a murine antibody produced by a hybridoma cell line having an ATCC Accession Number HB-12126, HB-12109, HB-12127 or HB-12101); or v a non-human, e.g., a murine, e.g., a J591 or J415, light or heavy chain variable region framework which has at least 5 amino acid replacements.

In some embodiments, the light chain variable region of the non-human anti-PSMA antibody or antigen-binding fragment thereof has at least one, two, three and preferably four amino acid sequences chosen from SEQ ID NO:13, 14, 15, and 16 (corresponding to deimmunized J591 light chain FR's 1–4; see FIG. 3B) or SEQ ID NO:41, 42, 43, and 44 (corresponding to deimmunized J415 light chain (J415DIVK5) FR's 1–4; see FIG. 7), or at least one, two, three and preferably four light chain framework regions from the antibody produced by the cell line having ATCC Accession Number PTA-3709 or PTA-4174. In other embodiments, the heavy chain variable region of the non-human anti-PSMA antibody or antigen binding portion thereof has at least one, two, three, and preferably four amino acid sequences chosen from SEQ ID NO:9, 10, 11, and 12 (corresponding to deimmunized J591 heavy chain FR's 1–4; see FIG. 3A) or SEQ ID NO:37, 38, 39, and 40

(corresponding to deimmunized J415 heavy chain (J415DIVH4) FR's 1–4; see FIG. 6), or at least one, two, three and preferably four heavy chain framework regions of the antibody produced by the cell line having ATCC Accession Number PTA-3709 or PTA-4174. In other embodiments, the heavy or light chain framework has an amino acid sequence which has at least 80%, 85%, 90%, 95%, 97%, 98%, 99% or more identity with SEQ ID NO:17 or SEQ ID NO:18, respectively (corresponding to deimmunized J591 framework sequence; see FIGS. 3A–3B), SEQ ID NO:45 or SEQ ID NO:46, respectively (corresponding to deimmunized J415 framework sequences J415DIVH4 and J415DIVK5; see FIG. 6 or 7), or with the heavy or light chain framework sequence of an antibody produced by the cell line having ATCC Accession Number PTA-3709 or PTA-4174. In still other embodiments, the heavy or light chain framework has an amino acid sequence which differs by at least 1, 2, 5, or more residues, but less than 10, 20, 30, or 40 residues, from the amino acid sequence of SEQ ID NO:17 or SEQ ID NO:18, respectively, SEQ ID NO:45 or SEQ ID NO:46, respectively, or the heavy or light chain framework sequence of the antibody produced by the cell line having ATCC Accession Number PTA-3709 or PTA-4174. Preferably, the heavy or light chain framework region includes the amino acid sequence shown in SEQ ID NO:17 or SEQ ID NO:18, respectively, SEQ ID NO:45 or SEQ ID NO:46, respectively, or the heavy or light chain framework sequence of the antibody produced by the cell line having ATCC Accession Number PTA-3709 or PTA-4174.

In other embodiments, the heavy or light chain variable region of the modified anti-PSMA antibody has an amino acid sequence which has at least 80%, 85%, 90%, 95%, 97%, 98%, 99% or more identity with SEQ ID NO:21 or SEQ ID NO:22, respectively (corresponding to the heavy and light chain variable regions of deimmunized J591; see FIGS. 3A–3B), SEQ ID NO:49 or SEQ ID NO:50, respectively (corresponding to the heavy and light chain variable regions of deimmunized J415, J415DIVH4 and J415DIVK5; see FIG. 6 or 7), or the heavy or light chain variable region sequence of the antibody produced by the cell line having ATCC Accession Number PTA-3709 or PTA-4174. In other embodiments, the heavy or light chain variable region of the modified anti-PSMA antibody has an amino acid sequence that differs by at least 1, 2, 5, or more residues, but less than 10, 20, 30, or 40 residues, from the amino acid sequence of SEQ ID NO:21 or SEQ ID NO:22, respectively, SEQ ID NO:49 or SEQ ID NO:50, respectively, or the heavy or light chain variable region sequence of the antibody produced by the cell line having ATCC Accession Number PTA-3709 or PTA-4174. Preferably, the light or heavy chain variable region includes the amino acid sequence shown in SEQ ID NO:21 or SEQ ID NO:22, respectively, SEQ ID NO:49 or SEQ ID NO:50, respectively, or the heavy or light chain variable region sequence of the antibody produced by the cell line having ATCC Accession Number PTA-3709 or PTA-4174.

Preferred modified anti-PSMA antibodies include at least one, preferably two, light chain variable regions and at least one, preferably two, heavy chain variable regions having the amino acid sequence shown in SEQ ID NO:21 and SEQ ID NO:22, respectively (corresponding to the heavy and light chain variable regions of deimmunized J591; see FIGS. 3A–3B), SEQ ID NO:49 and SEQ ID NO:50, respectively (corresponding to the heavy and light chain variable regions of deimmunized J415, J415DIVH4 and J415DIVK5; see FIGS. 6 and 7), or at least one, preferably two, modified light chain variable region sequences and at least one, preferably two, heavy chain variable region sequences of the antibody produced by the cell line having ATCC Accession Number PTA-3709 or PTA-4174.

In other embodiments, the light or heavy chain variable framework of the anti-PSMA antibody, or antigen-binding fragment thereof, includes at least one, two, three, four, five, six, seven, eight, nine, ten, fifteen, sixteen, or seventeen amino acid residues from a human light or heavy chain variable framework, e.g., a light or heavy chain variable framework residue from a mature human antibody, a human germline antibody sequence, or a consensus antibody sequence.

In some embodiments, the amino acid residue from the human light chain variable framework is the same as the residue found at the same position in a human germline antibody sequence. Preferably, the amino acid residue from the human light chain variable framework is the most common residue at the same position in the human germline antibody sequence. Preferably, the light chain variable framework of the modified anti-PSMA antibody, or antigen-binding fragment thereof, has at least one, two, three, five, seven, then amino acid residues which differ from the framework of the non-human anti-PSMA light chain variable region (e.g., the murine J591 light chain variable region), or which is from a human light chain variable framework (e.g., a human germline, mature, or consensus framework sequence), at a position selected from the group consisting of: residue 8, 9, 10, 11, 20, 22, 60, 63, 76, 77, 78, 80, 83, 87, 103, 104 and 106 (Kabat numbering as shown in Table 4). Preferably, the light chain variable framework of the modified anti-PSMA antibody, or antigen-binding fragment thereof, has at least one, two, three, five, seven, or ten amino acid residues from the human light chain variable framework selected from the group consisting of: residue 8 (proline), 9 (serine), 10 (serine), 11 (leucine), 20 (threonine), 22 (threonine), 60 (serine), 63 (serine), 76 (serine), 77 (serine), 78 (leucine), 80 (proline), 83 (phenylalanine), 87 (tyrosine), 103 (lysine), 104 (valine) and 106 (isoleucine) (Kabat numbering as shown in Table 4).

The amino acid replacements in the deimmunized J591 light chain variable region are provided below in Table 4. The left panel indicates the amino acid number according to Kabat, E. A., et al (1991) supra; the middle panel indicates the replacements of the residue in the mouse sequence and the corresponding mouse residues; and the right panel indicates the most common residue in the corresponding postion in the human germline.

TABLE 4

| Position Kabat No. | Substitution of mouse sequence | Most common in human germline |
|---|---|---|
| 3 | V→Q | V |
| 8 | H→P | P |
| 9 | K→S | S |
| 10 | F→S | S |
| 11 | M→L | L |
| 20 | S→T | T |
| 21 | I→L | I |
| 22 | I→T | T |
| 42 | Q→P | K |
| 58 | V→I | V |
| 60 | D→S | S |
| 63 | T→S | S |
| 76 | T→S | S |
| 77 | T→S | S |
| 78 | V→L | L |
| 80 | S→P | P |
| 83 | L→F | F |

TABLE 4-continued

| Position Kabat No. | Substitution of mouse sequence | Most common in human germline |
|---|---|---|
| 87 | F→Y | Y |
| 100 | A→P | Q |
| 103 | M→K | K |
| 104 | L→V | V |
| 106 | L→I | I |

In other embodiments, the light chain variable framework of the anti-PSMA antibody, or antigen-binding fragment thereof, has at least one, two, three, five, or seven amino acid residues which differ from the framework of a non-human anti-PSMA light chain variable region (e.g., the murine J415 light chain variable region), or which is from a human light chain variable framework (e.g., a human germline, mature, or consensus framework), at a position selected from the group consisting of: residue 13, 15, 19, 41, 63, 68, and 80 (linear numbering as shown in FIG. 7 and Table 5). Preferably, the light chain variable framework of the modified antibody, or antigen-binding fragment thereof, has at least one, two, three, five, or seven amino acid residues from the human consensus light chain variable framework selected from the group consisting of: residue 13 (alanine), 15 (alanine), 19 (methionine), 41 (threonine), 63 (serine), 68 (glycine), and 80 (alanine) (linear numbering as shown in FIG. 7 and Table 5).

The amino acid replacements in one of the deimmunized J415 light chain variable region are provided below in Table 5. The left panel indicates the amino acid number using linear numbering; the middle panel indicates the replacements of the residue in the mouse sequence and the corresponding mouse residues; and the right panel indicates the most common residue in the corresponding postion in the human germline.

TABLE 5

| Position Linear No | Substitution of mouse sequence | Most common in human germline |
|---|---|---|
| 13 | I→A | A |
| 15 | V→A | A |
| 19 | V→M | M |
| 41 | E→T | T |
| 63 | T→S | S |
| 68 | A→G | G |
| 80 | T→A | A |

In other embodiments, the light chain variable framework of the anti-PSMA antibody, or antigen-binding fragment thereof, includes at least 5, but no more than 80, amino acid residues from the light chain variable framework shown in SEQ ID NO:8 (from murine J591; see FIG. 2B), SEQ ID NO:36 (from murine J415; see FIG. 7), SEQ ID NO:114 (from murine J533; see FIG. 11A), or SEQ ID NO:124 (from murine E99; see FIG. 13A), or the light chain variable framework of an antibody produced by the hybridoma cell line having an ATCC Accession Number HB-12126, HB-12109, HB-12127 or HB-12101. Preferably, the light chain variable framework has at least 60%, 65%, 70%, 72%, 75%, 80%, 85%, 90%, or 94% identity with, or differs by at least 5, 7, 10, 20, or 30 but less than 10, 20, 30, or 40 amino acid residues from, the non-human light chain variable framework, e.g., the murine J591 or J415 light chain variable framework shown in SEQ ID NO:8 or SEQ ID NO:36, respectively, or the light chain variable framework of the antibody produced by the hybridoma cell line having an ATCC Accession Number HB-12126 or HB-12109. In other embodiments, the light chain variable framework is from murine J591 antibody (SEQ ID NO:8; see FIG. 2B), from murine J415 antibody (SEQ ID NO:36; see FIG. 7), from murine J533 antibody (SEQ ID NO:114; see FIG. 11A), or from murine E99 antibody (SEQ ID NO:124; see FIG. 13A), or the light chain variable framework of the antibody produced by the hybridoma cell line having an ATCC Accession Number HB-12126, HB-12109, HB-12127 or HB-12101.

In yet other embodiments, the light chain variable framework of the modified anti-PSMA antibody, or antigen-binding fragment thereof, includes a non-human (e.g., a murine) light chain variable framework (e.g., a murine J591 light chain variable framework as shown in SEQ ID NO:8 or the light chain variable framework of the antibody produced by the hybridoma cell line having an ATCC Accession Number HB-12126) which has at least 5, 10, 15, 16, 17, 18, 19, 20, 21, 22, or 23 amino acid replacements. In one embodiment, the non-human light chain variable framework includes one or more of:

a framework region 1 having at least 5, 6, 7, or 8 replacements;
a framework region 2 having at least one replacement;
a framework region 3 having at least 5, 6, 7, 8, or 9 replacements; or
a framework region 4 having at least 2, 3 or 4 replacements.

In yet other embodiments, the light chain variable framework of the modified anti-PSMA antibody, or antigen-binding fragment thereof, includes a non-human (e.g., a murine) light chain variable framework (e.g., a murine J415 light chain variable framework as shown in SEQ ID NO:36 or the light chain variable framework of the antibody produced by the hybridoma cell line having an ATCC Accession Number HB-12109) which has at least 1, 2, 3, 4, 5, 6, 7, 8, or 10 amino acid replacements. In some embodiments, the non-human light chain variable framework includes one or more of:

a framework region 1 having at least 1, 2 or 3 replacements;
a framework region 2 having at least one replacement; or
a framework region 3 having at least 1, 2 or 3 replacements.

The replacement can be selected from: a conservative substitution of a non-human residue, or a residue found in a human germline, mature or consensus framework sequence at the same position, e.g. the most common residue in the human germline sequence at the same position. In some embodiments, the light chain variable framework has at least 3, 4 and preferably 5 conservative substitutions. In other embodiments, the light chain variable framework has at least 5, 7, 10, 15, 16, or 17 amino acid replacements wherein the replacement amino acid residue is the most common residue in the human germline framework sequence at the same position.

In some embodiments, the non-human light chain variable framework (e.g., a murine J591 light chain variable framework as shown in SEQ ID NO:8 or the light chain variable framework of the antibody produced by the hybridoma cell line having an ATCC Accession No.: HB-12126) has at least one, two, three, five, seven, ten, eleven, fifteen, sixteen, seventeen, nineteen, twenty, twenty-one or twenty-two amino acid replacements at a position selected from the group consisting of: residue 3, 8, 9, 10, 11, 20, 21, 22, 42, 58, 60, 63, 76, 77, 78, 80, 83, 87, 100, 103, 104 and 106 (Kabat numbering as shown in Table 4). The replacement can be chosen from one or more of: residue 3 (glutamine), 8 (proline), 9 (serine), 10 (serine), 11 (leucine), 20 (threonine), 21 (leucine), 22 (threonine), 42 (proline), 58 (isoleucine), 60 (serine), 63 (serine), 76 (serine), 77 (serine), 78 (leucine), 80 (proline), 83 (phenylalanine), 87 (tyrosine), 100 (proline), 103 (lysine), 104 (valine) and 106 (isoleucine) (Kabat numbering as shown in Table 4).

In other embodiments, the non-human light chain variable framework (e.g., a murine J591 light chain variable framework as shown in SEQ ID NO:36 or the light chain variable framework of the antibody produced by the hybridoma cell line having an ATCC Accession No.: HB-12109) has at least one, two, three, five, or seven amino acid replacements at a position selected from the group consisting of: residue 13, 15, 19, 41, 63, 68 and 80 (linear numbering as shown in FIG. 7 and Table 5). Preferably, the light chain variable framework of the modified antibody, or antigen-binding fragment thereof, has at least one, two, three, five, seven amino acid residues from the human consensus light chain variable framework selected from the group consisting of: residue 13 (alanine), 15 (alanine), 19 (methionine), 41 (threonine), 63 (serine), 68 (glycine) and 80 (alanine) (linear numbering as shown in FIG. 7 and Table 5).

Preferably, the heavy chain variable framework of the modified anti-PSMA antibody, or antigen-binding fragment thereof, has at least one, two, three, five, seven, or eight amino acid residues, which differ from the framework of the non-human anti-PSMA heavy chain variable region (e.g., the murine J591 heavy chain variable region), or which is from a human heavy chain variable framework (e.g., a human germline framework), at a position selected from the group consisting of: residue 5, 40, 41, 44, 82a, 83, 87, and 108 (Kabat numbering as shown in Table 6). Preferably, the heavy chain variable framework of the recombinant antibody, or antigen-binding fragment thereof, has at least one amino acid residue from the human heavy chain variable framework selected from the group consisting of: residue 5 (valine), 40 (alanine), 41 (proline), 44 (glycine), 82a (serine), 83 (arginine), 87 (threonine), or 108 (leucine) (Kabat numbering as shown in Table 6).

The amino acid replacements in the deimmunized J591 heavy chain variable region are provided below in Table 6. The left panel indicates the amino acid number according to Kabat, E. A., et al. (1991) supra; the middle panel indicates the replacements of the residue in the mouse sequence and the corresponding mouse residues; and the right panel indicates the most common residue in the corresponding postion in the human germline.

TABLE 6

| Position Kabat No. | Substitution of mouse sequence | Most common in human germline |
|---|---|---|
| 5 | Q→V | V |
| 11 | L→V | L |
| 12 | V→K | V |
| 16 | T→A | G |
| 17 | S→T | S |
| 19 | R→K | R |
| 40 | S→A | A |
| 41 | H→P | P |
| 44 | S→G | G |
| 75 | S→T | K |
| 76 | S→D | N |
| 82a | R→S | S |
| 83 | T→R | R |
| 87 | S→T | T |
| 108 | T→L | L |

In other embodiments, the heavy chain variable framework of the modified anti-PSMA antibody, or antigen-binding fragment thereof, has at least one, two, three, four, five amino acid residues, which differ from the framework of a non-human anti-PSMA heavy chain variable region (e.g., the murine J415 heavy chain variable region), or which is from a human heavy chain variable framework (e.g., a human mature, consensus, or germline framework), at a position selected from the group consisting of: residue 20, 87, 94, 95, and 112 (linear numbering as shown in FIG. 6 and in Table 7). Preferably, the heavy chain variable framework of the recombinant antibody, or antigen-binding fragment thereof, has at least one, two, three, four, five amino acid residue from the human heavy chain variable framework selected from the group consisting of: residue 20 (isoleucine), 87 (serine), 94 (alanine), 95 (valine), and 112 (valine) (linear numbering as shown in FIG. 6 and in Table 7).

The amino acid replacements in one of the deimmunized J415 heavy chain variable region are provided below in Table 7. The left panel indicates the linear amino acid number; the middle panel indicates the replacements of the residue in the mouse sequence and the corresponding mouse residues; and the right panel indicates the most common reside in the corresponding postion in the human germline.

TABLE 7

| Position Kabat No | Substitution of mouse sequence | Most common in human germline |
|---|---|---|
| 20 | L→I | I |
| 87 | N→S | S |
| 94 | G→A | A |
| 95 | I→V | V |
| 112 | L→V | V |

In other embodiments, the heavy chain variable framework of the modified anti-PSMA antibody, or antigen-binding fragment thereof, includes at least 5 but no more than 75 or 82 amino acid residues from the heavy chain variable framework shown in SEQ ID NO:7 (from murine J591; see FIG. 2A), SEQ ID NO:35 (from murine J415; see FIG. 6), SEQ ID NO:109 (from murine J533; see FIG. 10A), or SEQ ID NO:119 (from murine E99; see FIG. 12A), or the heavy chain variable framework of the antibody produced by the hybridoma cell line having an ATCC Accession Number HB-12126, HB-12109, HB-12127 or HB-12101. Preferably, the heavy chain variable framework has at least 60%, 65%, 70%, 80%, 82%, 85%, 90%, or 94% identity with, or differs by at least 5, 10, 20, or 30 but less than 10, 20, 30, or 40 residues from, a non-human heavy chain variable framework, e.g., the murine J591 or J415 or heavy chain variable framework shown in SEQ ID NO:7 or SEQ ID NO:35, respectively, or a heavy chain variable framework of the antibody produced by the hybridoma cell line having an ATCC Accession Number HB-12126 or HB-12109, respectively. In other embodiments, the non-human heavy chain variable framework is from murine J591 antibody (SEQ ID NO:7; see FIG. 2A), from murine J415 antibody (SEQ ID NO:35; see FIG. 6), from murine J533 antibody (SEQ ID NO:109; see FIG. 10A), or from murine E99 antibody (SEQ ID NO:119; see FIG. 12A), or the heavy chain variable framework of the antibody produced by the hybridoma cell line having an ATCC Accession Number HB-12126, HB-12109, HB-12127 or HB-12101.

In yet other embodiments, the heavy chain variable framework of the modified anti-PSMA antibody, or antigen-binding fragment thereof, includes a non-human (e.g., a murine) heavy chain variable framework (e.g., a murine J591 heavy chain variable framework (SEQ ID NO:7, as shown FIG. 2A, or the heavy chain variable framework of the antibody produced by the hybridoma cell line having an ATCC Accession Number HB-12126) which has at least 3, 5, 10, 15, 16, 17, 18, or 19 amino acid replacements. In one embodiment, the non-human heavy chain variable framework of the modified anti-PSMA antibody includes one or more of:

a framework region 1 having at least 4, 5, or 6 replacements;

a framework region 2 having at least 1, 2, or 3 replacements;

a framework region 3 having at least 3, 4, or 5 replacements; or a framework region 4 having at least one replacement.

In yet other embodiments, the heavy chain variable framework of the modified anti-PSMA antibody, or antigen-binding fragment thereof, includes a non-human (e.g., a murine) heavy chain variable framework (e.g., a murine J415 heavy chain variable framework (SEQ ID NO:35, as shown in FIG. 6, or the heavy chain variable framework of the antibody produced by the hybridoma cell line having an ATCC Accession Number HB-12109) which has at least 1, 2, 3, 4, or 5 amino acid replacements. In one embodiment, the non-human heavy chain variable framework of the modified anti-PSMA antibody includes one or more of:

a framework region 1 having at least one replacement;

a framework region 3 having at least 1, 2, or 3 replacements; or a framework region 4 having at least one replacement.

The replacement can be chosen from: a conservative substitution of a non-human residue, or a residue found in a human germline, mature or consensus sequence at the same position, e.g. the most common residue in the human germline at the same position. In one embodiment, the heavy chain variable framework has at least 3, 4, 5, 6 and preferably 7 conservative substitutions. Preferably, the heavy chain variable framework has at least 5, 6, 7 and preferably 8 replacements by the most common residue in the human germline at the same position.

In some embodiments, the non-human heavy chain variable framework (e.g., a murine J591 heavy chain variable framework of SEQ ID NO:7 or the heavy chain variable framework of the antibody produced by the hybridoma cell line having an ATCC Accession Number HB-12126) has at least one amino acid replacement at a position selected from the group consisting of: residue 5, 11, 12, 16, 17, 19, 40, 41, 44, 75, 76, 82a, 83, 87, and 108 (Kabat numbering as shown in Table 6). The replacement can be chosen from one or more of: 5 (valine), 11 (valine), 12 (lysine), 16 (alanine), 17 (threonine), 19 (lysine), 40 (alanine), 41 (proline), 44 (glycine), 75 (threonine), 76 (aspartate), 82a (serine), 83 (arginine), 87 (threonine), and 108 (leucine) (Kabat numbering as shown in Table 6).

In other embodiments, the non-human heavy chain variable framework (e.g., a murine J415 heavy chain variable framework of SEQ ID NO:35 or the heavy chain variable framework of the antibody produced by the hybridoma cell line having an ATCC Accession Number HB-12109) has at least one amino acid replacement at a position selected from the group consisting of: residue 20, 87, 94, 95 and 112 (linear numbering as shown in FIG. 6 and in Table 7). The replacement can be chosen from one or more of: residue 20 (isoleucine), 87 (serine), 94 (alanine), 95 (valine), and 112 (valine) (linear numbering as shown in FIG. 6 and in Table 7).

The amino acid sequence of the framework regions of the light and heavy chains regions of antibodies J591, J415, J533 and E99 are provided in Table 8, below.

TABLE 8

Framework Sequences

| NAME | Organism | FIG. | SEQ ID NO | SEQUENCE |
|---|---|---|---|---|
| V_HFR1-FR4 J591 | *Mus musculus* | FIG. 2A | 7 | EVQLQQSGPELKKPGTSVRISCK TSWVKQSHGKSLEWIGKATLTV DKSSSTAYMELRSLTSEDSAVY YCAAWGQGTTLTVSS |
| V_LFR1-FR4 J591 | *Mus musculus* | FIG. 2B | 8 | DIVMTQSHKFMSTSVGDRVSIIC WYQQKPGQSPKLLIYGVPDRFT GSGSGTDFTLTITNVQSEDLADY FCFGAGTMLDLK |
| V_HFR1 (Deimm) J591 | Artificial - deimmunized heavy chain J591 | FIG. 3A | 9 | EVQLVQSGPEVKKPGATVKISC KTS |
| V_HFR2 (Deimm) J591 | Artificial - deimmunized heavy chain J591 | FIG. 3A | 10 | WVKQAPGKGLEWIG |
| V_HFR3 (Deimm) J591 | Artificial - deimmunized heavy chain J591 | FIG. 3A | 11 | KATLTVDKSTDTAYMELSSLRS EDTAVYYCAA |
| V_HFR4 (Deimm) J591 | Artificial - deimmunized heavy chain J591 | FIG. 3A | 12 | WGQGTLLTVSS |
| V_LFR1 (Deimm) J591 | Artificial - deimmunized light chain J591 | FIG. 3B | 13 | DIQMTQSPSSLSTSVGDRVTLTC |

TABLE 8-continued

Framework Sequences

| NAME | Organism | FIG. | SEQ ID NO: | SEQUENCE |
|---|---|---|---|---|
| V<sub>L</sub>FR2 (Deimm) J591 | Artificial - deimmunized light chain J591 | FIG. 3B | 14 | WYQQKPGPSPKLLIY |
| V<sub>L</sub>FR3 (Deimm) J591 | Artificial - deimmunized light chain J591 | FIG. 3B | 15 | GIPSRFSGSGSGTDFTLTISSLQPE DFADYYC |
| V<sub>L</sub>FR4 (Deimm) J591 | Artificial - deimmunized light chain J591 | FIG. 3B | 16 | FGPGTKVDIK |
| V<sub>H</sub>FR1-FR4 (Deimm) J591 | Artificial - deimmunized heavy chain J591 | FIG. 3A | 17 | EVQLVQSGPEVKKPGATVKISC KTSWVKQAPGKGLEWIGKATLT VDKSTDTAYMELSSLRSEDTAV YYCAAWGQGTLLTVSS |
| V<sub>L</sub>FR1-FR4 (Deimm) J591 | Artificial - deimmunized light chain J591 | FIG. 3B | 18 | DIQMTQSPSSLSTSVGDRVTLTC WYQQKPGPSPKLLIYGIPSRFSGS GSGTDFTLTISSLQPEDFADYYC FGPGTKVDIK |
| V<sub>H</sub>FR1-FR4 J415 | Mus musculus | FIG. 6 | 35 | EVKLEESGGGLVQPGGSMKLSC VASWVRQSPEKGLEWVARVIIS RDDSKSSVYLQMNNLRAEDTGI YYCTRWGQGTTLTVSS |
| V<sub>L</sub>FR1-FR4 J415 | Mus musculus | FIG. 6 | 36 | NIVMTQFPKSMSISVGERVTLTC WYQQKPEQSPKMLIYGVPDRFT GSGSATDFILTISSVQTEDLVDY YCFGGGTKLEMK |
| V<sub>H</sub>FR1 (Deimm) J415-4 | Artificial - deimmunized heavy chain J415-4 | FIG. 6 | 37 | EVKLEESGGGLVQPGGSMKISC VAS |
| V<sub>H</sub>FR2 (Deimm) J415-4 | Artificial - deimmunized heavy chain J415-4 | FIG. 6 | 38 | WVRQSPEKGLEWVA |
| V<sub>H</sub>FR3 (Deimm) J415-4 | Artificial - deimmunized heavy chain J415-4 | FIG. 6 | 39 | RVIISRDDSKSSVYLQMNSLRAE DTAVYYCTR |
| V<sub>H</sub>FR4 (Deimm) J415-4 | Artificial - deimmunized heavy chain J415-4 | FIG. 6 | 40 | WGQGTTVTVSS |
| V<sub>L</sub>FR1 (Deimm) J415-5 | Artificial - deimmunized light chain J415-5 | FIG. 7 | 41 | NIVMTQFPKSMSASAGERMTLT C |
| V<sub>L</sub>FR2 (Deimm) J415-5 | Artificial - deimmunized light chain J415-5 | FIG. 7 | 42 | WYQQKPTQSPKMLIY |
| V<sub>L</sub>FR3 (Deimm) J415-5 | Artificial - deimmunized light chain J415-5 | FIG. 7 | 43 | GVPDRFSGSGSGTDFILTISSVQA EDLVDYYC |
| V<sub>L</sub>FR4 (Deimm) J415-5 | Artificial - deimmunized light chain J415-5 | FIG. 7 | 44 | FGGGTKLEMK |
| V<sub>H</sub>FR1-FR4 (Deimm) J415-4 | Artificial - deimmunized heavy chain J415-4 | FIG. 7 | 45 | EVKLEESGGGLVQPGGSMKISC VASWVRQSPEKGLEWVARVIIS RDDSKSSVYLQMNSLRAEDTAV YYCTRWGQGTTVTVSS |
| V<sub>L</sub>FR1-FR4 (Deimm) J415-5 | Artificial - deimmunized light chain J415-5 | FIG. 7 | 46 | NIVMTQFPKSMSASAGERMTLT CWYQQKPTQSPKMLIYGVPDRF SGSGSGTDFILTISSVQAEDLVDY YCFGGGTKLEMK |
| V<sub>H</sub>FR1 J533 | Mus musculus | FIG. 10A | 105 | EVQLQQSGPELVKPGASVKMSC KAS |

TABLE 8-continued

Framework Sequences

| NAME | Organism | FIG. | SEQ ID NO | SEQUENCE |
|---|---|---|---|---|
| $V_H$FR2 J533 | Mus musculus | FIG. 10A | 106 | WVKQKPGQVLEWIG |
| $V_H$FR3 J533 | Mus musculus | FIG. 10A | 107 | KATLTSDKYSSTAYMELSGLTSE DSAVYYCAR |
| $V_H$FR4 J533 | Mus musculus | FIG. 10A | 108 | WGRGATLTVSS |
| $V_H$FR1-FR4 J533 | Mus musculus | FIG. 10A | 109 | EVQLQQSGPELVKPGASVKMSC KASWVKQKPGQVLEWIGKATLT SDKYSSTAYMELSGLTSEDSAV YYCARWGRGATLTVSS |
| $V_L$FR1 J533 | Mus musculus | FIG. 11A | 110 | DIVLTQSPASLAVSLGQRATISC |
| $V_L$FR2 J533 | Mus musculus | FIG. 11A | 111 | WYQQKPGQPPNLLIF |
| $V_L$FR3 J533 | Mus musculus | FIG. 11A | 112 | GIPARFSGSGSGTDFTLTIYPVEA DDVATYYC |
| $V_L$FR4 J533 | Mus musculus | FIG. 11A | 113 | FGGGTKLEIK |
| $V_L$FR1-FR4 J533 | Mus musculus | FIG. 11A | 114 | DIVLTQSPASLAVSLGQRATISC WYQQKPGQPPNLLIFGIPARFSG SGSGTDFTLTIYPVEADDVATYY CFGGGTKLEIK |
| $V_H$FR1 E99 | Mus musculus | FIG. 12A | 115 | QVQLKESGPGLVASSQSLSITCT VS |
| $V_H$FR2 E99 | Mus musculus | FIG. 12A | 116 | WVRQPPGKGLEWLG |
| $V_H$FR3 E99 | Mus musculus | FIG. 12A | 117 | RLNIFKDNSKNQVFLKMSSFQTD DTARYFCAR |
| $V_H$FR4 E99 | Mus musculus | FIG. 12A | 118 | WGQGTTLTVSS |
| $V_H$FR1-FR4 E99 | Mus musculus | FIG. 12A | 119 | QVQLKESGPGLVASSQSLSITCT VSWVRQPPGKGLEWLGRLNIFK DNSKNQVFLKMSSFQTDDTARY FCARWGQGTTLTVSS |
| $V_L$FR1 E99 | Mus musculus | FIG. 13A | 120 | NIVMTQSQKFMSTSPGDRVRVT C |
| $V_L$FR2 E99 | Mus musculus | FIG. 13A | 121 | WYQAKPGQSPRILIY |
| $V_L$FR3 E99 | Mus musculus | FIG. 13A | 122 | GVPDRFTAYGSGTDFTLTITNVQ SEDLTEYFC |
| $V_L$FR4 E99 | Mus musculus | FIG. 13A | 123 | FGAGTKLELK |

TABLE 8-continued

Framework Sequences

| NAME | Organism | FIG. | SEQ ID NO: | SEQUENCE |
|---|---|---|---|---|
| V$_L$FR1-FR4 E99 | Mus musculus | FIG. 13A | 124 | NIVMTQSQKFMSTSPGDRVRVT CWYQAKPGQSPRILIYGVPDRFT AYGSGTDFTLTITNVQSEDLTEY FCFGAGTKLELK |

In other embodiments, the anti-PSMA antibody, or antigen-binding fragment thereof, includes at least one light chain or heavy chain immunoglobulin or, preferably, at least one light chain immunoglobulin and at least one heavy chain immunoglobulin. Preferably, the light chain immunoglobulin includes a non-human light chain variable region comprising three CDRs from a non-human, e.g., murine, anti-PSMA light chain variable region (e.g., the murine J591 or J415 light chain variable region shown in SEQ ID NO:20 (see FIG. 2B) or SEQ ID NO:48 (see FIG. 7), respectively, or the light chain variable region of the antibody produced by the hybridoma cell line having an ATCC Accession Number HB-12126 or HB-12109) and a light chain framework which differs from the framework of the non-human, e.g., murine, anti-PSMA light chain framework (e.g., the murine J591 of J415 light chain framework shown in SEQ ID NO:8 (see FIG. 2B) or SEQ ID NO:36 (see FIG. 7), respectively, or the light chain variable framework of the antibody produced by the hybridoma cell line having an ATCC Accession Number HB-12126 or HB-12109) at one, two, three, four, five, six, seven or more positions selected from the group consisting of: residue 3, 8, 9, 10, 11, 20, 21, 22, 42, 58, 60, 63, 76, 77, 78, 80, 83, 87, 100, 103, 104 and 106 (Kabat numbering as in Table 4), or residues 13, 15, 19, 41, 63, 68, and 80 (linear numbering as in FIG. 7 and in Table 5).

In other preferred embodiments, the heavy chain immunoglobulin includes a non-human heavy chain variable region comprising three complementarity determining regions (CDRs) from a non-human, e.g., murine, anti-PSMA heavy chain variable region (e.g., the murine J591 or J415 heavy chain variable region shown in SEQ ID NO:19 (see FIG. 2A) or SEQ ID NO:47 (see FIG. 6), respectively, or the heavy chain variable region of the antibody produced by the hybridoma cell line having an ATCC Accession Number HB-12126 or HB-12109, respectively) and a modified heavy chain framework which differs from the framework of the non-human, e.g., murine, anti-PSMA heavy chain framework (e.g., the murine J591 or J415 heavy chain framework shown in SEQ ID NO:7 (see FIG. 2A) or SEQ ID NO:35 (see FIG. 6), respectively, or the heavy chain variable framework of the antibody produced by the hybridoma cell line having an ATCC Accession Number HB-12126 or HB-12109, respectively) at one, two, three, four, five or more positions selected from the group consisting of: residue 5, 11, 12, 16, 17, 19, 40, 41, 44, 75, 76, 82a, 83, 87, and 108 (Kabat numbering as in Table 5), or residue 20, 87, 94, 95 and 112 (linear numbering as in FIG. 6 and in Table 7).

In yet other embodiments, the modified anti-PSMA antibody, or antigen-binding fragment thereof, includes at least one light or heavy chain immunoglobulin or, more preferably, at least one light chain immunoglobulin and at least one heavy chain immunoglobulin. Preferably, the light chain immunoglobulin includes a modified non-human light chain variable region comprising three CDRs from a non-human, e.g., murine, anti-PSMA light chain variable region (e.g., the murine J591 light chain variable region shown in SEQ ID NO:20 (see FIG. 2B), or the light chain variable region of the antibody produced by the hybridoma cell line having an ATCC Accession Number HB-12126) and a modified light chain framework which differs from the framework of the non-human anti-PSMA light chain variable region, e.g., the murine J591 light chain variable region (SEQ ID NO:20 or the light chain variable region of the antibody produced by the hybridoma cell line having an ATCC Accession Number HB-12126), by at least one, two, three, four, five, six, seven, eight, nine, ten positions selected from the group consisting of:

a position within or adjacent to one or more of residues 1, 2, 3, 4, 5, 6, 7, 8, 9, 10, 11, 12 or 13, or a T cell epitope which includes one or more of residues 1–13 (numbering as in FIG. 4B);

a position within or adjacent to one or more of residues 8, 9, 10, 11, 12, 13, 14, 15, 16, 17, 18, 19 or 20, or a T cell epitope which includes one or more of residues 8–20 (numbering as in FIG. 4B);

a position within or adjacent to one or more of residues 17, 18, 19, 20, 21, 22, 23, 24, 25, 26, 27, 28 or 29, or a T cell epitope which includes one or more of residues 17–29 (numbering as in FIG. 4B);

a position within or adjacent to one or more of residues 27, 28, 29, 30, 31, 32, 33, 34, 35, 36, 37, 38 or 39, or a T cell epitope which includes one or more of residues 27–39 (numbering as in FIG. 4B);

a position within or adjacent to one or more of residues 30, 31, 32, 33, 34, 35, 36, 37, 38, 39, 40, 41, 42 or 43, or a T cell epitope which includes one or more of residues 30–43 (numbering as in FIG. 4B);

a position within or adjacent to one or more of residues 45, 46, 47, 48, 49, 50, 51, 52, 53, 54, 55, 56, or 57, or a T cell epitope which includes one or more of residues 45–57 (numbering as in FIG. 4B);

a position within or adjacent to one or more of residues 56, 57, 58, 59, 60, 61, 62, 63, 64, 65, 66, 67, or 68, or a T cell epitope which includes one or more of residues 56–68 (numbering as in FIG. 4B);

a position within or adjacent to one or more of residues 71, 72, 73, 74, 75, 76, 77, 78, 79, 80, 81, 82, or 83, or a T cell epitope which includes one or more of residues 71–83 (numbering as in FIG. 4B);

a position within or adjacent to one or more of residues 73, 74, 75, 76, 77, 78, 79, 80, 81, 82, 83, 84 or 85, or a T cell epitope which includes one or more of residues 73–85 (numbering as in FIG. 4B); and a position within or adjacent to one or more of residues 94, 95, 96, 97, 98, 99, 100, 101, 102, 103, 104, 105, or 106, or a T cell epitope which includes one or more of residues 94–106 (numbering as in FIG. 4B).

In yet other embodiments, the anti-PSMA antibody, or antigen-binding fragment thereof, includes at least one light or heavy chain immunoglobulin or, more preferably, at least one light chain immunoglobulin and at least one modified heavy chain immunoglobulin. Preferably, the light chain immunoglobulin includes a modified non-human light chain variable region comprising three CDRs from a non-human, e.g., murine, anti-PSMA light chain variable region (e.g., the murine J415 light chain variable region shown in SEQ ID NO:48 (FIG. 7), or the light chain variable region of the antibody produced by the hybridoma cell line having an ATCC Accession Number HB-12109) and a light chain framework which differs from the framework of the non-human anti-PSMA light chain variable region, e.g., the murine J415 light chain variable region (SEQ ID NO:48 or the light chain variable region of the antibody produced by the hybridoma cell line having an ATCC Accession Number HB-12109), by at least one, two, three, four, five, six, seven positions selected from the group consisting of:

a position within or adjacent to one or more of residues 5, 6, 7, 8, 9, 10, 11, 12, 13, 14, 15, 16, 17 or 18, or a T cell epitope which includes one or more of residues 5–18 (linear numbering as in FIG. 7);

a position within or adjacent to one or more of residues 11, 12, 13, 14, 15, 16, 17, 18, 19, 20, 21, 22, 23, or 24, or a T cell epitope which includes one or more of residues 11–24 (linear numbering as in FIG. 7);

a position within or adjacent to one or more of residues 13, 14, 15, 16, 17, 18, 19, 20, 21, 22, 23, 24, 25, or 26, or a T cell epitope which includes one or more of residues 13–26 (linear numbering as in FIG. 7);

a position within or adjacent to one or more of residues 17, 18, 19, 20, 21, 22, 23, 24, 25, 26, 27, 28, 29, or 30, or a T cell epitope which includes one or more of residues 17–30 (linear numbering as in FIG. 7);

a position within or adjacent to one or more of residues 27, 28, 29, 30, 31, 32, 33, 34, 35, 36, 37, 38, 39, or 40, or a T cell epitope which includes one or more of residues 27–40 (linear numbering as in FIG. 7);

a position within or adjacent to one or more of residues 31, 32, 33, 34, 35, 36, 37, 38, 39, 40, 41, 42, 43, or 44, or a T cell epitope which includes one or more of residues 31–44 (linear numbering as in FIG. 7);

a position within or adjacent to one or more of residues 56, 57, 58, 59, 60, 61, 62, 63, 64, 65, 66, 67, 68, or 69, or a T cell epitope which includes one or more of residues 56–69 (linear numbering as in FIG. 7);

a position within or adjacent to one or more of residues 60, 61, 62, 63, 64, 65, 66, 67, 68, 69, 70, 71, 72, or 73, or a T cell epitope which includes one or more of residues 60–73 (linear numbering as in FIG. 7);

a position within or adjacent to one or more of residues 70, 71, 72, 73, 74, 75, 76, 77, 78, 79, 80, 81, 82, or 83, or a T cell epitope which includes one or more of residues 70–83 (linear numbering as in FIG. 7);

a position within or adjacent to one or more of residues 71, 72, 73, 74, 75, 76, 77, 78, 79, 80, 81, 82, 83 or 84, or a T cell epitope which includes one or more of residues 71–84 (linear numbering as in FIG. 7);

a position within or adjacent to one or more of residues 73, 74, 75, 76, 77, 78, 79, 80, 81, 82, 83, 84, 85 or 86, or a T cell epitope which includes one or more of residues 73–86 (linear numbering as in FIG. 7);

a position within or adjacent to one or more of residues 76, 77, 78, 79, 80, 81, 82, 83, 84, 85, 86, 87, 88, 89, 90, 91, or 92, or a T cell epitope which includes one or more of residues 76–92 (linear numbering as in FIG. 7); and a position within or adjacent to one or more of residues 81, 82, 83, 84, 85, 86, 87, 88, 89, 90, 91, 92, 93, or 94, or a T cell epitope which includes one or more of residues 81–94 (linear numbering as in FIG. 7).

In other embodiments, the heavy chain immunoglobulin of the anti-PSMA antibody, or antigen-binding fragment thereof, includes a non-human heavy chain variable region comprising three CDRs from a non-human, e.g., murine, anti-PSMA heavy chain variable region (e.g., the murine J591 heavy chain variable region shown in SEQ ID NO:19 (see FIG. 2A), or the heavy chain variable region of the antibody produced by the hybridoma cell line having an ATCC Accession Number HB-12126) and a heavy chain framework which differs from the framework of the non-human anti-PSMA heavy chain variable region (e.g., the murine J591 heavy chain variable region of SEQ ID NO:19 or the heavy chain variable framework of the antibody produced by the hybridoma cell line having an ATCC Accession Number HB-12126), by at least one, two, three, five, seven, ten positions selected from the group consisting of:

a position within or adjacent to one or more of residues 2, 3, 4, 5, 6, 7, 8, 9, 10, 11, 12, 13, or 14, or a T cell epitope which includes one or more of residues 2–14 (numbering as in FIG. 4A);

a position within or adjacent to one or more of residues 10, 11, 12, 13, 14, 15, 16, 17, 18, 19, 20, 21, or 22, or a T cell epitope which includes one or more of residues 10–22 (numbering as in FIG. 4A);

a position within or adjacent to one or more of residues 16, 17, 18, 19, 20, 21, 22, 23, 24, 25, 26, 27, or 28, or a T cell epitope which includes one or more of residues 16–28 (numbering as in FIG. 4A);

a position within or adjacent to one or more of residues 30, 31, 32, 33, 34, 35, 36, 37, 38, 39, 40, 41, or 42, or a T cell epitope which includes one or more of residues 30–42 (numbering as in FIG. 4A);

a position within or adjacent to one or more of residues 32, 33, 34, 35, 36, 37, 38, 39, 40, 41, 42, 43, or 44, or a T cell epitope which includes one or more of residues 32–44 (numbering as in FIG. 4A);

a position within or adjacent to one or more of residues 43, 44, 45, 46, 47, 48, 49, 50, 51, 52, 53, 54, or 55, or a T cell epitope which includes one or more of residues 43–55 (numbering as in FIG. 4A);

a position within or adjacent to one or more of residues 46, 47, 48, 49, 50, 51, 52, 53, 54, 55, 56, 57, or 58, or a T cell epitope which includes one or more of residues 46–58 (numbering as in FIG. 4A);

a position within or adjacent to one or more of residues 58, 59, 60, 61, 62, 63, 64, 65, 66, 67, 68, 69, or 70, or a T cell epitope which includes one or more of residues 58–70 (numbering as in FIG. 4A);

a position within or adjacent to one or more of residues 62, 63, 64, 65, 66, 67, 68, 69, 70, 71, 72, 73 or 74, or a T cell epitope which includes one or more of residues 62–74 (numbering as in FIG. 4A);

a position within or adjacent to one or more of residues 70, 71, 72, 73, 74, 75, 76, 77, 78, 79, 80 or 81, or a T cell epitope which includes one or more of residues 70–81 (numbering as in FIG. 4A);

a position within or adjacent to one or more of residues 81, 82, 83, 84, 85, 86, 87, 88, 89, 90, 91, 92, or 93, or a T cell epitope which includes one or more of residues 81–93 (numbering as in FIG. 4A);

a position within or adjacent to one or more of residues 84, 85, 86, 87, 88, 89, 90, 91, 92, 93, 95, or 96, or a T cell epitope which includes one or more of residues 84–96 (numbering as in FIG. 4A);

a position within or adjacent to one or more of residues 91, 92, 93, 95, 96, 97, 98, 99, 100, 101, 102, or 103, or a T cell epitope which includes one or more of residues 91–103 (numbering as in FIG. 4A); and a position within or adjacent to one or more of residues 100, 101, 102, 103, 104, 105, 106, 107, 108, 109, 110, 111, or 112, or a T cell epitope which includes one or more of residues 100–112 (numbering as in FIG. 4A).

In other embodiments, the heavy chain immunoglobulin of the anti-PSMA antibody, or antigen-binding fragment thereof, includes a non-human heavy chain variable region comprising three CDRs from a non-human, e.g., murine, anti-PSMA heavy chain variable region (e.g., the murine J415 heavy chain variable region shown in SEQ ID NO:47 (see FIG. 6), or the heavy chain variable region of the antibody produced by the hybridoma cell line having an ATCC Accession Number HB-12109) and a heavy chain framework which differs from the framework of the non-human anti-PSMA heavy chain variable region, e.g., the murine J415 heavy chain variable region of SEQ ID NO:47 or the heavy chain variable framework of the antibody produced by the hybridoma cell line having an ATCC Accession Number HB-12109), by at least one, two, three, four, five positions selected from the group consisting of:

a position within or adjacent to one or more of residues 10, 11, 12, 13, 14, 15, 16, 17, 18, 19, 20, 21, 22 or 23, or a T cell epitope which includes one or more of residues 10–23 (numbering as in FIG. 6);

a position within or adjacent to one or more of residues 16, 17, 18, 19, 20, 21, 22, 23, 24, 25, 26, 27, 28, or 29, or a T cell epitope which includes one or more of residues 16–29 (numbering as in FIG. 6);

a position within or adjacent to one or more of residues 21, 22, 23, 24, 25, 26, 27, 28, 29, 30, 31, 32, 33, or 34, or a T cell epitope which includes one or more of residues 21–34 (numbering as in FIG. 6);

a position within or adjacent to one or more of residues 30, 31, 32, 33, 34, 35, 36, 37, 38, 39, 40, 41, 42, or 43, or a T cell epitope which includes one or more of residues 30–43 (numbering as in FIG. 6);

a position within or adjacent to one or more of residues 35, 36, 37, 38, 39, 40, 41, 42, 43, 44, 45, 46, 47, or 48, or a T cell epitope which includes one or more of residues 35–48 (numbering as in FIG. 6);

a position within or adjacent to one or more of residues 43, 44, 45, 46, 47, 48, 49, 50, 51, 52, 53, 54, 55, or 56, or a T cell epitope which includes one or more of residues 43–56 (numbering as in FIG. 6);

a position within or adjacent to one or more of residues 46, 47, 48, 49, 50, 51, 52, 53, 54, 55, 56, 57, 58 or 59, or a T cell epitope which includes one or more of residues 46–59 (numbering as in FIG. 6);

a position within or adjacent to one or more of residues 49, 50, 51, 52, 53, 54, 55, 56, 57, 58, 59, 60, 61, or 62, or a T cell epitope which includes one or more of residues 49–62 (numbering as in FIG. 6);

a position within or adjacent to one or more of residues 64, 65, 66, 67, 68, 69, 70, 71, 72, 73, 74, 75, 76, or 77, or a T cell epitope which includes one or more of residues 64–77 (numbering as in FIG. 6);

a position within or adjacent to one or more of residues 80, 81, 82, 83, 84, 85, 86, 87, 88, 89, 90, 91, 92, or 93, or a T cell epitope which includes one or more of residues 80–93 (numbering as in FIG. 6);

a position within or adjacent to one or more of residues 86, 87, 88, 89, 90, 91, 92, 93, 94, 95, 96, 97, 98, or 99, or a T cell epitope which includes one or more of residues 86–99 (numbering as in FIG. 6); and a position within or adjacent to one or more of residues 104, 105, 106, 107, 108, 109, 110, 111, 112, 113, 114, 115, 116, or 117, or a T cell epitope which includes one or more of residues 104–117 (numbering as in FIG. 6).

In yet other embodiments, the anti-PSMA antibody, or antigen-binding fragment thereof, includes at least one light or heavy chain immunoglobulin or, more preferably, at least one light chain immunoglobulin and at least one heavy chain immunoglobulin. Preferably, the light chain immunoglobulin includes a non-human light chain variable region comprising three CDRs from a non-human, e.g., murine, anti-PSMA light chain variable region (e.g., the murine J591 light chain variable region shown in SEQ ID NO:20 (FIG. 2B), or the light chain variable region of the antibody produced by the hybridoma cell line having an ATCC Accession Number HB-12126) and a light chain framework which differs from the framework of the non-human anti-PSMA light chain variable region, e.g., murine J591 light chain variable region, by at least one position while having a residue from the non-human anti-PSMA light chain variable region at least one, two, three, five, seven, ten, fifteen, or twenty residues selected from the group consisting of 1, 2, 4–7, 12–19, 23, 31–41, 43–49, 57, 59, 61, 62, 64–75, 79, 82, 83, 85–87, 89, 98, 99, 101, 102, 105, and 106 (numbering as in FIG. 4B). The light chain framework can differ at a positions chosen from one, two, three, four, five, six, seven, eight, nine, ten, eleven, twelve, thirteen, fourteen, fifteen, sixteen, nineteen, twenty or more residues selected from the group consisting of 3, 8, 9, 10, 11, 20, 21, 22, 42, 58, 60, 63, 76, 77, 78, 80, 83, 87, 100, 103, and 104 (numbering as in FIG. 4B).

In yet other embodiments, the anti-PSMA antibody, or antigen-binding fragment thereof, includes at least one light or heavy chain immunoglobulin or, more preferably, at least one light chain immunoglobulin and at least one heavy chain immunoglobulin. Preferably, the modified light chain immunoglobulin includes a non-human light chain variable region comprising three CDRs from a non-human, e.g., murine, anti-PSMA light chain variable region (e.g., the murine J415 light chain variable region shown in SEQ ID NO:48 (FIG. 7), or the light chain variable region of the antibody produced by the hybridoma cell line having an ATCC Accession Number HB-12109) and a light chain framework which differs from the framework of the non-human anti-PSMA light chain variable region, e.g., murine J415 light chain variable region, by at least one position while having a residue from the non-human anti-PSMA light chain variable region at least one, two, three, five, seven, ten, fifteen, or twenty residues selected from the group consisting of 1–12, 14, 16–18, 20–40, 42–62, 64–67, 69–79, and 81–107 (linear numbering as in FIG. 7). The modified light chain framework can differ at least one, two, three, four, five, six, or seven positions selected from the group consisting of 13, 15, 19, 41, 63, 68 and 80 (linear numbering as in FIG. 7).

In other embodiments, the heavy chain immunoglobulin of the modified anti-PSMA antibody, or antigen-binding fragment thereof, includes a non-human heavy chain variable region comprising three CDRs from a non-human, e.g., murine, anti-PSMA heavy chain variable region (e.g., the murine J591 heavy chain variable region shown in SEQ ID NO:19 (FIG. 2A), or the heavy chain variable region of the antibody produced by the hybridoma cell line having an ATCC Accession Number HB-12126) and a modified heavy chain framework which differs from the framework of the non-human anti-PSMA heavy chain variable region by at least one position while having a residue from the non-human anti-PSMA heavy chain variable region at least one, two, three, four, five, six, seven, eight, nine, ten, eleven, twelve, thirteen, or fourteen residues selected from the group consisting of 1–4,6–10, 13–15, 18, 20–25, 36–39, 42, 43, 45–49, 67–75, 78–83, 85, 86, 88–90, 92–98, 105–109, and 111–115 (numbering as in FIG. 4A). The modified heavy chain framework can differ at at least one, two, three, four, five, six, seven, eight, nine, ten, eleven, twelve, thirteen, or fourteen positions selected from the group consisting of 5, 11–12, 16–17, 19, 26–35, 40–41, 44, 50–66, 76–77, 84, 87, 91, 99–104, and 110 (numbering as in FIG. 4A).

In other embodiments, the heavy chain immunoglobulin of the anti-PSMA antibody, or antigen-binding fragment thereof, includes a non-human heavy chain variable region comprising three CDRs from a non-human, e.g., murine, anti-PSMA heavy chain variable region (e.g., the murine J415 heavy chain variable region shown in SEQ ID NO:47 (FIG. 6), or the heavy chain variable region of the antibody produced by the hybridoma cell line having an ATCC Accession Number HB-12109) and a heavy chain framework which differs from the framework of the non-human anti-PSMA heavy chain variable region by at least one position while having a residue from the non-human anti-PSMA heavy chain variable region at at least one, two, three, four, or five residues selected from the group consisting of 1–19, 21–86, 88–93, 96–111, and 113–116 (numbering as in FIG. 6). The heavy chain framework can differ at a positions selected from the group consisting of 20, 87, 94, 95 and 112 (numbering as in FIG. 6).

In yet another aspect, the heavy chain immunoglobulin of the anti-PSMA antibody, or antigen-binding fragment thereof, includes a heavy chain variable region comprising at least one, two, three, four, five, six, seven, eight, nine, ten, twenty, twenty-five, thirty, thirty-five, forty, forty-five, or fifty amino acid residues chosen from one or more of the following residues and located at a position chosen from one or more of: residue 1 (glutamate), 2 (valine), 4 (leucine), 7 (serine), 8 (glycine), 11 (leucine), 14 (proline), 15 (glycine), 19 (lysine), 20 (isoleucine), 21 (serine), 22 (cysteine), 25 (serine), 26 (glycine), 28 (threonine), 29 (phenylalanine), 32 (tyrosine), 36 (tryptophan), 37 (valine), 38 (arginine/lysine), 39 (glutamine), 41 (proline), 43 (lysine), 44 (glycine), 45 (leucine), 46 (glutamate), 47 (tryptophan), 51 (isoleucine), 67 (arginine/lysine), 73 (aspartate), 75 (serine), 80 (tyrosine), 85 (serine), 86 (leucine), 87 (arginine), 89 (glutamate), 90 (aspartate), 91 (threonine), 92 (alanine), 93 (valine), 94 (tyrosine), 95 (tyrosine), 96 (cysteine), 100 (tryptophan), 101 (asparagine), 105 (tryptophan), 106 (glycine), 107 (glutamine), 108 (glycine), 109 (threonine), 112 (threonine), 113 (valine), 114 (serine), or 115 (serine) (linear numbering as shown in FIG. 4A).

In one embodiment, the heavy chain immunoglobulin of the anti-PSMA antibody, or antigen-binding fragment thereof, includes one or more of:

a framework region 1 having at least one, two, three, four, five, six, seven, eight, nine, ten, eleven, twelve, thirteen amino acids selected from the group consisting of residue 1 (glutamate), 2 (valine), 4 (leucine), 7 (serine), 8 (glycine), 11 (leucine), 14 (proline), 15 (glycine), 19 (lysine), 20 (isoleucine), 21 (serine), 22 (cysteine), and 25 (serine) (linear numbering as shown in FIG. 4A);

a CDR1 having at least one, two, three, four amino acids selected from the group consisting of residue 26 (glycine), 28 (threonine), 29 (phenylalanine), and 32 (tyrosine) (linear numbering as shown in FIG. 4A);

a framework region 2 having at least one, two, three, four, five, six, seven, eight, nine, ten amino acids selected from the group consisting of residue 36 (tryptophan), 37 (valine), 38 (arginine/lysine), 39 (glutamine), 41 (proline), 43 (lysine), 44 (glycine), 45 (leucine), 46 (glutamate), and 47 (tryptophan) (linear numbering as shown in FIG. 4A);

a CDR2 having at least one isoleucine at position 51 (linear numbering as shown in FIG. 4A);

a framework region 3 having at least one, two, three, four, five, six, seven, eight, nine, ten, eleven, twelve, thirteen, fourteen amino acids selected from the group consisting of residue 67 (arginine/lysine), 73 (aspartate), 75 (serine), 80 (tyrosine), 85 (serine), 86 (leucine), 87 (arginine), 89 (glutamate), 90 (aspartate), 91 (threonine), 92 (alanine), 93 (valine), 94 (tyrosine), 95 (tyrosine), and 96 (cysteine) (linear numbering as shown in FIG. 4A);

a CDR3 having at least one, two amino acids selected from the group consisting of residue 100 (tryptophan) and 101 (asparagine) (linear numbering as shown in FIG. 4A); or a framework region 4 having at least one, two, three, four, five, six, seven, eight, nine amino acids selected from the group consisting of residue 105 (tryptophan), 106 (glycine), 107 (glutamine), 108 (glycine), 109 (threonine), 112 (threonine), 113 (valine), 114 (serine), and 115 (serine) (linear numbering as shown in FIG. 4A).

In yet another embodiment, the light chain immunoglobulin of the modified anti-PSMA antibody, or antigen-binding fragment thereof, includes a light chain variable region comprising at least one, two, three, four, five, six, seven, eight, nine, ten, eleven, twelve, thirteen, fourteen, twenty, thirty, forty, fifty, sixty, or seventy amino acids chosen from one or more of the following residues and located at a position chosen from one or more of: residue 2 (isoleucine), 4 (methionine), 5 (threonine), 6 (glutamine), 8 (proline), 10 (serine), 12 (serine), 14 (serine), 16 (glycine), 17 (glutamate/aspartate), 18 (arginine), 20 (threonine), 21 (leucine), 22 (threonine), 23 (cysteine), 24 (lysine), 25 (alanine), 26 (serine), 29 (valine), 30 (glycine), 31 (threonine), 33 (valine), 35 (tryptophan), 36 (tyrosine), 37 (glutamine), 38 (glutamine), 39 (lysine), 40 (proline), 43 (serine), 44 (proline), 45 (lysine), 47 (leucine), 48 (isoleucine), 49 (tyrosine), 51 (alanine), 52 (serine), 54 (arginine), 56 (threonine), 57 (glycine), 59 (proline), 61 (arginine), 62 (phenylalanine), 63 (serine), 64 (glycine), 65 (serine), 66 (glycine), 67 (serine), 68 (glycine), 69 (threonine), 70 (aspartate), 71 (phenylalanine), 73 (leucine), 74 (threonine), 75 (threonine), 76 (serine), 77 (serine), 79 (glutamine), 81 (glutamate), 82 (aspartate), 85 (aspartate), 86 (tyrosine), 87 (tyrosine), 88 (cysteine), 90 (glutamine), 95 (proline), 97 (threonine), 98 (phenylalanine), 99 (glycine), 101 (glycine), 102 (threonine), 103 (lysine), 105 (glutamate/aspartate), or 107 (lysine) (linear numbering as in FIG. 4B).

In one embodiment, the light chain immunoglobulin of the anti-PSMA antibody, or antigen-binding fragment thereof, includes one or more of:

a framework region 1 having at least one, two, three, four, five, six, seven, eight, nine, ten, eleven, twelve, fourteen, fifteen amino acids selected from the group consisting of residue 2 (isoleucine), 4 (methionine), 5 (threonine), 6 (glutamine), 8 (proline), 10 (serine), 12 (serine), 14 (serine), 16 (glycine), 17 (glutamate/aspartate), 18 (arginine), 20 (threonine), 21 (leucine), 22 (threonine), and 23 (cysteine) (linear numbering as shown in FIG. 4B);

a CDR1 having at least one, two, three, four, five, six, seven amino acids selected from the group consisting of residue 24 (lysine), 25 (alanine), 26 (serine), 29 (valine), 30 (glycine), 31 (threonine), and 33 (valine) (linear numbering as shown in FIG. 4B);

a framework region 2 having at least one, two, three, four, five, six, seven, eight, nine, ten, eleven, twelve amino acids selected from the group consisting of residue 35 (tryptophan), 36 (tyrosine), 37 (glutamine), 38 (glutamine), 39 (lysine), 40 (proline), 43 (serine), 44 (proline), 45 (lysine), 47 (leucine), 48 (isoleucine), and 49 (tyrosine) (linear numbering as shown in FIG. 4B);

a CDR2 having at least one, two, three, four amino acids selected from the group consisting of residue 51 (alanine), 52 (serine), 54 (arginine), and 56 (threonine) (linear numbering as shown in FIG. 4B);

a framework region 3 having at least one, two, three, four, five, six, seven, eight, nine, ten, eleven, twelve, thirteen, fourteen, fifteen, twenty, twenty-one, twenty-two, twenty-three, twenty-four amino acids selected from the group consisting of residue 59 (proline), 61 (arginine), 62 (phenylalanine), 63 (serine), 64 (glycine), 65 (serine), 66 (glycine), 67 (serine), 68 (glycine), 69 (threonine), 70 (aspartate), 71 (phenylalanine), 73 (leucine), 74 (threonine), 75 (threonine), 76 (serine), 77 (serine), 79 (glutamine), 81 (glutamate), 82 (aspartate), 85 (aspartate), 86 (tyrosine), 87 (tyrosine), and 88 (cysteine) (linear numbering as shown in FIG. 4B);

a CDR3 having at least one, two, three, four amino acids selected from the group consisting of residue 90 (glutamine), 95 (proline), 97 (threonine), and 98 (phenylalanine) (linear numbering as shown in FIG. 4B); or a framework region 4 having at least one, two, three, four, five, six amino acid selected from the group consisting of residue 99 (glycine), 101 (glycine), 102 (threonine), 103 (lysine), 105 (glutamate/aspartate), and 107 (lysine) (linear numbering as shown in FIG. 4B).

Other Methods of Producing Anti-PSMA Antibodies

Monoclonal anti-PSMA antibodies can also be generated by other methods known to those skilled in the art of recombinant DNA technology.

As used herein, "an in vitro generated" "antibody" or "immunoglobulin" refers to an immunoglobulin where all or part of the variable region, e.g., one or more or all CDRs, is generated in a non-immune cell selection, e.g., an in vitro phage display, protein chip or any other method in which candidate sequences can be tested for their ability to bind to an antigen.

An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al., 1991, *Biotechniques* 11:152–156). A similar strategy can also be used to amplify human heavy and light chain variable regions from human antibodies (Larrick et al., 1991, *Methods: Companion to Methods in Enzymology* 2:106–110).

In an illustrative embodiment, RNA is isolated from B lymphocytes, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J.* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible (Gly$_4$-Ser)$_3$ linker can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the antigen, or peptide fragment thereof, to identify and isolate packages that express an antibody having specificity for the antigen. Nucleic acid encoding the selected antibody can be recovered from the display package (e.g., from the phage genome) and subcloned into other expression vectors by standard recombinant DNA techniques.

Specific antibodies with high affinities for a surface protein can be made according to methods known to those in the art, e.g., methods involving screening of libraries (Ladner, R. C., et al., U.S. Pat. No. 5,233,409; Ladner, R. C., et al., U.S. Pat. No. 5,403,484). Further, the methods of these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence information, by a modeling procedure using previously determined three-dimensional structures from other antibodies obtained from NMR studies or crystallographic data. See for example Bajorath, J. and S. Sheriff, 1996, *Proteins: Struct., Funct., and Genet.* 24 (2), 152–157; Webster, D. M. and A. R. Rees, 1995, "Molecular modeling of antibody-combining sites," in S. Paul, Ed., *Methods in Molecular Biol.* 51, Antibody Engineering Protocols, Humana Press, Totowa, N.J., pp 17–49; and Johnson, G., Wu, T. T. and E. A. Kabat, 1995, "Seqhunt: A program to screen aligned nucleotide and amino acid sequences," in *Methods in Molecular Biol.* 51, *op. cit.*, pp 1–15.

An antigen-binding region can also be obtained by screening various types of combinatorial libraries with a desired binding activity, and to identify the active species, by methods that have been described.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are described above.

Other techniques include affinity chromatography with an appropriate "receptor" to isolate binding agents, followed by identification of the isolated binding agents or ligands by conventional techniques (e.g., mass spectrometry and NMR). Preferably, the soluble receptor is conjugated to a label (e.g., fluorophores, calorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library (see, e.g., W. C. Still et al., International Application WO 94/08051). In general, this method features the use of inert but readily detectable tags, that are attached to the solid support or to the compounds. When an active compound is detected, the identity of the compound is determined by identification of the unique accompanying tag. This tagging method permits the synthesis of large libraries of compounds which can be identified at very low levels among to total set of all compounds in the library.

Anti-PSMA antibody that are not intact antibodies are also useful in this invention. Such antibodies may be derived from any of the antibodies described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

Antibody fragments may also be produced by chemical methods, e.g., by cleaving an intact antibody with a protease, such as pepsin or papain, and optionally treating the cleaved product with a reducing agent. Alternatively, useful fragments may be produced by using host cells transformed with truncated heavy and/or light chain genes.

Monoclonal, chimeric and humanized antibodies, which have been modified by, e.g., deleting, adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others.

In one embodiment, the constant region of the antibody can be replaced by another constant region from, e.g., a different species. This replacement can be carried out using molecular biology techniques. For example, the nucleic acid encoding the VL or VH region of a antibody can be converted to a full-length light or heavy chain gene, respectively, by operatively linking the VH or VL-encoding nucleic acid to another nucleic acid encoding the light or heavy chain constant regions. The sequences of human light and heavy chain constant region genes are known in the art. Preferably, the constant region is human, but constant constant variable regions from other species, e.g., rodent (e.g., mouse or rat), primate, camel, rabbit, can also be used. Constant regions from these species are known in the art (see e.g., Kabat, E. A., et al. (1991) *Sequences of Proteins of Immunological Interest, Fifth Edition*, U.S. Department of Health and Human Services, NIH Publication No. 91-3242).

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and US 5,648,260, the contents of all of which are hereby incorporated by reference). Similar type of alterations could be described, which if applied to immunoglobulins of murine or other species, would reduce or eliminate these functions.

An anti-PSMA antibody, or antigen-binding fragment thereof, can be derivatized or linked to another functional molecule (e.g., another peptide or protein). Accordingly, the antibodies and antibody portions of the invention are intended to include derivatized and otherwise modified forms of the antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized (or labeled) to include fluorescent compounds, various enzymes, prosthetic groups, luminescent materials, bioluminescent materials, fluorescent emitting metal atoms, e.g., europium (Eu), and other anthamides, and radioactive materials (described below). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibodies can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An anti-PSMA antibody or antigen-binding fragment thereof may be conjugated to a another molecular entity, typically a label or a therapeutic (e.g., a cytotoxic or cytostatic) agent or moiety.

Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rb). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The anti-PSMA antibodies can be radiolabeled using techniques known in the art. For example, the method includes contacting an anti-PSMA antibody, e.g. an anti-PSMA antibody described herein, with a chelating agent, e.g., 1,4,7,10-tetraazacyclododecane-N,N',N",N'''-tetraacetic acid (DOTA), to thereby produce a conjugated antibody. The conjugated antibody is radiolabeled with a radioisotope, e.g., $^{111}$Indium, $^{90}$Yttrium and $^{177}$Lutetium, to thereby produce a labeled anti-PSMA antibody. Detailed procedures for radiolabeling an anti-PSMA antibody are described in more detail in the sections below and the appended examples. For example, the anti-PSMA antibodies can be radiolabeled with $^{111}$Indium, $^{90}$Yttrium and $^{177}$Lutetium by coupling with 1,4,7,10-tetraazacyclododecane-N,N',N",N'''-tetraacetic acid (DOTA) as described in U.S. Ser. No. 60/295,214, filed on Jun. 1, 2001, the contents of which are incorporated by reference in its entirety. Detailed experimental protocols for chelating anti-PSMA antibodies are described in Example 15 of U.S. Ser. No. 60/295,214, which is specifically incorporated by reference in the present application and is reproduced below in the examples.

As is discussed above, the antibody can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol or DM1 (see U.S. Pat. No. 5,208,020), CC-1065 (see U.S. Pat. Nos. 5,475,092, 5,585,499, 5,846,545) calicheamicin, and analogs or homologs thereof. The maytansinoid can be, for example, maytansinol or a maytansinol analogue. Examples of maytansinol analogues include those having a modified aromatic ring (e.g., C-19-decloro, C-20-demethoxy, C-20-acyloxy) and those having modifications at other positions (e.g., C-9-CH, C-14-alkoxymethyl, C-14-hydroxymethyl or aceloxymethyl, C-15-hydroxy/acyloxy, C-15-methoxy, C-18-N-demethyl, 4,5-deoxy). Maytansinol and maytansinol analogues are described, for example, in U.S. Pat. No. 6,333,410, the contents of which is incorporated herein by reference. The calicheamicin can be, for example, a bromo-complex calicheamicin (e.g., an alpha, beta or gamma bromo-complex), an iodo-complex calicheamicin (e.g., an alpha, beta or gamma iodo-complex), or analogs and mimics thereof. Bromo-complex calicheamicins include $\alpha_1$-BR, $\alpha_2$-BR, $\alpha_3$-BR, $\alpha_4$-BR, $\beta_1$-BR, $\beta_2$-BR and $\gamma_1$-BR. Iodo-complex calicheamicins include $\alpha_1$-I, $\alpha_2$-I, $\alpha_3$-I, $\beta_2$-I, $\beta_2$-I, $\delta_1$-I and $\gamma_1$-BR. Calicheamicin and mutants, analogs and mimics thereof are described, for example, in U.S. Pat. No. 4,970,198, issued Nov. 13, 1990, U.S. Pat. No. 5,264,586, issued Nov. 23, 1993, U.S. Pat. No. 5,550,246, issued Aug. 27, 1996, U.S. Pat. No. 5,712,374, issued Jan. 27, 1998, and U.S. Pat. No. 5,714,586, issued Feb. 3, 1998, the contents of which are incorporated herein by reference. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

The conjugates of the invention can be used for modifying a given biological response. The therapeutic agent is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Nucleic Acids, Vectors and Host Cells

Isolated nucleic acid, vector and host cell compositions that can be used for recombinant expression of the modified antibodies and antigen-binding fragments of the invention are disclosed. In one embodiment, a first and second isolated nucleic acid comprising a nucleotide sequence encoding heavy and light chain variable regions, respectively, of an anti-PSMA antibody, e.g., a modified anti-PSMA antibody (e.g., a deimmunized J591 or J415 anti-PSMA antibody), or an antigen fragment thereof, are provided.

The nucleotide and amino acid sequence of the modified (deimmunized) anti-PSMA J591 immunoglobulin light chain variable region is shown in FIGS. 5B (SEQ ID NO:25 and 22, respectively). The non-coding complementary nucleotide sequence is also shown in FIG. 5B (SEQ ID NO:26). The J591 deimmunized anti-PSMA antibody light chain variable region contains the following regions: an FR1 domain corresponding to about amino acid residues 1–23 of SEQ ID NO:22 (linear numbering; see also SEQ ID NO:13), which is encoded by about nucleotides 261–329 of SEQ ID NO:25; a CDR1 domain corresponding to about amino acid residues 24–34 of SEQ ID NO:22 (linear numbering; see also SEQ ID NO:4), which is encoded by about nucleotides 330–362 of SEQ ID NO:25; an FR2 domain corresponding to about amino acid residues 35–49 of SEQ ID NO:22 (linear numbering; see also SEQ ID NO:14), which is encoded by about nucleotides 363–407 of SEQ ID NO:25; a CDR2 domain corresponding to about amino acid residues 50–56 of SEQ ID NO:22 (linear numbering; see SEQ ID NO:5), which is encoded by about nucleotides 408–428 of SEQ ID NO:25; an FR3 domain corresponding to about amino acid residues 57–88 of SEQ ID NO:22 (linear numbering; see also SEQ ID NO:15), which is encoded by about nucleotides 429–524 of SEQ ID NO:25; a CDR3 domain corresponding to about amino acid residues 89–97 of SEQ ID NO:22 (linear numbering; see also SEQ ID NO:6), which is encoded by about nucleotides 525–551 of SEQ ID NO:25; and an FR4 domain corresponding to about amino acid residues 98–107 of SEQ ID NO:22 (linear numbering; see also SEQ ID NO:16), which is encoded by about nucleotides 552–581 of SEQ ID NO:25.

The nucleotide and amino acid sequence of the modified (deimmunized) anti-PSMA J591 immunoglobulin heavy chain variable region is shown in FIG. 5A (SEQ ID NO:23 and 21, respectively). The non-coding complementary sequence is also shown in FIG. 5A (SEQ ID NO:24). The J591 deimmunized anti-PSMA antibody heavy chain variable region contains the following regions: an FR1 domain corresponding to about amino acid residues 1–25 of SEQ ID NO:21 (linear numbering; see also SEQ ID NO:9), which is encoded by about nucleotides 261–335 of SEQ ID NO:23; a CDR1 domain corresponding to about amino acid residues 26–35 of SEQ ID NO:21 (linear numbering; see also SEQ ID NO:1), which is encoded by about nucleotides 336–365 of SEQ ID NO:23; an FR2 domain corresponding to about amino acid residues 36–49 of SEQ ID NO:21 (linear numbering; see also SEQ ID NO:10), which is encoded by about nucleotides 366–407 of SEQ ID NO:23; a CDR2 domain of corresponding to about amino acid residues 50–66 of SEQ ID NO:21 (linear numbering; see also SEQ ID NO:2), which is encoded by about nucleotides 408–458 of SEQ ID NO:23; an FR3 domain corresponding to about amino acid residues 67–98 of SEQ ID NO:21 (linear numbering; see also SEQ ID NO:11), which is encoded by about nucleotides 459–554 of SEQ ID NO:23; a CDR3 domain corresponding to about amino acid residues 99–104 of SEQ ID NO:21 (linear numbering; see also SEQ ID NO:3), which is encoded by about nucleotides 555–572 of SEQ ID NO:23; and an FR4 domain corresponding to about amino acid residues 105–115 of SEQ ID NO:21 (linear numbering; see also SEQ ID NO:9), which is encoded by about nucleotides 573–605 of SEQ ID NO:23.

The nucleotide and amino acid sequence of the modified (deimmunized) anti-PSMA J415 immunoglobulin light chain variable region (J415DIVK1) is shown in FIG. 8A (SEQ ID NO:56 and 57, respectively). The non-coding complementary nucleotide sequence of J415DIVK1 is also shown in FIG. 9A (SEQ ID NO:58). The J415 deimmunized anti-PSMA antibody light chain variable region contains the following regions: an FR1 domain corresponding to about amino acid residues 1–23 of SEQ ID NO:57 (linear numbering; see also SEQ ID NO:41), which is encoded by about nucleotides 261–329 of SEQ ID NO:56; a CDR1 domain corresponding to about amino acid residues 24–34 of SEQ ID NO:57 (linear numbering; see also SEQ ID NO:32), which is encoded by about nucleotides 330–362 of SEQ ID NO:56; an FR2 domain corresponding to about amino acid residues 35–49 of SEQ ID NO:57 (linear numbering; see also SEQ ID NO:42), which is encoded by about nucleotides 363–407 of SEQ ID NO:56; a CDR2 domain corresponding to about amino acid residues 50–56 of SEQ ID NO:57 (linear numbering; see also SEQ ID NO:33), which is encoded by about nucleotides 408–428 of SEQ ID NO:56; an FR3 domain corresponding to about amino acid residues 57–88 of SEQ ID NO:57 (linear numbering; see also SEQ ID NO:43), which is encoded by about nucleotides 429–524 of SEQ ID NO:56; a CDR3 domain corresponding to about amino acid residues 89–97 of SEQ ID NO:57 (linear numbering; see also SEQ ID NO:34), which is encoded by about nucleotides 525–551 of SEQ ID NO:56; and an FR4 domain corresponding to about amino acid residues 98–107 of SEQ ID NO:57 (linear numbering; see also SEQ ID NO:44), which is encoded by about nucleotides 552–581 of SEQ ID NO:56. The nucleotide and amino acid sequences of the preferred modified (deimmunized) anti-PSMA J415 immunoglobulin light chain variable region (J415DIVK5) are shown in SEQ ID NO:50 and 52, respectively; J415DIVK5 can be broken down into its component sequences in a manner identical to that shown above for J415DIVK1. 1002191 The nucleotide and amino acid sequence of the modified (deimmunized) anti-PSMA J415 immunoglobulin heavy chain variable region is shown in FIG. 8A (SEQ ID NO:53 and 54, respectively). The non-coding complementary sequence is also shown in FIG. 8A (SEQ ID NO:55). The J415 deimmunized anti-PSMA antibody heavy chain variable region contains the following regions: an FR1 domain corresponding to about amino acid residues 1–25 of SEQ ID NO:54 (linear numbering; see also SEQ ID NO:37), which is encoded by about nucleotides 261–335 of SEQ ID NO:53; a CDR1 domain corresponding to about amino acid residues 26–35 of SEQ ID NO:54 (linear numbering; see also SEQ ID NO:29), which is encoded by about nucleotides 336–365 of SEQ ID NO:53; an FR2 domain corresponding to about amino acid residues 36–49 of SEQ ID NO:54 (linear numbering; see also SEQ ID NO:38), which is encoded by about nucleotides 366–407 of SEQ ID NO:53; a CDR2 domain corresponding to about amino acid residues 50–68 of SEQ ID NO:54 (linear numbering; see also SEQ ID NO:30), which is encoded by about nucleotides 408–464 of SEQ ID NO:53; an FR3 domain corresponding to about amino acid residues 69–100 of SEQ ID NO:54 (linear numbering; see also SEQ ID NO:39), which is encoded by about nucleotides 465–560 of SEQ ID NO:53; a CDR3 domain corresponding to about amino acid residues 101–105 of SEQ ID NO:54 (linear numbering; see also SEQ ID NO:31), which is encoded by about nucleotides 561–575 of SEQ ID NO:53; and an FR4 domain corresponding to about amino acid residues 106–116 of SEQ ID NO:54 (linear numbering; see also SEQ ID NO:40), which is encoded by about nucleotides 576–608 of SEQ ID NO:53. The nucleotide and amino acid sequences of the preferred modified (deimmunized) anti-PSMA J415 immunoglobulin heavy chain variable region (J415DIVH4) are shown in SEQ ID NO:51 and 49, respectively; J415DIVH4 can be broken down into its component sequences in a manner identical to that shown above for J415DIVH1.

It will be appreciated by the skilled artisan that nucleotide sequences encoding anti-PSMA modified antibodies (e.g., FR domains, e.g., FR1–4), can be derived from the nucleotide and amino acid sequences described in the present application using the genetic code and standard molecular biology techniques.

In one embodiment, the isolated nucleic acid comprises an anti-PSMA modified antibody heavy chain variable region nucleotide sequence having a nucleotide sequence as shown in FIG. 5A (SEQ ID NO:23), FIG. 8A (SEQ ID NO:53) or SEQ ID NO:51 (for J415DIVH4) or a complement thereof (e.g., SEQ ID NO:24 or SEQ ID NO:55), the nucleotide sequence of the heavy chain variable region of the antibody produced by the NSO cell line having ATCC Accession Number PTA-3709 or PTA-4174 or a complement thereof; a sequence at least 85%, 90%, 95%, 99% or more identity thereto; or a sequence capable of hybridizing under stringent conditions described herein (e.g., highly stringent conditions) to a nucleotide sequence shown in FIG. 5A (SEQ ID NO:23), FIG. 8A (SEQ ID NO:53), SEQ ID NO:51, or a complement thereof (e.g., SEQ ID NO:24 or SEQ ID NO:55), or the nucleotide sequence of the heavy chain variable region of the antibody produced by the NSO cell line having ATCC Accession Number PTA-3709 or PTA-4174, or a complement thereof.

In another embodiment, the isolated nucleic acid encodes an anti-PSMA modified antibody heavy chain variable region amino acid sequence having an amino acid sequence as shown in FIG. 3A (SEQ ID NO:21) or FIG. 6 (e.g., SEQ ID NO:49), or the amino acid sequence of the heavy chain variable region of the antibody produced by the NSO cell line having ATCC Accession Number PTA-3709 or PTA-4174; a sequence at least 85%, 90%, 95%, 99% or more identical thereto; or a sequence capable of hybridizing under stringent conditions described herein (e.g., highly stringent conditions) to a nucleotide sequence encoding the amino acid sequence as shown in FIG. 3A (SEQ ID NO:21), FIG. 6 (e.g., SEQ ID NO:49), or the amino acid sequence of the heavy chain variable region of the antibody produced by the NSO cell line having ATCC Accession Number PTA-3709 or PTA-4174.

In another embodiment, the isolated nucleic acid comprises a nucleotide sequence encoding at least one, preferably two, and most preferably three, CDRs of the heavy chain variable region of the anti-PSMA antibody chosen from the amino acid sequences of SEQ ID NO:1, 2, and 3, or 29, 30 and 31, or 93, 94, and 95, or 99, 100 and 101, or a CDR sequence which differs by one or two amino acids from the sequences described herein. In yet another embodiment, the isolated nucleic acid comprises a nucleotide sequence encoding CDRs 1, 2, or 3 shown in FIG. 5A (SEQ ID NO:23), in SEQ ID NO:51, in FIG. 8A (SEQ ID NO:125), in FIG. 10A (SEQ ID NO:73), or in FIG. 12A (SEQ ID NO:83), or a complement thereof, or a sequence encoding a CDR that differs by one or two amino acids from the sequences described herein.

In another embodiment, the isolated nucleic acid comprises a nucleotide sequence encoding at least one, preferably two, three and most preferably four amino acid sequences from the heavy chain variable framework region of the anti-PSMA modified antibody chosen from SEQ ID NO:9, 10, 11 and 12, or 37, 38, 39 and 40, or a sequence at least 85%, 90%, 95%, 99% or more identical thereto.

In yet another embodiment, the isolated nucleic acid comprises an anti-PSMA modified antibody light chain variable region nucleotide sequence having a sequence as shown in FIG. 5B (SEQ ID NO:25), FIG. 9A (SEQ ID NO:56), or SEQ ID NO:52, or a complement thereof (e.g., SEQ ID NO:26 or 58), or the nucleotide sequence of the light chain variable region of the antibody produced by the NSO cell line having ATCC Accession Number PTA-3709 or PTA-4174; a sequence at least 85%, 90%, 95%, 99% or more identical thereto; or a sequence capable of hybridizing under stringent conditions described herein (e.g., highly stringent conditions) to the nucleotide sequence as shown in FIG. 5B (SEQ ID NO:25), FIG. 9A (SEQ ID NO:56), SEQ ID NO:52, or a complement thereof (e.g., SEQ ID NO:26 or 58), or the nucleotide sequence of the light chain variable region of the antibody produced by the NSO cell line having ATCC Accession Number PTA-3709 or PTA-4174, or a complement thereof. In another embodiment, the isolated nucleic acid encodes an anti-PSMA modified antibody light chain variable region amino acid sequence having a sequence as shown in FIG. 3B (SEQ ID NO:22) or in FIG. 7 (e.g., SEQ ID NO:50), the amino acid sequence of the light chain variable region of the antibody produced by the NSO cell line having ATCC Accession Number PTA-3709 or PTA-4174; a sequence at least 85%, 90%, 95%, 99% or more identity thereto; or a sequence capable of hybridizing under stringent conditions described herein (e.g., highly stringent conditions) to a nucleotide sequence encoding the amino acid sequence as shown in FIG. 3B (SEQ ID NO:22) or in FIG. 7 (SEQ ID NO:50), or the amino acid sequence of the light chain variable region of the antibody produced by the NSO cell line having ATCC Accession Number PTA-3709 or PTA-4174.

In another embodiment, the isolated nucleic acid comprises a nucleotide sequence encoding at least one, preferably two, and most preferably three, CDRs of the light chain variable region of the anti-PSMA antibody chosen from the amino acid sequences of SEQ ID NO:4, 5, and 6, or 32, 33, and 34, or 96, 97, and 98, or 102, 103, and 104, or a sequence encoding a CDR which differs by one or two amino acids from the sequences described herein.

In yet another embodiment, the isolated nucleic acid comprises a nucleotide sequence encoding CDRs 1–3 of the light chain variable nucleotide sequence shown in SEQ ID NO:25, or a sequence encoding a CDR which differs by one or two amino acids from the sequences described herein. In another embodiment, the isolated nucleic acid comprises a nucleotide sequence encoding at least one, preferably two, three and most preferably four amino acid sequences from the light chain variable framework region of the anti-PSMA modified antibody chosen from SEQ ID NO:13, 14, 15, and 16, or 41, 42, 43, and 44, or a sequence at least 85%, 90%, 95%, 99% or more identical thereto.

In a preferred embodiment, there is an isolated first and second nucleic acid which have nucleotide sequences encoding a light chain and the heavy chain variable regions of an anti-PSMA antibody, respectively, wherein each isolated nucleic acid has at least one, two, three, four, five and preferably all CDRs chosen from the amino acid sequences of SEQ ID NO:1, 2, 3, 4, 5, and 6, or 29, 30, 31, 32, 33 and 34, or 93, 94, 95, 96, 97, and 98, or 99, 100, 101, 102, 103, and 104, or sequence encoding a CDR which differs by one or two amino acids from the sequences described herein.

The nucleic acid can encode only the light chain or the heavy chain variable region, or can also encode an antibody light or heavy chain constant region, operatively linked to the corresponding variable region. In one embodiment, the light chain variable region is linked to a constant region chosen from a kappa or a lambda constant region. Preferably, the light chain constant region is from a lambda type (e.g., a human type lambda). In another embodiment, the heavy chain variable region is linked to a heavy chain constant region of an antibody isotype selected from the group consisting of IgG (e.g., IgG1, IgG2, IgG3, IgG4), IgM, IgA1, IgA2, IgD, and IgE. Preferably, the heavy chain constant region is from an IgG (e.g., an IgG1) isotype, e.g., a human IgG1.

Nucleic acids of the invention can be chosen for having codons, which are preferred, or non-preferred, for a particular expression system. For example, the nucleic acid can be one in which at least one codon, at preferably at least 10%, or 20% of the codons has been altered such that the sequence is optimized for expression in *E. coli*, yeast, human, insect, NSO, or CHO cells.

In a preferred embodiment, the nucleic acid differs (e.g., differs by substitution, insertion, or deletion) from that of the sequences provided, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences. The differences are, preferably, differences or changes at nucleotides encoding a non-essential residue(s) or a conservative substitution(s).

In one embodiment, the first and second nucleic acids are linked, e.g., contained in the same vector. In other embodiments, the first and second nucleic acids are unlinked, e.g., contained in different vectors.

In another aspect, the invention features host cells and vectors (e.g., recombinant expression vectors) containing the nucleic acids, e.g., the first and second nucleic acids, of the invention.

Prokaryotic or eukaryotic host cells may be used. The terms "host cell" and "recombinant host cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic, e.g., bacterial cells such as *E. coli*, or eukaryotic, e.g., insect cells, yeast, or preferably mammalian cells (e.g., cultured cell or a cell line). Other suitable host cells are known to those skilled in the art.

Preferred mammalian host cells for expressing the anti-PSMA antibodies, or antigen-binding fragments thereof, include Chinese Hamster Ovary (CHO cells) (including dhfr-CHO cells, described in Urlaub and Chasin, (1980) *Proc. Natl. Acad. Sci. USA* 77:4216–4220, used with a DHFR selectable marker, e.g., as described in R. J. Kaufman and P. A. Sharp (1982) *Mol. Biol.* 159:601–621), lymphocytic cell lines, e.g., NSO myeloma cells and SP2 cells, COS cells, and a cell from a transgenic animal, e.g., e.g., mammary epithelial cell.

In another aspect, the invention features a vector, e.g., a recombinant expression vector. The recombinant expression vectors of the invention can be designed for expression of the modified antibodies, or an antigen-binding fragment thereof, in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to an antibody encoded therein, usually to the constant region of the recombinant antibody.

In addition to the antibody chain genes, the recombinant expression vectors of the invention carry regulatory sequences that are operatively linked and control the expression of the antibody chain genes in a host cell.

In an exemplary system for recombinant expression of a modified antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Other PSMA Binding Agents

Also useful in the methods of this invention are PSMA mimetic agents. These agents, which include peptides, semi-peptidic compounds or non-peptidic compounds (e.g., small organic molecules), are inhibitors of PSMA activity.

In preferred embodiments, the agent is a member of a combinatorial library, e.g., a peptide or organic combinatorial library, or a natural product library. In a preferred embodiment, a plurality of test compounds, e.g., library members, includes at least 10, $10^2$, $10^3$, $10^4$, $10^5$, $10^6$, $10^7$, or $10^8$ compounds. In a preferred embodiment, the plurality of test compounds, e.g., library members, share a structural or functional characteristic.

In one embodiment, the invention provides libraries of PSMA binding agents. The synthesis of combinatorial libraries is well known in the art and has been reviewed (see, e.g., E. M. Gordon et al., *J. Med. Chem.* (1994) 37:1385–1401; DeWitt, S. H.; Czarnik, A. W. *Acc. Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds of the invention can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allow to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen-binding site. It will be appreciated that a wide variety of peptidic, peptidomimetic, or non-peptidic compounds can be readily generated in this way.

The "split-pool" strategy results in a library of peptides, e.g., inhibitors, which can be used to prepare a library of test compounds of the invention. In another illustrative synthesis, a "diversomer library" is created by the method of Hobbs DeWitt et al. (*Proc. Natl. Acad. Sci. U.S.A.* 90:6909 (1993)). Other synthesis methods, including the "tea-bag" technique of Houghten (see, e.g., Houghten et al., *Nature* 354:84–86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

In one embodiment, compounds of the invention can be screened for the ability to interact with PSMA polypeptide by assaying the activity of each compound to bind directly to the polypeptide, e.g., by incubating the test compound with a PSMA polypeptide and a lysate, in one well of a multiwell plate, such as a standard 96-well microtiter plate. In this embodiment, the activity of each individual compound can be determined. A well or wells having no test compound can be used as a control. After incubation, the activity of each test compound can be determined by assaying each well. Thus, the activities of a plurality of test compounds can be determined in parallel.

In still another embodiment, large numbers of test compounds can be simultaneously tested for binding activity. For example, test compounds can be synthesized on solid resin beads in a "one bead-one compound" synthesis; the compounds can be immobilized on the resin support through a photolabile linker. A plurality of beads (e.g., as many as 100,000 beads or more) can then be combined with yeast cells and sprayed into a plurality of "nano-droplets", in which each droplet includes a single bead (and, therefore, a single test compound). Exposure of the nano-droplets to UV light then results in cleavage of the compounds from the beads. It will be appreciated that this assay format allows the screening of large libraries of test compounds in a rapid format.

Combinatorial libraries of compounds can be synthesized with "tags" to encode the identity of each member of the library (see, e.g., W. C. Still et al., U.S. Pat. No. 5,565,324 and PCT Publication Nos. WO 94/08051 and WO 95/28640). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels. Such a tagging scheme can be useful, e.g., in the "nano-droplet" screening assay described above, to identify compounds released from the beads.

In preferred embodiments, the libraries of compounds of the invention contain at least 30 compounds, more preferably at least 100 compounds, and still more preferably at least 500 compounds. In preferred embodiments, the libraries of compounds of the invention contain fewer than $10^9$ compounds, more preferably fewer than $10^8$ compounds, and still more preferably fewer than $10^7$ compounds.

Pharmaceutical Compositions

In another aspect, the present invention provides compositions, e.g., pharmaceutically acceptable compositions, which include a PSMA binding agent described herein, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. The carrier is suitable for intravenous, intramuscular, subcutaneous, parenteral, spinal or epidermal administration (e.g., by injection or infusion). Depending on the route of administration, the active compound, i.e., the PSMA binding agent may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1–19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The composition may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection (e.g., by needleless injection). In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The PSMA binding agents can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In some embodiments, pharmaceutical compositions of PSMA binding agents, alone or in combination with other agent, can be delivered or administered topically or by transdermal patches for treating skin disorders, e.g., dermal psoriasis. In those embodiments where the binding agent is a small molecule, oral administration can be used. Additionally, the compositions can be delivered parenterally, especially for treatment of arthritis, such as psoriatic arthritis, and for direct injection of skin lesions. Parenteral therapy is typically intra-dermal, intra-articular, intramuscular or intravenous. PSMA binding agents can be applied, in a cream or oil based carrier, directly to the psoriatic lesions. Alternatively, an aerosol can be used topically. These compounds can also be orally administered.

In general, the route of administration is topical (including administration to the eye, scalp, and mucous membranes), oral, or parenteral. Topical administration is preferred in treatment of skin lesions, including lesions of the scalp, lesions of the cornea (keratitis), and lesions of mucous membranes where such direct application is practical. Shampoo formulations are sometimes advantageous for treating scalp lesions such as seborrheic dermatitis and psoriasis of the scalp. Mouthwash and oral paste formulations can be advantageous for mucous membrane lesions, such as oral lesions and leukoplakia.

Intra-articular injection is a preferred alternative in the case of treating one or only a few (such as 2–6) joints. Additionally, the therapeutic compounds are injected directly into lesions (intra-lesion administration) in appropriate cases. Intra-dermal administration is an alternative for dermal lesions such as those of psoriasis.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other implants, delivery systems, and modules are known to those skilled in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1–20 mg/kg, more preferably 1–10 mg/kg. In one embodiment, the anti-PSMA antibody is administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of a binding agent. A "therapeutically effective amount" refers to an amount effective, at dosages and for periods of time necessary, to achieve the desired therapeutic result. A therapeutically effective amount of the PSMA binding agent may vary according to factors such as the disease state, age, sex, and weight of the individual, and the ability of the antibody or antibody portion to elicit a desired response in the individual. A therapeutically effective amount is also one in which any toxic or detrimental effects of the PSMA binding agent is outweighed by the therapeutically beneficial effects. A "therapeutically effective dosage" preferably inhibits a measurable parameter, relative to untreated subjects. The ability of a compound to inhibit a measurable parameter, e.g., skin lesions, can be evaluated in an animal model system predictive of efficacy in human skin. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Kits

Also within the scope of the invention are kits including the PSMA binding agents of the invention along with instructions on how to use the PSMA agent or the combination of such agents to treat, prevent or detect a disorder described herein, e.g., a skin disorder. In some embodiments, the kit can include one or more other elements including: instructions for use; other reagents, e.g., a label, a therapeutic agent, or an agent useful for chelating, or otherwise coupling, an antibody to a label or therapeutic agent, or a radio protective composition; devices or other materials for preparing the antibody for administration; pharmaceutically acceptable carriers; and devices or other materials for administration to a subject. Instructions for use can include instructions for diagnostic applications of the PSMA binding agent, e.g., anti-PSMA antibodies (or antigen-binding fragment thereof), to detect PSMA, in vitro, e.g., in a sample, e.g., a biopsy or cells from a patient having psoriasis, or in vivo. The instructions can include instructions for therapeutic application including suggested dosages and/or modes of administration, e.g., in a patient with a skin disorder, e.g., psoriasis. Other instructions can include instructions on coupling of the antibody to a chelator, a label or a therapeutic agent, or for purification of a conjugated antibody, e.g., from unreacted conjugation components. As discussed above, the kit can include a label, e.g., any of the labels described herein. As discussed above, the kit can include a therapeutic agent, e.g., a therapeutic agent described herein. The kit can include a reagent useful for chelating or otherwise coupling a label or therapeutic agent to the antibody, e.g., a reagent discussed herein. For example, a macrocyclic chelating agent, preferably 1,4,7, 10-tetraazacyclododecane-N,N',N",N"'-tetraacetic acid (DOTA), can be included. The DOTA can be supplied as a separate component or the DOTA (or other chelator or conjugating agent) can be supplied already coupled to the antibody. Additional coupling agents, e.g., an agent such as N-hydroxysuccinimide (NHS), can be supplied for coupling the chelator, e.g., DOTA, to the antibody. In some applications the antibody will be reacted with other components, e.g., a chelator or a label or therapeutic agent, e.g., a radioisotope, e.g., yttrium or lutetium. In such cases, the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional PSMA binding agents, e.g., anti-PSMA antibodies (or fragments thereof), formulated as appropriate, in one or more separate pharmaceutical preparations.

The kit can further contain a radioprotectant. The radiolytic nature of isotopes, e.g., $^{90}$Yttrium ($^{90}$Y) is known. In order to overcome this radiolysis, radioprotectants may be included, e.g., in the reaction buffer, as long as such radioprotectants are benign, meaning that they do not inhibit or otherwise adversely affect the labeling reaction, e.g., of an isotope, such as of $^{90}$Y, to the antibody.

The formulation buffer of the present invention may include a radioprotectant such as human serum albumin (HSA) or ascorbate, which minimize radiolysis due to yttrium or other strong radionuclides. Other radioprotectants are known in the art and could also be used in the formulation buffer of the present invention, i.e., free radical scavengers (phenol, suffites, glutathione, cysteine, gentisic acid, nicotinic acid, ascorbyl palmitate, HOP(:O)H2I glycerol, sodium formaldehyde sulfoxylate, Na2S20., Na2S203, and S02, etc.). A preferred kit is one useful for radiolabeling a chelator-conjugated protein or peptide with a therapeutic radioisotope for administration to a patient. The kit includes (i) a vial containing chelator-conjugated antibody, (ii) a vial containing formulation buffer for stabilizing and administering the radiolabeled antibody to a patient, and (iii) instructions for performing the radiolabeling procedure. The kit provides for exposing a chelator-conjugated antibody to the radioisotope or a salt thereof for a sufficient amount of time under amiable conditions, e.g., as recommended in the instructions. A radiolabeled antibody having sufficient purity, specific activity and binding specificity is produced. The radiolabeled antibody may be diluted to an appropriate concentration, e.g., in formulation buffer, and administered directly to the patient without further purification. The chelator-conjugated antibody may be supplied in lyophilized form.

Therapeutic and Prophylactic Methods

The methods of this invention are useful to treat, e.g., ablate or kill, an aberrant cell, e.g., an aberrant PSMA-expressing epidermal or a dermal cell, or a non-malignant, non-prostatic, hyperproliferative cell. The method includes contacting the cell, or a vascular endothelial cell proximate to the cell, with a binding agent, e.g., an antibody or antigen-binding fragment thereof, that binds specifically PSMA in an amount sufficient to ablate or kill the cell.

The method of the invention can be used, for example, to treat or prevent a disorder, e.g., a skin disorder (e.g., psoriasis) or a non-malignant, non-prostatic hyperproliferative disorder, by administering to a subject a PSMA-binding agent, e.g., an anti-PSMA antibody or antigen-binding fragment thereof, in an amount effective to treat or prevent such disorder.

The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, e.g., a dermal endothelial, fibroblast, immune cell (e.g., mast cell or macrophage) found in a dermal layer, e.g., the papillary layer or the reticular layer.

The methods of the invention may be practiced on any subject, e.g., a mammal, a higher primate preferably on humans. As used herein, the term "subject" is intended to include human and non-human animals. Preferred human animals include a human patient having a skin disorder as described herein. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc.

Examples of skin disorders that can be treated or prevented using the methods of the invention include psoriasis, psoriatic arthritis, dermatitis (eczema), e.g., exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitites such as seborrheic dermatitis and solar dermatitis; keratoses such as seborrheic keratosis, senile keratosis, actinic keratosis. photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. Preferably, the disorder is dermatitis, e.g., atopic dermatitis or allergic dermatitis, or psoriasis.

Most preferably, the disorder is psoriasis. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

In other embodiments, the skin disorder is an inflammatory or a neoplastic disorder of the dermis. Examples of such disorders include acute febrile neutrophilic dermatosis (Sweet's Syndrome), erythema elevatum diutinum, cutaneous eosinophilic disease, granuloma, malignant atrophic papulosis, dermal neoplasm, dermal pseudoneoplasm, dermal hyperplasia, dermal vascular anomaly, Kaposi's sarcoma, anetoderma and atrophic disorder of the skin.

In yet other embodiments, the skin disorder is an epidermal precancerous or cancerous lesion. For example, the lesion can be chosen from one or more of: an epithelial precancerous lesion, squamous cell carcinoma, basal cell carcinoma, melanoma, benign neoplasia or hyperplasis of melanocytes, keratoacanthoma, a benign epithelial tumor, and cutaneous neuroendocrine carcinoma. Other examples of precancerous or cancerous lesion include cutaneous T cell lymphomas cutaneous T cell lymphoma (e.g., mycosis fungoides), systemic lymphomas with skin infiltrations, and cutaneous pseudolymphomas.

In other embodiments, the skin disorder is a cutaneous disorder of altered reactivity. Examples of such cutaneous disorders include urticaria and angioedema, graft-v-host disease, allergic contact dermatitis, autosensitization dermatitis, atopic dermatitis (atopic eczema), nummular eczematous dermatitis, and vesicular palmoplantar eczema.

In other embodiments, the skin disorder is a skin manifestation of an autoimmune disorder, e.g., a rheumatologic disorder. Examples of rheumatologic disorders that can be treated using the invention include lupus erythematosus, dermatomyositis, scleroderma, systemic necrotizing arteritis, cutaneous necrotizing venulitis, rheumatoid arthritis, Sjögren's Syndrome, Raynaud's phenomenon, and Reiter's syndrome.

In other embodiments, the skin disorder occurs in response to an irritant, e.g., a drug, an infectious agent, food, or environmental irritant. In one embodiment, the irritant is poison ivy.

In other embodiments, the methods of the invention can be used to treat non-malignant, non-prostatic hyperproliferative disorders. Examples of such disorders include autoimmune and inflammatory conditions, including, but not limited to, transplant rejection, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease (e.g., Crohn's disease and ulcerative colitis), aphthous ulcer, iritis, conjunctivitis, keratoconjunctivitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, and allergy such as, atopic allergy.

The methods and compositions of the invention can also be used to treat or prevent disorders involving aberrant activity of a PSMA-expressing cell, e.g., a kidney, liver or brain cell.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schonlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; and hepatic complications of organ or bone marrow transplantation, such as drug toxicity after bone marrow transplantation, graft-versus-host disease and liver rejection, and nonimmunologic damage to liver allografts.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Combination Therapy

The PSMA binding agents, e.g., anti-PSMA antibodies or antigen-binding fragments thereof, may be used in combination with other therapies. For example, the combination therapy can include a composition of the present invention coformulated with, and/or coadministered with, one or more additional therapeutic agents, e.g., one or more anti-cancer agents, cytotoxic or cytostatic agents and/or immunosuppressants. The terms "cytotoxic agent" and "cytostatic agent" are used interchangeably herein and refer to agents that have the property of inhibiting the growth or proliferation (e.g., a cytostatic agent), or inducing the killing, of hyperproliferative cells, e.g., an aberrant skin cell or a T cell.

For example, the PSMA binding agents may be coformulated with, and/or coadministered with, one or more additional antibodies that bind other targets (e.g., antibodies that bind other cytokines or that bind cell surface molecules), including naked antibodies, immunotoxins, and radioconjugates, one or more cytokines, or immunosuppressants, e.g., cyclosporin A or FK506.

For skin disorders, combination of PSMA binding agent with current therapeutic modalities for skin disorders are preferred. Examples of such modalities include light therapy (e.g., UVA, UVB or PUVA); chemotherapy (e.g., methotrexate; retinoid; cyclosporine; etretinate); or topical therapy (e.g., steroid, vitamin (e.g., vitamin D), tar, anthralin, or a macrolide, e.g., tacrolimus). Such combination therapy may advantageously utilize lower dosages of the therapeutic or prophylactic agents. Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

Combinations of PSMA binding agents, e.g., anti-PSMA antibodies, with one or more additional antibodies or ligands that bind other targets (e.g., antibodies that bind other cytokines or that bind cell surface molecules), including naked antibodies, fusion proteins, immunotoxins, and radioconjugates, can be used. Example of antibodies that can be used in combination with PSMA binding agents include antibodies against IL-8 (ABX-IL8 (Abgenix)); complement C5 protein (5G1.1 (Alexion)); CD2 (MEDI-507/BTI-322 (MedImmune/Bio Transplant)); E selectin (CDP 850 (Celltech)); TNF alpha (Remicaide (Centocor)); CD4 (HuMax-CD4 (Genmab)); IL15 (HuMax-IL15 (Genmab/Immunex)); ICAM-3 (ICM3 (Icos); CD64 (MDX-44 (Medarex)); IL2-receptor (Zenepax (PDL)); CD3 (Nuvion (PDL)); and CD11a (Xanelim (Genentech/Xoma)). In addition to the above, immunoglobulin fusion proteins that bind to other targets can be used. For example, immunoglobulin fusions that bind to CD2, e.g., LFA-3-Ig, can be used.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. E.g., the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In a preferred embodiment a delivery of the first treatment and a delivery of the second treatment occur within 1, 2, 5, 10, 15, or 30 days of one another.

The binding agents as described herein can be used as an adjunct to conventional treatments of skin conditions, such as psoriasis. For example, binding agents can be introduced prior to, concurrently with, or after sequential therapy of psoriasis (reviewed in Koo, J. (1999) *J Am Acad Dermatol.* 41(3 Pt 2):S25–8).

In other exemplary embodiments, a PSMA-binding agent can be administered over an extended period of time (e.g., a therapeutic treatment period of twelve weeks). During periods of remission or less active disease, the PSMA-binding agent can be administered alone or in combination with a topical agent (e.g., e.g., steroid, vitamin (e.g., vitamin D), tar, anthralin, or a macrolide, e.g., tacrolimus) and/or phototherapy (e.g., UVA, UVB or PUVA, but preferably, UVB). During periods of active disease, a rapidly acting, but toxic auxiliary agent, such as methotrexate and/or cyclosporin, can be administered for a short treatment period.

In a preferred embodiment, the PSMA-binding agent (e.g., anti-PSMA antibody) or a pharmaceutical composition containing the same is administered systemically (e.g., intravenously, intramuscularly, subcutaneously, intra-articularly, intrathecally, periostally, intratumorally, intralesionally, perilesionally by infusion (e.g., using an infusion device), orally, topically or by inhalation). Preferably, the PSMA-binding agent is administered intramuscularly or intravenously. In other embodiments, the PSMA-binding agent is administered locally (e.g., topically) to an affected area, e.g., a psoriatic lesion.

In one embodiment, the PSMA binding agent as disclosed herein is administered in combination with phototherapy (also referred to herein as "light therapy"). Phototherapy utilizes optical absorption of ultraviolet (UV) radiation by the skin to kill rapidly growing cells and arrest proliferation. At present, both UVA and UVB therapy, which expose the skin to UV radiation between 320–400 nm (UVA radiation) or 290–320 nm (UVB radiation), are effectively and widely used to treat skin conditions. In other embodiments, PUVA therapy, a form of photochemotherapy which involves repeated topical application of psoralen or a psoralen-based compound to an affected region of skin, followed by exposure of that region to UVA radiation, can also be used. In yet other embodiments, photodynamic therapy (PDT) can be used to treat skin conditions, particularly psoriasis and mycosis fungoides. In this method, a photosensitizing agent, which is a drug selectively retained in carcinoma cells, is administered to a subject. Following absorption of light (typically between 320–700 nm, depending on the drug) the photosensitizing agent undergoes a photochemical reaction, resulting in the production of cytotoxic singlet oxygen which eventually leads to tumor vessel destruction in the skin (Anderson, et al. (1992) Arch. Dermatol. 128:1631–1636).

Pharmacogenomics

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. See, for example, Eichelbaum, M. et al. (1996) Clin. Exp. Pharmacol. Physiol. 23:983–985 and Linder, M. W. et al. (1997) Clin. Chem. 43:254–266. Differences in metabolism of therapeutics can lead to severe toxicity or therapeutic failure by altering the relation between dose and blood concentration of the pharmacologically active drug. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment according to that individual's drug response genotype.

Information generated from pharmacogenomic research can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a composition consisting of one or more PSMA binding agents, or derivatized form(s) thereof, to a patient, as a means of treating a disorder, e.g., a skin disorder as described herein.

In one embodiment, a physician or clinician may consider applying knowledge obtained in relevant pharmacogenomics studies when determining whether to administer a pharmaceutical composition, e.g., a composition consisting of one or more PSMA-binding agents, or derivatized form(s) thereof, and optionally a second agent, to a subject. In another embodiment, a physician or clinician may consider applying such knowledge when determining the dosage, e.g., amount per treatment or frequency of treatments, of a pharmaceutical composition, e.g., a pharmaceutical composition as described herein, administered to a patient.

In yet another embodiment, a physician or clinician may determine the genotypes, at one or more genetic loci, of a group of subjects participating in a clinical trial, wherein the subjects display a disorder, e.g., a skin disorder as described herein, and the clinical trial is designed to test the efficacy of a pharmaceutical composition, e.g., a composition consisting of one or more PSMA-binding agents, and optionally a second agent, and wherein the physician or clinician attempts to correlate the genotypes of the subjects with their response to the pharmaceutical composition.

Diagnostic Uses

In one aspect, the present invention provides a diagnostic method for detecting the presence of a PSMA, in vitro (e.g., a biological sample, such as plasma, tissue, biopsy, e.g., a psoriatic tissue) or in vivo (e.g., in vivo imaging in a subject). The method includes: (i) contacting the sample with a PSMA binding agent, or administering to the subject, the PSMA binding agent; (ii) contacting a control sample (e.g., a control biological sample, such as plasma, tissue, biopsy) or a control subject)); and (iii) detecting formation of a complex between the PSMA binding agent, and the sample or subject, or the control sample or subject, wherein a statistically significant change in the formation of the complex in the sample or subject relative to the control sample or subject is indicative of the presence of the antigen in the sample.

Preferably, the PSMA binding agent is directly or indirectly labeled with a detectable substance to facilitate detection of the bound or unbound antibody. Suitable detectable substances include various enzymes, prosthetic groups, fluorescent materials, luminescent materials and radioactive materials, as described above. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

Complex formation between the PSMA binding agent and PSMA can be detected by measuring or visualizing either the antibody (or antibody fragment) bound to the PSMA antigen or unbound antibody (or antibody fragment). Conventional detection assays can be used, e.g., an enzyme linked immunosorbent assays (ELISA), an radioimmunoassay (RIA) or tissue immunohistochemistry.

Alternative to labeling the PSMA binding agent, the presence of PSMA can be assayed in a sample by a competition immunoassay utilizing standards labeled with a detectable substance and an unlabeled anti-PSMA antibody. In this assay, the biological sample, the labeled standards and the PSMA binding agent are combined and the amount of labeled standard bound to the unlabeled antibody is determined. The amount of PSMA in the sample is inversely proportional to the amount of labeled standard bound to the PSMA binding agent.

In still another embodiment, the invention provides a method for detecting the presence of a PSMA-expressing cell in vivo. The method comprises (i) administering to a subject (e.g., a psoriatic patient) a PSMA binding agent, conjugated to a detectable marker; (ii) exposing the subject to a means for detecting said detectable marker to the PSMA-expressing cells. Protocols for in vivo diagnostic assays are provided in PCT/US88/01941, EP 0 365 997 and U.S. Pat. No. 4,954,617.

Deposits

Hybridomas E99, J415, J533, and J591 have been deposited pursuant to, and in satisfaction of, the requirements of the Budapest Treaty on the International Recognition of the Deposit of Microorganisms for the Purposes of Patent Procedure with the American Type Culture Collection ("ATCC") at 10801 University Boulevard, Manassas, Va. 20110-2209. Hybridoma E99 was deposited on May 2, 1996, and received ATCC Designation Number HB-12101. Hybridoma J415 was deposited on May 30, 1996, and received ATCC Designation Number HB-12109. Hybridomas J533 and J591 were deposited on Jun. 6, 1996, and received ATCC Designation Numbers HB-12127 and HB-12126, respectively.

An NSO cell line producing deimmunized J591 was deposited with American Type Culture Collection ("ATCC"), 10801 University Boulevard, Manassas, Va. 20110-2209, on Sep. 18, 2001 and assigned Accession Number PTA-3709. An NSO cell line producing deimmunized J415 was deposited with American Type Culture Collection ("ATCC"), 10801 University Boulevard, Manassas, Va. 20110-2209, on Mar. 21, 2002 and assigned Accession Number PTA-4174. These deposits will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The following invention is further illustrated by the following examples, which should not be construed as further limiting. The contents of all references, pending patent applications and published patents, cited throughout this application are hereby expressly incorporated by reference.

EXAMPLES

Example 1

Treatment of Psoriasis Using Deimmunized J591 Antibody

A 72 year old male with metastatic kidney cancer involving the lungs and liver was noted to have multifocal areas of psoriasis encompassing large areas of his skin, particularly on his back and arms. A note in the patient's chart indicates that his long-standing psoriasis had "worsened in the last few months." The patient received a dose of 10 mg of deimmunized J591 by intravenous infusion over approximately 5 minutes. The deimmunized J591 was traced-labeled with 5 mCi of $^{111}$Indium for imaging purposes. Approximately 45 minutes after an uneventful infusion, the patient had shaking chills that were treated with benadryl and demerol. Due to development of wheezing and decreas-ing oxygen saturation, the patient also received 100 mg of solu-cortef, epinephrine and pepcid. The patient's symptoms resolved.

Approximately two weeks later, the patient was seen for his two-week follow-up appointment. The patient indicated that his psoriasis was "less itchy" and the progress note indicates that "the lesions on his back appear less raised and red."

The patient was due for a second dose of deimmunized J591 at the 2 week time point. However, due to the patient's reaction after infusion, it was elected not to administer a second dose of the antibody. The patient was seen again in follow-up about two weeks later. The chart indicates that, at that time, "the psoriasis on his back, trunk, arms has decreased with the lesions smaller and less irritated and itchy." A subsequent (one week later) chart note indicates that the patient's psoriasis had improved. The note also indicates that the patient was using A&D ointment, however, this is unlikely to account for the improvement in the patient's symptoms for several reasons. Firstly, A&D ointment is not known to be effective in psoriasis and, in addition, the patient did not (and could not) apply the ointment to all of his lesions, particularly on his back. Nevertheless, all of his lesions, regardless of location, improved after deimmunized J591 administration.

About three weeks later, the patient indicated that his psoriasis was "better than it had been in 10 years." At the time, the lesions were flat and of altered pigmentation but without scales or apparent inflammatory changes. The patient did indicate that he had been under treatment for his psoriasis for over 10 years without significant success.

Example 2

Treatment of Psoriasis Using Isotope-Conjugated Deimmunized J591 Antibody

A 76-year-old male with a long-standing history of psoriasis involving the left middle finger and bilateral inguinal areas received 20 mg of deimmunized J591 labeled with 10 mCi $^{111}$Indium. This initial dose was followed six days later with 20 mg deimmunized J591 labeled with $^{90}$Y (20 mCi/m2). Both administrations were by 5-minute intravenous infusions. A photograph of the psoriatic area involving the left middle finger was taken prior to the initial antibody dose (FIG. 14A). This area was unchanged at the time of the second infusion. The patient reports that within days of the second infusion, his itching virtually disappeared and over subsequent days the lesion completely healed. A follow up photograph was taken about a month after the initial dose (FIG. 14B). The patient's affected areas in the inguinal areas also substantially improved.

Example 3

Enhanced Expression of PSMA in Psoriatic Lesions

Figure 1:
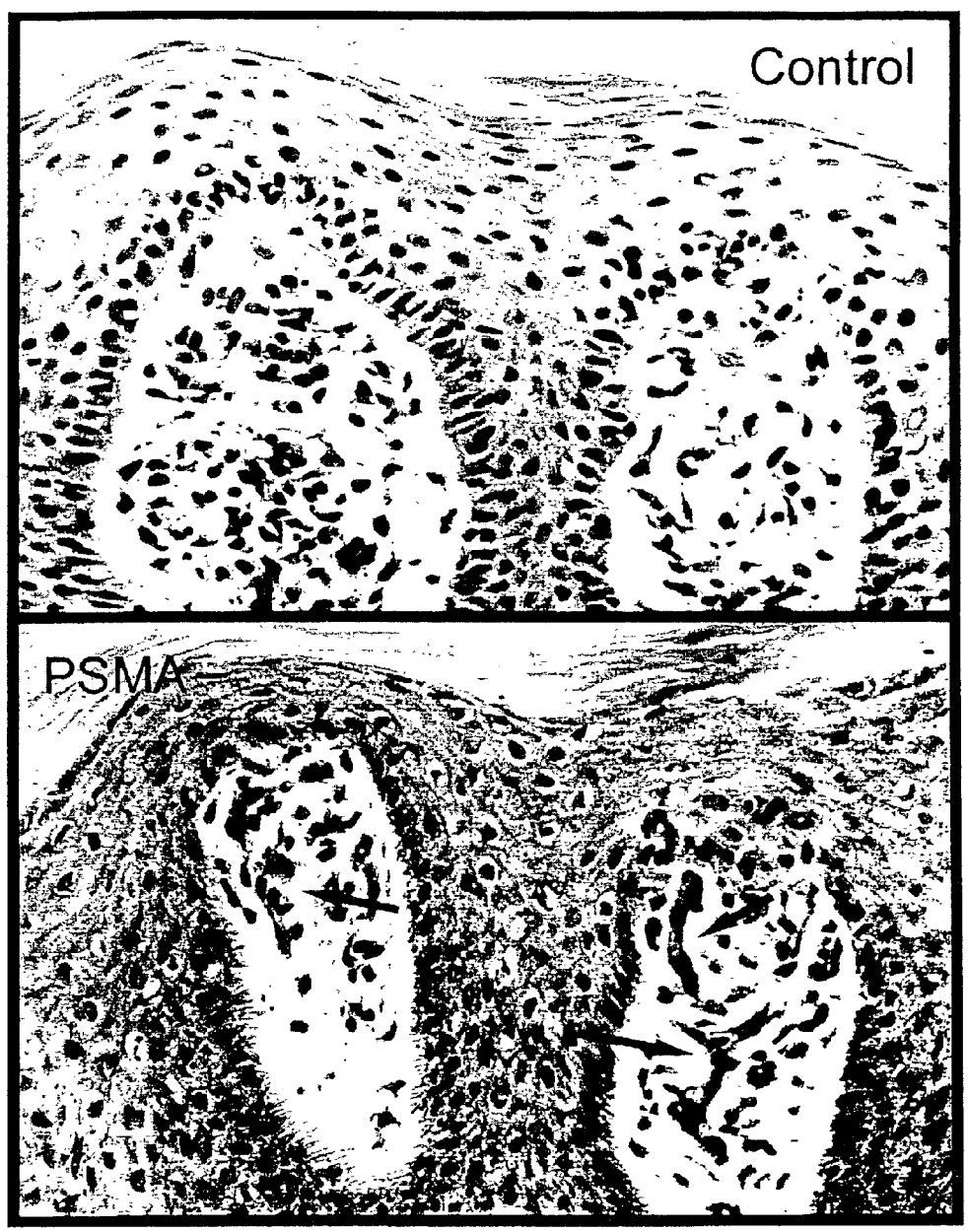
FIG. 1 depicts a photomicrograph of a human psoriatic biopsy (lower panel) stained for PSMA with murine J591 anti-PSMA antibody. PSMA expression was detected on the dermal vascular endothelium. The arrows indicate the regions showing enhanced PSMA expression in the dermal microvasculature. PSMA expression was also detected in keratinocytes. A control panel (upper panel), without antibody staining, showed only background staining.

Immunohistochemical stain of psoriatic lesions showed enhanced PSMA expression in basal and immediately suprabasal keratinocytes, and dermal endothelial cells, relative to non-lesional control (FIGS. 1 and 15). Increased staining was also detected in the surrounding blood vessels of psoriatic patients (FIG. 15).

Staining was performed by standard enzyme-linked immunohistochemistry. Briefly, frozen sections of skin from areas involved and uninvolved with psoriasis were washed and then incubated with murine J591 or control antibodies.

After a one-hour incubation, the slides were washed and incubated with a secondary, anti-mouse Ig-enzyme reagent for an hour. The slides were washed and incubated with substrate [AEC] which converts to a red color in the presence of the enzyme, indicating where the antibody has bound.

Example 4

Chelation of Anti-PSMA Antibodies To $^{111}$Indium, $^{90}$Yttrium and $^{177}$Lutetium The anti-PSMA monoclonal antibody of the present invention can be radiolabeled with $^{111}$Indium, $^{90}$Yttrium and $^{177}$Lutetium coupled with 1,4,7,10-tetraazacyclododecane-N,N',N'',N'''-tetraacetic acid (DOTA).

For example, as detailed below, the modified anti-PSMA monoclonal antibodies can be radiolabeled with $^{111}$Indium, $^{90}$Yttrium, or 177Lutetium by directly coupling one of the four carboxylic acid groups of the chelator 1,4,7,10-tetraaza-cyclododecane-N,N',N'',N'''-tetraacetic acid (DOTA) to primary amines present on the surface of the antibodies. The DOTA conjugated antibody is then purified, sterile filtered, and vialed. Prior to use, the purified antibodies can be mixed with the desired radiolabel which binds to DOTA.

Chelation Process

Monoclonal antibody deJ591 was conjugated with 1,4,7,10-tetraazacyclododecane-N,N',N'',N'''-tetraacetic acid (DOTA) and subsequently radiolabeled with $^{111}$In, $^{90}$Y and $^{177}$Lu. Radiolabeling and quality control tests were performed on three separate vials of clinical grade mAb deJ591.

All reagents used in the conjugation and purification of deJ591 were made from pyrogen-free water. In the specific case of NH$_4$OAC buffer and sodium phosphate buffer, the solutions were purified with Chelex 100 (Bio-Rad, CA) to remove any metal ions.

Conjugation of Antibody with 1,4,7,10-Tetraazacyclododecane-N,N',N'',N'''-tetraacetic acid (DOTA)

The monoclonal antibody deJ591 was modified with 1,4,7,10-tetraazacyclododecane-N,N',N'',N'''-tetraacetic acid (DOTA) as follows. Briefly, 25 mg of deJ591 was concentrated in a 30 kDa microsep centrifugal concentrator (Pall Filtron, Mass.) and washed with 5×4 mL of 1% DTPA (pH 5.0), over a period of 24 hours. The antibody buffer was then changed to 0.1 M phosphate (pH 7.0) using the same centrifugal technique. An active ester of DOTA was created by dissolving 146 mg DOTA (0.361 mmoles) and 36 mg N-hydroxysuccinimide (0.313 mmoles) in 2 ml of water and adjusting the pH to 7.3 with NaOH, prior to the addition of 10 mg of 1-ethyl-3-(3-dimethylaminopropyl)carbodiimide (see below). This reaction mixture was cooled on ice for 1 hour before being added to the deJ591 solution. The resultant DOTA-deJ591 was separated from the excess DOTA and other reactants by repeated washing with 0.3 M NH$_4$OAc (20×4 mL) and centrifugal concentration. The purified conjugate was then sterilized by filtration through a 0.22 μm filter and stored in a sterile polypropylene vial at 4° C.

The concentration of the DOTA-deJ591 conjugate was assayed by determining the UV absorption at 280 nm and two 50 μL aliquots mixed with either 20 or 30 μL of a 1.30 mM solution of InCl$_3$ (0.01 M HCl) spiked with a tracer amount of $^{111}$In. The mixture is incubated at 37° C. for 16 hours and then analyzed by ITLC, using silica gel impregnated glass fiber 10 cm strip (ITLC-SG, Gelman, prod. # 61885) and an eluant of 1% DTPA (pH 6.0). The antibody bound activity remains at the origin and free $^{111}$In moves with the solvent front as an [In-DTPA] complex. The relative amounts of $^{111}$In and $^{111}$In-DOTA-J591 is determined by cutting the ITLC strip at a R$_f$ of 0.5 and counting the two halves with a Na(Tl)I detector. The number of binding sites is calculated by considering the molar reaction ratio between $^{111}$In and DOTA-deJ591 and the observed ratio of $^{111}$In and $^{111}$In-DOTA-J591 detected. Typically, 5.1 molecules of DOTA are conjugated to deJ591. Table 9 shows the results from two conjugations of deJ591.

TABLE 9

Calculation of the Mean Number of DOTA Molecules Conjugated to deJ591

| Test number | Known $^{111}$In/DOTA-J591 Reaction ratio | Observed $^{111}$In/DOTA-J591 TLC ratio | Mean number of DOTA mols per mAb |
| --- | --- | --- | --- |
| A | 11.76 | 1.338 | 5.03 |
| B | 17.64 | 2.469 | 5.09 |

Radiolabeling

The following radiolabeling procedure is described for $^{111}$In, but may be used with other radiolabels such as $^{90}$Y or $^{177}$Lu. Radiolabeling was achieved by adding the $^{111}$In (in dilute HCl) to the ammonium acetate buffered DOTA-deJ591. To avoid the effects of autoradiolysis on the antibody, the reaction time was minimized and the reaction mixture purified with a size exclusion column prior to administration. Briefly, a mixture composed of 20 μL of $^{111}$InCl$_3$ (8 mCi, 0.01 M HCl, 400 μL DOTA-deJ591 (4 mg/ml, 0.3 M NH$_4$OAc, pH 7) was allowed to react at 37° C. for 20 minutes. The reaction mixture was then separated on a 16 mL Biogel-P6DG column (Bio-Rad, CA) equilibrated with 4×10 mL of sterile 1% HSA in PBS (HSA meets specification for US licensed albumin; manufactured by Central Laboratory Blood Transfusion Service Swiss Red Cross, Bern, Switzerland, License No. 647). Once the reaction mixture was loaded onto the column, it was washed with a further 2 mL of 1% HSA PBS, before the main $^{111}$In-DOTA-deJ591 fraction was eluted with 5 mL of 1% HSA PBS. The purified $^{111}$In-DOTA-deJ591 was then sterile filtered into a sterile evacuated vial. Using this method, specific activity of 7.6 mCi $^{111}$In/mg DOTA-deJ591 was achieved.

Radiochemical Purity

The amount of free $^{111}$In in radiolabeled DOTA-deJ591 preparations was evaluated using the instant thin layer chromatography method with a silica gel impregnated glass fiber support and a mobile phase of 1% DTPA (pH 5.5). Briefly, a portion of the radiolabeled DOTA-deJ591 was spotted on a 10 cm ITLC-SG strip (Gelman, prod. #61885) and developed in 1% DTPA (pH 5.5). Once the solvent front had reached the end of the strip, it was removed from the solvent and cut at a Rf of 0.5. The two portions were assayed for radioactivity and the radiochemical purity determined using the following equation:

Radiochemical purity=(Activity in between $R_f$ 0 and 0.5)/(Total activity in strip)

Immunoreactivity

The immunoreactivity of the $^{111}$In-DOTA-deJ591 preparations was assessed according to the method of Lindmo (Lindmo T. et al. (1994) *J. Immunol. Methods*, 72:77–89, 1994) that extrapolates the binding of the radiolabeled antibody at an infinite excess antigen. Briefly, five test solutions were prepared (in duplicate) containing 10,000 cpm of [111]In-DOTA-deJ591 and various amounts of LNCaP cells, in a total test volume of 250 μL of 0.2% BSA 10 mM HEPES. The solutions were incubated at 4° C. for 60 minutes prior to being isolated (by centrifugation) and washed with ice cold PBS. The membranes were then counted in a gamma counter with standards representing the total radioactivity added. The data was plotted using the Lindmo method as the reciprocal of the substrate concentration x-axis) against the reciprocal of the fraction bound (y-axis). The data was then fitted according to a least squares linear regression method (Sigma Plot) and the y intercept taken as the reciprocal of the immunoreactivity. A similar method using membranes derived from LNCaP cells, and subsequent centrifugation isolation of the membranes, gave similar results. The results gave an average immunoreactivity of 72% (see Table 9).

Immunohistochemistry

Immunohistochemistry was performed on the DOTA conjugated, partially purified, bulk intermediate deJ591. The results showed that the preparation was specific to prostate tissue and the reactivity was equivalent to the naked deJ591 antibody.

Sterility

The sterility of [111]In-DOTA-deJ591 preparations was determined using thioglycollate medium according to the U.S. Pat. No. 24/NF 19 method. Briefly, quadruplicate 0.1 mL samples of the [111]In-DOTA-deJ591 preparations were transferred to 15 mL of fluid thioglycollate medium and the mixture incubated at 35° C. for 14 days. The media were visually inspected on the 4th, 7th and 14 days of any signs of growth. All three preparations showed no growth (See Table 9).

Endotoxin

The endotoxin of [111]In-DOTA-deJ591 preparations was determined using the Limulus amebocyte lysate assay according to the U.S. Pat. No. 24/NF 19. Briefly, a Limulus amebocyte lysate kit (Bio Whittaker lot #7L3790, sensitivity 0.125EU/mL) was reconstituted with 0.25 mL of test sample. The quadruplicate test samples, artificially positive test samples, negative controls and positive controls were incubated at 37° C. for 60 minutes. Positive results were typified by the formation of a viscous gel that was unaffected by 180° inversion. The single preparation gave a value of less than 5 EU/mL. This assay can (and will) be repeated on the patient dose immediately prior to administration.

TABLE 10

Analytical Results of Radiolabeled [111]In-DOTA-deJ51

| Test | Result |
|---|---|
| Radiolabeling yield | 85% |
| Radiochemical Purity | >99% |
| Immunoreactivity | 72% |
| Endotoxin | <5 Eu/mL |
| Sterility | Sterile |

Lot # of deJ591: BIOV983.2-2

Large-Scale Manufacture/Process

The large-scale manufacture of the DOTA conjugated deJ591 antibody is described in the following paragraphs. The major differences from the above methodology were the use of a stirred cell, instead of a microsep centrifugal concentrator to concentrate and diafilter the antibody and the use of a Sephadex G-25 column to remove the unreacted DOTA and other reagents from the DOTA conjugated antibody. These changes were necessitated by the increase in scale. The ratios of the starting materials are given in Table 11 for a nominal 1000 milligram scale. The process may be scaled up using equivalent ratios of starting materials.

TABLE 11

Unit Ratios of Starting Materials

| Starting Material | Unit Ratio |
|---|---|
| deJ591 antibody | X mgs |
| 1,4,7,10-tetraazacyclododecane-N,N',N'',N'''-tetraacetic acid (DOTA) | 1.25 X mgs |
| N-hydroxysuccinimide (NHS) | 0.275 X mgs |
| 1-Ethyl-3-(3-dimethylaminopropyl) carbodiimide (EDC) | 0.3 X mgs |

Aseptic practices were observed in order to minimize contamination and environmental monitoring was conducted at periodic intervals during the manufacture. All solutions, buffers and reagents used in the conjugation and purification of DOTA-deJ591 antibody were made with Water For Injection (WFI). Throughout the process, metal free components were used in the manufacture in order to avoid the chelation of any free metal residues by the DOTA moiety. In the specific case of ammonium acetate buffer and sodium phosphate buffer, the solutions were purified with Chelex 100 to remove any metal ions. Sterile, pyrogen free and metal free containers were used to mix reactants. The final bulk sterile filtration was conducted in an area that meets Class 100 specifications.

The deJ591 was prepared by buffer exchanging the antibody into metal free, 0.1 M Sodium Phosphate, pH 7.1, over a Chelex 100 (BioRad or equivalent) column. The antibody was then concentrated to approximately 10 mg/mL using a Stirred Cell Unit (Millipore or equivalent) equipped with a 30 kD cut-off membrane. The concentrated antibody was then sterile-filtered through a 0.22 μm filter.

To conjugate one gram of antibody, the active ester of DOTA was prepared by adding 6.3 mL of 0.49 M DOTA in metal free, Sodium Phosphate Buffer, pH 7.1, to 2.7 mL of 0.87 M N-hydroxysuccinimide in metal free, Sodium Phosphate Buffer, pH 7.1. To this mixture, 0.1 N Sodium Hydroxide was added until the DOTA was completely dissolved (approximately a 1:1 ratio of 0.1 M Sodium Hydroxide to DOTA/NHS solution). The pH was between 6.9 and 7.2. The solution was cooled for not less than 30 minutes at 2–8° C. To the DOTA/NHS solution, 1.5 mL of 1.0 M of EDC in Sodium Phosphate Buffer, pH 7.1, was added and allowed to cool at 2–8° C. for not less than 1 hour.

The active DOTA ester was added to 1 gram of antibody and incubated overnight (12–14 hrs) at 2–8° C. The DOTA conjugated antibody was purified over a Sephadex G-25 column (Pharmacia or equivalent) in metal free, 0.3 M Ammonium Acetate Buffer, pH 7.2. The eluate fraction containing the DOTA conjugated antibody was concentrated using a Stirred Cell equipped with a 30 kD cut-off membrane to approximately 10 mg/mL. The DOTA conjugated deJ591 Antibody was then diafiltered in 0.3 M Ammonium Acetate, pH 7.2 to remove any excess reagents and diluted to a final concentration of 8.0 mg/mL prior to sterile filtering through a 0.22 μm filter.

DOTA conjugated deJ591 was tested for concentration, immunoreactivity, conjugation, endotoxin, and sterility. The endotoxin limit is based on the low clinical dose of the radiolabeled DOTA conjugated deJ591 antibody required, which ranges from 1 to 5 mg. Bioburden testing was performed on the bulk purified DOTA conjugated antibody instead of sterility because of the small batch sizes. Sterility (21 CFR 610) will be performed on the final vialed drug product. The target for immunoreactivity and number of DOTA moles per antibody was based on previous clinical experience. DOTA conjugated antibody with immunoreactivity values of as low as 72% have been successfully used in the clinic. The number of DOTA moles per antibody is based on the results from previous clinical lots.

Protein Concentration

A sample of DOTA-deJ591 was analyzed by optical density in a spectrophotometer at a wavelength of 280 nm. The extinction coefficient used for these calculations was $A_{280}$, $E_{1\ cm}^{0.1\%}=1.4$. The test sample was suitably diluted to give an absorbance reading in the working range of the assay (0.2 OD units to 1.2 OD units, linear, CV less than 2%). The acceptable limit for protein concentration is 8.0 mg/mL±0.5 mg/mL.

Endotoxin

Samples of DOTA-deJ591 were tested for pyrogens using a validated Limulus Amebocyte Lysate test (LAL) Gel Clot Assay (BioWhittaker or equivalent). A 0.06 EU/mL sensitivity Lysate was utilized and samples were diluted either 1:10 or 1:25 in Endotoxin free water for analysis in order to overcome the inhibition level of certain chemicals to the gel clot assay. Duplicate determinations were made for each buffer or intermediate sample during processing and the sample values needed to be equal to or less than the value obtained at the dilution level set for that buffer. A positive and negative control, as well as an inhibition control, was run with every sample. The proposed acceptable limits were not more than 5 EU per mg of DOTA-deJ591.

Bioburden

Aliquots of DOTA-deJ591 were directly inoculated in fluid thioglycollate and soybean-casein broth. The media were examined after fourteen days of incubation. As necessary, both media showed no growth after fourteen days.

Immunoreactivity

The immunoreactivity of the DOTA-deJ591 preparations was assessed according to the method of Lindmo (Lindmo T. et al. (1994) *J. Immunol. Methods* 72:77–89) which extrapolates the binding of the radiolabeled antibody at an infinite amount of excess antigen. Briefly five test solutions were prepared (in duplicate) containing 10,000 cpm of $^{111}$Indium labeled-DOTA-deJ591 and various amounts of LNCaP cells or cell membranes, in a total test volume of 250 µL of 0.2% BSA 10 mM HEPES. The solutions were incubated at 4° C. for 60 minutes prior to being isolated (by centrifugation) and washed with ice cold PBS. The membranes were then counted in a gamma counter with standards representing the total radioactivity added. The data was plotted using the Lindmo method as the reciprocal of the substrate concentration X-axis) against the reciprocal of the fraction bound (y-axis). The data was then fitted according to a least squares linear regression method (Sigma Plot) and the y intercept used as the reciprocal of the immunoreactivity. The target for immunoreactivity was not less than 75%.

Number of DOTA Moles per Antibody

The number of DOTA bound per antibody was determined using a saturation binding method with natural occurring isotope of Indium and $^{111}$Indium. Multiple aliquots (minimum two) of DOTA-deJ591 were mixed with various amounts, ranging from 10 to 30 µL, of a 3.0 mM solution of $InCl_3$ (0.01 M HCl) spiked with a tracer amount of $^{111}$In. The mixture was incubated at 37° C. for 16 hours and then analyzed by ITLC, using silica gel impregnated glass fiber 10 cm strip (ITLC-SG, Gelman, or equivalent) and an eluant of 1% DTPA (pH 6.0). The antibody bound activity remains at the origin and free $^{111}$In moves with the solvent front as an [In-DTPA] complex. The relative amounts of $^{111}$In and $^{111}$In-DOTA-J591 was determined by cutting the ITLC strip at a $R_f$ of 0.5 and counting the two halves with a Na(Tl)I detector. The number of binding sites was calculated by considering the molar reaction ratio between $^{111}$In and DOTA-deJ591 and the observed ratio of $^{111}$In and $^{111}$In-DOTA-J591 detected. The target number of DOTA molecules per antibody was between 4 and 6.

The analytical results for a sample lot of DOTA conjugated deJ591 antibody are shown below in Table 12.

TABLE 12

| Test | Proposed Acceptable Limits | Results |
|---|---|---|
| Appearance | Clear Colorless Solution | Clear Colorless Solution |
| Concentration | 8.0 mg/mL ± 0.5 mg/mL | 8.4 mg/mL |
| Endotoxin | NMT 5 EU per mg | <1.2 EU/mg |
| Bioburden | No growth | No growth |
| Immunoreactivity | For Information Only (Target NLT 75%) | 95% |
| Number of DOTA moles per Antibody | For Information Only (Target 4–6 DOTA per Antibody) | 6 |

The DOTA conjugation numbers for a previous lot of DOTA conjugated antibody (Biov983.2–2) and current Lot 243101 are shown in Table 13. The average number of DOTA moles per antibody for Lot Biov983.2–2 was 5.06 and for Lot 243101 was 5.96. Although the number of moles of DOTA conjugated per antibody was slightly higher for Lot 243101, the immunoreactivity was not affected as shown in Table 14. In fact, the immunoreactivity for Lot 243101 was higher than that for the comparison lot, which is beneficial. It should be noted that other small-scale clinical lots have had immunoreactivity values of greater than 90% (data not shown).

TABLE 13

Comparison of the Mean Number of DOTA Molecules Conjugated to deJ591 antibody

| Lot number | Known $^{111}$In/ DOTA-deJ591 Reaction ratio | Observed $^{111}$In/DOTA-deJ591 TLC ratio | Mean number of DOTA mols per mAb |
|---|---|---|---|
| BIOV983.2-2 | | | |
| A | 11.76 | 1.338 | 5.03 |
| B | 17.64 | 2.469 | 5.09 |
| Ave | | | 5.06 |
| Lot 243101 | | | |
| A | 10.98 | 0.8608 | 5.90 |
| B | 16.46 | 1.7301 | 6.03 |
| C | 21.95 | 2.8226 | 5.74 |
| D | 32.93 | 4.3498 | 6.15 |
| Ave | | | 5.96 |

A = 10 µL of In-natural/$^{111}$In solution, B = 15 µL of In-natural/$^{111}$In solution, C = 20 µL of In-natural/$^{111}$In solution, D = 30 µL of In-natural/$^{111}$In solution

TABLE 14

Comparison of Immunoreactivity of DOTA-deJ591

| Test | Lot BIOV983.2-2 | Lot 243101 |
|---|---|---|
| Immunoreactivity | 72% | 95% |

An alternative synthesis is as follows: 956.5 mg of deJ591 was diafiltered six times. The antibody was concentrated in a 30 kDa microsep centrifugal concentrator (Pall Filtron, Mass.) to approximately 15 mg/mL and diluted 12.5 fold with metal free 0.1 M Sodium phosphate at pH 7.1. This procedure is performed six times. An active ester of DOTA was created by mixing 598 mg DOTA (1.48 mmoles) in 5.95 mL 0.1 M metal free phosphate buffer and 132 mg N-hydroxysuccinimide (1.15 mmoles) in 2.7 ml of 0.1 M metal free phosphate buffer. The pH was adjusted to 6.9–7.2 with NaOH, prior to the addition of 144 mg (0.75 mmoles) of 1-ethyl-3-(3-dimethylaminopropyl)carbodiimide in 1.45 mL 0.1 M metal free phosphate buffer. This reaction mixture was filtered through a 0.2 micron sterile filter and cooled on ice for 1 hour before being added to the deJ591 solution and incubated overnight at 2–8 C. for 14–18 hours. The resultant DOTA-deJ591 was separated from the excess DOTA and other reactants by purifying it through a G-25 column equilibrated in 0.3 M metal free ammonium acetate. The purified conjugate was concentrated to 10 mg/mL in a stirred cell unit and washed with 0.3 M ammonium acetate, then sterilized by filtration through a 0.22 um filter and stored in a sterile polypropylene vial at 2–8° C.

Example 5

Use of the mAbs for Targeted Delivery of Cytotoxic Drugs to PSMA Expressing Cells Anti-PSMA antibodies can be conjugated to substances with high cytotoxic potential, such as drugs of the maytansinoid class. Maytansinoids exert their cytotoxic effects by interfering with the formation and stabilization of microtubules. They have 100-to 1000-fold greater cytotoxic potential than conventional chemotherapeutic agents (such as doxorubicin, methotrexate, and Vinca alkaloids) (Chari, R. V. J. et al. (1992) Cancer Res. 52: 127).

Both murine and deimmunized J591 antibodies have been conjugated to the maytansinoid, DM1, via a hindered disulfide bond. This bond is cleaved intracellularly allowing release of the drug. One or more lysine residues in the constant regions of the antibodies were conjugated to a linker containing a pyridyldithio group, which was, in turn, coupled to a maytansinoid toxin. A ratio of 3 to 4 moles of maytansinoid per mole of IgG is preferred.

The process for the DM1-linked J591 antibodies starts by reacting J591 with a linker that contains both a pyridyldithio group and a N-hydroxysuccinimide leaving group. In this case, the linker was N-succinimidyl 4-(2-pyridyldithio)propionate (or SPP), although other linkers can be used. The products of the reaction include modified J591 antibodies that contain one or more linker groups (4-(2-pyridyldithio) propionone) attached to surface exposed lysine groups, with the linker groups retaining the pyridyldithio reactive groups, and N-hydroxysuccinimide leaving groups. The J591 antibodies are then separated from the reaction mixture and N-hydroxysuccinimide by gel filtration, e.g., using sephadex G25. The modified J591 antibodies are reacted with DM1, which contains a thiol group that reacts with the pyridyldithio groups now present on the surface of the modified antibody, thereby producing J591-DM1 immunoconjugates and thiopyridine. The J591-DM1 immunoconjugate is isolated from the reaction mixture and thiopyridine by size exclusion chromatography, e.g., using a sephacryl S300 column. Methods for preparing maytansinoid conjugates are described in U.S. Pat. Nos. 5,208,020; 5,475,092; 5,585,499; 5,846,545; and 6,333,410, the contents of which are incorporated by reference.

Example 6

Conjugation of deJ591 to the Maytansinoid Cytotoxin DM1

This example describes a process for the production of the deJ591-DM1 immunoconjugate. The process is based on standard methods known in the art and can therefore be generalized to other antibodies, including other antibodies of the invention such as deJ415.

The methods of conjugation are based on several small scale experiments, including one experiment performed using 5 g of deJ591 starting material (Lot 1552-60S) and three experiments performed using between 6.7 g and 7.3 g of deJ591 starting material (Lots 1552-168, 1552-104, and 1610-036).

The steps involved in the methods of conjugation are as follows:

1) 5 g to 7.5 g of deJ591 antibody is concentrated by tangential flow filtration (10 kD NMWCO membranes) to 25–30 mg/ml and diafiltered against 5 volumes of 50 mM potassium phosphate, 2 mM EDTA, pH 6.0. The yeild is typically between 98% and 100%.

2) The concentrated antibody is filtered through a 0.2 μ filter, if opalescent, and then modified with N-succinimidyl 4-(2-pyridyldithio)propionate (SPP) at a concentration of 20–22 mg/ml antibody and 7 molecules of SPP per molecule of antibody. The modification is done in 50 mM potassium phosphate, 2 mM EDTA, 5% ethanol, pH 6.0, for 2.5+/−0.5 hours. The modification vessel is a 500 ml round bottom flask.

3) The modified antibody is separated from the reaction mixture of step 2) using gel filtration chromatography and a Sephadex G-25TM column. The column load represents about 25% of the column volume and the chromatography is done in 50 mM potassium phosphate, 2 mM EDTA, pH 6.0, at a flow rate of 50 cm/hr. The modified antibody elutes between 38–75% column volume. Typically the yeild of this step between 95% and 100% and the SPP to antibody ration is about 5.4 to 5.9 SPP molecule/antibody.

4) At a concentration of about 10 mg/ml, the modified antibody is conjugated with DM1 (using 1.7 molecules of DM1/molecule of SPP conjugated to the antibodies) for 20+/−4 hours. Typically, the reaction time is between 16.25 and 17.7 hours and is carried out in a IL round bottom glass flask equipped with a magnetic stirring bar. The conjugation reaction is done in 3% DMA, 10% sucrose (100 mg sucrose/ml of reaction). At the end of the reaction the conjugated antibody is filtered through a 2.0μ filter and a spectrophotometric reading is taken.

5) The conjugated antibody is seperated from unreacted DM1 by gel filtration chromatography using a Sephadex G-25™ column. The column load represents 22–23% of the column volume and the flow rate is about 50 cm/hr. The column is equilibrated and run in 20 mM succinate, 5% sucrose (50 mg/ml), pH 5.5. The antibody conjugate elutes between about 31% and 65% of column volume, and is collected from the start of the peak elution to the start of the peak trailing edge as a single fraction, followed by fractionation of the remaining peak material in 15×2% column volume fractions. All fractions are adjusted to 100 mg/ml of sucrose (10% sucrose) through the addition of appropriate amounts of 50% sucrose. The 2% column volume fractions are assayed by analytical sizing (TSK 3000SWL) and selected fractions (fractions 1 and 2) are pooled together with the main peak. The fractions are assayed using analytical sizing with the pooling criterion being the 24 minute peak representing <20% or the total peak area. Typically the yield of this step is between 60% and 65% with the exception of run 1552–104 where there was no sucrose present in the reaction and/or purification mixture. The eluted antibody concentration ranges from 3.8 to 4.2 mg/ml and the ration of DM1/antibody ranges from 3.6 to 3.9.

6) The antibody conjugate is then concentrated to 7–10 mg/ml using a 10 kD NMWCO tangential flow filtration membrane and diafiltered against 5 volumes of 50 mM succinate, 10% sucrose, pH 5.5 (Inlet Pressure<10 psi). Following diafiltration the antibody conjugate is adjusted to 5 mg/ml. Typical yield for this step is between 92% and 100%, with the final protein concentration being between 4.85 and 5.1 mg/ml.

7) Finally, the antibody conjugate is filtered through a 0.2 m filter and aliquoted to the specified volumes. Step yield is between 90% and 100% and the final DM1-antibody ratio is 3.5 to 3.8.

The resulting deJ591-DM1 conjugates were analyzed according to appearance, concentration, DM1/antibody ratio, endotoxin, non-specific cytotoxicity, acetone extractable DM1, analytical sizing, reduced and non-reduced SDS-PAGE, pH, bioburden, specific cytotoxicity, and IEF. Selected analytical results for lots 1552-168, 1552-104, and 1552-036 are shown in Table 15, below.

TABLE 15

| Lot No. | Amount Recovered | Concentration (mg/ml) | DM1/antibody | Process Recovery (%) |
|---|---|---|---|---|
| 1552-168 | 3.85 | 5.1 | 3.7 | 57.2 |
| 1552-104 | 2.75 | 4.85 | 3.5 | 37.8* |
| 1610-036 | 3.41 | 5.05 | 3.8 | 47.2 |
| Mean | 3.34 | 5.00 | 3.67 | 47.4 |
| Standard Dev. | 0.55 | 0.13 | 0.15 | 9.7 |
| % c.v. | 16.6 | 2.6 | 4.2 | 20.5 |

*Lower recovery due partly to the lack of sucrose in the conjugation reaction and the second G-25 gel filtration run and partly to the fact that the front end of the product peak was not collected due to a malfunction in the chart recorder.

Example 7

Radiolabeling of DOTA-deJ591 with $^{111}$In $^{90}$Y, and $^{177}$Lu a) Radiolabeling with $^{111}$In The following radiolabeling procedure can be used for the routine preparation of $^{111}$In-DOTA-J591 for clinical studies and stability studies. Radiolabeling is achieved by the addition of $^{111}$In chloride and Ammonium acetate buffer (1 M) to DOTA-J591 solution (8 mg/ml, 0.3 M Ammonium acetate, pH 7). To avoid the effects of autoradiolysis on the antibody, the reaction time has been minimized. The labeled $^{111}$In-DOTA-J591 is purified using a size exclusion column and sterile filtered using a 0.2μl Millipore membrane filter prior to administration to patients. Briefly, ammonium acetate, (10 μL for each mCi of $^{111}$In) is added to a reaction vial containing $^{111}$In-chloride solution. Subsequently, DOTA-J591 solution (30 μL or 0.24 mg for each mCi of $^{111}$In) is added to the reaction vial and the mixture is gently mixed and incubated at 37° C. for 20–30 min. An aliquot of the mixture is tested to determine labeling efficiency using ITLC (SG and 5 mM DTPA, pH 5). If the binding is optimal (>70%), the reaction is stopped by the addition of 10–40 PL of 5 mM DTPA.

In order to separate or purify $^{111}$In-DOTA-J591 from free $^{111}$In, the reaction mixture is applied on a Biogel-P6DG column (Bio-Rad, CA), prewashed with 4×10 ml of PBS containing 1% Human Serum Albumin (meets specification for US licensed albumin; manufactured by Central Laboratory Blood Transfusion Service Swiss Red Cross, Bern, Switzerland, License No. 647). The $^{111}$In-DOTA-J591 is eluted from the column using PBS with 1% HSA and the fractions containing the labeled antibody (typically 5–8 ml) are collected into a sterile container. Following determination of radiochemical purity using ITLC (as before), and if the labeling efficiency is >95%, the labeled complex is filtered into a sterile vial using 0.2μ Filter. The final specific activity is typically 3–5 mCi/mg of antibody.

b) Radiolabeling with $^{90}$Y

The procedure is identical to the procedure described above for $^{111}$In, except the incubation time is 10–15 min. Radiochemical purity of $^{90}$Y-DOTA-J591 must be >97%.

c) Radiolabeling with $^{177}$Lu

The procedure is similar to the procedure described above except for two changes. The amount of Ammonium acetate added is reduced (3–5 μL for each mCi of $^{177}$Lu) and the incubation time is only 5 min. Radiochemical purity of $^{177}$Lu-DOTA-J591 should be >97%.

Alternative Procedures a) Radiolabeling with $^{111}$In

The following radiolabeling procedure is described for $^{111}$In, but may be used with other radiolabels such as $^{90}$Y or $^{177}$Lu. Radiolabeling is achieved by adding $^{111}$In (in dilute HCl) to ammonium acetate buffered DOTA-deJ591. To avoid the effects of autoradiolysis on the antibody, the reaction time has been minimized and the reaction mixture purified with a size exclusion column prior to administration. Briefly, a mixture composed of 20 mL of $^{111}$In C13 (8 mCi, 0.01 M HCl, 400 mL DOTA-deJ591 (4 mg/ml, 0.3 M NH4OAc, pH 7) is allowed to react at 37° C. for 20 minutes. The reaction mixture is then separated on a 16 mL Biogel-P6DG column (Bio-Rad, CA) equilibrated with 4×10 mL of sterile 1% HSA in PBS (HAS meets specification for US licensed albumin; manufactured by Central Laboratory Blood Transfusion Service Swiss Red Cross, Bern, Switzerland, License No. 647). Once the reaction mixture is loaded onto the column, it is washed with a further 2 mL of 1% HSA PBS, before the main $^{111}$In-DOTA-deJ591 fraction is eluted with 5 mL of 1% HSA PBS. The purified $^{111}$In-DOTA-deJ591 is then sterile filtered into a sterile evacuated vial. Using this method, specific activity of 7.6 mCi $^{111}$In/mg DOTA-deJ591 is achieved.

b) Radiolabeling ($^{177}$Lu)

The radiolabeling of DOTA-huJ591 with $^{177}$Lu is achieved by adding the radionuclide (in dilute HCl) to ammonium acetate buffered DOTA-hu-J591. To avoid the effects of autoradiolysis on the antibody the reaction time has been minimized and the reaction mixture purified with a size exclusion column prior to administration. Briefly, a mixture composed of 20 μL of $^{177}$Lu (30 mCi, 0.01 M HCl, MURR), 1000 μL DOTA-hu-J591 (4 mg/ml, 0.3 M NH4OAc, pH 7) is allowed to react at 37 C for 10 minutes. The reaction mixture is then separated on a 18 mL Biogel-P6DG column (Bio-Rad, CA) equilibrated with 4×10 mL of sterile 1% HSA in PBS. Once the reaction mixture is loaded onto the column, it is washed with a further 4 mL of 1% HSA PBS, before the main 177Lu-DOTA-hu-J591 fraction is eluted with 2 mL of 1% HSA PBS. The purified $^{177}$Lu-DOTA-hu-J591 is then sterile filtered into a sterile evacuated vial. Using this method, specific activity of 8 mCi $^{177}$Lu /mg DOTA-hu-J591 have been achieved.

EQUIVALENTS

Those skilled in the art will recognize, or be able to ascertain using no more than routine experimentation, many equivalents of the specific embodiments of the invention described herein. Such equivalents are intended to be encompassed by the following claims.

---

SEQUENCE LISTING

```
<160> NUMBER OF SEQ ID NOS: 128

<210> SEQ ID NO 1
<211> LENGTH: 10
<212> TYPE: PRT
<213> ORGANISM: Mus musculus

<400> SEQUENCE: 1

Gly Tyr Thr Phe Thr Glu Tyr Thr Ile His
1               5                   10

<210> SEQ ID NO 2
<211> LENGTH: 17
<212> TYPE: PRT
<213> ORGANISM: Mus musculus

<400> SEQUENCE: 2

Asn Ile Asn Pro Asn Asn Gly Gly Thr Thr Tyr Asn Gln Lys Phe Glu
1               5                   10                  15

Asp

<210> SEQ ID NO 3
<211> LENGTH: 6
<212> TYPE: PRT
<213> ORGANISM: Mus musculus

<400> SEQUENCE: 3

Gly Trp Asn Phe Asp Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Val Gly Thr Ala Val Asp
1               5                   10

<210> SEQ ID NO 5
<211> LENGTH: 7
<212> TYPE: PRT
<213> ORGANISM: Mus musculus

<400> SEQUENCE: 5

Trp Ala Ser Thr Arg His Thr
1               5
```

<210> SEQ ID NO 6
<211> LENGTH: 9
<212> TYPE: PRT
<213> ORGANISM: Mus musculus

<400> SEQUENCE: 6

Gln Gln Tyr Asn Ser Tyr Pro Leu Thr
1               5

<210> SEQ ID NO 7
<211> LENGTH: 82
<212> TYPE: PRT
<213> ORGANISM: Mus musculus

<400> SEQUENCE: 7

Glu Val Gln Leu Gln Gln Ser Gly Pro Glu Leu Lys Lys Pro Gly Thr
1               5                   10                  15

Ser Val Arg Ile Ser Cys Lys Thr Ser Trp Val Lys Gln Ser His Gly
            20                  25                  30

Lys Ser Leu Glu Trp Ile Gly Lys Ala Thr Leu Thr Val Asp Lys Ser
        35                  40                  45

Ser Ser Thr Ala Tyr Met Glu Leu Arg Ser Leu Thr Ser Glu Asp Ser
    50                  55                  60

Ala Val Tyr Tyr Cys Ala Ala Trp Gly Gln Gly Thr Thr Leu Thr Val
65                  70                  75                  80

Ser Ser

<210> SEQ ID NO 8
<211> LENGTH: 80
<212> TYPE: PRT
<213> ORGANISM: Mus musculus

<400> SEQUENCE: 8

Asp Ile Val Met Thr Gln Ser His Lys Phe Met Ser Thr Ser Val Gly
1               5                   10                  15

Asp Arg Val Ser Ile Ile Cys Trp Tyr Gln Gln Lys Pro Gly Gln Ser
            20                  25                  30

Pro Lys Leu Leu Ile Tyr Gly Val Pro Asp Arg Phe Thr Gly Ser Gly
        35                  40                  45

Ser Gly Thr Asp Phe Thr Leu Thr Ile Thr Asn Val Gln Ser Glu Asp
    50                  55                  60

Leu Ala Asp Tyr Phe Cys Phe Gly Ala Gly Thr Met Leu Asp Leu Lys
65                  70                  75                  80

<210> SEQ ID NO 9
<211> LENGTH: 25
<212> TYPE: PRT
<213> ORGANISM: Artificial Sequence
<220> FEATURE:
<223> OTHER INFORMATION: deimmunized heavy chain J591

<400> SEQUENCE: 9

Glu Val Gln Leu Val Gln Ser Gly Pro Glu Val Lys Lys Pro Gly Ala
1               5                   10                  15

Thr Val Lys Ile Ser Cys Lys Thr Ser
            20                  25

<210> SEQ ID NO 10
<211> LENGTH: 14

```
<212> TYPE: PRT
<213> ORGANISM: Artificial Sequence
<220> FEATURE:
<223> OTHER INFORMATION: deimmunized heavy chain J591

<400> SEQUENCE: 10

Trp Val Lys Gln Ala Pro Gly Lys Gly Leu Glu Trp Ile Gly
 1               5                  10

<210> SEQ ID NO 11
<211> LENGTH: 32
<212> TYPE: PRT
<213> ORGANISM: Artificial Sequence
<220> FEATURE:
<223> OTHER INFORMATION: deimmunized heavy chain J591

<400> SEQUENCE: 11

Lys Ala Thr Leu Thr Val Asp Lys Ser Thr Asp Thr Ala Tyr Met Glu
 1               5                  10                  15

Leu Ser Ser Leu Arg Ser Glu Asp Thr Ala Val Tyr Tyr Cys Ala Ala
                20                  25                  30

<210> SEQ ID NO 12
<211> LENGTH: 11
<212> TYPE: PRT
<213> ORGANISM: Artificial Sequence
<220> FEATURE:
<223> OTHER INFORMATION: deimmunized heavy chain J591

<400> SEQUENCE: 12

Trp Gly Gln Gly Thr Leu Leu Thr Val Ser Ser
 1               5                  10

<210> SEQ ID NO 13
<211> LENGTH: 23
<212> TYPE: PRT
<213> ORGANISM: Artificial Sequence
<220> FEATURE:
<223> OTHER INFORMATION: deimmunized light chain J591

<400> SEQUENCE: 13

Asp Ile Gln Met Thr Gln Ser Pro Ser Ser Leu Ser Thr Ser Val Gly
 1               5                  10                  15

Asp Arg Val Thr Leu Thr Cys
                20

<210> SEQ ID NO 14
<211> LENGTH: 15
<212> TYPE: PRT
<213> ORGANISM: Artificial Sequence
<220> FEATURE:
<223> OTHER INFORMATION: deimmunized light chain J591

<400> SEQUENCE: 14

Trp Tyr Gln Gln Lys Pro Gly Pro Ser Pro Lys Leu Leu Ile Tyr
 1               5                  10                  15

<210> SEQ ID NO 15
<211> LENGTH: 32
<212> TYPE: PRT
<213> ORGANISM: Artificial Sequence
<220> FEATURE:
<223> OTHER INFORMATION: deimmunized light chain J591

<400> SEQUENCE: 15

Gly Ile Pro Ser Arg Phe Ser Gly Ser Gly Ser Gly Thr Asp Phe Thr
```

```
                 1               5                  10                 15
Leu Thr Ile Ser Ser Leu Gln Pro Glu Asp Phe Ala Asp Tyr Tyr Cys
                20                  25                 30

<210> SEQ ID NO 16
<211> LENGTH: 10
<212> TYPE: PRT
<213> ORGANISM: Artificial Sequence
<220> FEATURE:
<223> OTHER INFORMATION: deimmunized light chain J591

<400> SEQUENCE: 16

Phe Gly Pro Gly Thr Lys Val Asp Ile Lys
 1               5                  10

<210> SEQ ID NO 17
<211> LENGTH: 82
<212> TYPE: PRT
<213> ORGANISM: Artificial Sequence
<220> FEATURE:
<223> OTHER INFORMATION: deimmunized heavy chain J591

<400> SEQUENCE: 17

Glu Val Gln Leu Val Gln Ser Gly Pro Glu Val Lys Lys Pro Gly Ala
 1               5                  10                 15

Thr Val Lys Ile Ser Cys Lys Thr Ser Trp Val Lys Gln Ala Pro Gly
                20                  25                 30

Lys Gly Leu Glu Trp Ile Gly Lys Ala Thr Leu Thr Val Asp Lys Ser
            35                  40                 45

Thr Asp Thr Ala Tyr Met Glu Leu Ser Ser Leu Arg Ser Glu Asp Thr
        50                  55                 60

Ala Val Tyr Tyr Cys Ala Ala Trp Gly Gln Gly Thr Leu Leu Thr Val
65                  70                  75                 80

Ser Ser

<210> SEQ ID NO 18
<211> LENGTH: 80
<212> TYPE: PRT
<213> ORGANISM: Artificial Sequence
<220> FEATURE:
<223> OTHER INFORMATION: deimmunized light chain J591

<400> SEQUENCE: 18

Asp Ile Gln Met Thr Gln Ser Pro Ser Ser Leu Ser Thr Ser Val Gly
 1               5                  10                 15

Asp Arg Val Thr Leu Thr Cys Trp Tyr Gln Gln Lys Pro Gly Pro Ser
                20                  25                 30

Pro Lys Leu Leu Ile Tyr Gly Ile Pro Ser Arg Phe Ser Gly Ser Gly
            35                  40                 45

Ser Gly Thr Asp Phe Thr Leu Thr Ile Ser Ser Leu Gln Pro Glu Asp
        50                  55                 60

Phe Ala Asp Tyr Tyr Cys Phe Gly Pro Gly Thr Lys Val Asp Ile Lys
65                  70                  75                 80

<210> SEQ ID NO 19
<211> LENGTH: 115
<212> TYPE: PRT
<213> ORGANISM: Mus musculus

<400> SEQUENCE: 19

Glu Val Gln Leu Gln Gln Ser Gly Pro Glu Leu Lys Lys Pro Gly Thr
```

-continued

```
                1               5                   10                  15
Ser Val Arg Ile Ser Cys Lys Thr Ser Gly Tyr Thr Phe Thr Glu Tyr
                20                  25                  30

Thr Ile His Trp Val Lys Gln Ser His Gly Lys Ser Leu Glu Trp Ile
                35                  40                  45

Gly Asn Ile Asn Pro Asn Asn Gly Gly Thr Thr Tyr Asn Gln Lys Phe
                50                  55                  60

Glu Asp Lys Ala Thr Leu Thr Val Asp Lys Ser Ser Ser Thr Ala Tyr
65                      70                  75                  80

Met Glu Leu Arg Ser Leu Thr Ser Glu Asp Ser Ala Val Tyr Tyr Cys
                    85                  90                  95

Ala Ala Gly Trp Asn Phe Asp Tyr Trp Gly Gln Gly Thr Thr Leu Thr
                    100                 105                 110

Val Ser Ser
        115
```

<210> SEQ ID NO 20
<211> LENGTH: 107
<212> TYPE: PRT
<213> ORGANISM: Mus musculus

<400> SEQUENCE: 20

```
Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
                20                  25                  30

Val Asp Trp Tyr Gln Gln Lys Pro Gly Gln Ser Pro Lys Leu Leu Ile
                35                  40                  45

Tyr Trp Ala Ser Thr Arg His Thr Gly Val Pro Asp Arg Phe Thr Gly
                50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                    85                  90                  95

Thr Phe Gly Ala Gly Thr Met Leu Asp Leu Lys
                100                 105
```

<210> SEQ ID NO 21
<211> LENGTH: 115
<212> TYPE: PRT
<213> ORGANISM: Artificial Sequence
<220> FEATURE:
<223> OTHER INFORMATION: deimmunized heavy chain J591

<400> SEQUENCE: 21

```
Glu Val Gln Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
                20                  25                  30

Thr Ile His Trp Val Lys Gln Ala Pro Gly Lys Gly Leu Glu Trp Ile
                35                  40                  45

Gly Asn Ile Asn Pro Asn Asn Gly Gly Thr Thr Tyr Asn Gln Lys Phe
                50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                    85                  90                  95
```

```
Ala Ala Gly Trp Asn Phe Asp Tyr Trp Gly Gln Gly Thr Leu Leu Thr
            100                 105                 110

Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: deimmunized light chain J591

<400> SEQUENCE: 22

Asp Ile Gln Met Thr Gln Ser Pro Ser Leu Ser Thr Ser Val Gly
 1               5                  10                  15

Asp Arg Val Thr Leu Thr Cys Lys Ala Ser Gln Asp Val Gly Thr Ala
             20                  25                  30

Val Asp Trp Tyr Gln Gln Lys Pro Gly Ser Pro Lys Leu Leu Ile
         35                  40                  45

Tyr Trp Ala Ser Thr Arg His Thr Gly Ile Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                 85                  90                  95

Thr Phe Gly Pro Gly Thr Lys Val Asp Ile Lys
            100                 105

<210> SEQ ID NO 23
<211> LENGTH: 807
<212> TYPE: DNA
<213> ORGANISM: Artificial Sequence
<220> FEATURE:
<221> NAME/KEY: CDS
<222> LOCATION: (122)...(166)
<220> FEATURE:
<221> NAME/KEY: CDS
<222> LOCATION: (249)...(605)
<223> OTHER INFORMATION: deimmunized heavy chain J591

<400> SEQUENCE: 23
aagcttatga atatgcaaat cctctgaatc tacatggtaa atataggttt gtctatacca      60
caaacagaaa aacatgagat cacagttctc tctacagtta ctgagcacac aggacctcac    120 c atg gga tgg agc tgt atc atc ctc ttc ttg gta gca aca gct aca          166
  Met Gly Trp Ser Cys Ile Ile Leu Phe Leu Val Ala Thr Ala Thr
   1               5                  10                  15 ggtaagggc tcacagtagc aggcttgagg tctggacata tatatgggtg acaatgacat     226
ccactttgcc tttctctcca ca ggt gtc cac tcc gag gtc caa ctg gta cag     278
                         Gly Val His Ser Glu Val Gln Leu Val Gln
                                          20                  25 tct gga cct gaa gtg aag aag cct ggg gct aca gtg aag ata tcc tgc      326
Ser Gly Pro Glu Val Lys Lys Pro Gly Ala Thr Val Lys Ile Ser Cys
                 30                  35                  40 aag act tct gga tac aca ttc act gaa tat acc ata cac tgg gtg aag      374
Lys Thr Ser Gly Tyr Thr Phe Thr Glu Tyr Thr Ile His Trp Val Lys
             45                  50                  55 cag gcc cct gga aag ggc ctt gag tgg att gga aac atc aat cct aac      422
Gln Ala Pro Gly Lys Gly Leu Glu Trp Ile Gly Asn Ile Asn Pro Asn
 60                  65                  70
```

|  |  |  |  |  |  |  |  |  |  |  |  |  |  |  |  |
|---|---|---|---|---|---|---|---|---|---|---|---|---|---|---|---|
| aat | ggt | ggt | acc | acc | tac | aat | cag | aag | ttc | gag | gac | aag | gcc | aca | cta | 470 |
| Asn | Gly | Gly | Thr | Thr | Tyr | Asn | Gln | Lys | Phe | Glu | Asp | Lys | Ala | Thr | Leu |
|  | 75 |  |  |  | 80 |  |  |  |  | 85 |  |  |  |  |  |

|  |  |  |  |  |  |  |  |  |  |  |  |  |  |  |  |
|---|---|---|---|---|---|---|---|---|---|---|---|---|---|---|---|
| act | gta | gac | aag | tcc | acc | gat | aca | gcc | tac | atg | gag | ctc | agc | agc | cta | 518 |
| Thr | Val | Asp | Lys | Ser | Thr | Asp | Thr | Ala | Tyr | Met | Glu | Leu | Ser | Ser | Leu |
| 90 |  |  |  |  | 95 |  |  |  |  | 100 |  |  |  |  | 105 |

|  |  |  |  |  |  |  |  |  |  |  |  |  |  |  |  |
|---|---|---|---|---|---|---|---|---|---|---|---|---|---|---|---|
| aga | tct | gag | gat | act | gca | gtc | tat | tat | tgt | gca | gct | ggt | tgg | aac | ttt | 566 |
| Arg | Ser | Glu | Asp | Thr | Ala | Val | Tyr | Tyr | Cys | Ala | Ala | Gly | Trp | Asn | Phe |
|  |  |  |  | 110 |  |  |  |  | 115 |  |  |  |  | 120 |  |

|  |  |  |  |  |  |  |  |  |  |  |  |  |
|---|---|---|---|---|---|---|---|---|---|---|---|---|
| gac | tac | tgg | ggc | caa | ggg | acc | ctg | ctc | acc | gtc | tcc | tca | ggtgagtcct | 615 |
| Asp | Tyr | Trp | Gly | Gln | Gly | Thr | Leu | Leu | Thr | Val | Ser | Ser |  |
|  |  |  | 125 |  |  |  |  | 130 |  |  |  |  |  |

```
tacaacctct ctcttctatt cagcttaaat agattttact gcatttgttg gggggaaat      675 gtgtgtatct gaatttcagg tcatgaagga ctagggacac cttgggagtc agaaagggtc     735
attgggagcc cgggctgatg cagacagaca tcctcagctc ccagacttca tggccagaga    795
tttataggat cc                                                         807

<210> SEQ ID NO 24
<211> LENGTH: 807
<212> TYPE: DNA
<213> ORGANISM: Artificial Sequence
<220> FEATURE:
<223> OTHER INFORMATION: deimmunized heavy chain J591

<400> SEQUENCE: 24
ggatcctata aatctctggc catgaagtct gggagctgag gatgtctgtc tgcatcagcc      60
cgggctccca atgacccttt ctgactccca aggtgtccct agtccttcat gacctgaaat     120
tcagatacac acatttcccc cccaacaaat gcagtaaaat ctatttaagc tgaatagaag    180
agagaggttg taaggactca cctgaggaga cggtgagcag ggtcccttgg ccccagtagt    240
caaagttcca accagctgca caataataga ctgcagtatc ctcagatctt aggctgctga    300
gctccatgta ggctgtatcg gtggacttgt ctacagttag tgtggccttg tcctcgaact    360
tctgattgta ggtggtacca ccattgttag gattgatgtt tccaatccac tcaaggccct    420 ttccagggc ctgcttcacc cagtgtatgg tatattcagt gaatgtgtat ccagaagtct    480
tgcaggatat cttcactgta gccccaggct tcttcacttc aggtccagac tgtaccagtt    540
ggacctcgga gtggacacct gtggagagaa aggcaaagtg gatgtcattg tcacccatat    600
atatgtccag acctcaagcc tgctactgtg agcccttac ctgtagctgt tgctaccaag    660
aagaggatga tacagctcca tcccatggtg aggtcctgtg tgctcagtaa ctgtagagag    720
aactgtgatc tcatgttttt ctgtttgtgg tatagacaaa cctatattta ccatgtagat    780
tcagaggatt tgcatattca taagctt                                         807

<210> SEQ ID NO 25
<211> LENGTH: 620
<212> TYPE: DNA
<213> ORGANISM: Artificial Sequence
<220> FEATURE:
<221> NAME/KEY: CDS
<222> LOCATION: (122)...(166)
<220> FEATURE:
<221> NAME/KEY: CDS
<222> LOCATION: (249)...(581)
<223> OTHER INFORMATION: deimmunized light chain J591

<400> SEQUENCE: 25
aagcttatga atatgcaaat cctctgaatc tacatggtaa atataggttt gtctatacca      60
```

```
caaacagaaa aacatgagat cacagttctc tctacagtta ctgagcacac aggacctcac      120 c atg gga tgg agc tgt atc atc ctc ttc ttg gta gca aca gct aca          166
  Met Gly Trp Ser Cys Ile Ile Leu Phe Leu Val Ala Thr Ala Thr
  1               5                   10                  15 ggtaagggc tcacagtagc aggcttgagg tctggacata tatatgggtg acaatgacat       226
ccactttgcc tttctctcca ca ggt gtc cac tcc gac atc cag atg acc cag       278
                         Gly Val His Ser Asp Ile Gln Met Thr Gln
                                             20                  25 tct ccc tca tcc ctg tcc aca tca gta gga gac agg gtc acc ctc acc        326
Ser Pro Ser Ser Leu Ser Thr Ser Val Gly Asp Arg Val Thr Leu Thr
                30                  35                  40 tgt aag gcc agt caa gat gtg ggt act gct gta gac tgg tat caa cag        374
Cys Lys Ala Ser Gln Asp Val Gly Thr Ala Val Asp Trp Tyr Gln Gln
                45                  50                  55 aaa cca gga cca tct cct aaa cta ctg att tat tgg gca tcc act cgg        422
Lys Pro Gly Pro Ser Pro Lys Leu Leu Ile Tyr Trp Ala Ser Thr Arg
        60                  65                  70 cac act gga atc cct agt cgc ttc tca ggc agt gga tct ggg aca gac        470
His Thr Gly Ile Pro Ser Arg Phe Ser Gly Ser Gly Ser Gly Thr Asp
    75                  80                  85 ttc act ctc acc att tct agt ctt cag cct gaa gac ttt gca gat tat        518
Phe Thr Leu Thr Ile Ser Ser Leu Gln Pro Glu Asp Phe Ala Asp Tyr
90                  95                  100                 105 tac tgt cag caa tat aac agc tat cct ctc acg ttc ggt cct ggg acc        566
Tyr Cys Gln Gln Tyr Asn Ser Tyr Pro Leu Thr Phe Gly Pro Gly Thr
                110                 115                 120 aag gtg gac atc aaa cgtgagtaga atttaaactt tgcttcctca gttggatcc         620
Lys Val Asp Ile Lys
            125

<210> SEQ ID NO 26
<211> LENGTH: 620
<212> TYPE: DNA
<213> ORGANISM: Artificial Sequence
<220> FEATURE:
<223> OTHER INFORMATION: deimmunized light chain J591

<400> SEQUENCE: 26
ggatccaact gaggaagcaa agtttaaatt ctactcacgt ttgatgtcca ccttggtccc       60
aggaccgaac gtgagaggat agctgttata ttgctgacag taataatctg caaagtcttc     120
aggctgaaga ctagaaatgg tgagagtgaa gtctgtccca gatccactgc ctgagaagcg     180
actagggatt ccagtgtgcc gagtggatgc caataaatc agtagtttag gagatggtcc      240
tggtttctgt tgataccagt ctacagcagt acccacatct tgactggcct tacaggtgag     300
ggtgaccctg tctcctactg atgtggacag ggatgaggga ctagggtca tctggatgtc       360 ggagtggaca cctgtggaga aaaggcaaa gtggatgtca ttgtcaccca tatatatgtc      420
cagacctcaa gcctgctact gtgagcccct tacctgtagc tgttgctacc aagaagagga     480
tgatacagct ccatcccatg gtgaggtcct gtgtgctcag taactgtaga gagaactgtg     540
atctcatgtt tttctgtttg tggtatagac aaacctatat ttaccatgta gattcagagg     600
atttgcatat tcataagctt                                                  620

<210> SEQ ID NO 27
<211> LENGTH: 134
<212> TYPE: PRT
<213> ORGANISM: Artificial Sequence
<220> FEATURE:
<223> OTHER INFORMATION: deimmunized heavy chain J591
```

```
<400> SEQUENCE: 27

Met Gly Trp Ser Cys Ile Ile Leu Phe Leu Val Ala Thr Ala Thr Gly
 1               5                  10                  15

Val His Ser Glu Val Gln Leu Val Gln Ser Gly Pro Glu Val Lys Lys
             20                  25                  30

Pro Gly Ala Thr Val Lys Ile Ser Cys Lys Thr Ser Gly Tyr Thr Phe
         35                  40                  45

Thr Glu Tyr Thr Ile His Trp Val Lys Gln Ala Pro Gly Lys Gly Leu
     50                  55                  60

Glu Trp Ile Gly Asn Ile Asn Pro Asn Asn Gly Thr Thr Tyr Asn
 65                  70                  75                  80

Gln Lys Phe Glu Asp Lys Ala Thr Leu Thr Val Asp Lys Ser Thr Asp
                 85                  90                  95

Thr Ala Tyr Met Glu Leu Ser Ser Leu Arg Ser Glu Asp Thr Ala Val
            100                 105                 110

Tyr Tyr Cys Ala Ala Gly Trp Asn Phe Asp Tyr Trp Gly Gln Gly Thr
        115                 120                 125

Leu Leu Thr Val Ser Ser
        130

<210> SEQ ID NO 28
<211> LENGTH: 126
<212> TYPE: PRT
<213> ORGANISM: Artificial Sequence
<220> FEATURE:
<223> OTHER INFORMATION: deimmunized light chain J591

<400> SEQUENCE: 28

Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Thr
             20                  25                  30

Ser Val Gly Asp Arg Val Thr Leu Thr Cys Lys Ala Ser Gln Asp Val
         35                  40                  45

Gly Thr Ala Val Asp Trp Tyr Gln Gln Lys Pro Gly Pro Ser Pro Lys
     50                  55                  60

Leu Leu Ile Tyr Cys Ala Ser Thr Arg His Thr Gly Ile Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Asp Tyr Tyr Cys Gln Gln Tyr Asn Ser
            100                 105                 110

Tyr Pro Leu Thr Phe Gly Pro Gly Thr Lys Val Asp Ile Lys
        115                 120                 125

<210> SEQ ID NO 29
<211> LENGTH: 10
<212> TYPE: PRT
<213> ORGANISM: Mus musculus

<400> SEQUENCE: 29

Gly Phe Thr Phe Ser Asn Tyr Trp Met Asn
 1               5                  10

<210> SEQ ID NO 30
<211> LENGTH: 19
<212> TYPE: PRT
```

<213> ORGANISM: Mus musculus

<400> SEQUENCE: 30

Glu Ile Arg Ser Gln Ser Asn Asn Phe Ala Thr His Tyr Ala Glu Ser
1               5                   10                  15
Val Lys Gly

<210> SEQ ID NO 31
<211> LENGTH: 5
<212> TYPE: PRT
<213> ORGANISM: Mus musculus

<400> SEQUENCE: 31

Arg Trp Asn Asn Phe
1               5

<210> SEQ ID NO 32
<211> LENGTH: 11
<212> TYPE: PRT
<213> ORGANISM: Mus musculus

<400> SEQUENCE: 32

Lys Ala Ser Glu Asn Val Gly Thr Tyr Val Ser
1               5                   10

<210> SEQ ID NO 33
<211> LENGTH: 7
<212> TYPE: PRT
<213> ORGANISM: Mus musculus

<400> SEQUENCE: 33

Gly Ala Ser Asn Arg Phe Thr
1               5

<210> SEQ ID NO 34
<211> LENGTH: 9
<212> TYPE: PRT
<213> ORGANISM: Mus musculus

<400> SEQUENCE: 34

Gly Gln Ser Tyr Thr Phe Pro Tyr Thr
1               5

<210> SEQ ID NO 35
<211> LENGTH: 82
<212> TYPE: PRT
<213> ORGANISM: Mus musculus

<400> SEQUENCE: 35

Glu Val Lys Leu Glu Glu Ser Gly Gly Gly Leu Val Gln Pro Gly Gly
1               5                   10                  15
Ser Met Lys Leu Ser Cys Val Ala Ser Trp Val Arg Gln Ser Pro Glu
            20                  25                  30
Lys Gly Leu Glu Trp Val Ala Arg Val Ile Ile Ser Arg Asp Asp Ser
        35                  40                  45
Lys Ser Ser Val Tyr Leu Gln Met Asn Asn Leu Arg Ala Glu Asp Thr
    50                  55                  60
Gly Ile Tyr Tyr Cys Thr Arg Trp Gly Gln Gly Thr Thr Leu Thr Val
65                  70                  75                  80
Ser Ser

<210> SEQ ID NO 36
<211> LENGTH: 80
<212> TYPE: PRT
<213> ORGANISM: Mus musculus

<400> SEQUENCE: 36

Asn Ile Val Met Thr Gln Phe Pro Lys Ser Met Ser Ile Ser Val Gly
1               5                   10                  15

Glu Arg Val Thr Leu Thr Cys Trp Tyr Gln Gln Lys Pro Glu Gln Ser
            20                  25                  30

Pro Lys Met Leu Ile Tyr Gly Val Pro Asp Arg Phe Thr Gly Ser Gly
        35                  40                  45

Ser Ala Thr Asp Phe Ile Leu Thr Ile Ser Ser Val Gln Thr Glu Asp
    50                  55                  60

Leu Val Asp Tyr Tyr Cys Phe Gly Gly Gly Thr Lys Leu Glu Met Lys
65                  70                  75                  80

<210> SEQ ID NO 37
<211> LENGTH: 25
<212> TYPE: PRT
<213> ORGANISM: Artificial Sequence
<220> FEATURE:
<223> OTHER INFORMATION: deimmunized heavy chain J415-4

<400> SEQUENCE: 37

Glu Val Lys Leu Glu Glu Ser Gly Gly Gly Leu Val Gln Pro Gly Gly
1               5                   10                  15

Ser Met Lys Ile Ser Cys Val Ala Ser
            20                  25

<210> SEQ ID NO 38
<211> LENGTH: 14
<212> TYPE: PRT
<213> ORGANISM: Artificial Sequence
<220> FEATURE:
<223> OTHER INFORMATION: deimmunized heavy chain J415-4

<400> SEQUENCE: 38

Trp Val Arg Gln Ser Pro Glu Lys Gly Leu Glu Trp Val Ala
1               5                   10

<210> SEQ ID NO 39
<211> LENGTH: 32
<212> TYPE: PRT
<213> ORGANISM: Artificial Sequence
<220> FEATURE:
<223> OTHER INFORMATION: deimmunized heavy chain J415-4

<400> SEQUENCE: 39

Arg Val Ile Ile Ser Arg Asp Asp Ser Lys Ser Ser Val Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 40
<211> LENGTH: 11
<212> TYPE: PRT
<213> ORGANISM: Artificial Sequence
<220> FEATURE:
<223> OTHER INFORMATION: deimmunized heavy chain J415-4

<400> SEQUENCE: 40

Trp Gly Gln Gly Thr Thr Val Thr Val Ser Ser
1               5                   10

```
<210> SEQ ID NO 41
<211> LENGTH: 23
<212> TYPE: PRT
<213> ORGANISM: Artificial Sequence
<220> FEATURE:
<223> OTHER INFORMATION: deimmunized light chain J415-5

<400> SEQUENCE: 41

Asn Ile Val Met Thr Gln Phe Pro Lys Ser Met Ser Ala Ser Ala Gly
 1               5                  10                  15

Glu Arg Met Thr Leu Thr Cys
            20

<210> SEQ ID NO 42
<211> LENGTH: 15
<212> TYPE: PRT
<213> ORGANISM: Artificial Sequence
<220> FEATURE:
<223> OTHER INFORMATION: deimmunized light chain J415-5

<400> SEQUENCE: 42

Trp Tyr Gln Gln Lys Pro Thr Gln Ser Pro Lys Met Leu Ile Tyr
 1               5                  10                  15

<210> SEQ ID NO 43
<211> LENGTH: 32
<212> TYPE: PRT
<213> ORGANISM: Artificial Sequence
<220> FEATURE:
<223> OTHER INFORMATION: deimmunized light chain J415-5

<400> SEQUENCE: 43

Gly Val Pro Asp Arg Phe Ser Gly Ser Gly Ser Gly Thr Asp Phe Ile
 1               5                  10                  15

Leu Thr Ile Ser Ser Val Gln Ala Glu Asp Leu Val Asp Tyr Tyr Cys
            20                  25                  30

<210> SEQ ID NO 44
<211> LENGTH: 10
<212> TYPE: PRT
<213> ORGANISM: Artificial Sequence
<220> FEATURE:
<223> OTHER INFORMATION: deimmunized light chain J415-5

<400> SEQUENCE: 44

Phe Gly Gly Gly Thr Lys Leu Glu Met Lys
 1               5                  10

<210> SEQ ID NO 45
<211> LENGTH: 82
<212> TYPE: PRT
<213> ORGANISM: Artificial Sequence
<220> FEATURE:
<223> OTHER INFORMATION: deimmunized heavy chain J415-4

<400> SEQUENCE: 45

Glu Val Lys Leu Glu Glu Ser Gly Gly Gly Leu Val Gln Pro Gly Gly
 1               5                  10                  15

Ser Met Lys Ile Ser Cys Val Ala Ser Trp Val Arg Gln Ser Pro Glu
            20                  25                  30

Lys Gly Leu Glu Trp Val Ala Arg Val Ile Ile Ser Arg Asp Asp Ser
        35                  40                  45

Lys Ser Ser Val Tyr Leu Gln Met Asn Ser Leu Arg Ala Glu Asp Thr
```

```
                          50                  55                  60
Ala Val Tyr Tyr Cys Thr Arg Trp Gly Gln Gly Thr Thr Val Thr Val
 65                  70                  75                  80

Ser Ser

<210> SEQ ID NO 46
<211> LENGTH: 80
<212> TYPE: PRT
<213> ORGANISM: Artificial Sequence
<220> FEATURE:
<223> OTHER INFORMATION: deimmunized light chain J415-5

<400> SEQUENCE: 46

Asn Ile Val Met Thr Gln Phe Pro Lys Ser Met Ser Ala Ser Ala Gly
  1               5                  10                  15

Glu Arg Met Thr Leu Thr Cys Trp Tyr Gln Gln Lys Pro Thr Gln Ser
                 20                  25                  30

Pro Lys Met Leu Ile Tyr Gly Val Pro Asp Arg Phe Ser Gly Ser Gly
             35                  40                  45

Ser Gly Thr Asp Phe Ile Leu Thr Ile Ser Ser Val Gln Ala Glu Asp
         50                  55                  60

Leu Val Asp Tyr Tyr Cys Phe Gly Gly Thr Lys Leu Glu Met Lys
 65                  70                  75                  80

<210> SEQ ID NO 47
<211> LENGTH: 116
<212> TYPE: PRT
<213> ORGANISM: Mus musculus

<400> SEQUENCE: 47

Glu Val Lys Leu Glu Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
             35                  40                  45

Ala Glu Ile Arg Ser Gln Ser Asn Asn Phe Ala Thr His Tyr Ala Glu
         50                  55                  60

Ser Val Lys Gly Arg Val Ile Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg Arg Trp Asn Asn Phe Trp Gly Gln Gly Thr Thr Leu
                100                 105                 110

Thr Val Ser Ser
        115

<210> SEQ ID NO 48
<211> LENGTH: 107
<212> TYPE: PRT
<213> ORGANISM: Mus musculus

<400> SEQUENCE: 48

Asn Ile Val Met Thr Gln Phe Pro Lys Ser Met Ser Ile Ser Val Gly
  1               5                  10                  15

Glu Arg Val Thr Leu Thr Cys Lys Ala Ser Glu Asn Val Gly Thr Tyr
                 20                  25                  30

Val Ser Trp Tyr Gln Gln Lys Pro Glu Gln Ser Pro Lys Met Leu Ile
```

```
                35                  40                  45
Tyr Gly Ala Ser Asn Arg Phe Thr Gly Val Pro Asp Arg Phe Thr Gly
     50                  55                  60

Ser Gly Ser Ala Thr Asp Phe Ile Leu Thr Ile Ser Ser Val Gln Thr
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 49
<211> LENGTH: 116
<212> TYPE: PRT
<213> ORGANISM: Artificial Sequence
<220> FEATURE:
<223> OTHER INFORMATION: deimmunized heavy chain J415-4

<400> SEQUENCE: 49

Glu Val Lys Leu Glu Glu Ser Gly Gly Gly Leu Val Gln Pro Gly Gly
 1               5                  10                  15

Ser Met Lys Ile Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Ser Gln Ser Asn Asn Phe Ala Thr His Tyr Ala Glu
     50                  55                  60

Ser Val Lys Gly Arg Val Ile Ile Ser Arg Asp Asp Ser Lys Ser Ser
 65                  70                  75                  80

Val Tyr Leu Gln Met Asn Ser Leu Arg Ala Glu Asp Thr Ala Val Tyr
                 85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 50
<211> LENGTH: 107
<212> TYPE: PRT
<213> ORGANISM: Artificial Sequence
<220> FEATURE:
<223> OTHER INFORMATION: deimmunized light chain J415-5

<400> SEQUENCE: 50

Asn Ile Val Met Thr Gln Phe Pro Lys Ser Met Ser Ala Ser Ala Gly
 1               5                  10                  15

Glu Arg Met Thr Leu Thr Cys Lys Ala Ser Glu Asn Val Gly Thr Tyr
                20                  25                  30

Val Ser Trp Tyr Gln Gln Lys Pro Thr Gln Ser Pro Lys Met Leu Ile
            35                  40                  45

Tyr Gly Ala Ser Asn Arg Phe Thr Gly Val Pro Asp Arg Phe Ser Gly
     50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105
```

<210> SEQ ID NO 51
<211> LENGTH: 348
<212> TYPE: DNA
<213> ORGANISM: Artificial Sequence
<220> FEATURE:
<223> OTHER INFORMATION: deimmunized heavy chain J415-4

<400> SEQUENCE: 51

```
gaagtgaaac ttgaggagtc tggaggaggc ttggtgcaac ctggagggtc catgaaaatc      60
tcctgtgttg cctctggatt cactttcagt aattactgga tgaactgggt ccgccagtct     120
ccagagaagg ggcttgagtg ggttgctgaa attagatcgc aatctaataa ttttgcaaca     180
cattatgcgg agtctgtgaa agggagggtc atcatctcaa gagatgattc caagagtagt     240
gtctacctgc aaatgaacag tttgagagct gaagacactg ccgttttatta ctgtaccagg     300
cgatggaata atttctgggg ccaaggcacc actgtcacag tctcctca                   348
```

<210> SEQ ID NO 52
<211> LENGTH: 321
<212> TYPE: DNA
<213> ORGANISM: Artificial Sequence
<220> FEATURE:
<223> OTHER INFORMATION: deimmunized light chain J415-5

<400> SEQUENCE: 52

```
aacattgtaa tgacccaatt tcccaaatcc atgtccgcct cagcaggaga gaggatgacc      60
ttgacctgca aggccagtga aaatgtgggt acttatgtgt cctggtatca acagaaacca     120
acacagtctc ctaagatgtt gatatacggg gcatccaacc ggttcactgg ggtcccagat     180
cgcttctccg gcagtggatc tggaacagat ttcattctga ccatcagcag tgtgcaggca     240
gaagaccttg tagattatta ctgtggacag agttacacct ttccgtacac gttcggaggg     300
gggaccaagc tggaaatgaa g                                               321
```

<210> SEQ ID NO 53
<211> LENGTH: 810
<212> TYPE: DNA
<213> ORGANISM: Artificial Sequence
<220> FEATURE:
<223> OTHER INFORMATION: deimmunized heavy chain J415-1
<220> FEATURE:
<221> NAME/KEY: CDS
<222> LOCATION: (122)...(160)
<220> FEATURE:
<221> NAME/KEY: CDS
<222> LOCATION: (249)...(608)

<400> SEQUENCE: 53

```
aagcttatga atatgcaaat cctctgaatc tacatggtaa atataggttt gtctatacca      60
caaacagaaa aacatgagat cacagttctc tctacagtta ctgagcacac aggacctcac     120
c atg gga tgg agc tgt atc atc ctc ttc ttg gta gca aca gctacaggta      170
  Met Gly Trp Ser Cys Ile Ile Leu Phe Leu Val Ala Thr
   1               5                  10 agggctcac agtagcaggc ttgaggtctg acatatata tggtgacaa tgacatccac        230
tttgcctttc tctccaca ggt gtc cac tcc gaa gtg aaa ctt gag gag tct        281
                    Gly Val His Ser Glu Val Lys Leu Glu Glu Ser
                                 15                  20 gga gga ggc ttg gtg caa cct gga ggg tcc atg aaa atc tcc tgt aaa        329
Gly Gly Gly Leu Val Gln Pro Gly Gly Ser Met Lys Ile Ser Cys Lys
 25                  30                  35                  40 gcc tct gga ttc act ttc agt aat tac tgg atg aac tgg gtc cgc cag        377
```

```
                Ala Ser Gly Phe Thr Phe Ser Asn Tyr Trp Met Asn Trp Val Arg Gln
                             45                  50                  55 act cca gag aag ggg ctt gag tgg gtt gct ctt att aga tcg caa tct         425
Thr Pro Glu Lys Gly Leu Glu Trp Val Ala Leu Ile Arg Ser Gln Ser
             60                  65                  70 aat aat ttt gca aca cat tat gcg gag tct gtg aaa ggg agg gtc atc         473
Asn Asn Phe Ala Thr His Tyr Ala Glu Ser Val Lys Gly Arg Val Ile
     75                  80                  85 atc tca aga gat gat tcc aag agt agt gtc tac ctg caa atg aac agt         521
Ile Ser Arg Asp Asp Ser Lys Ser Ser Val Tyr Leu Gln Met Asn Ser
 90                  95                 100 ttg aga gct gaa gac act gcc gtt tat tac tgt acc agg cga tgg aat         569
Leu Arg Ala Glu Asp Thr Ala Val Tyr Tyr Cys Thr Arg Arg Trp Asn
105                 110                 115                 120 aat ttc tgg ggc caa ggc acc act gtc aca gtc tcc tca ggtgagtcct          618
Asn Phe Trp Gly Gln Gly Thr Thr Val Thr Val Ser Ser
                125                 130 tacaacctct ctcttctatt cagcttaaat agatttact gcatttgttg gggggaaat         678 gtgtgtatct gaatttcagg tcatgaagga ctagggacac cttgggagtc agaaagggtc      738
attgggagcc cgggctgatg cagacagaca tcctcagctc ccagacttca tggccagaga      798
tttataggat cc                                                           810
```

```
<210> SEQ ID NO 54
<211> LENGTH: 133
<212> TYPE: PRT
<213> ORGANISM: Artificial Sequence
<220> FEATURE:
<223> OTHER INFORMATION: deimmunized heavy chain J415-1

<400> SEQUENCE: 54

Met Gly Trp Ser Cys Ile Ile Leu Phe Leu Val Ala Thr Gly Val His
 1               5                  10                  15

Ser Glu Val Lys Leu Glu Glu Ser Gly Gly Leu Val Gln Pro Gly
             20                  25                  30

Gly Ser Met Lys Ile Ser Cys Lys Ala Ser Gly Phe Thr Phe Ser Asn
         35                  40                  45

Tyr Trp Met Asn Trp Val Arg Gln Thr Pro Glu Lys Gly Leu Glu Trp
 50                  55                  60

Val Ala Leu Ile Arg Ser Gln Ser Asn Asn Phe Ala Thr His Tyr Ala
 65                  70                  75                  80

Glu Ser Val Lys Gly Arg Val Ile Ile Ser Arg Asp Asp Ser Lys Ser
                 85                  90                  95

Ser Val Tyr Leu Gln Met Asn Ser Leu Arg Ala Glu Asp Thr Ala Val
            100                 105                 110

Tyr Tyr Cys Thr Arg Arg Trp Asn Asn Phe Trp Gly Gln Gly Thr Thr
        115                 120                 125

Val Thr Val Ser Ser
        130
```

```
<210> SEQ ID NO 55
<211> LENGTH: 810
<212> TYPE: DNA
<213> ORGANISM: Artificial Sequence
<220> FEATURE:
<223> OTHER INFORMATION: deimmunized heavy chain J415-1

<400> SEQUENCE: 55
ggatcctata aatctctggc catgaagtct gggagctgag gatgtctgtc tgcatcagcc      60
```

-continued

```
cgggctccca atgacccttt ctgactccca aggtgtccct agtccttcat gacctgaaat      120
tcagatacac acatttcccc cccaacaaat gcagtaaaat ctatttaagc tgaatagaag      180
agagaggttg taaggactca cctgaggaga ctgtgacagt ggtgccttgg ccccagaaat      240
tattccatcg cctggtacag taataaacgg cagtgtcttc agctctcaaa ctgttcattt      300
gcaggtagac actactcttg gaatcatctc ttgagatgat gaccctccct ttcacagact      360
ccgcataatg tgttgcaaaa ttattagatt gcgatctaat aagagcaacc cactcaagcc      420
ccttctctgg agtctggcgg acccagttca tccagtaatt actgaaagtg aatccagagg      480
ctttacagga gattttcatg gaccctccag gttgcaccaa gcctcctcca gactcctcaa      540
gtttcacttc ggagtggaca cctgtggaga aaaggcaaa gtggatgtca ttgtcaccca      600
tatatatgtc cagacctcaa gcctgctact gtgagcccct acctgtagc tgttgctacc       660 aagaagagga tgatacagct ccatcccatg gtgaggtcct gtgtgctcag taactgtaga      720
gagaactgtg atctcatgtt tttctgtttg tggtatagac aaacctatat ttaccatgta      780
gattcagagg atttgcatat tcataagctt                                       810
```

<210> SEQ ID NO 56
<211> LENGTH: 620
<212> TYPE: DNA
<213> ORGANISM: Artificial Sequence
<220> FEATURE:
<223> OTHER INFORMATION: deimmunized light chain J415-1
<220> FEATURE:
<221> NAME/KEY: CDS
<222> LOCATION: (122)...(160)
<220> FEATURE:
<221> NAME/KEY: CDS
<222> LOCATION: (249)...(581)

<400> SEQUENCE: 56

```
aagcttatga atatgcaaat cctctgaatc tacatggtaa atataggttt gtctatacca       60
caaacagaaa aacatgagat cacagttctc tctacagtta ctgagcacac aggacctcac      120 c atg gga tgg agc tgt atc atc ctc ttc ttg gta gca aca gctacaggta      170
  Met Gly Trp Ser Cys Ile Ile Leu Phe Leu Val Ala Thr
  1               5                  10 agggctcac agtagcaggc ttgaggtctg gacatatata tgggtgacaa tgacatccac      230
tttgcctttc tctccaca ggt gtc cac tcc aac att gta atg acc caa tcc      281
                    Gly Val His Ser Asn Ile Val Met Thr Gln Ser
                               15                  20 ccc aaa tcc atg tcc gcc tca gca gga gag agg atg acc ttg acc tgc       329
Pro Lys Ser Met Ser Ala Ser Ala Gly Glu Arg Met Thr Leu Thr Cys
25                  30                  35                  40 aag gcc agt gag aat tcc ggt act tat gtg tcc tgg tat caa cag aaa       377
Lys Ala Ser Glu Asn Ser Gly Thr Tyr Val Ser Trp Tyr Gln Gln Lys
                45                  50                  55 cca aca cag tct cct aag atg ttg ata tac ggg gca tcc aac cgg ttc       425
Pro Thr Gln Ser Pro Lys Met Leu Ile Tyr Gly Ala Ser Asn Arg Phe
            60                  65                  70 act ggg gtc cca gat cgc ttc tcc ggc agt gga tct gga aca gat ttc       473
Thr Gly Val Pro Asp Arg Phe Ser Gly Ser Gly Ser Gly Thr Asp Phe
        75                  80                  85 att ctg acc gcc agc agt gtg cag gca gaa gac cct gta gat tat tac       521
Ile Leu Thr Ala Ser Ser Val Gln Ala Glu Asp Pro Val Asp Tyr Tyr
    90                  95                 100 tgt gga cag agt tac acc ttt ccg tac acg ttc gga ggg ggg acc aag       569
Cys Gly Gln Ser Tyr Thr Phe Pro Tyr Thr Phe Gly Gly Gly Thr Lys
```

```
                 105                 110                 115                 120
ctg gaa atg aag cgtgagtaga atttaaactt tgcttcctca gttggatcc              620
Leu Glu Met Lys
```

<210> SEQ ID NO 57
<211> LENGTH: 124
<212> TYPE: PRT
<213> ORGANISM: Artificial Sequence
<220> FEATURE:
<223> OTHER INFORMATION: deimmunized light chain J415-1

<400> SEQUENCE: 57

```
Met Gly Trp Ser Cys Ile Ile Leu Phe Leu Val Ala Thr Gly Val His
 1               5                  10                  15

Ser Asn Ile Val Met Thr Gln Ser Pro Lys Ser Met Ser Ala Ser Ala
                20                  25                  30

Gly Glu Arg Met Thr Leu Thr Cys Lys Ala Ser Glu Asn Ser Gly Thr
            35                  40                  45

Tyr Val Ser Trp Tyr Gln Gln Lys Pro Thr Gln Ser Pro Lys Met Leu
        50                  55                  60

Ile Tyr Gly Ala Ser Asn Arg Phe Thr Gly Val Pro Asp Arg Phe Ser
65                  70                  75                  80

Gly Ser Gly Ser Gly Thr Asp Phe Ile Leu Thr Ala Ser Ser Val Gln
                85                  90                  95

Ala Glu Asp Pro Val Asp Tyr Tyr Cys Gly Gln Ser Tyr Thr Phe Pro
            100                 105                 110

Tyr Thr Phe Gly Gly Gly Thr Lys Leu Glu Met Lys
        115                 120
```

<210> SEQ ID NO 58
<211> LENGTH: 620
<212> TYPE: DNA
<213> ORGANISM: Artificial Sequence
<220> FEATURE:
<223> OTHER INFORMATION: deimmunized light chain J415-1

<400> SEQUENCE: 58

```
ggatccaact gaggaagcaa agtttaaatt ctactcacgc ttcatttcca gcttggtccc         60
ccctccgaac gtgtacggaa aggtgtaact ctgtccacag taataatcta cagggtcttc       120
tgcctgcaca ctgctggcgg tcagaatgaa atctgttcca gatccactgc cggagaagcg       180
atctgggacc ccagtgaacc ggttggatgc cccgtatatc aacatcttag agactgtgt        240 tggtttctgt tgataccagg acacataagt accggaattc tcactggcct tgcaggtcaa       300
ggtcatcctc tctcctgctg aggcggacat ggatttgggg gattgggtca ttacaatgtt       360
ggagtggaca cctgtggaga gaaaggcaaa gtggatgtca ttgtcaccca tatatatgtc       420
cagacctcaa gcctgctact gtgagcccct tacctgtagc tgttgctacc aagaagagga       480
tgatacagct ccatcccatg gtgaggtcct gtgtgctcag taactgtaga gagaactgtg       540
atctcatgtt tttctgtttg tggtatagac aaacctatat ttaccatgta gattcagagg       600
atttgcatat tcataagctt                                                    620
```

<210> SEQ ID NO 59
<211> LENGTH: 116
<212> TYPE: PRT
<213> ORGANISM: Artificial Sequence
<220> FEATURE:
<223> OTHER INFORMATION: deimmunized heavy chain J415-2

-continued

```
<400> SEQUENCE: 59

Glu Val Lys Leu Glu Glu Ser Gly Gly Gly Leu Val Gln Pro Gly Gly
 1               5                  10                  15

Ser Met Lys Ile Ser Cys Val Ala Ser Gly Phe Thr Phe Ser Asn Tyr
             20                  25                  30

Trp Met Asn Trp Val Arg Gln Thr Pro Glu Lys Gly Leu Glu Trp Val
         35                  40                  45

Ala Leu Ile Arg Ser Gln Ser Asn Asn Phe Ala Thr His Tyr Ala Glu
     50                  55                  60

Ser Val Lys Gly Arg Val Ile Ile Ser Arg Asp Asp Ser Lys Ser Ser
 65                  70                  75                  80

Val Tyr Leu Gln Met Asn Ser Leu Arg Ala Glu Asp Thr Ala Val Tyr
                 85                  90                  95

Tyr Cys Thr Arg Arg Trp Asn Asn Phe Trp Gly Gln Gly Thr Thr Val
            100                 105                 110

Thr Val Ser Ser
            115

<210> SEQ ID NO 60
<211> LENGTH: 116
<212> TYPE: PRT
<213> ORGANISM: Artificial Sequence
<220> FEATURE:
<223> OTHER INFORMATION: deimmunized heavy chain J415-3

<400> SEQUENCE: 60

Glu Val Lys Leu Glu Glu Ser Gly Gly Gly Leu Val Gln Pro Gly Gly
 1               5                  10                  15

Ser Met Lys Ile Ser Cys Val Ala Ser Gly Phe Thr Phe Ser Asn Tyr
             20                  25                  30

Trp Met Asn Trp Val Arg Gln Thr Pro Glu Lys Gly Leu Glu Trp Val
         35                  40                  45

Ala Glu Ile Arg Ser Gln Ser Asn Asn Phe Ala Thr His Tyr Ala Glu
     50                  55                  60

Ser Val Lys Gly Arg Val Ile Ile Ser Arg Asp Asp Ser Lys Ser Ser
 65                  70                  75                  80

Val Tyr Leu Gln Met Asn Ser Leu Arg Ala Glu Asp Thr Ala Val Tyr
                 85                  90                  95

Tyr Cys Thr Arg Arg Trp Asn Asn Phe Trp Gly Gln Gly Thr Thr Val
            100                 105                 110

Thr Val Ser Ser
            115

<210> SEQ ID NO 61
<211> LENGTH: 116
<212> TYPE: PRT
<213> ORGANISM: Artificial Sequence
<220> FEATURE:
<223> OTHER INFORMATION: majority sequence

<400> SEQUENCE: 61

Glu Val Lys Leu Glu Glu Ser Gly Gly Gly Leu Val Gln Pro Gly Gly
 1               5                  10                  15

Ser Met Lys Ile Ser Cys Val Ala Ser Gly Phe Thr Phe Ser Asn Tyr
             20                  25                  30

Trp Met Asn Trp Val Arg Gln Thr Pro Glu Lys Gly Leu Glu Trp Val
         35                  40                  45
```

```
Ala Glu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Ser Leu Arg Ala Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
            115

<210> SEQ ID NO 62
<211> LENGTH: 107
<212> TYPE: PRT
<213> ORGANISM: Artificial Sequence
<220> FEATURE:
<223> OTHER INFORMATION: deimmunized light chain J415-2

<400> SEQUENCE: 62

Asn Ile Val Met Thr Gln Ser Pro Lys Ser Met Ser Ala Ser Ala Gly
1               5                   10                  15

Glu Arg Met Thr Leu Thr Cys Lys Ala Ser Glu Asn Val Gly Thr Tyr
                20                  25                  30

Val Ser Trp Tyr Gln Gln Lys Pro Thr Gln Ser Pro Lys Met Leu Ile
            35                  40                  45

Tyr Gly Ala Ser Asn Arg Phe Thr Gly Val Pro Asp Arg Phe Ser Gly
        50                  55                  60

Ser Gly Ser Gly Thr Asp Phe Ile Leu Thr Ala Ser Ser Val Gln Ala
65                  70                  75                  80

Glu Asp Pro Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: deimmunized light chain J415-3

<400> SEQUENCE: 63

Asn Ile Val Met Thr Gln Ser Pro Lys Ser Met Ser Ala Ser Ala Gly
1               5                   10                  15

Glu Arg Met Thr Leu Thr Cys Lys Ala Ser Glu Asn Val Gly Thr Tyr
                20                  25                  30

Val Ser Trp Tyr Gln Gln Lys Pro Thr Gln Ser Pro Lys Met Leu Ile
            35                  40                  45

Tyr Gly Ala Ser Asn Arg Phe Thr Gly Val Pro Asp Arg Phe Ser Gly
        50                  55                  60

Ser Gly Ser Gly Thr Asp Phe Ile Leu Thr Ala Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 64
```

-continued

```
<211> LENGTH: 107
<212> TYPE: PRT
<213> ORGANISM: Artificial Sequence
<220> FEATURE:
<223> OTHER INFORMATION: deimmunized light chain J415-4

<400> SEQUENCE: 64

Asn Ile Val Met Thr Gln Ser Pro Lys Ser Met Ser Ala Ser Ala Gly
  1               5                  10                  15

Glu Arg Met Thr Leu Thr Cys Lys Ala Ser Glu Asn Val Gly Thr Tyr
             20                  25                  30

Val Ser Trp Tyr Gln Gln Lys Pro Thr Gln Ser Pro Lys Met Leu Ile
         35                  40                  45

Tyr Gly Ala Ser Asn Arg Phe Thr Gly Val Pro Asp Arg Phe Ser Gly
 50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
             85                  90                  95

Thr Phe Gly Gly Gly Thr Lys Leu Glu Met Lys
            100                 105

<210> SEQ ID NO 65
<211> LENGTH: 107
<212> TYPE: PRT
<213> ORGANISM: Artificial Sequence
<220> FEATURE:
<223> OTHER INFORMATION: deimmunized light chain J415-6

<400> SEQUENCE: 65

Asn Ile Val Met Thr Gln Phe Pro Lys Ser Met Ser Ala Ser Ala Gly
  1               5                  10                  15

Glu Arg Met Thr Leu Thr Cys Lys Ala Ser Glu Asn Val Gly Thr Tyr
             20                  25                  30

Val Ser Trp Tyr Gln Gln Lys Pro Glu Gln Ser Pro Lys Met Leu Ile
         35                  40                  45

Tyr Gly Ala Ser Asn Arg Phe Thr Gly Val Pro Asp Arg Phe Ser Gly
 50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
             85                  90                  95

Thr Phe Gly Gly Gly Thr Lys Leu Glu Met Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: deimmunized light chain J415-7

<400> SEQUENCE: 66

Asn Ile Val Met Thr Gln Phe Pro Lys Ser Met Ser Ala Ser Ala Gly
  1               5                  10                  15

Glu Arg Val Thr Leu Thr Cys Lys Ala Ser Glu Asn Val Gly Thr Tyr
             20                  25                  30

Val Ser Trp Tyr Gln Gln Lys Pro Thr Gln Ser Pro Lys Met Leu Ile
         35                  40                  45
```

-continued

Tyr Gly Ala Ser Asn Arg Phe Thr Gly Val Pro Asp Arg Phe Ser Gly
            50                  55                  60

Ser Gly Ser Gly Thr Asp Phe Ile Leu Thr Ile Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 67
<211> LENGTH: 107
<212> TYPE: PRT
<213> ORGANISM: Artificial Sequence
<220> FEATURE:
<223> OTHER INFORMATION: deimmunized light chain J415-8

<400> SEQUENCE: 67

Asn Ile Val Met Thr Gln Phe Pro Lys Ser Met Ser Ala Ser Ala Gly
1               5                   10                  15

Glu Arg Met Thr Leu Thr Cys Lys Ala Ser Glu Asn Ser Gly Thr Tyr
            20                  25                  30

Val Ser Trp Tyr Gln Gln Lys Pro Glu Gln Ser Pro Lys Met Leu Ile
        35                  40                  45

Tyr Gly Ala Ser Asn Arg Phe Thr Gly Val Pro Asp Arg Phe Ser Gly
            50                  55                  60

Ser Gly Ser Gly Thr Asp Phe Ile Leu Thr Ile Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 68
<211> LENGTH: 107
<212> TYPE: PRT
<213> ORGANISM: Artificial Sequence
<220> FEATURE:
<223> OTHER INFORMATION: majority sequence

<400> SEQUENCE: 68

Asn Ile Val Met Thr Gln Phe Pro Lys Ser Met Ser Ala Ser Ala Gly
1               5                   10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
            50                  55                  60

Ser Gly Ser Gly Thr Asp Phe Ile Leu Thr Ile Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 69
<211> LENGTH: 123
<212> TYPE: PRT
<213> ORGANISM: Mus musculus

```
<400> SEQUENCE: 69

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Thr Gly Gly Tyr Gly Gly Arg Arg Ser Trp Phe Ala Tyr
            100                 105                 110

Trp Gly Gln Gly Thr Leu Val Thr Val Ser Ser
        115                 120

<210> SEQ ID NO 70
<211> LENGTH: 123
<212> TYPE: PRT
<213> ORGANISM: Artificial Sequence
<220> FEATURE:
<223> OTHER INFORMATION: majority sequence

<400> SEQUENCE: 70

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Gln Ser Asp Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Thr Gly Gly Tyr Gly Gly Arg Arg Ser Trp Asn Ala Phe
            100                 105                 110

Trp Gly Gln Gly Thr Leu Val Thr Val Ser Ser
        115                 120

<210> SEQ ID NO 71
<211> LENGTH: 113
<212> TYPE: PRT
<213> ORGANISM: Mus musculus

<400> SEQUENCE: 71

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
```

-continued

```
            50                  55                  60
Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110
Lys
```

<210> SEQ ID NO 72
<211> LENGTH: 113
<212> TYPE: PRT
<213> ORGANISM: Artificial Sequence
<220> FEATURE:
<223> OTHER INFORMATION: majority sequence

<400> SEQUENCE: 72

```
Asp Ile Val Met Thr Gln Ser Pro Ser Ser Leu Ala Val Ser Ala Gly
1               5                   10                  15

Glu Lys Val Thr Leu Ser Cys Lys Ala Ser Glu Ser Leu Leu Asn Val
                20                  25                  30

Gly Asn Gln Lys Thr Tyr Val Ala Trp Tyr Gln Gln Lys Pro Gly Gln
            35                  40                  45

Ser Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Ile Leu Thr
65                  70                  75                  80

Ile Ser Ser Val Gln Ala Glu Asp Leu Ala Val Tyr Tyr Cys Gly Asn
                85                  90                  95

Ser Tyr Ser Phe Pro Leu Thr Phe Gly Gly Gly Thr Lys Leu Glu Leu
            100                 105                 110
Lys
```

<210> SEQ ID NO 73
<211> LENGTH: 354
<212> TYPE: DNA
<213> ORGANISM: Mus musculus
<220> FEATURE:
<221> NAME/KEY: CDS
<222> LOCATION: (1)...(354)

<400> SEQUENCE: 73

```
gag gtc cag ctg cag cag tct gga cct gag ctg gtt aag cct ggg gct    48
Glu Val Gln Leu Gln Gln Ser Gly Pro Glu Leu Val Lys Pro Gly Ala
1               5                   10                  15 tca gtg aag atg tcc tgc aag gct tct gga tac aca ttc act ggc tat    96
Ser Val Lys Met Ser Cys Lys Ala Ser Gly Tyr Thr Phe Thr Gly Tyr
                20                  25                  30 gtt atg cac tgg gtg aag cag aag cct gga cag gtc ctt gag tgg att    144
Val Met His Trp Val Lys Gln Lys Pro Gly Gln Val Leu Glu Trp Ile
            35                  40                  45 gga tat att aat cct tac aat gat gtt act agg tat aat ggg aag ttc    192
Gly Tyr Ile Asn Pro Tyr Asn Asp Val Thr Arg Tyr Asn Gly Lys Phe
        50                  55                  60 aaa ggc aag gcc aca ctg acc tca gac aaa tat tcc agc aca gcc tac    240
Lys Gly Lys Ala Thr Leu Thr Ser Asp Lys Tyr Ser Ser Thr Ala Tyr
65                  70                  75                  80 atg gag ctc agc ggc ctg acc tct gag gac tct gcg gtc tat tac tgt    288
Met Glu Leu Ser Gly Leu Thr Ser Glu Asp Ser Ala Val Tyr Tyr Cys
                85                  90                  95
```

```
gca aga ggg gag aac tgg tac tac ttt gac tcc tgg ggc cga ggc gcc      336
Ala Arg Gly Glu Asn Trp Tyr Tyr Phe Asp Ser Trp Gly Arg Gly Ala
            100                 105                 110 act ctc aca gtc tcc tca                                              354
Thr Leu Thr Val Ser Ser
        115
```

<210> SEQ ID NO 74
<211> LENGTH: 118
<212> TYPE: PRT
<213> ORGANISM: Mus musculus

<400> SEQUENCE: 74

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Gly Tyr
            20                  25                  30

Val Met His Trp Val Lys Gln Lys Pro Gly Gln Val Leu Glu Trp Ile
        35                  40                  45

Gly Tyr Ile Asn Pro Tyr Asn Asp Val Thr Arg Tyr Asn Gly Lys Phe
    50                  55                  60

Lys Gly Lys Ala Thr Leu Thr Ser Asp Lys Tyr Ser Ser Thr Ala Tyr
65                  70                  75                  80

Met Glu Leu Ser Gly Leu Thr Ser Glu Asp Ser Ala Val Tyr Tyr Cys
                85                  90                  95

Ala Arg Gly Glu Asn Trp Tyr Tyr Phe Asp Ser Trp Gly Arg Gly Ala
            100                 105                 110

Thr Leu Thr Val Ser Ser
        115
```

<210> SEQ ID NO 75
<211> LENGTH: 354
<212> TYPE: DNA
<213> ORGANISM: Mus musculus

<400> SEQUENCE: 75

```
tgaggagact gtgagagtgg cgcctcggcc ccaggagtca agtagtacc agttctcccc      60 tcttgcacag taatagaccg cagagtcctc agaggtcagg ccgctgagct ccatgtaggc    120
tgtgctggaa tatttgtctg aggtcagtgt ggccttgcct ttgaacttcc cattatacct    180
agtaacatca ttgtaaggat taatatatcc aatccactca aggacctgtc caggcttctg    240
cttcacccag tgcataacat agccagtgaa tgtgtatcca gaagccttgc aggacatctt    300
cactgaagcc caggcttaa ccagctcagg tccagactgc tgcagctgga cctc            354
```

<210> SEQ ID NO 76
<211> LENGTH: 333
<212> TYPE: DNA
<213> ORGANISM: Mus musculus
<220> FEATURE:
<221> NAME/KEY: CDS
<222> LOCATION: (1)...(333)

<400> SEQUENCE: 76

```
gac att gtg ctg acc caa tct cca gct tct ttg gct gtg tct cta gga       48
Asp Ile Val Leu Thr Gln Ser Pro Ala Ser Leu Ala Val Ser Leu Gly
1               5                   10                  15 cag agg gcc acc ata tcc tgc aga gcc agt gaa agt att gat agt tat       96
Gln Arg Ala Thr Ile Ser Cys Arg Ala Ser Glu Ser Ile Asp Ser Tyr
            20                  25                  30
```

```
gac aat act ttt atg cac tgg tac cag cag aaa cca gga cag cca ccc      144
Asp Asn Thr Phe Met His Trp Tyr Gln Gln Lys Pro Gly Gln Pro Pro
        35                  40                  45 aac ctc ctc atc ttt cgt gca tcc atc cta gaa tct ggg atc cct gcc      192
Asn Leu Leu Ile Phe Arg Ala Ser Ile Leu Glu Ser Gly Ile Pro Ala
 50                  55                  60 agg ttc agt ggc agt ggg tct ggg aca gac ttc acc ctc acc att tat      240
Arg Phe Ser Gly Ser Gly Ser Gly Thr Asp Phe Thr Leu Thr Ile Tyr
 65                  70                  75                  80 cct gtg gag gct gat gat gtt gca acc tat tac tgt cac caa agt att      288
Pro Val Glu Ala Asp Asp Val Ala Thr Tyr Tyr Cys His Gln Ser Ile
                 85                  90                  95 gag gat ccg tac acg ttc gga ggg ggg acc aag ctg gaa ata aaa          333
Glu Asp Pro Tyr Thr Phe Gly Gly Gly Thr Lys Leu Glu Ile Lys
            100                 105                 110
```

<210> SEQ ID NO 77
<211> LENGTH: 111
<212> TYPE: PRT
<213> ORGANISM: Mus musculus

<400> SEQUENCE: 77

```
Asp Ile Val Leu Thr Gln Ser Pro Ala Ser Leu Ala Val Ser Leu Gly
 1               5                   10                  15

Gln Arg Ala Thr Ile Ser Cys Arg Ala Ser Glu Ser Ile Asp Ser Tyr
            20                  25                  30

Asp Asn Thr Phe Met His Trp Tyr Gln Gln Lys Pro Gly Gln Pro Pro
        35                  40                  45

Asn Leu Leu Ile Phe Arg Ala Ser Ile Leu Glu Ser Gly Ile Pro Ala
 50                  55                  60

Arg Phe Ser Gly Ser Gly Ser Gly Thr Asp Phe Thr Leu Thr Ile Tyr
 65                  70                  75                  80

Pro Val Glu Ala Asp Asp Val Ala Thr Tyr Tyr Cys His Gln Ser Ile
                 85                  90                  95

Glu Asp Pro Tyr Thr Phe Gly Gly Gly Thr Lys Leu Glu Ile Lys
            100                 105                 110
```

<210> SEQ ID NO 78
<211> LENGTH: 333
<212> TYPE: DNA
<213> ORGANISM: Mus musculus

<400> SEQUENCE: 78

```
ttttatttcc agcttggtcc cccctccgaa cgtgtacgga tcctcaatac tttggtgaca    60
gtaataggtt gcaacatcat cagcctccac aggataaatg gtgagggtga agtctgtccc   120
agacccactg ccactgaacc tggcagggat cccagattct aggatggatg cacgaaagat   180
gaggaggttg ggtggctgtc ctggtttctg ctggtaccag tgcataaaag tattgtcata   240
actatcaata ctttcactgg ctctgcagga tatggtggcc ctctgtccta gagacacagc   300
caaagaagct ggagattggg tcagcacaat gtc                                333
```

<210> SEQ ID NO 79
<211> LENGTH: 125
<212> TYPE: PRT
<213> ORGANISM: Mus musculus

<400> SEQUENCE: 79

Glu Val Gln Leu Gln Gln Ser Gly Pro Glu Leu Val Lys Pro Gly Ala

```
                1               5                   10                  15
Ser Val Lys Ile Ser Cys Lys Ala Ser Gly Tyr Thr Phe Thr Asp Tyr
                    20                  25                  30

Tyr Met Asn Asn Trp Val Lys Gln Ser Pro Gly Lys Ser Leu Glu Trp
                    35                  40                  45

Ile Gly Asp Ile Asn Pro Gly Asn Gly Gly Thr Ser Tyr Asn Gln Lys
    50                  55                  60

Phe Lys Gly Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Tyr
                    85                  90                  95

Cys Ala Arg Gly Tyr Tyr Ser Ser Tyr Met Ala Tyr Tyr Ala Phe
                    100                 105                 110

Asp Tyr Trp Gly Gln Gly Thr Thr Val Thr Val Ser Ser
            115                 120                 125
```

<210> SEQ ID NO 80
<211> LENGTH: 125
<212> TYPE: PRT
<213> ORGANISM: Artificial Sequence
<220> FEATURE:
<223> OTHER INFORMATION: majority sequence

<400> SEQUENCE: 80

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
                    20                  25                  30

Val Met Asn Asn Trp Val Lys Gln Ser Pro Gly Gln Val Leu Glu Trp
                    35                  40                  45

Ile Gly Asp Ile Asn Pro Gly Asn Gly Gly Thr Ser Tyr Asn Gly Lys
    50                  55                  60

Phe Lys Gly Lys Ala Thr Leu Thr Val Asp Lys Ser Ser Ser Thr Ala
65                  70                  75                  80

Tyr Met Glu Leu Ser Gly Leu Thr Ser Glu Asp Ser Ala Val Tyr Tyr
                    85                  90                  95

Cys Ala Arg Gly Glu Asn Ser Ser Tyr Met Ala Tyr Tyr Ala Phe
                    100                 105                 110

Asp Ser Trp Gly Gln Gly Ala Thr Val Thr Val Ser Ser
            115                 120                 125
```

<210> SEQ ID NO 81
<211> LENGTH: 112
<212> TYPE: PRT
<213> ORGANISM: Mus musculus

<400> SEQUENCE: 81

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                    20                  25                  30

Gly Asn Ser Phe Met His Trp Tyr Gln Gln Lys Pro Gly Gln Pro Pro
                    35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80
```

```
Pro Val Glu Glu Asp Asp Ala Ala Thr Tyr Tyr Cys Gln Gln Ser Asn
                85                  90                  95

Glu Asp Pro Pro Trp Thr Phe Gly Gly Gly Thr Lys Leu Glu Ile Lys
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: majority sequence

<400> SEQUENCE: 82

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
         35                  40                  45

Asn Leu Leu Ile Phe Ala Ala Ser Ile Leu Glu Ser Gly Val Pro Ala
     50                  55                  60

Arg Phe Ser Gly Ser Gly Ser Gly Thr Asp Phe Thr Leu Thr Ile His
 65                  70                  75                  80

Pro Val Glu Ala Asp Asp Ala Ala Thr Tyr Tyr Cys Gln Gln Ser Ile
                85                  90                  95

Glu Asp Pro Pro Tyr Thr Phe Gly Gly Gly Thr Lys Leu Glu Ile Lys
            100                 105                 110

<210> SEQ ID NO 83
<211> LENGTH: 363
<212> TYPE: DNA
<213> ORGANISM: Mus musculus
<220> FEATURE:
<221> NAME/KEY: CDS
<222> LOCATION: (1)...(363)

<400> SEQUENCE: 83 cag gtg cag cta aag gag tca gga cct ggc ctg gtg gcg tcc tca cag      48
Gln Val Gln Leu Lys Glu Ser Gly Pro Gly Leu Val Ala Ser Ser Gln
  1               5                  10                  15 agc ctg tcc atc aca tgc acc gtc tca gga ttc tca tta acc gcc tat      96
Ser Leu Ser Ile Thr Cys Thr Val Ser Gly Phe Ser Leu Thr Ala Tyr
             20                  25                  30 ggt att aac tgg gtt cgc cag cct cca gga aag ggt ctg gag tgg ctg     144
Gly Ile Asn Trp Val Arg Gln Pro Pro Gly Lys Gly Leu Glu Trp Leu
         35                  40                  45 gga gtg ata tgg cct gat gga aac aca gac tat aat tca act ctc aaa     192
Gly Val Ile Trp Pro Asp Gly Asn Thr Asp Tyr Asn Ser Thr Leu Lys
     50                  55                  60 tcc aga ctg aac atc ttc aag gac aac tcc aag aac caa gtt ttc tta     240
Ser Arg Leu Asn Ile Phe Lys Asp Asn Ser Lys Asn Gln Val Phe Leu
 65                  70                  75                  80 aaa atg agc agt ttc caa act gat gac aca gcc aga tac ttc tgt gcc     288
Lys Met Ser Ser Phe Gln Thr Asp Asp Thr Ala Arg Tyr Phe Cys Ala
                85                  90                  95 aga gat tcg tat ggt aac ttc aag agg ggt tgg ttt gac ttc tgg ggc     336
Arg Asp Ser Tyr Gly Asn Phe Lys Arg Gly Trp Phe Asp Phe Trp Gly
            100                 105                 110 cag ggc acc act ctc aca gtc tcc tca                                 363
Gln Gly Thr Thr Leu Thr Val Ser Ser
```

-continued

<210> SEQ ID NO 84
<211> LENGTH: 121
<212> TYPE: PRT
<213> ORGANISM: Mus musculus

<400> SEQUENCE: 84

Gln Val Gln Leu Lys Glu Ser Gly Pro Gly Leu Val Ala Ser Ser Gln
1               5                   10                  15

Ser Leu Ser Ile Thr Cys Thr Val Ser Gly Phe Ser Leu Thr Ala Tyr
            20                  25                  30

Gly Ile Asn Trp Val Arg Gln Pro Pro Gly Lys Gly Leu Glu Trp Leu
        35                  40                  45

Gly Val Ile Trp Pro Asp Gly Asn Thr Asp Tyr Asn Ser Thr Leu Lys
    50                  55                  60

Ser Arg Leu Asn Ile Phe Lys Asp Asn Ser Lys Asn Gln Val Phe Leu
65                  70                  75                  80

Lys Met Ser Ser Phe Gln Thr Asp Asp Thr Ala Arg Tyr Phe Cys Ala
                85                  90                  95

Arg Asp Ser Tyr Gly Asn Phe Lys Arg Gly Trp Phe Asp Phe Trp Gly
            100                 105                 110

Gln Gly Thr Thr Leu Thr Val Ser Ser
        115                 120

<210> SEQ ID NO 85
<211> LENGTH: 363
<212> TYPE: DNA
<213> ORGANISM: Mus musculus

<400> SEQUENCE: 85
tgaggagact gtgagagtgg tgccctggcc ccagaagtca aaccaacccc tcttgaagtt      60
accatacgaa tctctggcac agaagtatct ggctgtgtca tcagtttgga aactgctcat    120
ttttaagaaa acttggttct tggagttgtc cttgaagatg ttcagtctgg atttgagagt    180
tgaattatag tctgtgtttc catcaggcca tatcactccc agccactcca gacccttttcc   240 tggaggctgg cgaacccagt taataccata ggcggttaat gagaatcctg agacggtgca    300
tgtgatggac aggctctgtg aggacgccac caggccaggt cctgactcct ttagctgcac    360
ctg                                                                  363

<210> SEQ ID NO 86
<211> LENGTH: 321
<212> TYPE: DNA
<213> ORGANISM: Mus musculus
<220> FEATURE:
<221> NAME/KEY: CDS
<222> LOCATION: (1)...(321)

<400> SEQUENCE: 86 aac att gtg atg acc cag tct caa aaa ttc atg tcc aca tca cca gga       48
Asn Ile Val Met Thr Gln Ser Gln Lys Phe Met Ser Thr Ser Pro Gly
1               5                   10                  15 gac agg gtc agg gtc acc tgc aag gcc agt cag aat gtg ggt tct gat       96
Asp Arg Val Arg Val Thr Cys Lys Ala Ser Gln Asn Val Gly Ser Asp
            20                  25                  30 gta gcc tgg tat caa gcg aaa cca gga caa tct cct aga ata ctg att     144
Val Ala Trp Tyr Gln Ala Lys Pro Gly Gln Ser Pro Arg Ile Leu Ile
        35                  40                  45

-continued

| | |
|---|---|
| tac tcg aca tcc tac cgt tac agt ggg gtc cct gat cgc ttc aca gcc<br>Tyr Ser Thr Ser Tyr Arg Tyr Ser Gly Val Pro Asp Arg Phe Thr Ala<br>     50                   55                   60 | 192 |
| tat gga tct ggg aca gat ttc act ctc acc att acc aat gtg cag tct<br>Tyr Gly Ser Gly Thr Asp Phe Thr Leu Thr Ile Thr Asn Val Gln Ser<br>65                   70                   75                   80 | 240 |
| gaa gac ttg aca gag tat ttc tgt cag caa tat aat agc tat cct ctc<br>Glu Asp Leu Thr Glu Tyr Phe Cys Gln Gln Tyr Asn Ser Tyr Pro Leu<br>                  85                   90                   95 | 288 |
| acg ttc ggt gct ggg acc aag ctg gag ctg aaa<br>Thr Phe Gly Ala Gly Thr Lys Leu Glu Leu Lys<br>          100                  105 | 321 |

<210> SEQ ID NO 87
<211> LENGTH: 107
<212> TYPE: PRT
<213> ORGANISM: Mus musculus

<400> SEQUENCE: 87

Asn Ile Val Met Thr Gln Ser Gln Lys Phe Met Ser Thr Ser Pro Gly
1               5                   10                  15

Asp Arg Val Arg Val Thr Cys Lys Ala Ser Gln Asn Val Gly Ser Asp
                20                  25                  30

Val Ala Trp Tyr Gln Ala Lys Pro Gly Gln Ser Pro Arg Ile Leu Ile
            35                  40                  45

Tyr Ser Thr Ser Tyr Arg Tyr Ser Gly Val Pro Asp Arg Phe Thr Ala
        50                  55                  60

Tyr Gly Ser Gly Thr Asp Phe Thr Leu Thr Ile Thr Asn Val Gln Ser
65                  70                  75                  80

Glu Asp Leu Thr Glu Tyr Phe Cys Gln Gln Tyr Asn Ser Tyr Pro Leu
                85                  90                  95

Thr Phe Gly Ala Gly Thr Lys Leu Glu Leu Lys
            100                 105

<210> SEQ ID NO 88
<211> LENGTH: 321
<212> TYPE: DNA
<213> ORGANISM: Mus musculus

<400> SEQUENCE: 88

| | |
|---|---|
| tttcagctcc agcttggtcc cagcaccgaa cgtgagagga tagctattat attgctgaca | 60 |
| gaaatactct gtcaagtctt cagactgcac attggtaatg gtgagagtga aatctgtccc | 120 |
| agatccatag gctgtgaagc gatcagggac cccactgtaa cggtaggatg tcgagtaaat | 180 |
| cagtattcta ggagattgtc ctggtttcgc ttgataccag gctacatcag aacccacatt | 240 |
| ctgactggcc ttgcaggtga ccctgaccct gtctcctggt gatgtggaca tgaattttg | 300 |
| agactgggtc atcacaatgt t | 321 |

<210> SEQ ID NO 89
<211> LENGTH: 121
<212> TYPE: PRT
<213> ORGANISM: Mus musculus

<400> SEQUENCE: 89

Gln Val Gln Leu Lys Glu Ser Gly Pro Gly Leu Val Ala Ser Ser Gln
1               5                   10                  15

Ser Leu Ser Ile Thr Cys Thr Val Ser Gly Phe Ser Leu Thr Ala Tyr
                20                  25                  30

```
Gly Ile Asn Trp Val Arg Gln Pro Pro Gly Lys Gly Leu Glu Trp Leu
            35                  40                  45

Gly Val Ile Trp Pro Asp Gly Asn Thr Asp Tyr Asn Ser Thr Leu Lys
    50                  55                  60

Ser Arg Leu Asn Ile Phe Lys Asp Asn Ser Lys Asn Gln Val Phe Leu
65                  70                  75                  80

Lys Met Ser Ser Phe Gln Thr Asp Asp Thr Ala Arg Tyr Phe Cys Ala
                85                  90                  95

Arg Asp Ser Tyr Gly Asn Phe Lys Arg Gly Trp Phe Asp Phe Trp Gly
                100                 105                 110

Gln Gly Thr Thr Leu Thr Val Ser Ser
            115                 120

<210> SEQ ID NO 90
<211> LENGTH: 121
<212> TYPE: PRT
<213> ORGANISM: Artificial Sequence
<220> FEATURE:
<223> OTHER INFORMATION: majority sequence

<400> SEQUENCE: 90

Gln Val Gln Leu Lys Glu Ser Gly Pro Gly Leu Val Ala Ser Ser Gln
1               5                   10                  15

Ser Leu Ser Ile Thr Cys Thr Val Ser Gly Phe Ser Leu Thr Ala Tyr
            20                  25                  30

Gly Ile Asn Trp Val Arg Gln Pro Pro Gly Lys Gly Leu Glu Trp Leu
            35                  40                  45

Gly Val Ile Trp Pro Asp Gly Asn Thr Asp Tyr Asn Ser Thr Leu Lys
    50                  55                  60

Ser Arg Leu Asn Ile Phe Lys Asp Asn Ser Lys Asn Gln Val Phe Leu
65                  70                  75                  80

Lys Met Ser Ser Phe Gln Thr Asp Asp Thr Ala Arg Tyr Phe Cys Ala
                85                  90                  95

Arg Asp Ser Tyr Gly Asn Phe Lys Arg Gly Trp Phe Asp Phe Trp Gly
                100                 105                 110

Gln Gly Thr Thr Leu Thr Val Ser Ser
            115                 120

<210> SEQ ID NO 91
<211> LENGTH: 113
<212> TYPE: PRT
<213> ORGANISM: Mus musculus

<400> SEQUENCE: 91

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
```

-continued

```
                 100                 105                 110
Lys

<210> SEQ ID NO 92
<211> LENGTH: 115
<212> TYPE: PRT
<213> ORGANISM: Artificial Sequence
<220> FEATURE:
<223> OTHER INFORMATION: majority sequence

<400> SEQUENCE: 92

Asp Ile Val Met Thr Gln Ser Gln Ser Ser Leu Ala Val Ser Ala Gly
  1               5                  10                  15

Asp Lys Val Thr Val Ser Cys Lys Ala Ser Gln Ser Leu Leu Asn Val
             20                  25                  30

Gly Ser Asp Lys Asn Tyr Val Ala Trp Tyr Gln Ala Lys Pro Gly Gln
         35                  40                  45

Ser Pro Lys Leu Leu Ile Tyr Ser Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Phe Cys Gln Asn
                 85                  90                  95

Asp Asn Ser Tyr Pro Leu Thr Phe Gly Ala Gly Thr Lys Leu Glu Leu
                100                 105                 110

Lys Arg Ala
        115

<210> SEQ ID NO 93
<211> LENGTH: 10
<212> TYPE: PRT
<213> ORGANISM: Mus musculus

<400> SEQUENCE: 93

Gly Tyr Thr Phe Thr Gly Tyr Val Met His
  1               5                  10

<210> SEQ ID NO 94
<211> LENGTH: 17
<212> TYPE: PRT
<213> ORGANISM: Mus musculus

<400> SEQUENCE: 94

Tyr Ile Asn Pro Tyr Asn Asp Val Thr Arg Tyr Asn Gly Lys Phe Lys
  1               5                  10                  15

Gly

<210> SEQ ID NO 95
<211> LENGTH: 9
<212> TYPE: PRT
<213> ORGANISM: Mus musculus

<400> SEQUENCE: 95

Gly Glu Asn Trp Tyr Tyr Phe Asp Ser
  1               5

<210> SEQ ID NO 96
<211> LENGTH: 15
<212> TYPE: PRT
<213> ORGANISM: Mus musculus
```

```
<400> SEQUENCE: 96

Arg Ala Ser Glu Ser Ile Asp Ser Tyr Asp Asn Thr Phe Met His
 1               5                  10                  15

<210> SEQ ID NO 97
<211> LENGTH: 7
<212> TYPE: PRT
<213> ORGANISM: Mus Musculus

<400> SEQUENCE: 97

Arg Ala Ser Ile Leu Glu Ser
 1               5

<210> SEQ ID NO 98
<211> LENGTH: 9
<212> TYPE: PRT
<213> ORGANISM: Mus musculus

<400> SEQUENCE: 98

His Gln Ser Ile Glu Asp Pro Tyr Thr
 1               5

<210> SEQ ID NO 99
<211> LENGTH: 10
<212> TYPE: PRT
<213> ORGANISM: Mus musculus

<400> SEQUENCE: 99

Gly Phe Ser Leu Thr Ala Tyr Gly Ile Asn
 1               5                  10

<210> SEQ ID NO 100
<211> LENGTH: 16
<212> TYPE: PRT
<213> ORGANISM: Mus musculus

<400> SEQUENCE: 100

Val Ile Trp Pro Asp Gly Asn Thr Asp Tyr Asn Ser Thr Leu Lys Ser
 1               5                  10                  15

<210> SEQ ID NO 101
<211> LENGTH: 13
<212> TYPE: PRT
<213> ORGANISM: Mus musculus

<400> SEQUENCE: 101

Asp Ser Tyr Gly Asn Phe Lys Arg Gly Trp Phe Asp Phe
 1               5                  10

<210> SEQ ID NO 102
<211> LENGTH: 11
<212> TYPE: PRT
<213> ORGANISM: Mus musculus

<400> SEQUENCE: 102

Lys Ala Ser Gln Asn Val Gly Ser Asp Val Ala
 1               5                  10

<210> SEQ ID NO 103
<211> LENGTH: 7
<212> TYPE: PRT
<213> ORGANISM: Mus musculus

<400> SEQUENCE: 103
```

-continued

Ser Thr Ser Tyr Arg Tyr Ser
1               5

<210> SEQ ID NO 104
<211> LENGTH: 9
<212> TYPE: PRT
<213> ORGANISM: Mus musculus

<400> SEQUENCE: 104

Gln Gln Tyr Asn Ser Tyr Pro Leu Thr
1               5

<210> SEQ ID NO 105
<211> LENGTH: 25
<212> TYPE: PRT
<213> ORGANISM: Mus musculus

<400> SEQUENCE: 105

Glu Val Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 106
<211> LENGTH: 14
<212> TYPE: PRT
<213> ORGANISM: Mus musculus

<400> SEQUENCE: 106

Trp Val Lys Gln Lys Pro Gly Gln Val Leu Glu Trp Ile Gly
1               5                   10

<210> SEQ ID NO 107
<211> LENGTH: 32
<212> TYPE: PRT
<213> ORGANISM: Mus musculus

<400> SEQUENCE: 107

Lys Ala Thr Leu Thr Ser Asp Lys Tyr Ser Ser Thr Ala Tyr Met Glu
1               5                   10                  15

Leu Ser Gly Leu Thr Ser Glu Asp Ser Ala Val Tyr Tyr Cys Ala Arg
            20                  25                  30

<210> SEQ ID NO 108
<211> LENGTH: 11
<212> TYPE: PRT
<213> ORGANISM: Mus musculus

<400> SEQUENCE: 108

Trp Gly Arg Gly Ala Thr Leu Thr Val Ser Ser
1               5                   10

<210> SEQ ID NO 109
<211> LENGTH: 82
<212> TYPE: PRT
<213> ORGANISM: Mus musculus

<400> SEQUENCE: 109

Glu Val Gln Leu Gln Gln Ser Gly Pro Glu Leu Val Lys Pro Gly Ala
1               5                   10                  15

Ser Val Lys Met Ser Cys Lys Ala Ser Trp Val Lys Gln Lys Pro Gly
            20                  25                  30

Gln Val Leu Glu Trp Ile Gly Lys Ala Thr Leu Thr Ser Asp Lys Tyr

```
            35                  40                  45
Ser Ser Thr Ala Tyr Met Glu Leu Ser Gly Leu Thr Ser Glu Asp Ser
        50                  55                  60
Ala Val Tyr Tyr Cys Ala Arg Trp Gly Arg Gly Ala Thr Leu Thr Val
65                  70                  75                  80

Ser Ser

<210> SEQ ID NO 110
<211> LENGTH: 23
<212> TYPE: PRT
<213> ORGANISM: Mus musculus

<400> SEQUENCE: 110

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 111
<211> LENGTH: 15
<212> TYPE: PRT
<213> ORGANISM: Mus musculus

<400> SEQUENCE: 111

Trp Tyr Gln Gln Lys Pro Gly Gln Pro Pro Asn Leu Leu Ile Phe
1               5                   10                  15

<210> SEQ ID NO 112
<211> LENGTH: 32
<212> TYPE: PRT
<213> ORGANISM: Mus musculus

<400> SEQUENCE: 112

Gly Ile Pro Ala Arg Phe Ser Gly Ser Gly Ser Gly Thr Asp Phe Thr
1               5                   10                  15

Leu Thr Ile Tyr Pro Val Glu Ala Asp Asp Val Ala Thr Tyr Tyr Cys
            20                  25                  30

<210> SEQ ID NO 113
<211> LENGTH: 10
<212> TYPE: PRT
<213> ORGANISM: Mus musculus

<400> SEQUENCE: 113

Phe Gly Gly Gly Thr Lys Leu Glu Ile Lys
1               5                   10

<210> SEQ ID NO 114
<211> LENGTH: 80
<212> TYPE: PRT
<213> ORGANISM: Mus musculus

<400> SEQUENCE: 114

Asp Ile Val Leu Thr Gln Ser Pro Ala Ser Leu Ala Val Ser Leu Gly
1               5                   10                  15

Gln Arg Ala Thr Ile Ser Cys Trp Tyr Gln Gln Lys Pro Gly Gln Pro
            20                  25                  30

Pro Asn Leu Leu Ile Phe Gly Ile Pro Ala Arg Phe Ser Gly Ser Gly
        35                  40                  45

Ser Gly Thr Asp Phe Thr Leu Thr Ile Tyr Pro Val Glu Ala Asp Asp
    50                  55                  60
```

-continued

Val Ala Thr Tyr Tyr Cys Phe Gly Gly Thr Lys Leu Glu Ile Lys
65                  70                  75                  80

<210> SEQ ID NO 115
<211> LENGTH: 25
<212> TYPE: PRT
<213> ORGANISM: Mus musculus

<400> SEQUENCE: 115

Gln Val Gln Leu Lys Glu Ser Gly Pro Gly Leu Val Ala Ser Ser Gln
1               5                   10                  15

Ser Leu Ser Ile Thr Cys Thr Val Ser
            20                  25

<210> SEQ ID NO 116
<211> LENGTH: 14
<212> TYPE: PRT
<213> ORGANISM: Mus musculus

<400> SEQUENCE: 116

Trp Val Arg Gln Pro Pro Gly Lys Gly Leu Glu Trp Leu Gly
1               5                   10

<210> SEQ ID NO 117
<211> LENGTH: 32
<212> TYPE: PRT
<213> ORGANISM: Mus musculus

<400> SEQUENCE: 117

Arg Leu Asn Ile Phe Lys Asp Asn Ser Lys Asn Gln Val Phe Leu Lys
1               5                   10                  15

Met Ser Ser Phe Gln Thr Asp Asp Thr Ala Arg Tyr Phe Cys Ala Arg
            20                  25                  30

<210> SEQ ID NO 118
<211> LENGTH: 11
<212> TYPE: PRT
<213> ORGANISM: Mus musculus

<400> SEQUENCE: 118

Trp Gly Gln Gly Thr Thr Leu Thr Val Ser Ser
1               5                   10

<210> SEQ ID NO 119
<211> LENGTH: 82
<212> TYPE: PRT
<213> ORGANISM: Mus musculus

<400> SEQUENCE: 119

Gln Val Gln Leu Lys Glu Ser Gly Pro Gly Leu Val Ala Ser Ser Gln
1               5                   10                  15

Ser Leu Ser Ile Thr Cys Thr Val Ser Trp Val Arg Gln Pro Pro Gly
            20                  25                  30

Lys Gly Leu Glu Trp Leu Gly Arg Leu Asn Ile Phe Lys Asp Asn Ser
        35                  40                  45

Lys Asn Gln Val Phe Leu Lys Met Ser Ser Phe Gln Thr Asp Asp Thr
    50                  55                  60

Ala Arg Tyr Phe Cys Ala Arg Trp Gly Gln Gly Thr Thr Leu Thr Val
65                  70                  75                  80

Ser Ser

-continued

```
<210> SEQ ID NO 120
<211> LENGTH: 23
<212> TYPE: PRT
<213> ORGANISM: Mus musculus

<400> SEQUENCE: 120

Asn Ile Val Met Thr Gln Ser Gln Lys Phe Met Ser Thr Ser Pro Gly
1               5                   10                  15

Asp Arg Val Arg Val Thr Cys
            20

<210> SEQ ID NO 121
<211> LENGTH: 15
<212> TYPE: PRT
<213> ORGANISM: Mus musculus

<400> SEQUENCE: 121

Trp Tyr Gln Ala Lys Pro Gly Gln Ser Pro Arg Ile Leu Ile Tyr
1               5                   10                  15

<210> SEQ ID NO 122
<211> LENGTH: 32
<212> TYPE: PRT
<213> ORGANISM: Mus musculus

<400> SEQUENCE: 122

Gly Val Pro Asp Arg Phe Thr Ala Tyr Gly Ser Gly Thr Asp Phe Thr
1               5                   10                  15

Leu Thr Ile Thr Asn Val Gln Ser Glu Asp Leu Thr Glu Tyr Phe Cys
            20                  25                  30

<210> SEQ ID NO 123
<211> LENGTH: 10
<212> TYPE: PRT
<213> ORGANISM: Mus musculus

<400> SEQUENCE: 123

Phe Gly Ala Gly Thr Lys Leu Glu Leu Lys
1               5                   10

<210> SEQ ID NO 124
<211> LENGTH: 80
<212> TYPE: PRT
<213> ORGANISM: Mus musculus

<400> SEQUENCE: 124

Asn Ile Val Met Thr Gln Ser Gln Lys Phe Met Ser Thr Ser Pro Gly
1               5                   10                  15

Asp Arg Val Arg Val Thr Cys Trp Tyr Gln Ala Lys Pro Gly Gln Ser
            20                  25                  30

Pro Arg Ile Leu Ile Tyr Gly Val Pro Asp Arg Phe Thr Ala Tyr Gly
        35                  40                  45

Ser Gly Thr Asp Phe Thr Leu Thr Ile Thr Asn Val Gln Ser Glu Asp
    50                  55                  60

Leu Thr Glu Tyr Phe Cys Phe Gly Ala Gly Thr Lys Leu Glu Leu Lys
65                  70                  75                  80

<210> SEQ ID NO 125
<211> LENGTH: 348
<212> TYPE: DNA
<213> ORGANISM: Mus musculus
```

```
<400> SEQUENCE: 125
gaagtgaagc ttgaggagtc tggaggaggc ttggtgcaac ctggaggatc catgaaactc      60
tcctgtgttg cctctggatt cactttcagt aattactgga tgaactgggt ccgccagtct     120
ccagagaagg ggcttgagtg ggttgctgaa attagatcgc aatctaataa ttttgcaaca     180
cattatgcgg agtctgtgaa agggagggtc atcatctcaa gagatgattc caagagtagt     240
gtctacctgc aaatgaacaa cttgagagct gaagacactg catttatta ctgtaccagg      300 cgatggaata atttctgggg ccaaggcacc actctcacag tctcctca                 348

<210> SEQ ID NO 126
<211> LENGTH: 348
<212> TYPE: DNA
<213> ORGANISM: Mus musculus

<400> SEQUENCE: 126
tgaggagact gtgagagtgg tgccttggcc ccagaaatta ttccatcgcc tggtacagta      60
ataaatgcca gtgtcttcag ctctcaagtt gttcatttgc aggtagacac tactcttgga     120
atcatctctt gagatgatga ccctcccttt cacagactcc gcataatgtg ttgcaaaatt     180
attagattgc gatctaattt cagcaaccca ctcaagcccc ttctctggag actggcggac     240
ccagttcatc cagtaattac tgaaagtgaa tccagaggca acacaggaga gtttcatgga     300
tcctccaggt tgcaccaagc tcctccaga ctcctcaagc ttcacttc                   348

<210> SEQ ID NO 127
<211> LENGTH: 321
<212> TYPE: DNA
<213> ORGANISM: Mus musculus

<400> SEQUENCE: 127
aacattgtaa tgacccaatt tcccaaatcc atgtccattt cagtaggaga gagggtcacc      60
ttgacctgca aggccagtga gaatgtgggt acttatgtgt cctggtatca acagaaacca     120
gaacagtctc ctaagatgtt gatatacggg gcatccaacc ggttcactgg ggtccccgat     180
cgcttcacag gcagtggatc tgcaacagat ttcattctga ccatcagcag tgtgcagact     240
gaagaccttg tagattatta ctgtggacag agttacacct ttccgtacac gttcggaggg     300
gggaccaagc tggaaatgaa g                                              321

<210> SEQ ID NO 128
<211> LENGTH: 321
<212> TYPE: DNA
<213> ORGANISM: Mus musculus

<400> SEQUENCE: 128
cttcatttcc agcttggtcc cccctccgaa cgtgtacgga aggtgtaac tctgtccaca       60 gtaataatct acaaggtctt cagtctgcac actgctgatg gtcagaatga atctgttgc      120 agatccactg cctgtgaagc gatcggggac cccagtgaac cggttggatg ccccgtatat     180
caacatctta ggagactgtt ctggtttctg ttgataccag gacacataag tacccacatt     240
ctcactggcc ttgcaggtca aggtgaccct ctcctcctact gaaatggaca tggatttggg   300
aaattgggtc attacaatgt t                                              321
```

What is claimed is:

1. A method of treating a subject having psoriasis, comprising:
   administering to the subject an antibody, or an antigen-binding fragment thereof, which binds specifically to the extracellular domain of PSMA, to thereby treat psoriasis.

2. The method of claim 1, wherein the antibody, or antigen-binding fragment thereof, is a monoclonal antibody or is derived from a monoclonal antibody.

3. The method of claim 2, wherein the antibody, or antigen-binding fragment thereof, is a murine or a human antibody or an antigen-binding fragment thereof.

4. The method of claim 1, wherein the antibody, or antigen-binding fragment thereof, is a chimeric, a humanized, a deimmunized, or an in vitro generated antibody or an antigen-binding fragment thereof.

5. The method of claim 1, wherein the antibody, or antigen-binding fragment thereof, binds to the extracellular domain of human PSMA with an affinity constant between $10^8$ $M^{-1}$ and $10^{10}$ $M^{-1}$.

6. The method of claim 1, wherein the antibody, or antigen-binding fragment thereof, competitively inhibits the binding of a monoclonal antibody selected from the group consisting of E99, J415, J533 and J591.

7. The method of claim 1, wherein the antibody, or antigen-binding fragment thereof, competitively inhibits the binding of a monoclonal antibody selected from the group consisting of deJ591 and deJ415.

8. The method of claim 1, wherein the antibody, or antigen-binding fragment thereof, is a murine monoclonal antibody or an antigen-binding fragment of a murine monoclonal antibody selected from the group consisting of E99, J415, J533 and J591.

9. The method of claim 1, wherein the antibody, or antigen-binding fragment thereof, is produced by a hybridoma cell line having an ATCC Accession Number selected from the group consisting of HB-12101, HB-12109, HB-12127, and HB-12126.

10. The method of claim 1, wherein the antibody, or antigen-binding fragment thereof, is produced by a hybridoma cell line having an ATCC Accession Number selected from the group consisting of PTA 3709 and PTA 4174.

11. The method of claim 4, wherein the antibody, or antigen-binding fragment thereof, comprises a heavy and light chain constant region of human origin.

12. The method of claim 11, wherein the heavy chain constant region is a human IgG1 constant region or portion thereof.

13. The method of claim 1, wherein the antibody, or antigen-binding fragment thereof, comprises all six CDRs from murine J591.

14. The method of claim 1, wherein the antibody, or antigen-binding fragment thereof, comprises all six CDRs from murine J415.

15. The method of claim 1, wherein the antibody, or antigen-binding fragment thereof, comprises a light chain variable region having an amino acid sequence of SEQ ID NO: 22.

16. The method of claim 1, wherein the antibody, or antigen-binding fragment thereof, comprises a heavy chain variable region having an amino acid sequence of SEQ ID NO: 21.

17. The method of claim 1, wherein the antibody, or antigen-binding fragment thereof, comprises a light chain variable region having an amino acid sequence of SEQ ID NO:50.

18. The method of claim 1, wherein the antibody, or antigen-binding fragment thereof, comprises a heavy chain variable region having an amino acid sequence of SEQ ID NO:49.

19. The method of claim 1, wherein the antibody, or antigen-binding fragment thereof, comprises:
   a light chain variable region comprising the amino acid sequence shown as SEQ ID NO:22, or the light chain variable region amino acid sequence of the antibody produced by the NS0 cell line having ATCC Accession Number PTA-3709; and
   a heavy chain variable region comprising the amino acid sequence shown as SEQ ID NO:21, or the heavy chain variable region amino acid sequence of the antibody produced by the NS0 cell line having ATCC Accession Number PTA-3709.

20. The method of claim 1, wherein the antibody or antigen-binding fragment thereof, comprises:
   a light chain variable region comprising the amino acid sequence shown as SEQ ID NO:50, or the light chain variable region amino acid sequence of the antibody produced by the NS0 cell line having ATCC Accession Number PTA-4174; and
   a heavy chain variable region comprising the amino acid sequence shown as SEQ ID NO:49, or the heavy chain variable region amino acid sequence of the antibody produced by the NS0 cell line having ATCC Accession Number PTA-4174.

21. The method of claim 19 or claim 20, wherein the antibody, or antigen-binding fragment thereof, comprises two heavy chains and two light chains.

22. The method of claim 19 or claim 20, wherein the antibody further comprises a heavy chain constant region of human isotype IgG1 or a portion thereof.

23. The method of claim 19, wherein the antibody, or antigen-binding fragment thereof, comprises:
   a light chain variable region comprising the amino acid sequence shown as SEQ ID NO:22, and
   a heavy chain variable region comprising the amino acid sequence shown as SEQ ID NO:21.

24. The method of claim 19, wherein the antibody, or antigen-binding fragment thereof, comprises:
   the light chain variable region amino acid sequence of the antibody produced by the NS0 cell line having ATCC Accession Number PTA-3709; and
   the heavy chain variable region amino acid sequence of the antibody produced by the NS0 cell line having ATCC Accession Number PTA-3709.

25. The method of claim 19, wherein the antibody, or antigen-binding fragment thereof, comprises:
   a light chain variable region comprising the amino acid sequence shown as SEQ ID NO:22; and
   the heavy chain variable region amino acid sequence of the antibody produced by the NS0 cell line having ATCC Accession Number PTA-3709.

26. The method of claim 19, wherein the antibody, or antigen-binding fragment thereof, comprises:
   the light chain variable region amino acid sequence of the antibody produced by the NS0 cell line having ATCC Accession Number PTA-3709; and
   a heavy chain variable region comprising the amino acid sequence shown as SEQ ID NO:21.

27. The method of claim 20, wherein the antibody, or antigen-binding fragment thereof, comprises:
   a light chain variable region comprising the amino acid sequence shown as SEQ ID NO:50; and a heavy chain variable region comprising the amino acid sequence shown as SEQ ID NO:49.

28. The method of claim 20, wherein the antibody, or antigen-binding fragment thereof, comprises:
the light chain variable region amino acid sequence of the antibody produced by the NS0 cell line having ATCC Accession Number PTA-4174; and
the heavy chain variable region amino acid sequence of the antibody produced by the NS0 cell line having ATCC Accession Number PTA-4174.

29. The method of claim 20, wherein the antibody, or antigen-binding fragment thereof, comprises:
a light chain variable region comprising the amino acid sequence shown as SEQ ID NO:50; and
the heavy chain variable region amino acid sequence of the antibody produced by the NS0 cell line having ATCC Accession Number PTA-4174.

30. The method of claim 20, wherein the antibody, or antigen-binding fragment thereof, comprises:
the light chain variable region amino acid sequence of the antibody produced by the NS0 cell line having ATCC Accession Number PTA-4174; and
a heavy chain variable region comprising the amino acid sequence shown as SEQ ID NO:49.

31. The method of claim 1, wherein the antibody, or antigen-binding fragment thereof, is coupled to a therapeutic agent.

32. The method of claim 31, wherein the therapeutic agent is a cytotoxic moiety selected from the group consisting of a cytotoxin and a radioactive isotope.

33. The method of claim 32, wherein the radioactive isotope is yttrium ($^{90}$Y) or lutetium ($^{177}$Lu).

34. The method of claim 32, wherein the cytotoxic moiety is maytansinoid.

35. The method of claim 34, wherein the maytansinoid is maytansinol or a maytansinol analogue.

36. The method of claim 34, wherein the maytansinoid is DM1.

37. The method of claim 32, wherein the antibody, or antigen-binding fragment thereof, is coupled to the cytotoxic moiety by a chelating agent or a linker.

38. The method of claim 37, wherein the chelating agent is 1,4,7,10-tetraazacyclododecane-N, N', N'', N'''-tetraacetic acid (DOTA).

39. The method of claim 37, wherein the linker is N-succinimidyl 4-(2-pyridyldithio) pentanoate (SPP).

40. The method of claim 32, wherein the cytotoxic moiety is selected from the group consisting of: a compound that emits radiation, a molecule of plant, fungal or bacterial origin, and a biological protein.

41. The method of claim 40, wherein the cytotoxic moiety is a molecule of bacterial origin.

42. The method of claim 32, wherein the radioactive isotope is an α-emitter, a β-emitter, a γ-emitter, or a β- and γ-emitter.

43. The method of claim 38, wherein cytotoxic moiety is a radioactive isotope selected from the group consisting of: yttrium ($^{90}$Y) and lutetium ($^{177}$Lu).

44. The method of claim 39, wherein the cytotoxic moiety is a maytansinoid.

45. The method of claim 44, wherein the maytansinoid is maytansinol or a maytansinol analogue.

46. The method of claim 44, wherein the maytansinoid is DM1.

47. The method of claim 32, wherein the cytotoxic moiety is a taxane.

48. The method of claim 32, wherein the cytotoxic moiety is a calicheamicin.

49. The method of claim 1, wherein the antigen-binding fragment is selected from the group consisting of Fab, F(ab')$_2$, Fv, and single chain Fv fragments.

50. The method of claim 1, wherein the subject is a mammal.

51. The method of claim 50, wherein the mammal is a human.

52. The method of claim 1, further comprising administering to the subject a cytotoxic agent in an amount effective to treat psoriasis in the subject.

53. The method of claim 52, wherein the antibody, or antigen-binding fragment thereof, and the cytotoxic agent are administered simultaneously or sequentially.

54. The method of claim 52, wherein the cytotoxic agent is selected from the group consisting of an antimetabolite, an alkylating agent, cyclothosphamide, busulfan, dibromomannitol, streptozotocin, mitomycin C, cis-dichlorodiamine platinum (II) (DDP) cisplatin), anthracyclines, and an antimitotic agent.

55. The method of claim 52, wherein cytotoxic agent is selected from the group consisting of phototherapy therapy, methotrexate, retinoids, macrolides, cyclosporine, etretinate, nonsteroidal anti-inflammatory drugs (NSAIDs), gold salts, and sulfasalizine.

56. The method of claim 55, wherein the cytotoxic agent is PUVA or UV radiation.

57. The method of claim 56, wherein the UV radiation is UVA or UVB radiation.

58. The method of claim 1, wherein the antibody, or antigen-binding fragment thereof, is administered systemically, parenterally or topically.

59. The method of claim 58, wherein the antibody, or antigen-binding fragment thereof, is administered intravenously, intramuscularly, subcutaneously, transdermally, or by inhalation.

60. The method of claim 58, further comprising administering to the subject a topically applied agent selected from the group consisting of a steroid, vitamin, tar, keratolytic agent and anthralin.

61. The method of claim 60, wherein the topically applied agent is a steroid selected from the group consisting of a glucocorticoid and a retinoid.

62. The method of claim 58, further comprising administering to the subject systemic agents selected from the group consisting of systemic glucocorticoids, sulfones, aminoquinolines, cytotoxic agents, antimetabolic agents, retinoids, antihistamines, immunosuppressive drugs, immunomodulatory drugs, and thalidomide.

* * * * *